United States Patent
Cox et al.

(10) Patent No.: US 11,771,677 B2
(45) Date of Patent: Oct. 3, 2023

(54) IMMUNOMODULATING UREA AZALIDES

(71) Applicant: Zoetis Services LLC, Parsippany, NJ (US)

(72) Inventors: Mark R. Cox, Kalamazoo, MI (US); Timothy L. Stuk, Mattawan, MI (US); Todd M. Maddux, Kalamazoo, MI (US); Richard Andrew Ewin, Kalamazoo, MI (US); Paul D. Johnson, Kalamazoo, MI (US); Tomasz Respondek, Kalamazoo, MI (US); Graham M. Kyne, Kalamazoo, MI (US); Rajendran Vairagoundar, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 365 days.

(21) Appl. No.: 17/198,863

(22) Filed: Mar. 11, 2021

(65) Prior Publication Data
US 2021/0290591 A1 Sep. 23, 2021

Related U.S. Application Data

(60) Provisional application No. 62/988,492, filed on Mar. 12, 2020.

(51) Int. Cl.
| | |
|---|---|
| *A61K 31/351* | (2006.01) |
| *C07D 498/04* | (2006.01) |
| *C07D 519/00* | (2006.01) |
| *C07H 17/08* | (2006.01) |
| *A61K 31/7048* | (2006.01) |
| *A61P 29/00* | (2006.01) |
| *A61P 37/02* | (2006.01) |
| *A61P 11/00* | (2006.01) |
| *A61P 31/04* | (2006.01) |

(52) U.S. Cl.
CPC ............ *A61K 31/351* (2013.01); *A61P 11/00* (2018.01); *A61P 29/00* (2018.01); *A61P 31/04* (2018.01); *A61P 37/02* (2018.01); *C07D 498/04* (2013.01); *C07D 519/00* (2013.01); *C07H 17/08* (2013.01)

(58) Field of Classification Search
CPC .............. A61K 31/351; A61K 31/7048; C07D 498/04; C07D 519/00; C07H 17/08; A61P 11/00; A61P 29/00; A61P 31/04; A61P 37/02
See application file for complete search history.

(56) References Cited

U.S. PATENT DOCUMENTS

| | | | |
|---|---|---|---|
| 6,667,393 B2 | 12/2003 | Boettner | |
| 7,507,721 B2 * | 3/2009 | Mereu | A61P 11/00 536/7.2 |
| 8,124,744 B2 | 2/2012 | Kashimura | |
| 2013/0045939 A1 | 2/2013 | Vu | |
| 2016/0031925 A1 | 2/2016 | Gardarsson | |

FOREIGN PATENT DOCUMENTS

| | | | |
|---|---|---|---|
| WO | WO 2009/023196 A1 | 2/2009 | |
| WO | WO-2011116312 A1 * | 9/2011 | ....... A61K 47/48038 |

OTHER PUBLICATIONS

Mereu A., et al., "Design, synthesis and in vivo activity of 9-(S)-dihydroerythromycin derivatives as potent anti-inflammatory agents," Bioorganic & Medicinal Chemistry Letters, 16 (2006) pp. 5801-5804.

* cited by examiner

*Primary Examiner* — Amanda L. Aguirre
*Assistant Examiner* — Sagar Patel
(74) *Attorney, Agent, or Firm* — Paul M. Misiak

(57) ABSTRACT

Defined herein are immunomodulating Formula (1) compounds wherein R, $R^0$, $R^1$, $R^2$, (1)

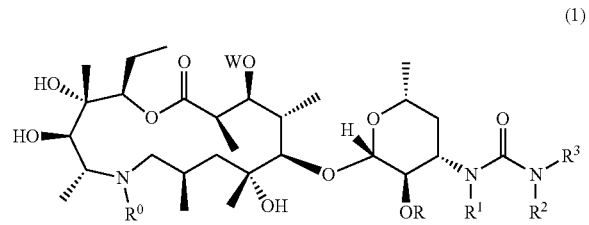

$R^3$ and W are as defined herein, stereoisomers thereof, and pharmaceutically acceptable salts thereof; and compositions comprising said compounds. The invention also includes methods for treating an inflammatory and/or immunological disease or disorder in an animal by administering a therapeutically effective amount of a Formula (1) compound, stereoisomer thereof, and a pharmaceutically acceptable salt thereof; or use of said compound of Formula (1) to prepare a medicament for treating an inflammatory and/or immunological disease or disorder in an animal.

11 Claims, 13 Drawing Sheets

FIGURE 1. Mechanism of an Immunomodulator in Context of BRD Progression
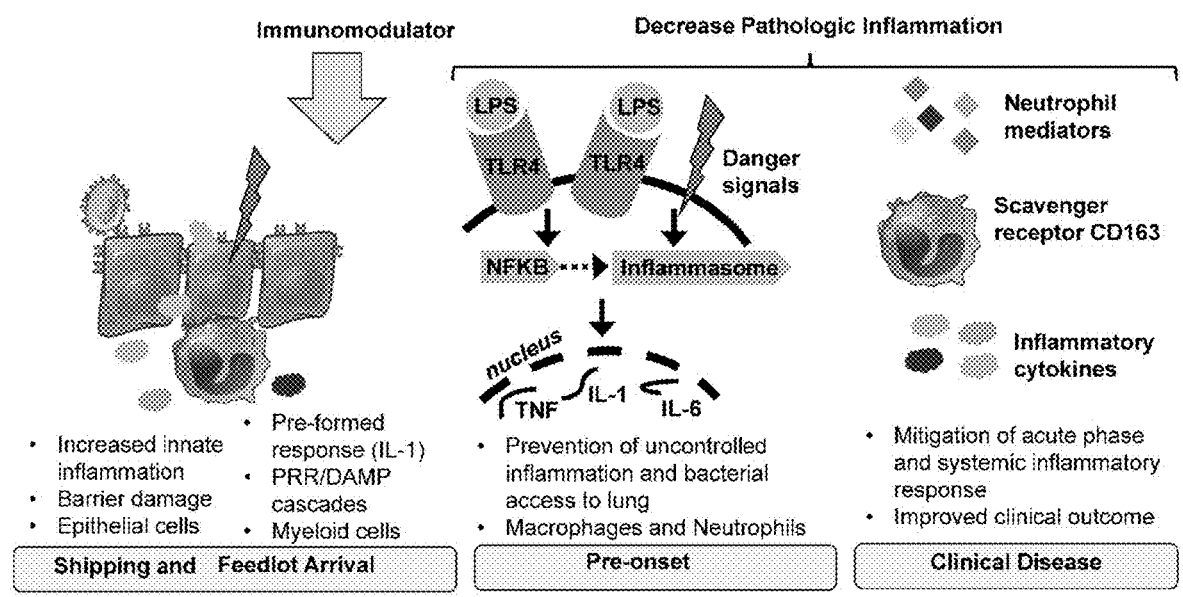

FIGURE 2. Clinical and Genomics Temporal Data Summary
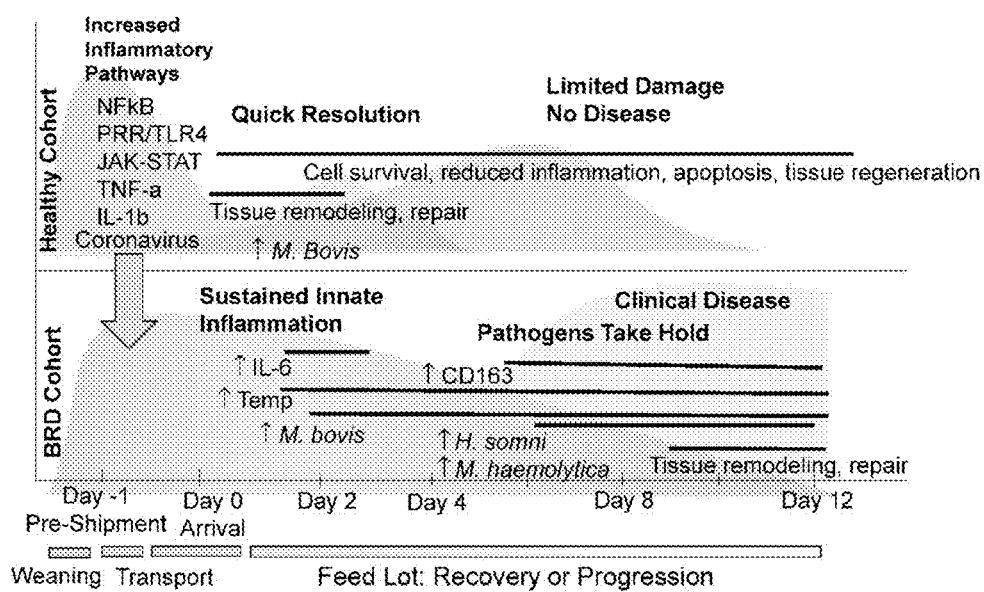

FIGURE 3. Plasma Cytokine (IL-6, IL-8, IL-10 and IFN-γ) Levels upon Arrival to the Feedlot for Calves at Risk for BRD
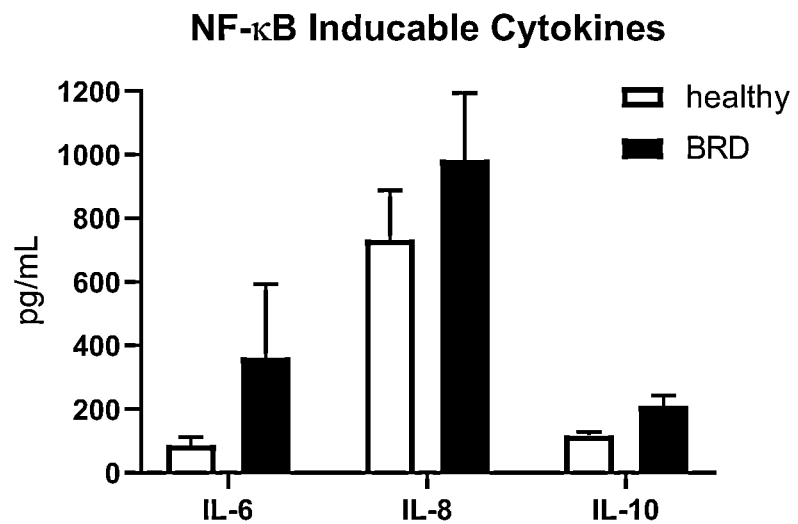
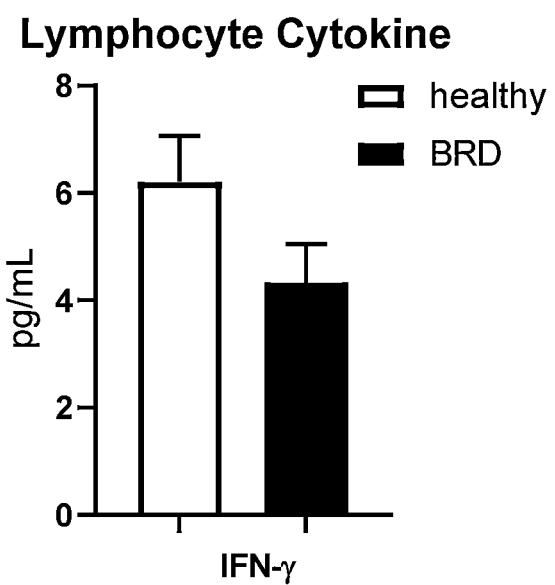

FIGURE 4. Example H-11 Dose-Dependent Cytokine Inhibition in Bovine Whole Blood; IL-6 (A), TNF-α (B) and IL-1β (C)
(A)
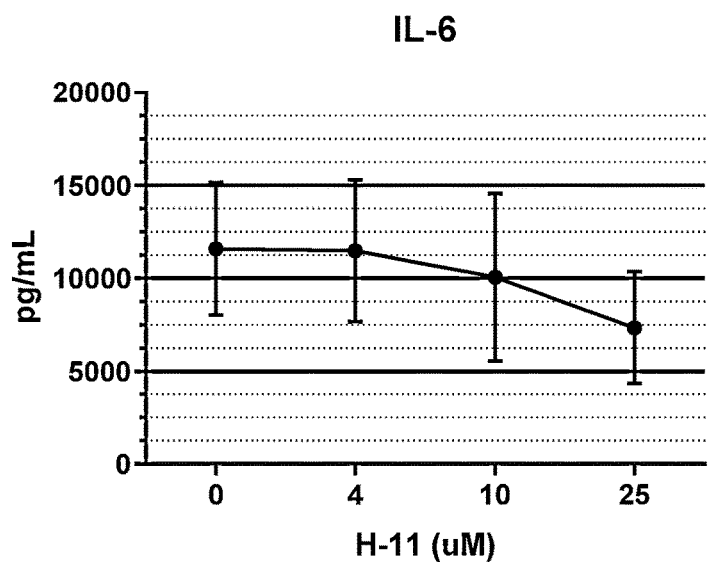
(B)
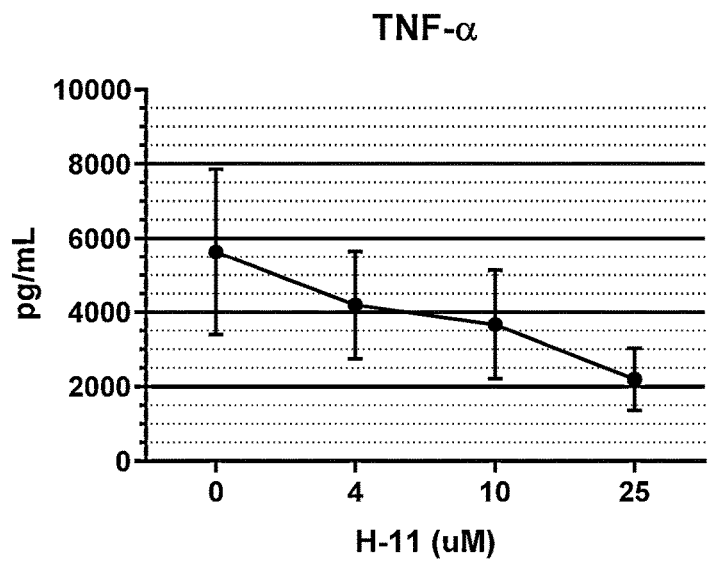

FIGURE 4. Example H-11 Dose-Dependent Cytokine Inhibition in Bovine Whole Blood
(C)
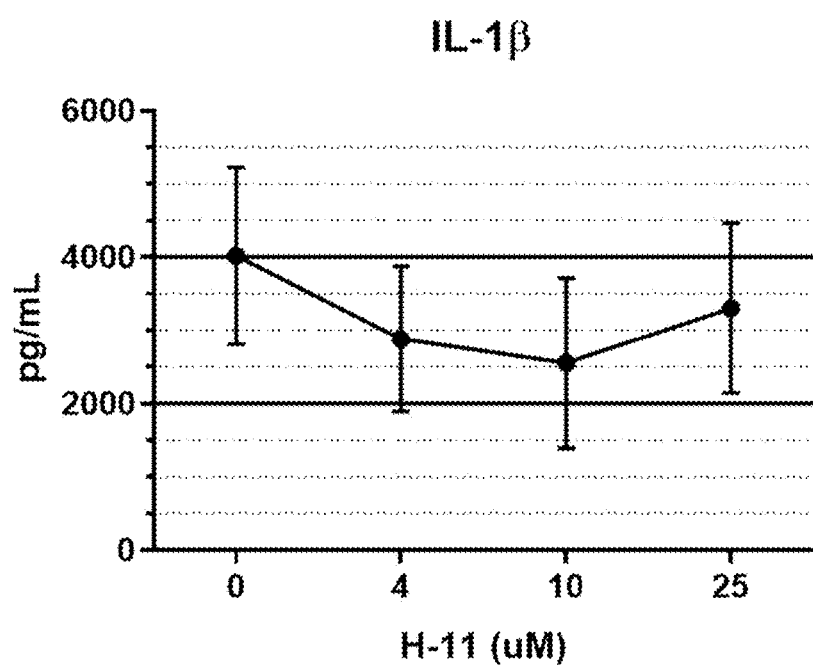

FIGURE 5. IL-36RA Change (%) During the Natural Infection Bovine Studies with Examples H-11 and H-91
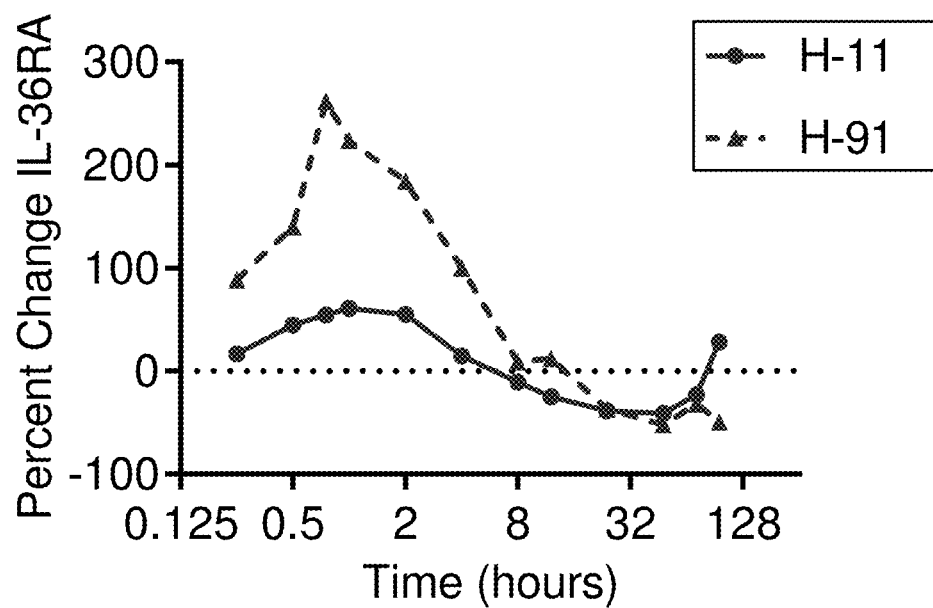

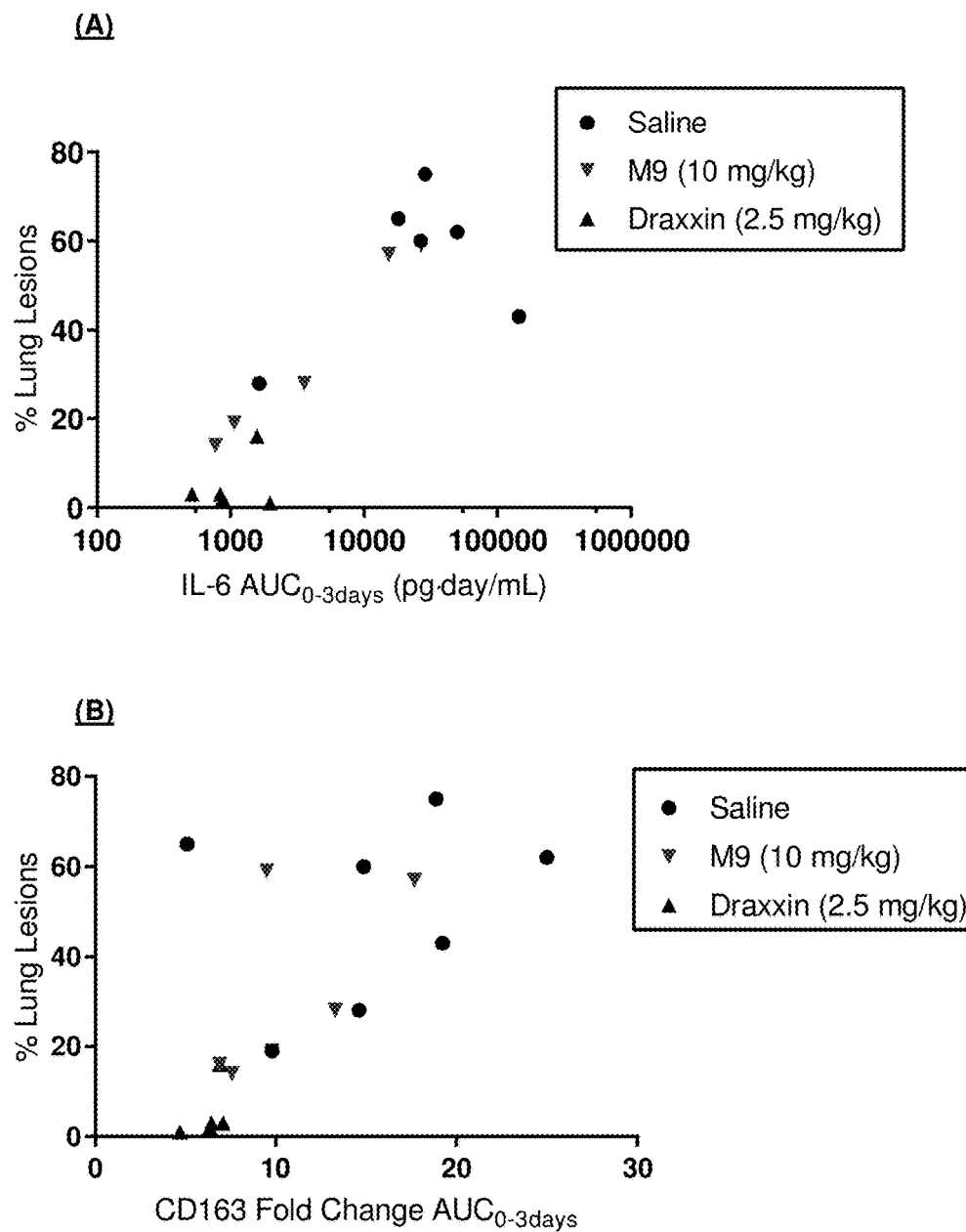
FIGURE 6. Biomarker Evaluation for M9 and Draxxin Intratracheal Lung Challenge; IL-6 (A) and CD163 Biomarker (B) Results FIGURE 7. Biomarker Evaluation for Example H-91 Intratracheal Lung Challenge: IL-6 (A) and CD163 Biomarker (B) Results
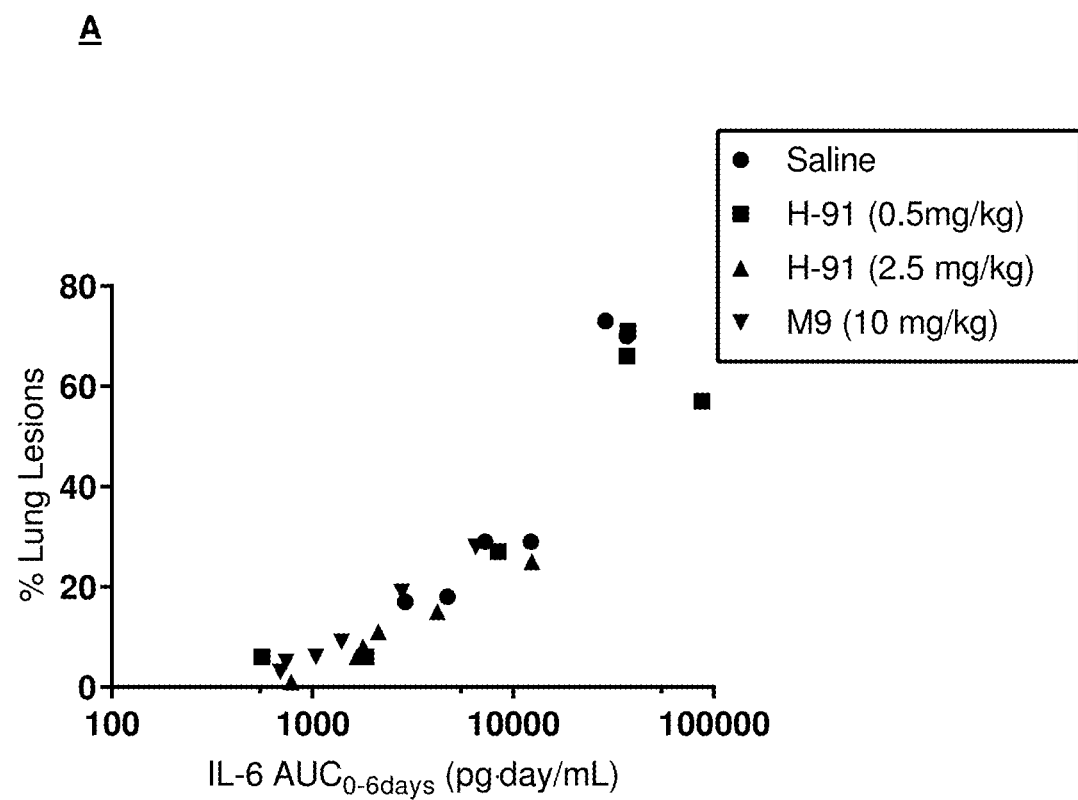

FIGURE 7. Biomarker Evaluation for Example H-91 Intratracheal Lung Challenge: IL-6 (A) and CD163 Biomarker (B) Results
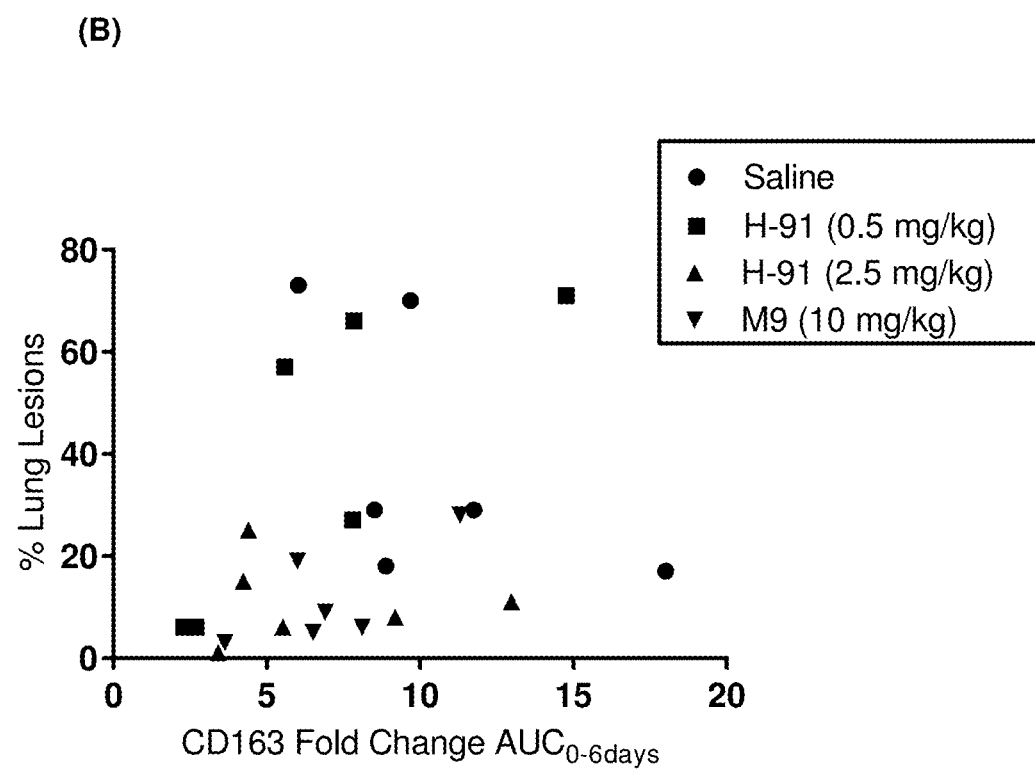

FIGURE 8. Biomarker Evaluation for Example H-11 Intratracheal Lung Challenge: Neutrophils (A), IL-6 (B) and CD163 (C) Results
A
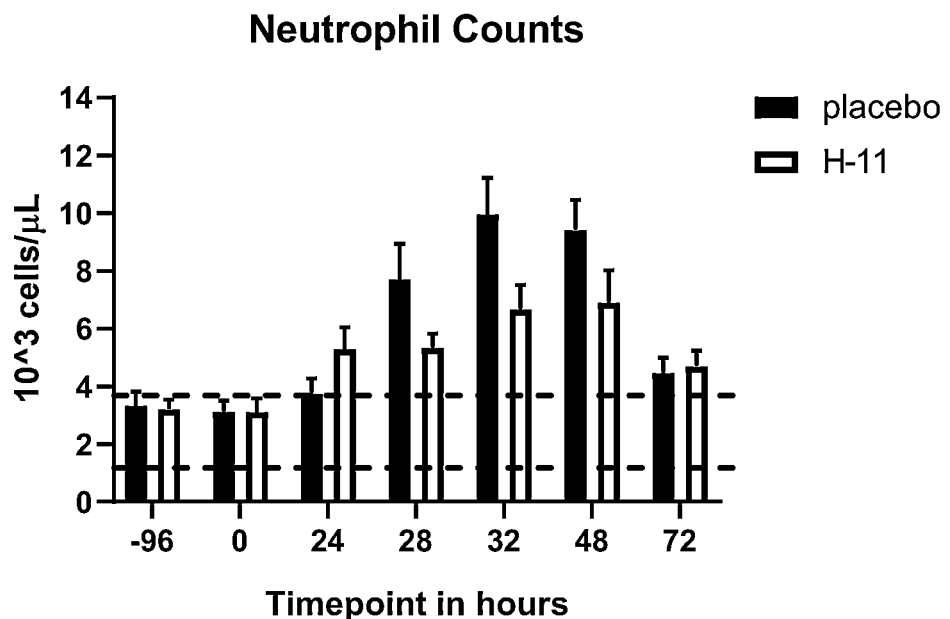
B
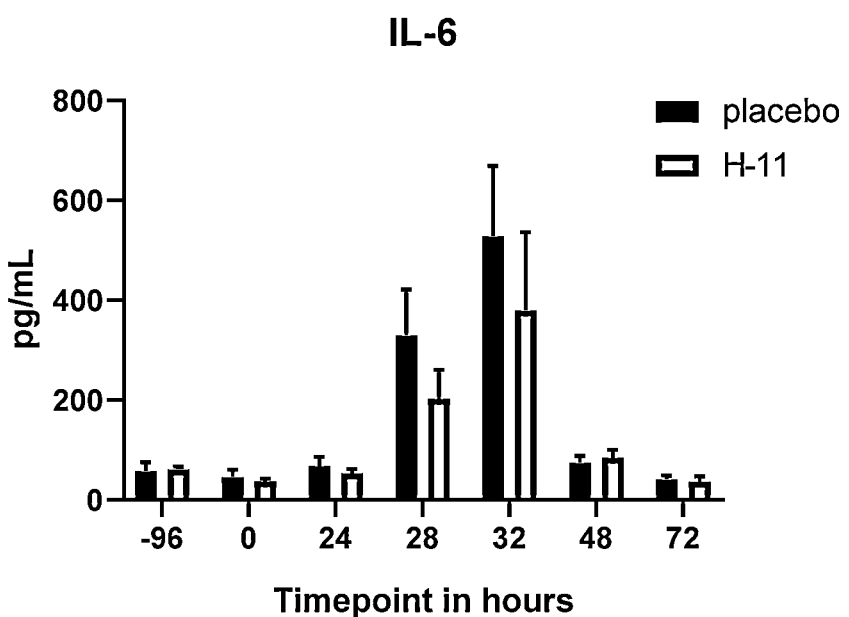

FIGURE 8. Biomarker Evaluation for Example H-11 Intratracheal Lung Challenge: Neutrophils (A), IL-6 (B) and CD163 (C) Results
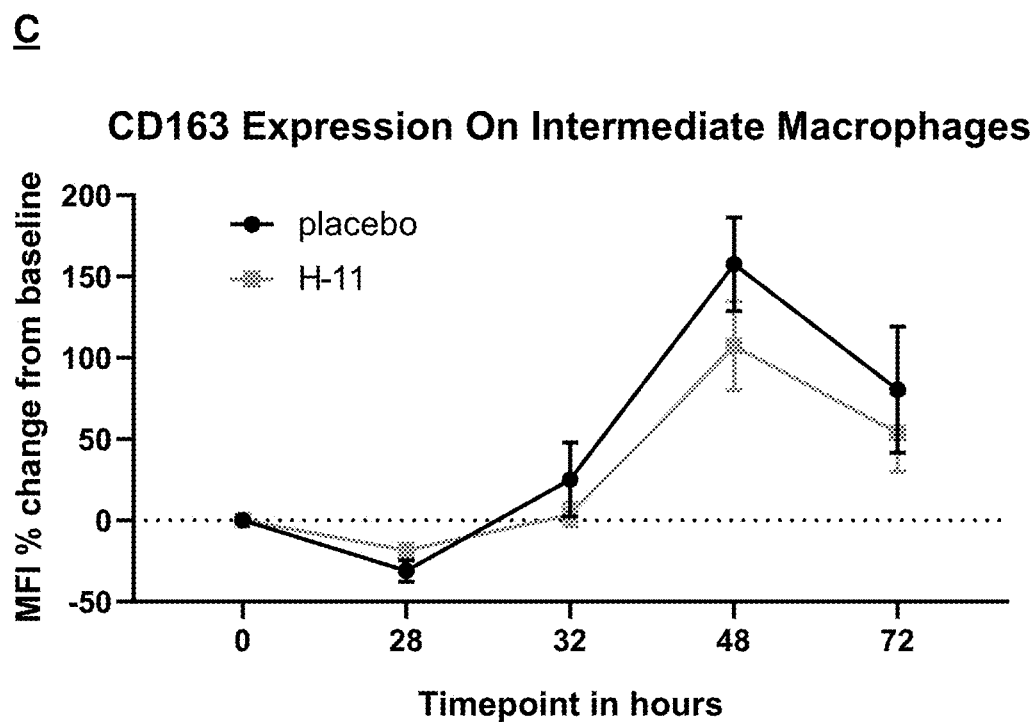

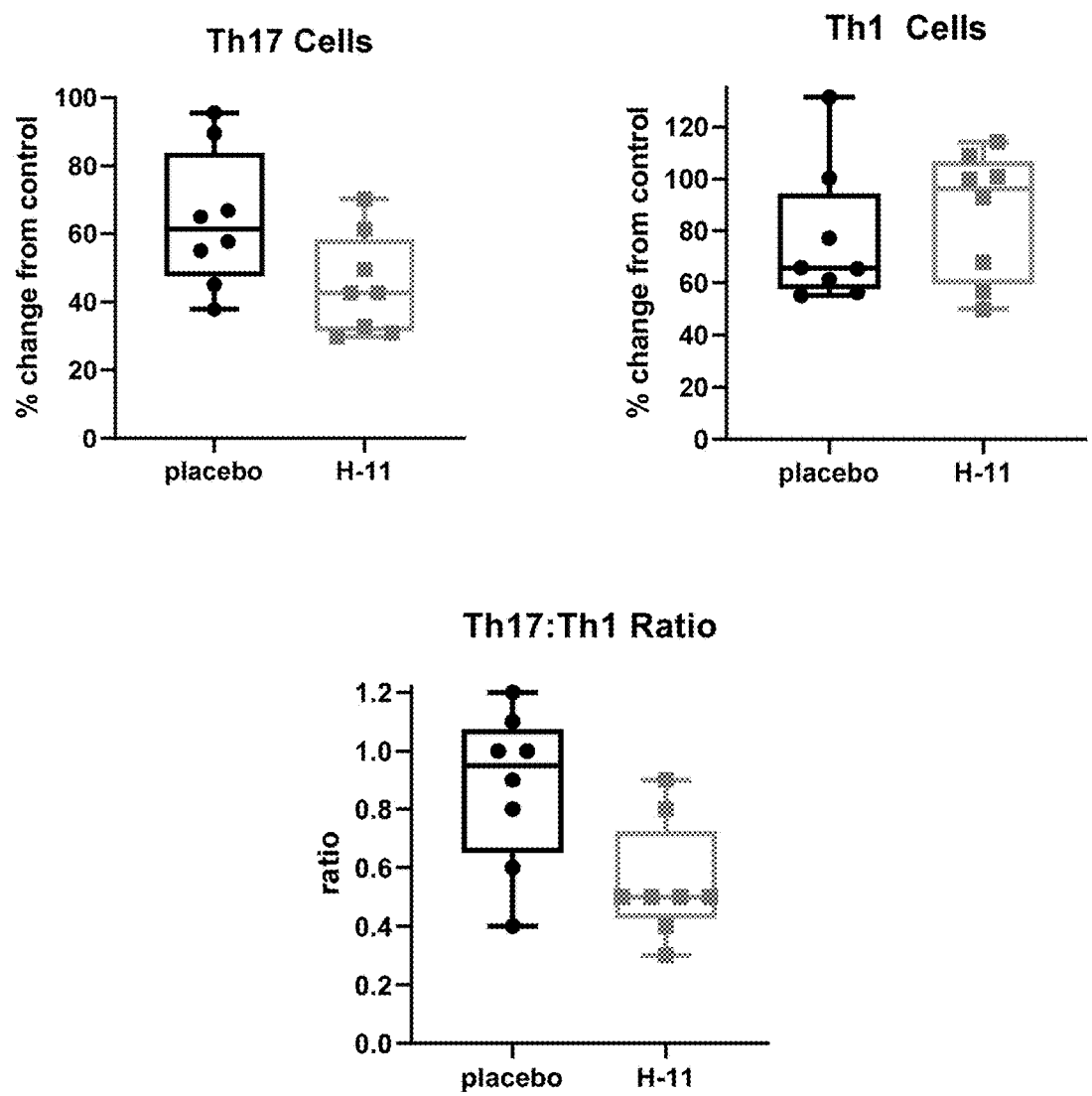
FIGURE 9. Intracellular Flow Cytometric Characterization of CD4+ T Helper Cell Subtypes FIGURE 10. IL-17 Levels from the Airway of Animals Challenged with *M. haemolytica* Administered Example H-11

IMMUNOMODULATING UREA AZALIDES

FIELD OF THE INVENTION

Defined herein are anti-inflammatory and immune-modulating compounds; non-antibacterial, anti-inflammatory and immune-modulating compounds; stereoisomers thereof, and pharmaceutically acceptable salts thereof. The invention includes the respective 13-membered macrolide ring compounds that are in equilibrium with the 15-membered macrolide ring compounds. The invention also includes pharmaceutical compositions comprising a compound of the invention and methods for treating an inflammatory and/or immunological disease or disorder in an animal. The compounds of the invention are azalides.

BACKGROUND OF THE INVENTION

Macrolides are antibacterial compounds that consist of a large macrocyclic lactone ring containing 12 to 16 atoms, which are attached, via glycosidic bonds, to at least one or two deoxy sugars. Azalides are a class of macrolide wherein the lactone ring contains a nitrogen atom. Draxxin© is a semi-synthetic macrolide (azalide) antibiotic that is sold as a ready to use sterile parenteral preparation containing tulathromycin. The preparation consists of an equilibrated mixture of two isomeric forms of tulathromycin in a 9:1 (Tula-A:Tula-B) ratio. Tula-A is a 15-membered lactone ring structure wherein Tula-B is a 13-membered lactone ring structure. Equilibrium is pH and time dependent. Tulathromycin is marketed for bovine respiratory disease (BRD) and swine respiratory disease (SRD) under the tradename, Draxxin©.

Macrolides are known for inhibiting protein synthesis in bacteria (Gram positive and Gram negative) by reversibly binding to the P site of the 50S unit of the ribosome. They tend to be bacteriostatic and may be bactericidal against some pathogens. Their activity against the Gram-negative pathogens of BRD and ability to concentrate in lung tissue make them an excellent therapeutic. They are the first-line treatment against BRD and are also used to treat respiratory infections in humans.

Known macrolide antibiotics include, for example, erythromycin, tilmicosin, azithromycin, clarithromycin, gamithromycin, fidaxomicin, roxithromycin, tulathromycin and others. In addition, some macrolides have been shown to have anti-inflammatory and immune-modulating properties. For example, azithromycin, a broad-spectrum antibiotic, suppresses interleukin 12p40 expression in lipopolysaccharide (LPS) and interferon-gamma stimulated macrophages and attenuates LPS induced induction of CXCL8 (IL-8) and GM-CSF from primary bronchial epithelial cells; and in epithelial cells, interactions with phospholipids and Erk1/2, are followed by down-regulation of transcription factors AP-1, NFκB, inflammatory cytokines and mucin release following LPS stimulation. US2016-0031925 describes certain azithromycin analogues that are immune-modulating but have been modified to reduce or eliminate the antibiotic effect. Clarithromycin has an immunomodulatory effect on ERJ-mediated inflammation induced by *Pseudomonas aeruginosa* flagellin. Erythromycin inhibits interleukin-6 and interleukin-8 expression and promotes apoptosis of activated human neutrophils in vitro. Tilmicosin modulates COX-2 and iNOS gene expression and production of cytokines in LPS-stimulated macrophages and monocytes. Roxithromycin down-regulates Th2 chemokine production by keratinocytes and chemokine receptor expression on Th2 cells. Tulathromycin promotes apoptosis and down-regulates pro-inflammatory mediators like leukotriene B4 and CXCL8; and induces production of anti-inflammatory and pro-resolving lipid lipoxin A4. Research findings demonstrate that these anti-bacterial macrolides modulate certain excessive immune responses which in turn cascade into certain anti-inflammatory benefits.

Inflammation and pro-inflammatory mediators negatively affect production in the food animal industry by reducing growth, feed and water intake, reproduction, milk production and metabolic health. Increased clinical use of macrolide antibiotics is linked with an increase in pneumococcal macrolide resistance and resistance in BRD pathogens. Recent concerns by global governmental agencies and the general public relative to use of antibiotics in food producing animals (e.g., cattle and swine) has been thought to lead to cross resistance to human pathogens. Bovine respiratory disease (BRD) remains a major problem in modern day cattle production and judicious management is vitally important for both animal welfare and human food safety. In fact, *Mannheimia haemolytica* is a principle bacterium isolated from respiratory disease in feedlot cattle and is a significant component of enzootic pneumonia in neonatal calves. One of the hallmarks of BRD is a heightened inflammatory response in the host that promotes progression to the full BRD complex. Inhibiting or reversing the inflammation in the host has the ability to prevent or control the development of BRD in cattle and other inflammatory diseases or disorders in animals. Therefore, there is an unmet desire to develop a new anti-inflammatory and immune-modulating agent that lacks the antibacterial effects of the known macrolides. The compounds of the invention have been shown to be non-antibacterial in multiple bacterial species and possess upwards of 5-20 times greater immune-modulating activity at lower dosages than current macrolides (e.g., azithromycin, erythromycin and tulathromycin). Therefore, the compounds can be used to control or prevent the onset of a bacterial infection or viral infection which is enabled by an inflammatory and/or immune response due to a stressful event or other environmental factor(s) thereby preventing or mitigating the pathobiological cascade from advancing to the full disease complex. The compounds of the invention presented herein are non-antibiotic, anti-inflammatory and immune-modulating macrolides for the reduction of an inflammatory state in animals with the potential for reducing the use of antibiotics in animals.

SUMMARY OF THE INVENTION

In one aspect of the invention, is an anti-inflammatory and immune-modulating Formula (1) azalide compound; or a non-antibacterial, anti-inflammatory and immune-modulating Formula (1) azalide compound; stereoisomers thereof, and pharmaceutically acceptable salts thereof,

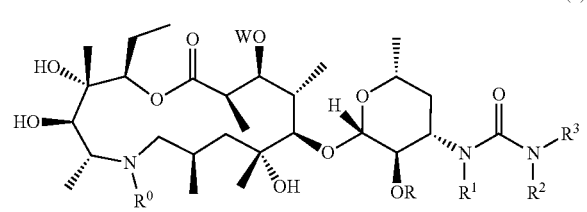

(1)

wherein W is H or Formula (A)

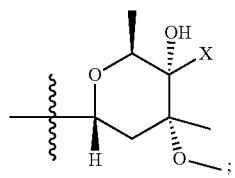

wherein X is —$R^a$, —$R^cNR^5R^6$, —$R^cOR^7$, —$R^cSR^7$, —$R^cN_3$, —$R^cCN$ or —$R^cX'$;
X is F, Cl, I or Br;
R is H, $C_1$-$C_3$alkyl, —C(O)$NR^aR^d$ or —C(O)$OR^8$;
$R^a$, $R^b$, $R^0$ and $R^1$ are each independently H or $C_1$-$C_6$alkyl; or $R^1$ is benzyl optionally substituted with at least one $R^9$ substituent;
or $R^1$ is —$CH_2$Het wherein Het is a 5-6 membered heteroaryl ring containing at least one heteroatom selected from N, S and O; and wherein the heteroaryl ring is optionally substituted with at least one $R^9$ substituent;
$R^c$ is $C_1$-$C_4$alkyl;
$R^d$ is H, $C_1$-$C_6$alkyl, $C_3$-$C_6$cycloalkyl, or phenyl optionally substituted with $C_1$-$C_3$alkyl, $C_1$-$C_3$alkoxy, halogen, cyano, hydroxy, amino, —$NHCH_3$, —$N(CH_3)_2$, $C_1$-$C_3$haloalkyl or $C_1$-$C_3$haloalkoxy;
$R^2$ and $R^3$ are each independently is H, $C_1$-$C_6$alkyl, $R^cN$-$R^aR^b$, $C_0$-$C_3$alkyl$C_3$-$C_6$cycloalkyl, $C_0$-$C_3$alkylaryl, $C_0$-$C_3$alkylheterocycle wherein the heterocycle is a 5-6 membered saturated or partially saturated heterocycle ring; or $C_0$-$C_3$alkylheteroaryl wherein the heteroaryl is a 5-6 membered heteroaryl ring; wherein the heterocycle ring and the heteroaryl ring each contain at least one heteroatom selected from N, O and S; and wherein the cycloalkyl, aryl, heterocyclic and heteroaryl rings are each optionally substituted with at least one $R^9$ substituent;
or $R^2$ and $R^3$ taken together with the nitrogen atom to which they are attached form Ring A, a 4-8 membered heterocyclic ring or a 5-membered heteroaryl ring, each optionally containing at least one additional heteroatom selected from N, O and S; each ring is optionally substituted with at least one $R^{10}$ substituent; and wherein each ring is optionally fused with Y;
$R^5$ and $R^6$ are each independently selected from H; $C_1$-$C_6$alkyl or $C_1$-$C_6$alkoxy each optionally substituted with at least one hydroxy; or cyano, $C_1$-$C_6$haloalkyl, $C_1$-$C_6$haloalkoxy, —C(O)$R^8$, —C(O)$NR^aR^8$, —C(O)$R^cN$-$R^aR^b$, —C(O)$OR^cR^8$, —C(O)$ONR^aR^b$, —$R^cNR^aC(O)R^8$, —$R^cC(O)OH$, —$R^cC(O)NR^aR^b$, —$R^cNR^aC(O)H$, —$R^cS(O)_pR^8$, —$R^cNR^aR^b$, —$R^cOR^a$, —$S(O)_pR^8$, —$S(O)_pR^8NR^aR^b$, —$R^cS(O)_pNR^aR^b$ or —$R^cNR^aS(O)_pR^8$; or $C_0$-$C_4$alkylaryl, $C_0$-$C_4$alkyl$C_3$-$C_6$cycloalkyl, $C_0$-$C_4$alkylheterocycle or $C_0$-$C_4$alkylheteroaryl, wherein the heterocycle and heteroaryl rings are each a 5-6 membered monocyclic ring or a 9-10 membered fused ring, each containing at least one heteroatom selected from the group consisting of N, O and S; and wherein the aryl, cycloalkyl, heterocycle and heteroaryl rings are optionally substituted with at least one $R^{10}$ substituent;
or $R^5$ and $R^6$ taken together with the nitrogen atom to which they are attached form Ring B, a 4-8 membered heterocyclic ring or a 5 membered heteroaryl ring, each optionally containing at least one additional heteroatom selected from N, O and S; each ring is optionally substituted with at least one $R^9$ substituent; and wherein each ring is optionally fused with Y;
$R^7$ is H, $C_1$-$C_6$alkyl, —$R^cNR^aR^b$, —$R^cOR^a$, —$R^cS(O)_pR^a$, —$R^cNR^aC(O)R^b$, —$R^cC(O)NR^aR^b$, —$R^cNR^aC(O)NR^aR^b$ or —$R^cNR^aC(O)OR^b$;
$R^8$ is $C_1$-$C_6$alkyl, $C_1$-$C_6$haloalkyl, $C_0$-$C_4$alkyl$C_3$-$C_6$cycloalkyl, —$NR^aR^b$, phenyl, a 5-6 membered heterocyclic ring containing at least one heteroatom selected from N, O and S, or a 5-6 membered heteroaryl ring containing at least one heteroatom selected from N, O, and S; and wherein the cycloalkyl, phenyl, heterocycle and heteroaryl are each optionally substituted with at least one substituent selected from $C_1$-$C_4$alkyl, halogen, $C_1$-$C_4$alkoxy, $C_1$-$C_4$haloalkyl and $C_1$-$C_4$haloalkoxy;
$R^9$ is independently selected from the group consisting of $C_1$-$C_6$alkyl, $C_1$-$C_6$alkoxy, $C_0$-$C_4$alkyl$C_3$-$C_6$cycloalkyl, halogen, oxo, hydroxy, cyano, —$NR^aR^b$, $C_1$-$C_6$haloalkyl, $C_1$-$C_6$haloalkoxy, —$S(O)_pR^8$, phenyl, and a 5-6 membered monocyclic heterocyclic or heteroaryl ring each containing at least one heteroatom selected from the group consisting of N, O and S;
$R^{10}$ is independently selected from the group consisting of $C_1$-$C_3$alkyl, $C_1$-$C_3$alkoxy, $C_1$-$C_3$haloalkyl, $C_1$-$C_3$haloalkoxy, $C_0$-$C_4$alkyl$C_3$-$C_6$cycloalkyl, halogen, —$NR^aR^b$, —$S(O)_pR^8$, nitro, oxo, cyano, —C(O)H, —C(O)$R^8$, —C(O)$OR^a$, —OC(O)$OR^a$, —$NHR^cC(O)R^a$, —C(O)$NR^aR^b$, hydroxy, a 5-6 membered heterocyclic ring, a 5-6 membered heteroaryl ring, a 9-10 membered fused heteroaryl ring wherein each heterocyclic and heteroaryl ring each contain at least one heteroatom selected from the group consisting of N, O and S; and phenyl; and wherein the phenyl, heterocyclic and heteroaryl ring are each optionally substituted with at least one $R^9$ substituent;
Y is phenyl, pyridinyl, pyrimidyl, pyrazolyl, thienyl, thiazolyl, triazolyl, isothiazolyl, pyrrolyl, oxazolyl, oxadiazolyl, imidazolyl, furanyl, indolyl, benzothienyl or naphthyl; p is the integer 0, 1, or 2; stereoisomers thereof, and pharmaceutically acceptable salts thereof.

In another aspect, is a composition comprising a Formula (1) compound, stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1) compound, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNFα and IL-6 in the animal.

In another aspect, is the use of a Formula (1) compound, stereoisomers thereof, and pharmaceutically acceptable salts thereof; to prepare a medicament for treating or preventing an inflammatory response in an animal wherein the inflammatory response is due to a bacterial, viral, or fungal infection, stress, and/or an environmental factor. In another aspect of the use, the use of the medicament for treating or and preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNFα and IL-6 in the animal.

In another aspect of the invention, $R^a$ and $R^b$ are each independently H, methyl, ethyl, propyl, isopropyl, isobutyl, n-butyl or t-butyl. In another aspect, $R^a$ and $R^b$ are each independently H, methyl, ethyl, propyl or isopropyl. In another aspect, $R^a$ and $R^b$ are each independently H, methyl, ethyl or propyl. In another aspect, $R^a$ and $R^b$ are each independently H or methyl.

In another aspect of the invention, $R^c$ is methyl, ethyl, propyl, isopropyl, n-butyl, or t-butyl. In another aspect of the invention, $R^c$ is methyl, ethyl, propyl, isopropyl, or t-butyl. In another aspect of the invention, $R^c$ is methyl, ethyl, propyl, or isopropyl. In another aspect of the invention, $R^c$ is methyl, ethyl or propyl. In another aspect, $R^c$ is methyl. In another aspect, $R^c$ is ethyl. In another aspect, $R^c$ is propyl.

In another aspect of the invention, $R^d$ is $C_1$-$C_6$alkyl, $C_3$-$C_6$cycloalkyl or phenyl optionally substituted with $C_1$-$C_3$alkyl, $C_1$-$C_3$alkoxy, halogen, cyano, hydroxy, amino, —NHCH$_3$, —N(CH$_3$)$_2$, $C_1$-$C_3$haloalkyl or $C_1$-$C_3$haloalkoxy. In another aspect, $R^d$ is $C_1$-$C_6$alkyl, $C_3$-$C_6$cycloalkyl or phenyl optionally substituted with $C_1$-$C_3$alkyl, $C_1$-$C_3$alkoxy, halogen, cyano, hydroxy, amino, —NHCH$_3$, —N(CH$_3$)$_2$, —CF$_3$ or —OCF$_3$. In another aspect, $R^d$ is methyl, ethyl, cyclopropyl, cyclobutyl or phenyl optionally substituted with methyl, ethyl, methoxy, ethoxy, F, Cl, cyano, hydroxy, amino, —NHCH$_3$, —N(CH$_3$)$_2$, —CHF$_2$, —CF$_3$ or —OCF$_3$. In another aspect, $R^d$ is methyl, ethyl or phenyl optionally substituted with methyl, ethyl, methoxy, ethoxy, F, Cl, cyano, hydroxy, amino, —NHCH$_3$, —N(CH$_3$)$_2$, —CHF$_2$, —CF$_3$ or —OCF$_3$.

In another aspect of the invention, $R^0$ and $R^1$ are each independently H, methyl, ethyl, propyl, isopropyl, isobutyl, n-butyl or t-butyl; or $R^1$ is benzyl, —CH$_2$pyridine, —CH$_2$pyrimidine, —CH$_2$pyridazine, —CH$_2$pyrazine, —CH$_2$pyrrole, —CH$_2$furan, —CH$_2$thiophene, —CH$_2$pyrazole, —CH$_2$imidazole, —CH$_2$-triazole, —CH$_2$tetrazole, —CH$_2$oxazole, —CH$_2$isoxazole, —CH$_2$thiazole, —CH$_2$isothiazole or —CH$_2$oxadiazole, each optionally substituted with at least one $R^9$ substituent selected from methyl, ethyl, propyl, methoxy, ethoxy, F, Cl, oxo, hydroxy, cyano, —NR$^a$R$^b$, —CF$_3$ and —OCF$_3$. In another aspect, $R^0$ and $R^1$ are each independently H, methyl, ethyl, propyl or isopropyl; or $R^1$ is benzyl, —CH$_2$pyridine, —CH$_2$pyrimidine, —CH$_2$pyrazole, —CH$_2$imidazole, —CH$_2$-triazole, —CH$_2$tetrazole, —CH$_2$oxazole, —CH$_2$isoxazole, —CH$_2$thiazole, —CH$_2$isothiazole or —CH$_2$oxadiazole, each optionally substituted with at least one $R^9$ substituent selected from methyl, ethyl, propyl, methoxy, ethoxy, F, Cl, hydroxy, cyano, —NH$_2$, —CF$_3$ and —OCF$_3$. In another aspect, $R^0$ is H, methyl, ethyl or propyl; $R^1$ is methyl, ethyl, propyl, isopropyl; or $R^1$ is benzyl, —CH$_2$pyridine, —CH$_2$pyrimidine, —CH$_2$pyrazole or —CH$_2$imidazole, each optionally substituted with at least one $R^9$ substituent selected from methyl, ethyl, methoxy, ethoxy, F, Cl, hydroxy, —CF$_3$ and —OCF$_3$. In another aspect, $R^0$ is H, methyl, ethyl or propyl; and $R^1$ is methyl, ethyl, propyl or isopropyl. In another aspect, $R^0$ is H or methyl; and $R^1$ is methyl, ethyl, propyl or isopropyl. In another aspect, $R^0$ is H or methyl and $R^1$ is methyl.

In another aspect of the invention, $R^2$ and $R^3$ are each independently H, $C_1$-$C_6$alkyl, R$^c$NR$^a$R$^b$, $C_0$-$C_3$alkylC$_3$-$C_6$cycloalkyl, $C_0$-$C_3$alkylphenyl, $C_0$-$C_3$alkylheterocycle, or $C_0$-$C_3$alkylheteroaryl; wherein the heterocycle moiety is pyrrolidinyl, piperadinyl, piperazinyl, tetrahydropyran, morpholinyl or thiomorpholinyl; and wherein the heteroaryl moiety is pyrrolyl, pyrazolyl, imidazolyl, thiazolyl, oxazolyl, pyridinyl, pyrimidinyl, pyridazinyl, pyrazinyl, triazolyl, tetrazolyl or 6,7-dihydro-5H-cyclopenta[d]pyrimidine; and wherein the cycloalkyl, phenyl, heterocycle and heteroaryl rings are each optionally substituted with at least one $R^9$ substituent selected from the group consisting of $C_1$-$C_3$alkyl, $C_1$-$C_3$alkoxy, hydroxy, halogen, cyclopropyl, cyclobutyl, cyano, amino, —NHCH$_3$, —N(CH$_3$)$_2$, $C_1$-$C_3$haloalkyl and $C_1$-$C_3$haloalkoxy. In another aspect of the invention, $R^2$ and $R^3$ are each independently H, $C_1$-$C_6$alkyl, —CH$_2$N(CH$_3$)$_2$, —CH$_2$CH$_2$N(CH$_3$)$_2$; or $C_0$-$C_2$cyclopropyl, $C_0$-$C_2$cyclobutyl, $C_0$-$C_2$cyclopentyl, $C_0$-$C_2$cyclohexyl, $C_0$-$C_2$phenyl, $C_0$-$C_2$piperadinyl, piperazinyl, morpholinyl, tetrahydropyran, pyrrolyl, pyrazolyl, triazolyl, tetrazolyl, pyridinyl, pyrimidinyl, pyridazinyl or pyrazinyl, each of which is optionally substituted with at least one $R^9$ substituent selected from the group consisting of methyl, ethyl, propyl, isopropyl, t-butyl, hydroxy, methoxy, ethoxy, F, Cl, Br, cyano, amino, —N(CH$_3$)$_2$, —CHF$_2$, —CF$_3$, —OCHF$_2$ and —OCF$_3$. In another aspect of the invention, $R^2$ and $R^3$ are each independently H, $C_1$-$C_6$alkyl; —CH$_2$N(CH$_3$)$_2$, —CH$_2$CH$_2$N(CH$_3$)$_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-pyran, pyrrolyl, pyrazolyl, triazolyl, pyridinyl, pyrimidinyl, pyridazinyl or pyrazinyl, each of which is optionally substituted with at least one $R^9$ substituent selected from the group consisting of methyl, ethyl, propyl, isopropyl, t-butyl, hydroxy, methoxy, ethoxy, F, Cl, Br, cyano, amino, —N(CH$_3$)$_2$, —CHF$_2$, —CF$_3$, —OCHF$_2$ and —OCF$_3$. In another aspect, $R^2$ and $R^3$ are each independently H, $C_1$-$C_6$alkyl; —CH$_2$N(CH$_3$)$_2$, —CH$_2$CH$_2$N(CH$_3$)$_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, triazolyl, pyridinyl, pyrimidinyl, pyridazinyl or pyrazinyl, each of which is optionally substituted with at least one $R^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$. In another aspect, $R^2$ and $R^3$ are each independently H, $C_1$-$C_6$alkyl; —CH$_2$N(CH$_3$)$_2$, —CH$_2$CH$_2$N(CH$_3$)$_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, pyridinyl, pyrimidinyl, pyridazinyl or pyrazinyl, each of which is optionally substituted with at least one $R^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$. In another aspect, $R^2$ is H, methyl, ethyl, isopropyl, cyclopropyl, —CF$_3$, —CHF$_2$, —CH$_2$F, —CH$_2$CF$_3$ or phenyl. In another aspect, $R^2$ is H, methyl, ethyl, cyclopropyl or phenyl. In another aspect, $R^2$ is H, methyl or ethyl. In another aspect, $R^2$ is H or methyl. In another aspect, $R^2$ is H. In another aspect, $R^2$ is methyl. In another aspect, $R^3$ is H, methyl, ethyl, propyl, isopropyl, t-butyl; —$CH_2N(CH_3)_2$, —$CH_2CH_2N(CH_3)_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl or pyridinyl, and wherein each ring is optionally substituted with at least one $R^9$ substituent selected from the group consisting of methyl, ethyl, hydroxy, methoxy, ethoxy, F, Cl, cyano, amino, —$N(CH_3)_2$ and —$CF_3$.

In another aspect of the invention, $R^2$ and $R^3$ are taken together with the nitrogen atom to which they are attached form Ring A, a 4-8 membered heterocyclic ring or a 5-membered heteroaryl ring, each optionally containing at least one additional heteroatom selected from N, O and S; and wherein each ring is optionally substituted with at least one $R^{10}$ substituent; and wherein each ring is further optionally fused to Y which is phenyl, pyridinyl, pyrimidyl, pyrazolyl, thienyl, thiazolyl or triazolyl. In another aspect, $R^2$ and $R^3$ taken together with the nitrogen atom to which they are attached form Ring A, a 4-8 membered heterocyclic or 5-membered heteroaryl ring, each optionally containing at least one additional heteroatom selected from N, O and S; and wherein each ring is optionally substituted with at least one $R^{10}$ substituent, and wherein each ring is further optionally fused to Y which is phenyl, pyridinyl or pyrimidyl. In another aspect, $R^2$ and $R^3$ taken together with the nitrogen atom to which they are attached form Ring A which is azetidinyl, pyrrolyl, pyrazolyl, imidazolyl, triazolyl, tetrazolyl, pyrrolidinyl, piperidinyl, piperazinyl, morpholinyl, or thiomorpholinyl, each optionally substituted with at least one $R^{10}$ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; and wherein each ring is further optionally fused with Y which is phenyl, pyridinyl or pyrimidyl. In another aspect, $R^2$ and $R^3$ taken together with the nitrogen atom to which they are attached form Ring A which is pyrrolyl, pyrazolyl, imidazolyl, triazolyl, tetrazolyl, pyrrolidinyl, piperidinyl, piperazinyl, morpholinyl, or thiomorpholinyl, each optionally substituted with at least one $R^{10}$ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; and wherein each ring is further optionally fused with Y which is phenyl, pyridinyl or pyrimidinyl. In another aspect, $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; and wherein each ring is further optionally fused with Y which is phenyl or pyridinyl. In another aspect, $R^2$ and $R^3$ taken together with the nitrogen atom to which they are attached form Ring A which is pyrrolyl, pyrazolyl, pyrrolidinyl, piperidinyl, piperazinyl, morpholinyl, or thiomorpholinyl, each optionally substituted with at least one $R^{10}$ substituent selected from methyl, ethyl, F, Cl, oxo, and —$CF_3$; and wherein each ring is further optionally fused with Y which is phenyl. In another aspect, $R^2$ and $R^3$ taken together with the nitrogen atom to which they are attached form Ring A which is pyrrolyl, pyrazolyl, pyrrolidinyl, piperidinyl, piperazinyl, morpholinyl, or thiomorpholinyl, each optionally substituted with at least one $R^{10}$ substituent selected from methyl, ethyl, F, Cl, oxo, and —$CF_3$; or Ring A is indolinyl, isoindolinyl, tetrahydroisoquinolinyl, dihydropyrrolopyrazinyl, tetrahydroisoquinolinyl, dihydrobenzooxazinyl or dihydrobenzothiazinyl optionally substituted with at least one oxo. In another aspect, $R^2$ and $R^3$ taken together with the nitrogen atom to which they are attached form Ring A which is pyrrolyl, pyrazolyl, pyrrolidinyl, piperidinyl, piperazinyl, morpholinyl, or thiomorpholinyl, each optionally substituted with at least one $R^{10}$ substituent selected from methyl, ethyl, F, Cl, oxo, and —$CF_3$; or Ring A is indolinyl, isoindolinyl, tetrahydroquinolinyl, dihydrobenzooxazinyl or dihydrobenzothiazinyl optionally substituted with at least one oxo. In another aspect, $R^2$ and $R^3$ taken together with the nitrogen atom to which they are attached form Ring A which is pyrrolyl, pyrazolyl, pyrrolidinyl, piperidinyl, piperazinyl, morpholinyl, or thiomorpholinyl, each optionally substituted with at least one $R^{10}$ substituent selected from methyl, ethyl, F, Cl, oxo, and —$CF_3$.

In another aspect of the invention, $R^5$ and $R^6$ are each independently H; $C_1$-$C_6$alkyl or $C_1$-$C_6$alkoxy each optionally substituted with at least one hydroxy; cyano, $C_1$-$C_6$haloalkyl, $C_1$-$C_6$haloalkoxy, —$C(O)R^8$, —$C(O)NR^aR^8$, —$C(O)R^cNR^aR^b$, —$C(O)OR^cR^8$, —$C(O)ONR^aR^b$, —$R^cNR^aC(O)R^8$, —$R^cC(O)OH$, —$R^cC(O)NR^aR^b$, —$R^cNR^aC(O)H$, —$R^cS(O)_pR^8$, —$R^cNR^aR^b$, —$R^cOR^a$, —$S(O)_pR^8$, —$S(O)_pR^8NR^aR^b$, —$R^cS(O)_pNR^aR^b$, —$R^cNR^aS(O)_pR^8$; $C_0$-$C_4$alkylphenyl, $C_0$-$C_4$alkyl$C_3$-$C_6$cycloalkyl, $C_0$-$C_4$alkylheterocycle, $C_0$-$C_4$alkylheteroaryl, wherein the heterocycle and heteroaryl rings are each 5-6 membered monocyclic rings and wherein each heterocycle and heteroaryl ring each contain at least one heteroatom selected from the group consisting of N, O and S; and wherein the phenyl, cycloalkyl ring, heterocycle ring and heteroaryl ring are each optionally substituted with at least one $R^{10}$ substituent. In another aspect, $R^5$ and $R^6$ are each independently H; $C_1$-$C_6$alkyl or $C_1$-$C_6$alkoxy, each optionally substituted with at least one hydroxy; cyano, $C_1$-$C_6$haloalkyl, $C_1$-$C_6$haloalkoxy, —$C(O)R^8$, —$C(O)NR^aR^8$, —$C(O)R^cNR^aR^b$, —$C(O)OR^cR^8$, —$C(O)ONR^aR^b$, —$R^cNR^aC(O)R^8$, —$R^cC(O)OH$, —$R^cC(O)NR^aR^b$, —$R^cNR^aC(O)H$, —$R^cS(O)_pR^8$, —$R^cNR^aR^b$, —$R^cOR^a$, —$S(O)_pR^8$, —$S(O)_pR^8NR^aR^b$, —$R^cS(O)_pNR^aR^b$, —$R^cNR^aS(O)_pR^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, $C_1$-$C_2$alkylcyclopentyl, $C_1$-$C_2$alkylcyclohexyl, tetrahydrofuranyl, tetrahydropyranyl, oxazolidinyl, pyrrolidinyl, piperidinyl, piperazinyl, morpholinyl, $C_1$-$C_2$alkyltetrahydro-furanyl, $C_1$-$C_2$alkyloxazolidinyl, $C_1$-$C_2$alkyltetrahydropyranyl, $C_1$-$C_2$alkylpyrrolidinyl, $C_1$-$C_2$alkylpiperidinyl, $C_1$-$C_2$alkylpiperazinyl, $C_1$-$C_2$morpholinyl; pyrazolyl, imidazolyl, triazolyl, tetrazolyl, oxazolyl, pyridinyl, pyridazinyl, pyrimidinyl, pyrazinyl, $C_1$-$C_2$alkylpyrazolyl, $C_1$-$C_2$alkylimidazolyl, $C_1$-$C_2$alkyltriazolyl, $C_1$-$C_2$alkyltetrazolyl, $C_1$-$C_2$alkyloxazolyl, $C_1$-$C_2$alkylpyridinyl, $C_1$-$C_2$alkylpyridazinyl, $C_1$-$C_2$alkylpyrimidinyl or $C_1$-$C_2$alkylpyrazinyl; and wherein the phenyl, cycloalkyl ring, heterocycle ring and heteroaryl ring are each optionally substituted with at least one $R^{10}$ substituent. In another aspect, $R^5$ and $R^6$ are each independently H; $C_1$-$C_6$alkyl or $C_1$-$C_6$alkoxy each optionally substituted with at least one hydroxy; cyano, $C_1$-$C_6$haloalkyl, $C_1$-$C_6$haloalkoxy, —$C(O)R^8$, —$C(O)NR^aR^8$, —$C(O)R^cN-R^aR^b$, —$C(O)ONR^aR^b$, —$R^cNR^aC(O)R^8$, —$R^cC(O)NR^aR^b$, —$R^cNR^aC(O)H$, —$R^cS(O)_pR^8$, —$R^cNR^aR^b$, $S(O)_pR^8$, —$S(O)_pR^8NR^aR^b$, —$R^cS(O)_pNR^aR^b$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydrofuranyl, tetrahydropyranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydrofuran, $C_1$-$C_2$tetrahydropyran, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each optionally substituted with at least one $R^{10}$ substituent each independently selected from methyl, ethyl, propyl, methoxy, ethoxy, —$CHF_2$, —$CF_3$, —$OCF_3$, F, Cl, amino, —$NHCH_3$, —$N(CH_3)_2$, —$S(O)_2CH_3$, nitro, cyano, —$C(O)CH_3$, —$NHCH_2C(O)CH_3$, —$NHCH_2CH_2C(O)CH_3$, —$C(O)NHCH_3$, hydroxy and phenyl. In another aspect, $R^5$ and $R^6$ are each independently H; $C_1$-$C_6$alkyl or $C_1$-$C_6$alkoxy each optionally substituted with at least one hydroxy; $C_1$-$C_6$haloalkyl, $C_1$-$C_6$haloalkoxy, —$C(O)R^8$, —$C(O)NR^aR^8$, —$C(O)R^cNR^aR^b$, —$R^cS(O)_pR^8$, —$R^cNR^aR^b$, —$R^cOR^a$, —$S(O)_pR^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$piperadinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each optionally substituted with at least one $R^{10}$ substituent each independently selected from methyl, ethyl, methoxy, ethoxy, —$CHF_2$, —$CF_3$, —$OCF_3$, F, Cl, —$NHCH_3$, —$N(CH_3)_2$, —$S(O)_2CH_3$, cyano and hydroxy. In another aspect, $R^5$ and $R^6$ are each independently H; $C_1$-$C_6$alkyl or $C_1$-$C_6$alkoxy each optionally substituted with at least one hydroxy; $C_1$-$C_6$haloalkyl, —$OCF_3$, —$C(O)NR^aR^8$, —$R^cS(O)_pR^8$, —$R^cNR^aR^b$, —$R^cOR^a$, —$S(O)_pR^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each optionally substituted with at least one $R^{10}$ substituent each independently selected from methyl, ethyl, methoxy, ethoxy, —$CHF_2$, —$CF_3$, —$OCF_3$, F, Cl, amino, —$NHCH_3$, —$N(CH_3)_2$, —$S(O)_2CH_3$, cyano and hydroxy. In another aspect, $R^5$ is H, $C_1$-$C_6$alkyl, morpholinyl, piperadinyl, —$CH_2$morpholinyl, —$CH_2$piperadinyl, —$(CH_2)_2$morpholinyl or $(CH_2)_2$piperadinyl. In another aspect, $R^5$ is H, methyl, ethyl, propyl, isopropyl, —$CH_2$morpholinyl, —$CH_2$piperadinyl, —$(CH_2)_2$morpholinyl or $(CH_2)_2$piperadinyl. In another aspect, $R^5$ is H, methyl, ethyl, propyl or isopropyl. In another aspect, $R^6$ is H; $C_1$-$C_6$alkyl or $C_1$-$C_6$alkoxy each optionally substituted with at least one hydroxy; $C_1$-$C_6$haloalkyl, —$OCF_3$, —$C(O)NR^aR^8$, —$R^cS(O)_pR^8$, —$R^cNR^aR^b$, —$R^cOR^a$, —$S(O)_pR^8$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each optionally substituted with at least one $R^{10}$ substituent each independently selected from methyl, ethyl, methoxy, ethoxy, —$CHF_2$, —$CF_3$, —$OCF_3$, F, Cl, —$NHCH_3$, —$N(CH_3)_2$, —$S(O)_2CH_3$, cyano and hydroxy. In another aspect, $R^6$ is H, methyl, ethyl, propyl, isopropyl, butyl, isobutyl, t-butyl, methoxy, ethoxy, —$CH_2CF_3$, —$CF_3$, —$OCF_3$; —$C(O)NR^aR^8$ wherein $R^a$ is H or methyl and $R^8$ is H, methyl, cyclopropyl, phenyl optionally substituted with F, Cl or —$CF_3$; —$(CH_2)S(O)_2R^8$ wherein $R^8$ is methyl or phenyl; —$CH_2NR^aR^b$ or —$(CH_2)_2NR^aR^b$ wherein $R^a$ and $R^b$ are each independently H or methyl; —$(CH_2)_2OCH_3$, —$(CH_2)_3OCH_3$; phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, pyrrolidinyl, piperidinyl, piperazinyl, morpholinyl, tetrahydropyranyl, tetrahydrofuranyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl; and wherein the phenyl, cycloalkyl ring, heterocycle ring and heteroaryl ring are each optionally substituted with at least one $R^{10}$ substituent each independently selected from methyl, ethyl, methoxy, ethoxy, —$CHF_2$, —$CF_3$, —$OCF_3$, F, Cl, amino, —$NHCH_3$, —$N(CH_3)_2$, —$S(O)_2CH_3$, cyano and hydroxy.

In another aspect of the invention, $R^5$ and $R^6$ taken together with the nitrogen atom to which they are attached form Ring B, a 4-8 membered heterocyclic or a 5-membered heteroaryl ring, each optionally containing at least one additional heteroatom selected from N, O and S; and wherein each ring is optionally substituted with at least one $R^9$ substituent; and wherein each ring is further optionally fused with Y which is phenyl, pyridinyl, pyrimidyl, pyrazolyl, thienyl, thiazolyl or triazolyl. In another aspect, $R^5$ and $R^6$ taken together with the nitrogen atom to which they are attached form Ring B, a 4-8 membered heterocyclic ring or a 5-membered heteroaryl ring, each optionally containing at least one additional heteroatom selected from N, O and S; and wherein each ring is optionally substituted with at least one $R^9$ substituent; and wherein each ring is further optionally fused with Y which is phenyl, pyridinyl or pyrimidyl. In another aspect, $R^5$ and $R^6$ taken together with the nitrogen atom to which they are attached form Ring B which is azetidinyl, pyrrolyl, pyrazolyl, imidazolyl, triazolyl, tetrazolyl, pyrrolidinyl, piperidinyl, piperazinyl, morpholinyl, or thiomorpholinyl, each of which is optionally substituted with at least one $R^9$ substituent selected from methyl, ethyl, propyl, isopropyl, cyclopropyl, methoxy, F, Cl, Br, CN, —$N(CH_3)_2$, hydroxy, —$CHF_2$, —$CF_3$, —$OCHF_2$, —$OCF_3$ and oxo; and wherein each ring is further optionally fused with Y which is phenyl or pyridinyl. In another aspect, $R^5$ and $R^6$ taken together with the nitrogen atom to which they are attached form Ring B which is pyrrolyl, pyrazolyl, imidazolyl, triazolyl, tetrazolyl, pyrrolidinyl, piperidinyl, piperazinyl, morpholinyl or thiomorpholinyl, each of which is optionally substituted with at least one $R^9$ substituent selected from methyl, ethyl, propyl, isopropyl, cyclopropyl, methoxy, F, Cl, Br, CN, —N(CH$_3$)$_2$, hydroxy, —CHF$_2$, —CF$_3$, —OCHF$_2$, —OCF$_3$ and oxo; and wherein each ring is further optionally fused with Y which is phenyl. In another aspect, $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each of which is optionally substituted with at least one $R^9$ substituent selected from methyl, ethyl, propyl, isopropyl, cyclopropyl, methoxy, F, Cl, Br, CN, —N(CH$_3$)$_2$, hydroxy, —CHF$_2$, —CF$_3$, —OCHF$_2$, —OCF$_3$ and oxo; and wherein each ring is further optionally fused with Y which is phenyl. In another aspect, $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each of which is optionally substituted with at least one $R^9$ substituent selected from methyl, ethyl, propyl, isopropyl, cyclopropyl, methoxy, F, Cl, Br, CN, —N(CH$_3$)$_2$, hydroxy, —CHF$_2$, —CF$_3$, —OCHF$_2$, —OCF$_3$ and oxo; or Ring B is indolinyl, isoindolinyl, tetrahydroquinolinyl, dihydropyrrolopyrazinyl or tetrahydroisoquinolinyl, dihydrobenzooxazinyl or dihydrobenzothiazinyl optionally substituted with at least one oxo. In another aspect, $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each of which is optionally substituted with at least one $R^9$ substituent selected from methyl, ethyl, propyl, isopropyl, cyclopropyl, methoxy, F, Cl, Br, CN, —N(CH$_3$)$_2$, hydroxy, —CHF$_2$, —CF$_3$, —OCHF$_2$, —OCF$_3$ and oxo.

In another aspect of the invention, $R^7$ is H, $C_1$-$C_6$alkyl, —(CH$_2$)$_m$NH$_2$, —(CH$_2$)$_m$NHCH$_3$, —(CH$_2$)$_m$N(CH$_3$)$_2$, —(CH$_2$)$_m$C(O)H, —(CH$_2$)$_m$C(O)CH$_3$, —(CH$_2$)$_m$S(O)$_p$CH$_3$, —(CH$_2$)$_m$NHC(O)CH$_3$, —(CH$_2$)$_m$NHC(O)NHCH$_3$, —(CH$_2$)$_m$NHC(O)N(CH$_3$)$_2$ or —(CH$_2$)$_m$NHC(O)CH$_3$; wherein m is the integer 1, 2, or 3. In another aspect, $R^7$ is H, $C_1$-$C_6$alkyl, —(CH$_2$)$_m$NH$_2$, —(CH$_2$)$_m$NHCH$_3$, —(CH$_2$)$_m$N(CH$_3$)$_2$, —(CH$_2$)$_m$C(O)CH$_3$, —(CH$_2$)$_m$S(O)$_p$CH$_3$ or —(CH$_2$)$_m$NHC(O)CH$_3$; wherein m is the integer 1 or 2. In another aspect of the invention, $R^7$ is H, $C_1$-$C_6$alkyl, —(CH$_2$)NH$_2$, —(CH$_2$)NHCH$_3$, —(CH$_2$)N(CH$_3$)$_2$, —(CH$_2$)C(O)CH$_3$, —(CH$_2$)S(O)$_p$CH$_3$ or —(CH$_2$)NHC(O)CH$_3$. In another aspect, $R^7$ is H, methyl, ethyl, propyl, isopropyl, t-butyl, —(CH$_2$)$_m$NH$_2$, —(CH$_2$)NHCH$_3$, —(CH$_2$)N(CH$_3$)$_2$, —(CH$_2$)C(O)CH$_3$, —(CH$_2$)S(O)$_p$CH$_3$ or —(CH$_2$)NHC(O)CH$_3$. In another aspect, $R^7$ is H, methyl, ethyl, propyl, isopropyl, t-butyl, —CH$_2$NH$_2$, —CH$_2$NHCH$_3$ or —CH$_2$N(CH$_3$)$_2$. In another aspect, $R^7$ is H, methyl, ethyl, propyl, isopropyl or —CH$_2$N(CH$_3$)$_2$. In another aspect, $R^7$ is H, methyl, ethyl or propyl.

In another aspect of the invention, $R^8$ is $C_1$-$C_6$alkyl, $C_1$-$C_6$haloalkyl, —NR$^a$R$^b$; or $C_0$-$C_4$alkylC$_3$-$C_6$cycloalkyl, phenyl, pyrrolyl, pyrazolyl, pyridinyl or pyrimidinyl each optionally substituted with at least one substituent selected from $C_1$-$C_6$alkyl, $C_1$-$C_6$haloalkyl, —NH$_2$, —NHCH$_3$, —N(CH$_3$)$_2$, halogen, $C_1$-$C_4$alkoxy, $C_1$-$C_4$haloalkyl and $C_1$-$C_4$haloalkoxy. In another aspect, $R^8$ is methyl, ethyl, propyl; or cyclopropyl, $C_1$alkylcyclopropyl, phenyl or pyridinyl each optionally substituted with at least one substituent selected from $C_1$-$C_4$alkyl, halogen, $C_1$-$C_4$alkoxy, —CF$_3$ and —OCF$_3$. In another aspect, $R^8$ is methyl, ethyl; or cyclopropyl or phenyl each optionally substituted with at least one substituent selected from $C_1$-$C_4$alkyl, halogen, $C_1$-$C_4$alkoxy, —CF$_3$ and —OCF$_3$.

In another aspect of the invention, each $R^9$ is independently selected from the group consisting of $C_1$-$C_6$alkyl, $C_1$-$C_6$alkoxy, halogen, oxo, hydroxy, nitro, cyano, —NR$^a$R$^b$, $C_1$-$C_6$haloalkyl, $C_1$-$C_6$haloalkoxy, —S(O)$_p$R$^8$, phenyl, tetrahydrofuranyl, tetrahydrothiophenyl, pyrrolidinyl, tetrahydropyranyl, tetrahydrothiopyranyl, piperidinyl, morpholinyl, piperazinyl, pyrrolyl, furanyl thiophenyl, pyrazolyl, imidazolyl, isoxazolyl, oxazolyl, isothiazolyl, thiazolyl, triazolyl, oxadiazolyl, thiadiazolyl, pyridinyl, pyridazinyl, pyrimidinyl and pyrazinyl. In yet another aspect, each $R^9$ is independently selected from the group consisting of $C_1$-$C_6$alkyl, $C_1$-$C_6$alkoxy, halogen, oxo, hydroxy, nitro, cyano, —NR$^a$R$^b$, $C_1$-$C_6$haloalkyl, $C_1$-$C_6$haloalkoxy, —S(O)$_p$R$^8$, phenyl, tetrahydrofuranyl, pyrrolidinyl, tetrahydropyranyl, piperidinyl, morpholinyl, piperazinyl, pyrrolyl, furanyl, thiophenyl pyrazolyl, imidazolyl, isoxazolyl, pyridinyl, pyrimidinyl, and pyrazinyl. In yet another aspect, each $R^9$ is independently selected from the group consisting of $C_1$-$C_6$alkyl, $C_1$-$C_6$alkoxy, halogen, oxo, hydroxy, nitro, cyano, —NR$^a$R$^b$, $C_1$-$C_6$haloalkyl, $C_1$-$C_6$haloalkoxy, —S(O)$_p$R$^8$, phenyl, piperidinyl, morpholinyl, piperazinyl and pyridinyl. In yet another aspect, $R^9$ is independently selected from the group consisting of $C_1$-$C_6$alkyl, $C_1$-$C_6$alkoxy, halogen, oxo, hydroxy, cyano, —NHCH$_3$, —N(CH$_3$)$_2$, —N(CH$_2$CH$_3$)$_2$, —CHF$_2$, —CF$_3$, —OCHF$_2$, —OCF$_3$, —S(O)$_2$CH$_3$, phenyl, piperidinyl, morpholinyl, piperazinyl and pyridinyl. In yet another aspect, $R^9$ is independently selected from the group consisting of methyl, ethyl, propyl, isopropyl, methoxy, ethoxy, isopropoxy, F, Cl, Br, oxo, hydroxy, cyano, —NHCH$_3$, —N(CH$_3$)$_2$, —N(CH$_2$CH$_3$)$_2$, —CHF$_2$, —CF$_3$, —OCHF$_2$, —OCF$_3$, —S(O)$_2$CH$_3$, phenyl, piperidinyl, morpholinyl, piperazinyl and pyridinyl. In yet another aspect, $R^9$ is independently selected from the group consisting of methyl, ethyl, methoxy, ethoxy, isopropoxy, F, Cl, Br, oxo, hydroxy, nitro, cyano, —NHCH$_3$, —N(CH$_3$)$_2$, —N(CH$_2$CH$_3$)$_2$, —CHF$_2$, —CF$_3$, —OCHF$_2$, —OCF$_3$, —S(O)$_2$CH$_3$, phenyl, piperidinyl, morpholinyl, piperazinyl and pyridinyl. In yet another aspect, each $R^9$ is independently selected from the group consisting of methyl, ethyl, propyl, methoxy, ethoxy, F, Cl, oxo, hydroxy, nitro, cyano, —NR$^a$R$^b$, —CF$_3$ and —OCF$_3$. In yet another aspect, each $R^9$ is independently selected from the group consisting of methyl, ethyl, propyl, methoxy, ethoxy, F, Cl, oxo, hydroxy, nitro, cyano, —NH$_2$, —NHCH$_3$, —N(CH$_3$)$_2$, CF$_3$ and —OCF$_3$. In another aspect, at least one $R^9$ substituent refers to the integer (n) which is 1, 2 or 3.

In another aspect of the invention, each $R^{10}$ is independently selected from $C_1$-$C_3$alkyl, $C_1$-$C_3$alkoxy, $C_1$-$C_3$haloalkyl, $C_1$-$C_3$haloalkoxy, halogen, —NR$^a$R$^b$, —S(O)$_p$R$^8$, nitro, oxo, cyano, —C(O)R$^a$, —C(O)OR$^a$, —OC(O)OR$^a$, —NR$^c$C(O)R$^a$, —C(O)NR$^a$R$^b$, hydroxy, a 5-6 membered heterocyclic ring, a 5-6 membered heteroaryl ring, wherein each heterocyclic and heteroaryl ring each contain at least one heteroatom selected from the group consisting of N, O and S; and phenyl; and wherein the phenyl, heterocyclic and heteroaryl ring are each optionally substituted with at least one $R^9$ substituent selected from the group consisting of $C_1$-$C_6$alkyl, $C_1$-$C_6$alkoxy, halogen, oxo, hydroxy, cyano, —NHCH$_3$, —N(CH$_3$)$_2$, —N(CH$_2$CH$_3$)$_2$, —CHF$_2$, —CF$_3$, —OCHF$_2$, —OCF$_3$, —S(O)$_2$CH$_3$, phenyl, piperidinyl, morpholinyl, piperazinyl and pyridinyl. In another aspect, each $R^{10}$ is independently selected from $C_1$-$C_3$alkyl, $C_1$-$C_3$alkoxy, $C_1$-$C_3$haloalkyl, $C_1$-$C_3$haloalkoxy, halogen, —NHCH$_3$, —N(CH$_3$)$_2$, —S(O)$_2$CH$_3$, nitro, oxo, cyano, —C(O)CH$_3$, —C(O)OCH$_3$, —NHCH$_2$C(O)CH$_3$, —NHCH$_2$CH$_2$C(O)CH$_3$, —C(O)NHCH$_3$ and hydroxy; phenyl, tetrahydrofuranyl, pyrrolidinyl, tetrahydropyranyl, piperidinyl, morpholinyl, piperazinyl, pyrrolyl, furanyl, pyrazolyl, imidazolyl, pyridinyl and pyrazinyl, each optionally and independently substituted with at least one $R^9$ substituent selected from the group consisting of methyl, ethyl, propyl, isopropyl, methoxy, ethoxy, halogen, oxo, hydroxy, cyano, —NHCH$_3$, —N(CH$_3$)$_2$, —N(CH$_2$CH$_3$)$_2$, —CHF$_2$, —CF$_3$, —OCHF$_2$, —OCF$_3$ and —S(O)$_2$CH$_3$. In another aspect, each $R^{10}$ is independently selected from methyl, ethyl, propyl, methoxy, ethoxy, —CHF$_2$, —CF$_3$, —OCF$_3$, F, Cl, —NHCH$_3$, —N(CH$_3$)$_2$, —S(O)$_2$CH$_3$, nitro, cyano, —C(O)CH$_3$, —NHC(O)CH$_3$, —NHCH$_2$CH$_2$C(O)CH$_3$, —C(O)NHCH$_3$ and hydroxy; phenyl, pyrrolidinyl, piperidinyl, morpholinyl, piperazinyl, and pyridinyl, each optionally and independently substituted with at least one $R^9$ substituent selected from the group consisting of methyl, ethyl, propyl, isopropyl, methoxy, ethoxy, halogen, oxo, hydroxy, cyano, —NHCH$_3$, —N(CH$_3$)$_2$, —N(CH$_2$CH$_3$)$_2$, —CHF$_2$, —CF$_3$, —OCHF$_2$, —OCF$_3$ and —S(O)$_2$CH$_3$. In another aspect, each $R^{10}$ is independently selected from methyl, ethyl, propyl, methoxy, ethoxy, —CHF$_2$, —CF$_3$, —OCF$_3$, F, Cl, —NHCH$_3$, —N(CH$_3$)$_2$, —S(O)$_2$CH$_3$, nitro, cyano, —C(O)CH$_3$, —NHCH$_2$C(O)CH$_3$, —NHCH$_2$CH$_2$C(O)CH$_3$, —C(O)NHCH$_3$ and hydroxy. In another aspect, at least one $R^{10}$ substituent refers to the integer (n) which is 1, 2 or 3.

In another aspect, R is H, —C(O)NR$^a$R$^d$ or —C(O)OR$^8$. In another aspect, R is H, —C(O)NH$_2$, —C(O)NHCH$_3$, —C(O)N(CH$_3$)$_2$, —C(O)NHCH$_2$CH$_3$, —C(O)NHCH(CH$_3$)$_2$, —C(O)NHC(CH$_3$)$_3$ or —C(O)NHphenyl, wherein the phenyl is optionally substituted with at least one substituent independently selected from F, Cl, —CF$_3$, cyano, methoxy, ethoxy and —OCF$_3$. In another aspect, R is H, —C(O)NHCH$_3$, —C(O)N(CH$_3$)$_2$ or —C(O)NHphenyl, wherein the phenyl is optionally substituted with at least one substituent independently selected from F, Cl, —CF$_3$, cyano, methoxy, ethoxy and —OCF$_3$. In another aspect, R is H or —C(O)NHphenyl, wherein the phenyl is optionally substituted with at least one substituent independently selected from F, Cl, —CF$_3$, cyano, methoxy, ethoxy and —OCF$_3$. In another aspect, R is H or —C(O)NHphenyl. In another aspect, R is H.

In yet another aspect, Y is phenyl, pyridinyl, pyrimidyl, pyrazolyl, thienyl, thiazolyl, triazolyl, isothiazolyl or pyrrolyl. In yet another aspect, Y is phenyl, pyridinyl, pyrimidyl or pyrazolyl. In yet another aspect, Y is phenyl, pyridinyl or pyrimidyl. In yet another aspect, Y is phenyl or pyridinyl. In another aspect, Y is phenyl. In yet another aspect, Y is pyridinyl. In yet another aspect, when optionally substituted Ring A or Ring B is fused with Y, Ring A or Ring B is optionally substituted indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine.

In another aspect, X' is F, Cl or Br. In another aspect, X' is F or Cl. In another aspect, X' is F. In another aspect, X' is Cl.

In another aspect of the invention, X is $R^a$, —(CH$_2$)$_m$NR$^5$R$^6$, —(CH$_2$)$_m$OR$^7$, —(CH$_2$)$_m$SR$^7$, —(CH$_2$)$_m$N$_3$, —(CH$_2$)$_m$CN or —(CH$_2$)$_m$X'; wherein m is the integer 1 or 2. In another aspect, X is $R^a$. In another aspect, X is —CH$_2$NR$^5$R$^6$. In another aspect, X is —CH$_2$OR$^7$. In another aspect, X is —CH$_2$SR$^7$. In another aspect, X is —CH$_2$N$_3$. In another aspect, X is —CH$_2$CN. In another aspect, X is —CH$_2$X'.

In another aspect of the invention, p is the integer 0. In another aspect, p is the integer 1. In another aspect, p is the integer 2. In another aspect of the invention, n is the integer 0, 1 or 2. In yet another aspect, n is the integer 0 or 1. In yet another aspect, n is the integer 0. In yet another aspect, n is the integer 1. In yet another aspect, n is the integer 2. In yet another aspect, n is the integer 3.

In another aspect of the invention, is a Formula (1) compound wherein R is H and W is Formula (A) that is a Formula (1A) compound wherein $R^0$, $R^1$, $R^2$, $R^3$ and X

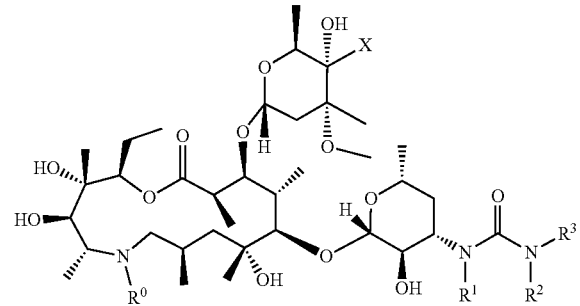

(1A)

are as defined herein, stereoisomers thereof, and pharmaceutically acceptable salts thereof.

In another aspect of the invention, Formula (A) is selected from the group consisting of: Formula (A0), Formula (A1), Formula (A2), Formula (A3), Formula (A4), Formula (A5) or Formula (A6)

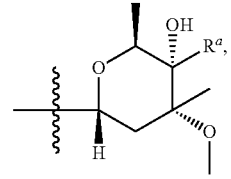

(A0)

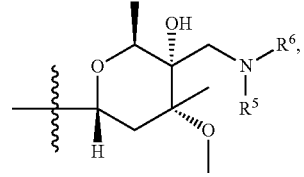

(A1)

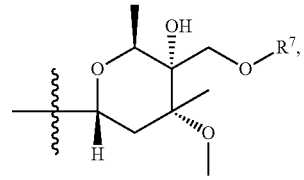

(A2)

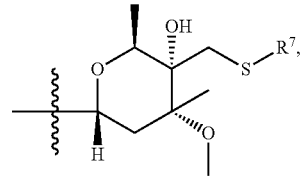

(A3)

-continued

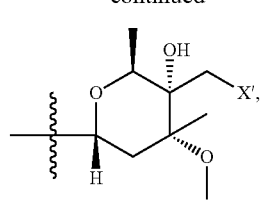

(A4)

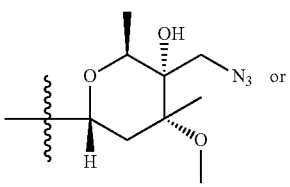

(A5)

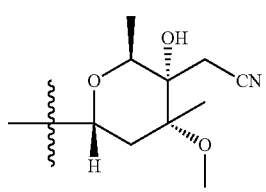

(A6)

stereoisomers thereof, and pharmaceutically acceptable salts thereof. In another aspect, Formula (A) compound is Formula (A0). In another aspect, Formula (A) is Formula (A1). In another aspect, Formula (A) is Formula (A2). In another aspect, Formula (A) is Formula (A3) compound. In another aspect, Formula (A) is Formula (A4). In another aspect, Formula (A) is Formula (A5). In another aspect, Formula (A) is Formula (A6). In another aspect, the preferred Formula (A) is Formula (A1).

In another aspect of the invention, is a Formula (1) compound wherein R and W are both H; that is a descladinose Formula (1.1) compound;

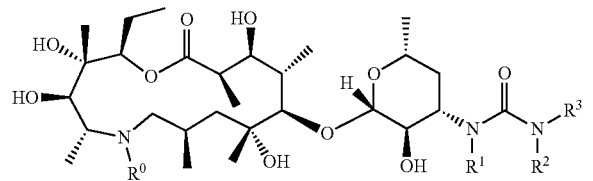

(1.1)

and wherein $R^0$, $R^1$, $R^2$ and $R^3$ are as defined herein; stereoisomers thereof, and pharmaceutically acceptable salts thereof. In another aspect, is a Formula (1.1) compound wherein $R^0$ is H, methyl, ethyl or propyl; and $R^1$, $R^2$ and $R^3$ are as defined herein, stereoisomers thereof, and pharmaceutically acceptable salts thereof. In another aspect, is a Formula (1.1) compound wherein $R^0$ is H or methyl; and $R^1$, $R^2$ and $R^3$ are as defined herein, stereoisomers thereof, and pharmaceutically acceptable salts thereof. In another aspect, is a Formula (1.1) compound wherein $R^0$ is H or methyl; $R^1$ is methyl; and $R^2$ and $R^3$ are as defined herein, stereoisomers thereof, and pharmaceutically acceptable salts thereof. In another aspect, is a Formula (1.1) compound wherein $R^0$ is H or methyl; $R^1$ is methyl; and $R^2$ and $R^3$ are each independently H, $C_1$-$C_6$alkyl, —$CH_2N(CH_3)_2$, —$CH_2CH_2N(CH_3)_2$; or $C_0$-$C_2$cyclopropyl, $C_0$-$C_2$cyclobutyl, $C_0$-$C_2$cyclopentyl, $C_0$-$C_2$cyclohexyl, $C_0$-$C_2$phenyl, $C_0$-$C_2$piperadinyl, piperazinyl, morpholinyl, tetrahydropyran, pyrrolyl, pyrazolyl, triazolyl, tetrazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, amino, —$N(CH_3)_2$, —$CHF_2$, —$CF_3$, —$OCHF_2$ and —$OCF_3$; or $R^2$ and $R^3$ taken together with the nitrogen atom to which they are attached form Ring A which is azetidinyl, pyrrolyl, pyrazolyl, imidazolyl, triazolyl, tetrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; and wherein each ring is further optionally substituted with Y which is phenyl, pyridinyl or pyrimidinyl; stereoisomers thereof, and pharmaceutically acceptable salts thereof. In another aspect, is a Formula (1.1) compound wherein $R^0$ is H is methyl; $R^1$ is methyl; and $R^2$ and $R^3$ are each independently H, $C_1$-$C_6$alkyl, —$CH_2N(CH_3)_2$, —$CH_2CH_2N(CH_3)_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, triazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, cyclopropyl, amino, —$N(CH_3)_2$, —$CHF_2$, —$CF_3$, —$OCHF_2$ and —$OCF_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; stereoisomers thereof, and pharmaceutically acceptable salts thereof. In another aspect, is a Formula (1.1) compound wherein $R^0$ is H or methyl; $R^1$ is methyl; $R^2$ is H, methyl, ethyl, isopropyl, cyclopropyl, —$CF_3$, —$CHF_2$, —$CH_2F$, —$CH_2CF_3$ or phenyl; and $R^3$ is H, methyl, ethyl, propyl, isopropyl, t-butyl; —$CH_2N(CH_3)_2$, —$CH_2CH_2N(CH_3)_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl, or pyridinyl, each optionally substituted with at least one $R^9$ substituent selected from the group consisting of methyl, ethyl, hydroxy, methoxy, ethoxy, F, Cl, cyano, amino, —$N(CH_3)_2$ and —$CF_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, F, Cl, oxo and —$CF_3$; stereoisomers thereof, and pharmaceutically acceptable salts thereof. In another aspect, is a Formula (1.1) Table A compound, stereoisomers thereof, and pharmaceutically acceptable salts thereof.

In another aspect, is a composition comprising a Formula (1.1) compound stereoisomers thereof, and pharmaceutically acceptable salts thereof. In another aspect, is a composition comprising a Formula (1.1) Table A compound, stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1.1) compound, stereoisomers thereof, and pharmaceutically acceptable salts thereof. In another aspect, is a method of treating or preventing an inflammatory response in an animal by administering to said animal in need thereof, a therapeutically effective amount of a Formula (1.1) Table A compound, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNF-α and IL-6 in the animal.

In another aspect, is the use of a Formula (1.1) compound, stereoisomers thereof, and pharmaceutically acceptable salts thereof; to prepare a medicament for treating or preventing an inflammatory response in an animal. In another aspect, is the use of a Formula (1.1) Table A compound, stereoisomers thereof, and pharmaceutically acceptable salts thereof; to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1) compound wherein R is H and W is Formula (A), and Formula (A) is Formula (A0); that is a Formula (1-A0)

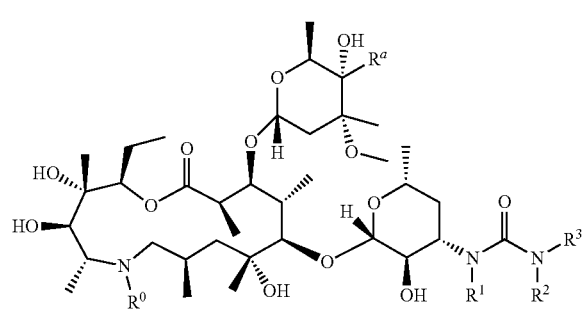

(1-A0)

compound, and wherein $R^a$, $R^0$, $R^1$, $R^2$ and $R^3$ are as defined herein; stereoisomers thereof, and pharmaceutically acceptable salts thereof. In another aspect, is a Formula (1-A0) compound wherein $R^0$ is H, methyl, ethyl or propyl; and $R^a$, $R^1$, $R^2$ and $R^3$ are as defined herein, stereoisomers thereof, and pharmaceutically acceptable salts thereof. In another aspect, is a Formula (1-A0) compound wherein $R^0$ is H, methyl, ethyl or propyl; $R^a$ is H or methyl; and $R^1$, $R^2$ and $R^3$ are as defined herein, stereoisomers thereof, and pharmaceutically acceptable salts thereof. In another aspect, is a Formula (1-A0) compound wherein $R^0$ is H or methyl; $R^a$ is H or methyl; and $R^1$ is H or methyl; and $R^2$ and $R^3$ are as defined herein, stereoisomers thereof, and pharmaceutically acceptable salts thereof. In another aspect, is a Formula (1-A0) compound wherein $R^0$ is H or methyl; $R^1$ is methyl; and $R^2$ and $R^3$ are as defined herein, stereoisomers thereof, and pharmaceutically acceptable salts thereof. In another aspect, is a Formula (1-A0) compound wherein $R^0$ is H or methyl; $R^1$ is methyl; and $R^2$ and $R^3$ are each independently H, $C_1$-$C_6$alkyl, —$CH_2N(CH_3)_2$, —$CH_2CH_2N(CH_3)_2$; or $C_0$-$C_2$cyclopropyl, $C_0$-$C_2$cyclobutyl, $C_0$-$C_2$cyclopentyl, $C_0$-$C_2$cyclohexyl, $C_0$-$C_2$phenyl, $C_0$-$C_2$piperadinyl, piperazinyl, morpholinyl, tetrahydropyran, pyrrolyl, pyrazolyl, triazolyl, tetrazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, amino, —$N(CH_3)_2$, —$CHF_2$, —$CF_3$, —$OCHF_2$ and —$OCF_3$; or $R^2$ and $R^3$ taken together with the nitrogen atom to which they are attached form Ring A, a 4-8 membered heterocyclic or 5-membered heteroaryl ring, each optionally containing at least one additional heteroatom selected from N, O and S; and wherein each ring is optionally substituted with at least one $R^{10}$ substituent, and wherein each ring is further optionally fused with Y which is phenyl, pyridinyl or pyrimidyl; stereoisomers thereof, and pharmaceutically acceptable salts thereof. In another aspect, is a Formula (1-A0) compound wherein $R^0$ is H or methyl; $R^1$ is methyl; and $R^2$ and $R^3$ are each independently H, $C_1$-$C_6$alkyl; —$CH_2N(CH_3)_2$, —$CH_2CH_2N(CH_3)_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, triazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, cyclopropyl, amino, —$N(CH_3)_2$, —$CHF_2$, —$CF_3$, —$OCHF_2$ and —$OCF_3$; or $R^2$ and $R^3$ taken together with the nitrogen atom to which they are attached form Ring A which is pyrrolyl, pyrazolyl, imidazolyl, triazolyl, tetrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; stereoisomers thereof, and pharmaceutically acceptable salts thereof. In another aspect, is a Formula (1-A0) compound wherein $R^0$ is H or methyl; $R^1$ is methyl; $R^2$ is H or methyl; and $R^3$ is H, methyl, ethyl or propyl; —$CH_2N(CH_3)_2$, —$CH_2CH_2N(CH_3)_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl or pyridinyl, each optionally substituted with at least one $R^9$ substituent selected from the group consisting of methyl, ethyl, hydroxy, methoxy, ethoxy, F, Cl, cyano, —$N(CH_3)_2$ and —CF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R$^{10}$ substituent selected from methyl, ethyl, F, Cl, oxo and —CF$_3$; stereoisomers thereof, and pharmaceutically acceptable salts thereof. In another aspect, is a Formula (1-A0) Table B compound, stereoisomers thereof, and pharmaceutically acceptable salts thereof. In another aspect, is a non-antibacterial Formula (1-A0) Table B compound, stereoisomers thereof, and pharmaceutically acceptable salts thereof.

In another aspect, is a composition comprising a Formula (1-A0) compound, stereoisomers thereof, and pharmaceutically acceptable salts thereof. In another aspect, is a composition comprising a Formula (1-A0) Table B compound, stereoisomers thereof, and pharmaceutically acceptable salts thereof. In another aspect, is a composition comprising a non-antibacterial Formula (1-A0) Table B compound, stereoisomers thereof, and pharmaceutically acceptable salts thereof.

In another aspect, is a composition comprising a Formula (1-A0) compound, stereoisomers thereof, and pharmaceutically acceptable salts thereof. In another aspect, is a composition comprising a Formula (1-A0) Table B compound, stereoisomers thereof, and pharmaceutically acceptable salts thereof. In another aspect, is a composition comprising a non-antibacterial Formula (1-A0) Table B compound, stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A0) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A0) Table B compound, stereoisomers thereof, and pharmaceutically acceptable salts thereof. In another aspect, is a method of treating or preventing an inflammatory response in an animal by administering to said animal in need thereof, a therapeutically effective amount of a non-antibacterial Formula (1-A0) Table B compound, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNF-α and IL-6 in the animal.

In another aspect, is the use of a Formula (1-A0) compound, stereoisomers thereof, and pharmaceutically acceptable salts thereof; to prepare a medicament for treating or preventing an inflammatory response in an animal. In another aspect, is the use of a Formula (1-A0) Table B compound, stereoisomers thereof, and pharmaceutically acceptable salts thereof; to prepare a medicament for treating or preventing an inflammatory response in an animal. In another aspect, is the use of a non-antibacterial Formula (1-A0) Table B compound, stereoisomers thereof, and pharmaceutically acceptable salts thereof; to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1) compound wherein R is H and W is Formula (A), and Formula (A) is Formula (A2); that is a Formula (1-A2)

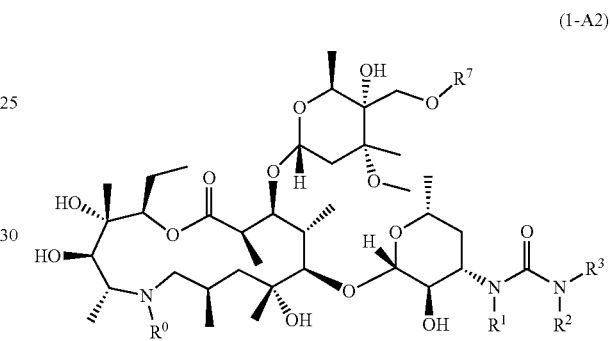

(1-A2)

compound; wherein R$^0$, R$^1$, R$^2$, R$^3$ and R$^7$ are as defined herein; stereoisomers thereof, and pharmaceutically acceptable salts thereof. In another aspect, is a Formula (1-A2) compound; wherein R$^0$ is H, methyl, ethyl or propyl; R$^1$ is H or methyl; and R$^2$, R$^3$ and R$^7$ are as defined herein; stereoisomers thereof, and pharmaceutically acceptable salts thereof. In another aspect, is a Formula (1-A2) compound; wherein R$^0$ is H or methyl; R$^1$ is H or methyl; and R$^2$ and R$^3$ are each independently H, C$_1$-C$_6$alkyl; —CH$_2$N(CH$_3$)$_2$, —CH$_2$CH$_2$N(CH$_3$)$_2$; or cyclopropyl, C$_1$cyclopropyl, cyclobutyl, C$_1$cyclobutyl, cyclopentyl, C$_1$cyclopentyl, cyclohexyl, C$_1$cyclohexyl, phenyl, C$_1$phenyl, piperadinyl, C$_1$-piperadinyl, C$_2$piperadinyl, piperazinyl, morpholinyl, tetrahydro-2H-pyran, pyrrolyl, pyrazolyl, pyridinyl, pyrimidinyl, pyridazinyl or pyrazinyl, each optionally substituted with at least one R$^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R$^{10}$ substituent selected from methyl, ethyl, propyl, isopropyl, cyclopropyl, methoxy, F, Cl, Br, CN, —N(CH$_3$)$_2$, hydroxyl, —CHF$_2$, —CF$_3$, —OCHF$_2$, —OCF$_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; and R$^7$ is H, C$_1$-C$_6$alkyl, —(CH$_2$)$_m$NH$_2$, —(CH$_2$)$_m$NHCH$_3$, —(CH$_2$)$_m$N(CH$_3$)$_2$, —(CH$_2$)$_m$C(O)CH$_3$, —(CH$_2$)$_m$S(O)$_p$CH$_3$ or —(CH$_2$)$_m$NHC(O)CH$_3$; wherein m is the integer 1 or 2; stereoisomers thereof, and pharmaceutically acceptable salts thereof. In another aspect, is a Formula (1-A2) wherein R$^0$ is H or methyl; R$^1$ is methyl; R$^2$ is H, methyl, ethyl, cyclopropyl or phenyl; R$^3$ is H, methyl, ethyl, propyl, isopropyl, isobutyl, —CH$_2$N(CH$_3$)$_2$, —CH$_2$CH$_2$N(CH$_3$)$_2$; or cyclopropyl, cyclobutyl, phenyl, C$_1$phenyl, piperadinyl, C$_1$-piperadinyl, C$_2$piperadinyl, piperazinyl, morpholinyl, tetrahydro-2H-pyran, pyrazolyl, or pyridinyl, each optionally substituted with at least one R$^9$ substituent selected from the group consisting of methyl, ethyl, hydroxy, methoxy, ethoxy, F, Cl, nitro, cyano, —N(CH$_3$)$_2$ and —CF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R$^{10}$ substituent selected from methyl, ethyl, F, Cl, oxo and —CF$_3$; and R$^7$ is H, methyl, ethyl, propyl, isopropyl, t-butyl, —CH$_2$NH$_2$, —CH$_2$NHCH$_3$ or —CH$_2$N(CH$_3$)$_2$, stereoisomers thereof, and pharmaceutically acceptable salts thereof. In another aspect, is a Formula (1-A2) Table C compound, stereoisomers thereof, and pharmaceutically acceptable salts thereof.

In another aspect of the invention, is a Formula (1) compound wherein R is H and W is Formula (A), and Formula (A) is Formula (A3); that is a Formula (1-A3) compound,

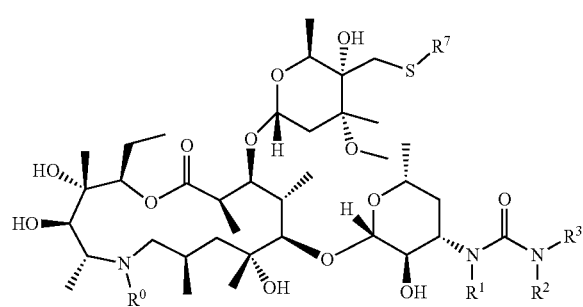

(1-A3)

wherein R$^0$, R$^1$, R$^2$, R$^3$ and R$^7$ are as defined herein; stereoisomers thereof, and pharmaceutically acceptable salts thereof. In another aspect, is a Formula (1-A3) compound; wherein R$^0$ is H, methyl, ethyl or propyl; and R$^1$, R$^2$, R$^3$ and R$^7$ are as defined herein; stereoisomers thereof, and pharmaceutically acceptable salts thereof. In another aspect, is a Formula (1-A3) compound; wherein R$^0$ is H, methyl, ethyl or propyl; R$^1$ is H or methyl; and R$^2$, R$^3$ and R$^7$ are as defined herein; stereoisomers thereof, and pharmaceutically acceptable salts thereof. In another aspect, is a Formula (1-A3) compound; wherein R$^0$ is H or methyl; R$^1$ is H or methyl; and R$^2$ and R$^3$ are each independently H, C$_1$-C$_6$alkyl; —CH$_2$N(CH$_3$)$_2$, —CH$_2$CH$_2$N(CH$_3$)$_2$; or cyclopropyl, C$_1$cyclopropyl, cyclobutyl, C$_1$cyclobutyl, cyclopentyl, C$_1$cyclopentyl, cyclohexyl, C$_1$cyclohexyl, phenyl, C$_1$phenyl, piperadinyl, C$_1$-piperadinyl, C$_2$piperadinyl, piperazinyl, morpholinyl, tetrahydro-2H-pyran, pyrrolyl, pyrazolyl, pyridinyl, pyrimidinyl, pyridazinyl or pyrazinyl, each optionally substituted with at least one R$^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R$^{10}$ substituent selected from methyl, ethyl, propyl, isopropyl, cyclopropyl, methoxy, F, Cl, Br, CN, —N(CH$_3$)$_2$, hydroxyl, —CHF$_2$, —CF$_3$, —OCHF$_2$, —OCF$_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; and R$^7$ is H, C$_1$-C$_6$alkyl, —(CH$_2$)$_m$NH$_2$, —(CH$_2$)$_m$NHCH$_3$, —(CH$_2$)$_m$N(CH$_3$)$_2$, —(CH$_2$)$_m$C(O)CH$_3$, —(CH$_2$)$_m$S(O)$_p$CH$_3$ or —(CH$_2$)$_m$NHC(O)CH$_3$; wherein m is the integer 1 or 2; stereoisomers thereof, and pharmaceutically acceptable salts thereof. In another aspect, is a Formula (1-A3) wherein R$^0$ is H or methyl; R$^1$ is methyl; R$^2$ is H, methyl, ethyl, cyclopropyl or phenyl; R$^3$ is H, methyl, ethyl, propyl, isopropyl, t-butyl, —CH$_2$N(CH$_3$)$_2$, —CH$_2$CH$_2$N(CH$_3$)$_2$; or cyclopropyl, cyclobutyl, phenyl, C$_1$phenyl, piperadinyl, C$_1$-piperadinyl, C$_2$piperadinyl, piperazinyl, morpholinyl, tetrahydro-2H-pyran, pyrazolyl, or pyridinyl, each optionally substituted with at least one R$^9$ substituent selected from the group consisting of methyl, ethyl, hydroxy, methoxy, ethoxy, F, Cl, nitro, cyano, —N(CH$_3$)$_2$ and —CF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl, or thiomorpholinyl, each optionally substituted with at least one R$^{10}$ substituent selected from methyl, ethyl, F, Cl, oxo and —CF$_3$; and R$^7$ is H, methyl, ethyl, propyl, isopropyl, t-butyl, —CH$_2$NH$_2$, —CH$_2$NHCH$_3$ or —CH$_2$N(CH$_3$)$_2$, stereoisomers thereof, and pharmaceutically acceptable salts thereof. In another aspect, is a Formula (1-A3) Table D compound, stereoisomers thereof, and pharmaceutically acceptable salts thereof. In another aspect, is a non-antibacterial Formula (1-A3) Table D compound, stereoisomers thereof, and pharmaceutically acceptable salts thereof.

In another aspect of the invention, is a Formula (1) compound wherein R is H and W is Formula (A), and Formula (A) is Formula (A4); that is a Formula (1-A4) compound

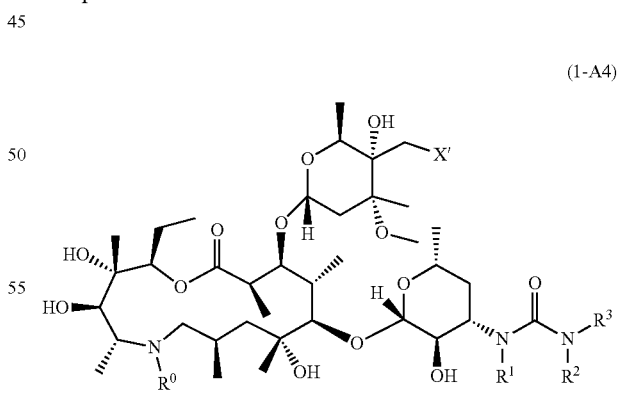

(1-A4)

wherein R$^0$, R$^1$, R$^2$, R$^3$ and X' are as defined herein; stereoisomers thereof, and pharmaceutically acceptable salts thereof. In another aspect, is a Formula (1-A4) compound; wherein R$^0$ is H, methyl, ethyl or propyl; and R$^1$, R$^2$, R$^3$ and X' are as defined herein; stereoisomers thereof, and pharmaceutically acceptable salts thereof. In another aspect, is a Formula (1-A4) compound; wherein R$^0$ is H, methyl, ethyl or propyl; $R^1$ is H or methyl; and $R^2$, $R^3$ and X' are as defined herein; stereoisomers thereof, and pharmaceutically acceptable salts thereof. In another aspect, is a Formula (1-A4) compound; wherein $R^0$ is H or methyl; $R^1$ is H or methyl; and $R^2$ and $R^3$ are each independently H, $C_1$-$C_6$alkyl; —CH$_2$N(CH$_3$)$_2$, —CH$_2$CH$_2$N(CH$_3$)$_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —N(CH$_3$)$_2$, hydroxyl, —CHF$_2$, —CF$_3$, —OCHF$_2$, —OCF$_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; and X is F, Cl, or Br; stereoisomers thereof, and pharmaceutically acceptable salts thereof. In another aspect, is a Formula (1-A4) wherein $R^0$ is H or methyl; $R^1$ is methyl; $R^2$ is H, methyl, ethyl, cyclopropyl or phenyl; $R^3$ is H, methyl, ethyl, propyl, isopropyl, t-butyl, —CH$_2$N(CH$_3$)$_2$, —CH$_2$CH$_2$N(CH$_3$)$_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl, or pyridinyl, each optionally substituted with at least one $R^9$ substituent selected from the group consisting of methyl, ethyl, hydroxy, methoxy, ethoxy, F, Cl, nitro, cyano, —N(CH$_3$)$_2$ and —CF$_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, F, Cl, oxo and —CF$_3$; and X is F or Cl; stereoisomers thereof, and pharmaceutically acceptable salts thereof. In another aspect, is a Formula (1-A4) Table E compound, stereoisomers thereof, and pharmaceutically acceptable salts thereof.

In another aspect of the invention, is a Formula (1) compound wherein R is H and W is Formula (A), and Formula (A) is Formula (A5); that is a Formula (1-A5)

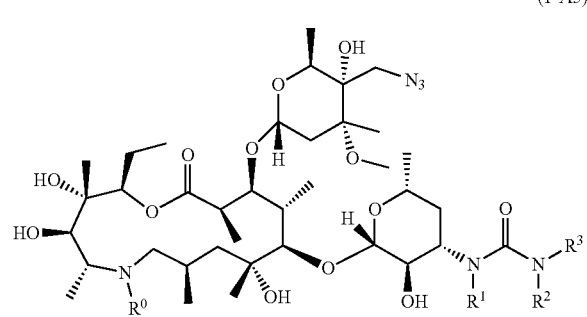

(1-A5)

compound; wherein $R^0$, $R^1$, $R^2$ and $R^3$ are as defined herein; stereoisomers thereof, and pharmaceutically acceptable salts thereof. In another aspect, is a Formula (1-A5) compound; wherein $R^0$ is H, methyl, ethyl or propyl; and $R^1$, $R^2$ and $R^3$ are as defined herein; stereoisomers thereof, and pharmaceutically acceptable salts thereof. In another aspect, is a Formula (1-A5) compound; wherein $R^0$ is H, methyl, ethyl or propyl; $R^1$ is H or methyl; and $R^2$ and $R^3$ are as defined herein; stereoisomers thereof, and pharmaceutically acceptable salts thereof. In another aspect, is a Formula (1-A5) compound; wherein $R^0$ is H or methyl; $R^1$ is H or methyl; and $R^2$ and $R^3$ are each independently H, $C_1$-$C_6$alkyl; —CH$_2$N(CH$_3$)$_2$, —CH$_2$CH$_2$N(CH$_3$)$_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —N(CH$_3$)$_2$, hydroxyl, —CHF$_2$, —CF$_3$, —OCHF$_2$, —OCF$_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; stereoisomers thereof, and pharmaceutically acceptable salts thereof. In another aspect, is a Formula (1-A5) wherein $R^0$ is H or methyl; $R^1$ is methyl; $R^2$ is H, methyl, ethyl, cyclopropyl or phenyl; $R^3$ is H, methyl, ethyl, propyl, isopropyl, t-butyl, —CH$_2$N(CH$_3$)$_2$, —CH$_2$CH$_2$N (CH$_3$)$_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl, or pyridinyl, each optionally substituted with at least one $R^9$ substituent selected from the group consisting of methyl, ethyl, hydroxy, methoxy, ethoxy, F, Cl, nitro, cyano, —N(CH$_3$)$_2$ and —CF$_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, F, Cl, oxo and —CF$_3$; stereoisomers thereof, and pharmaceutically acceptable salts thereof. In another aspect, is a Formula (1-A5) Table F compound, stereoisomers thereof, and pharmaceutically acceptable salts thereof. In another aspect, is a non-antibacterial Formula (1-A5) Table F compound, stereoisomers thereof, and pharmaceutically acceptable salts thereof.

In another aspect, is a Formula (1) compound, wherein R is H, W if Formula (A) and Formula (A) is Formula (A6) that is a Formula (1-A6) compound, wherein $R^0$, $R^1$,

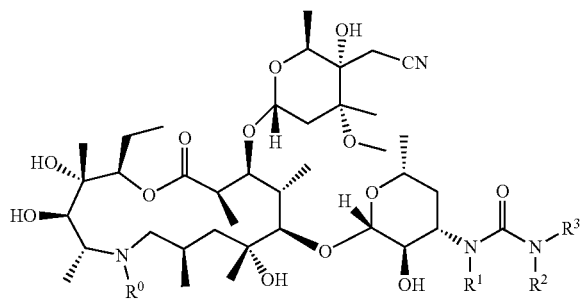

(1-A6)

R² and R³ are as defined herein; stereoisomers thereof, and pharmaceutically acceptable salts thereof. In another aspect, is a Formula (1-A6) compound, wherein R⁰ is H, methyl, ethyl or propyl; and R¹, R² and R³ are as defined herein; stereoisomers thereof, and pharmaceutically acceptable salts thereof. In another aspect, is a Formula (1-A6) compound; wherein R⁰ is H, methyl, ethyl or propyl; R¹ is H or methyl; and R² and R³ are as defined herein; stereoisomers thereof, and pharmaceutically acceptable salts thereof. In another aspect, is a Formula (1-A6) compound; wherein R⁰ is H or methyl; R¹ is H or methyl; and R² and R³ are each independently H, $C_1$-$C_6$alkyl; —$CH_2N(CH_3)_2$, —$CH_2CH_2N(CH_3)_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-2H-pyran, pyrrolyl, pyrazolyl, pyridinyl, pyrimidinyl, pyridazinyl or pyrazinyl, each optionally substituted with at least one R⁹ substituent selected from the group consisting of methyl, ethyl, propyl, isopropyl, t-butyl, hydroxy, methoxy, ethoxy, F, Cl, Br, cyano, cyclopropyl, amino, —$N(CH_3)_2$, —$CHF_2$, —$CF_3$, —$OCHF_2$ and —$OCF_3$; or R² and R³ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R¹⁰ substituent selected from methyl, ethyl, propyl, isopropyl, cyclopropyl, methoxy, F, Cl, Br, CN, —$N(CH_3)_2$, hydroxyl, —$CHF_2$, —$CF_3$, —$OCHF_2$, —$OCF_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; stereoisomers thereof, and pharmaceutically acceptable salts thereof. In another aspect, is a Formula (1-A6) wherein R⁰ is H or methyl; R¹ is methyl; R² is H, methyl, ethyl, cyclopropyl or phenyl; R³ is H, methyl, ethyl, propyl, isopropyl, t-butyl, —$CH_2N(CH_3)_2$, —$CH_2CH_2N(CH_3)_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl or pyridinyl, each optionally substituted with at least one R⁹ substituent selected from the group consisting of methyl, ethyl, hydroxy, methoxy, ethoxy, F, Cl, nitro, cyano, —$N(CH_3)_2$ and —$CF_3$; or R² and R³ taken together with the nitrogen atom to which they are attached form Ring A which is pyrrolyl, pyrazolyl, pyrrolidinyl, piperidinyl, piperazinyl, morpholinyl, or thiomorpholinyl, each optionally substituted with at least one R¹⁰ substituent selected from methyl, ethyl, F, Cl, oxo and —$CF_3$; stereoisomers thereof, and pharmaceutically acceptable salts thereof. In another aspect, is a Formula (1-A6) Table G compound, stereoisomers thereof, and pharmaceutically acceptable salts thereof.

In another aspect, is a composition comprising a Formula (1-A2) compound, stereoisomers thereof, and pharmaceutically acceptable salts thereof. In another aspect, is a composition comprising a Formula (1-A2) Table C compound, stereoisomers thereof, and pharmaceutically acceptable salts thereof. In another aspect, is a composition comprising a Formula (1-A3) compound, stereoisomers thereof, and pharmaceutically acceptable salts thereof. In another aspect, is a composition comprising a Formula (1-A3) Table D compound, stereoisomers thereof, and pharmaceutically acceptable salts thereof. In another aspect, is a composition comprising a non-antibacterial Formula (1-A3) compound, stereoisomers thereof, and pharmaceutically acceptable salts thereof. In another aspect, is a composition comprising a Formula (1-A4) compound, stereoisomers thereof, and pharmaceutically acceptable salts thereof. In another aspect, is a composition comprising a Formula (1-A4) Table E compound, stereoisomers thereof, and pharmaceutically acceptable salts thereof. In another aspect, is a composition comprising a Formula (1-A5) compound, stereoisomers thereof, and pharmaceutically acceptable salts thereof. In another aspect, is a composition comprising a non-antibacterial Formula (1-A5) Table F compound, stereoisomers thereof, and pharmaceutically acceptable salts thereof. In another aspect, is a composition comprising a Formula (1-A6) compound, stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A2) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A2) Table C compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A3) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A3) Table D compound, stereoisomers thereof, and pharmaceutically acceptable salts thereof. In another aspect, is a method of treating or preventing an inflammatory response in an animal by administering to said animal in need thereof, a therapeutically effective amount of a non-antibacterial Formula (1-A3) Table D compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A4) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A4) Table E compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A5) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A5) Table F compound, stereoisomers thereof, and pharmaceutically acceptable salts thereof. In another aspect, is a method of treating or preventing an inflammatory response in an animal by administering to said animal in need thereof, a therapeutically effective amount of a non-antibacterial Formula (1-A5) Table F compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A6) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A6) Table G compound, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNF-α and IL-6 in the animal.

In another aspect, is the use of a Formula (1-A2) compound, stereoisomers thereof, and pharmaceutically acceptable salts thereof; to prepare a medicament for treating or preventing an inflammatory response in an animal. In another aspect, is the use of a Formula (1-A2) Table C compound, stereoisomers thereof, and pharmaceutically acceptable salts thereof; to prepare a medicament for treating or preventing an inflammatory response in an animal. In another aspect, is the use of a Formula (1-A3) compound, stereoisomers thereof, and pharmaceutically acceptable salts thereof; to prepare a medicament for treating or preventing an inflammatory response in an animal. In another aspect, is the use of a non-antibacterial Formula (1-A3) Table D compound, stereoisomers thereof, and pharmaceutically acceptable salts thereof; to prepare a medicament for treating or preventing an inflammatory response in an animal. In another aspect, is the use of a Formula (1-A4) compound, stereoisomers thereof, and pharmaceutically acceptable salts thereof; to prepare a medicament for treating or preventing an inflammatory response in an animal. In another aspect, is the use of a Formula (1-A4) Table E compound, stereoisomers thereof, and pharmaceutically acceptable salts thereof; to prepare a medicament for treating or preventing an inflammatory response in an animal. In another aspect, is the use of a Formula (1-A5) compound, stereoisomers thereof, and pharmaceutically acceptable salts thereof; to prepare a medicament for treating or preventing an inflammatory response in an animal. In another aspect, is the use of a non-antibacterial Formula (1-A5) compound, stereoisomers thereof, and pharmaceutically acceptable salts thereof; to prepare a medicament for treating or preventing an inflammatory response in an animal. In another aspect, is the use of a Formula (1-A6) compound, stereoisomers thereof, and pharmaceutically acceptable salts thereof; to prepare a medicament for treating or preventing an inflammatory response in an animal. In another aspect, is the use of a Formula (1-A6) Table G compound, stereoisomers thereof, and pharmaceutically acceptable salts thereof; to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1) compound wherein R is H and W is Formula (A), Formula (A) is Formula (A1); that is a Formula (1-A1) compound;

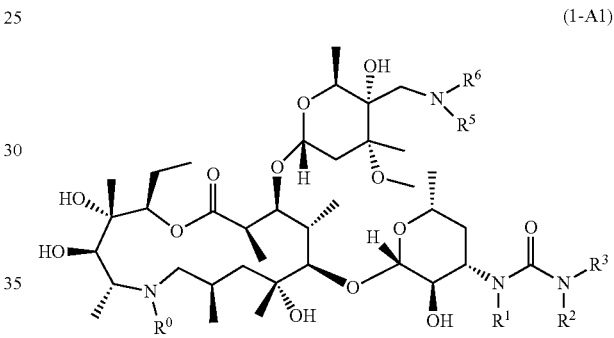

(1-A1)

and wherein $R^0$, $R^1$, $R^2$, $R^3$, $R^5$ and $R^6$ are as defined herein; stereoisomers thereof, and pharmaceutically acceptable salts thereof. In another aspect, is a Formula (1-A1) compound wherein $R^0$ is H, methyl, ethyl or propyl; and $R^1$, $R^2$, $R^3$, $R^5$ and $R^6$ are as defined herein, stereoisomers thereof, and pharmaceutically acceptable salts thereof. In another aspect, is a Formula (1-A1) compound wherein $R^0$ is H, methyl; ethyl or propyl; $R^1$ is H or methyl; and $R^2$, $R^3$, $R^5$ and $R^6$ are as defined herein, stereoisomers thereof, and pharmaceutically acceptable salts thereof. In another aspect, is a Formula (1-A1) compound wherein $R^0$ and $R^1$ are each independently H or methyl; $R^2$, $R^3$, $R^5$ and $R^6$ are as defined herein, stereoisomers thereof, and pharmaceutically acceptable salts thereof. In another aspect, is a Formula (1-A1) compound wherein $R^0$ is H or methyl; $R^1$ is methyl; and $R^2$, $R^3$, $R^5$ and $R^6$ are as defined herein, stereoisomers thereof, and pharmaceutically acceptable salts thereof. In another aspect, is a Formula (1-A1) compound wherein $R^0$ is H or methyl; $R^1$ is methyl; $R^2$ and $R^3$ are each independently H, $C_1$-$C_6$alkyl; —$CH_2N(CH_3)_2$, —$CH_2CH_2N(CH_3)_2$; or cyclopropyl, $C_1$cyclopropyl, cyclobutyl, $C_1$cyclobutyl, cyclopentyl, $C_1$cyclopentyl, cyclohexyl, $C_1$cyclohexyl, phenyl, $C_1$phenyl, piperadinyl, $C_1$-piperadinyl, $C_2$piperadinyl, piperazinyl, morpholinyl, tetrahydro-pyran, pyrrolyl, pyrazolyl, triazolyl, pyridinyl, pyrimidinyl, pyridazinyl or pyrazinyl, each optionally substituted with at least one $R^9$ substituent selected from the group consisting of methyl, ethyl, propyl, isopropyl, t-butyl, hydroxy, methoxy, ethoxy, F, Cl, Br, cyano, amino, —$N(CH_3)_2$, —$CHF_2$, —$CF_3$, —$OCHF_2$ and —OCF$_3$; or R$^2$ and R$^3$ taken together with the nitrogen atom to which they are attached form Ring A which is pyrrolyl, pyrazolyl, imidazolyl, triazolyl, tetrazolyl, pyrrolidinyl, piperidinyl, piperazinyl, morpholinyl or thiomorpholinyl, each optionally substituted with at least one R$^{10}$ substituent selected from methyl, ethyl, propyl, isopropyl, cyclopropyl, methoxy, F, Cl, Br, CN, —N(CH$_3$)$_2$, hydroxyl, —CHF$_2$, —CF$_3$, —OCHF$_2$, —OCF$_3$ and oxo; and wherein each ring is further optionally fused with Y which is phenyl, pyridinyl or pyrimidinyl; R$^5$ and R$^6$ are each independently H; C$_1$-C$_6$alkyl or C$_1$-C$_6$alkoxy each optionally substituted with at least one hydroxy; C$_1$-C$_6$haloalkyl, C$_1$-C$_6$haloalkoxy, —C(O)R$^8$, —C(O)NR$^a$R$^8$, —C(O)R$^c$NR$^a$R$^b$, —R$^c$S(O)$_p$R$^8$, —R$^c$NR$^a$R$^b$, —R$^c$OR$^a$, —S(O)$_p$R$^8$; or phenyl, C$_1$alkylphenyl, cyclopropyl, cyclobutyl, cyclopentyl, cyclohexyl, C$_1$-C$_2$alkylcyclopropyl, C$_1$-C$_2$alkylcyclobutyl, oxazolidinyl, pyrrolidinyl, piperidinyl, piperazinyl, morpholinyl, tetrahydropyranyl, tetrahydrofuranyl, C$_1$-C$_2$alkyloxazolidinyl, C$_1$-C$_2$alkylpyrrolidinyl, C$_1$-C$_2$alkylpiperidinyl, C$_1$-C$_2$alkylpiperazinyl, C$_1$-C$_2$morpholinyl, C$_1$-C$_2$morpholinyl, C$_1$-C$_2$piperadinyl, C$_1$-C$_2$tetrahydropyranyl, C$_1$-C$_2$tetrahydrofuranyl, pyrazolyl, imidazolyl, pyridinyl, pyrimidinyl, pyrazinyl, C$_1$-C$_2$alkylpyrazolyl, C$_1$-C$_2$alkylimidazolyl, C$_1$-C$_2$alkylpyridinyl, C$_1$-C$_2$alkylpyrimidinyl, or C$_1$-C$_2$alkylpyrazinyl, each optionally substituted with at least one R$^{10}$ substituent each independently selected from methyl, ethyl, methoxy, ethoxy, —CHF$_2$, —CF$_3$, —OCF$_3$, F, Cl, —NHCH$_3$, —N(CH$_3$)$_2$, —S(O)$_2$CH$_3$, cyano and hydroxy; or R$^5$ and R$^6$ taken together with the nitrogen atom to which they are attached form Ring B which is pyrrolyl, pyrazolyl, imidazolyl, triazolyl, tetrazolyl, pyrrolidinyl, piperidinyl, piperazinyl, morpholinyl or thiomorpholinyl, each optionally substituted with at least one R$^9$ substituent selected from methyl, ethyl, propyl, isopropyl, cyclopropyl, methoxy, F, Cl, Br, CN, —N(CH$_3$)$_2$, hydroxy, —CHF$_2$, —CF$_3$, —OCHF$_2$, —OCF$_3$ and oxo; and wherein each ring is further optionally fused with Y which is phenyl, pyridinyl or pyrimidinyl; stereoisomers thereof, and pharmaceutically acceptable salts thereof. In another aspect, is a Formula (1-A1) compound wherein R$^0$ is H or methyl; R$^1$ is methyl; R$^2$ and R$^3$ are each independently H, C$_1$-C$_6$alkyl; —CH$_2$N(CH$_3$)$_2$, —CH$_2$CH$_2$N(CH$_3$)$_2$; or cyclopropyl, C$_1$cyclopropyl, cyclobutyl, C$_1$cyclobutyl, cyclopentyl, C$_1$cyclopentyl, cyclohexyl, C$_1$cyclohexyl, phenyl, C$_1$phenyl, piperadinyl, C$_1$-piperadinyl, C$_2$piperadinyl, piperazinyl, morpholinyl, tetrahydro-2H-pyran, pyrrolyl, pyrazolyl, pyridinyl, pyrimidinyl, pyridazinyl or pyrazinyl, each optionally substituted with at least one R$^9$ substituent selected from the group consisting of methyl, ethyl, propyl, isopropyl, t-butyl, hydroxy, methoxy, ethoxy, F, Cl, Br, cyano, cyclopropyl, amino, —N(CH$_3$)$_2$, —CHF$_2$, —CF$_3$, —OCHF$_2$ and —OCF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R$^{10}$ substituent selected from methyl, ethyl, F, Cl, oxo and —CF$_3$; and wherein each ring is further optionally fused with Y which is phenyl; R$^5$ and R$^6$ are each independently H; C$_1$-C$_6$alkyl or C$_1$-C$_6$alkoxy each optionally substituted with at least one hydroxy; C$_1$-C$_6$haloalkyl, —OCF$_3$, —C(O)NR$^a$R$^8$, —R$^c$S(O)$_p$R$^8$, —R$^c$NR$^a$R$^b$, —R$^c$OR$^a$, —S(O)$_p$R$^8$; or phenyl, C$_1$alkylphenyl, cyclopropyl, cyclobutyl, cyclopentyl, cyclohexyl, C$_1$-C$_2$alkylcyclopropyl and C$_1$-C$_2$alkylcyclobutyl, oxazolidinyl, pyrrolidinyl, piperidinyl, piperazinyl, morpholinyl, tetrahydropyranyl, tetrahydrofuranyl, C$_1$-C$_2$alkyloxazolidinyl, C$_1$-C$_2$alkylpyrrolidinyl, C$_1$-C$_2$alkylpiperidinyl, C$_1$-C$_2$alkylpiperazinyl, C$_1$-C$_2$morpholinyl, C$_1$-C$_2$tetrahydropyranyl, C$_1$-C$_2$tetrahydrofuranyl, pyrazolyl, imidazolyl, pyridinyl, pyrimidinyl, pyrazinyl, C$_1$-C$_2$alkylpyrazolyl, C$_1$-C$_2$alkylimidazolyl, C$_1$-C$_2$alkylpyridinyl, C$_1$-C$_2$alkylpyrimidinyl or C$_1$-C$_2$alkylpyrimidinyl or C$_1$-C$_2$alkylpyrazinyl, each optionally substituted with at least one R$^{10}$ substituent each independently selected from methyl, ethyl, methoxy, ethoxy, —CHF$_2$, —CF$_3$, —OCF$_3$, F, Cl, amino, —NHCH$_3$, —N(CH$_3$)$_2$, —S(O)$_2$CH$_3$, cyano and hydroxy; or R$^5$ and R$^6$ taken together with the nitrogen atom to which they are attached form Ring B which is pyrrolyl, pyrazolyl, pyrrolidinyl, piperidinyl, piperazinyl, morpholinyl or thiomorpholinyl, each optionally substituted with at least one R$^9$ substituent selected from methyl, ethyl, F, Cl, cyano, hydroxy, oxo and —CF$_3$; and wherein each ring is further optionally fused with Y which is phenyl; stereoisomers thereof, and pharmaceutically acceptable salts thereof. In another aspect, is a Formula (1-A1) compound wherein R$^0$ is H or methyl; R$^1$ is methyl; R$^2$ is H, methyl, ethyl, isopropyl, cyclopropyl, —CF$_3$, —CHF$_2$, —CH$_2$F, —CH$_2$CF$_3$ or phenyl; R$^3$ is H, methyl, ethyl, propyl, isopropyl, t-butyl, —CH$_2$N(CH$_3$)$_2$, —CH$_2$CH$_2$N(CH$_3$)$_2$; or cyclopropyl, cyclobutyl, phenyl, C$_1$phenyl, piperadinyl, C$_1$-piperadinyl, C$_2$piperadinyl, piperazinyl, morpholinyl, tetrahydro-2H-pyran, pyrazolyl or pyridinyl, each optionally substituted with at least one R$^9$ substituent selected from the group consisting of methyl, ethyl, hydroxy, methoxy, ethoxy, F, Cl, cyano, amino, —N(CH$_3$)$_2$ and —CF$_3$; or R$^2$ and R$^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one R$^{10}$ substituent selected from methyl, ethyl, F, Cl, oxo and —CF$_3$; or Ring B is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; R$^5$ is H, C$_1$-C$_6$alkyl, morpholinyl, piperadinyl, —CH$_2$morpholinyl, —CH$_2$piperadinyl, —(CH$_2$)$_2$morpholinyl or (CH$_2$)$_2$piperadinyl; R$^6$ is H, methyl, ethyl, propyl, isopropyl, butyl, isobutyl, t-butyl, methoxy, ethoxy, —CH$_2$CF$_3$, —CF$_3$ or —OCF$_3$; —C(O)NR$^a$R$^8$ wherein R$^a$ is H or methyl and R$^8$ is H, methyl, cyclopropyl, phenyl optionally substituted with F, Cl or —CF$_3$; —(CH$_2$)S(O)$_2$R$^8$ wherein R$^8$ is methyl or phenyl; —CH$_2$NR$^a$R$^b$ or —(CH$_2$)$_2$NR$^a$R$^b$wherein R$^a$ and R$^b$ are each independently H or methyl; —(CH$_2$)$_2$OCH$_3$, —(CH$_2$)$_3$OCH$_3$; or phenyl, C$_1$alkylphenyl, cyclopropyl, cyclobutyl, cyclopentyl, cyclohexyl, C$_1$-C$_2$alkylcyclopropyl, C$_1$-C$_2$alkylcyclobutyl, pyrrolidinyl, piperidinyl, piperazinyl, morpholinyl, tetrahydropyranyl, tetrahydrofuranyl, C$_1$-C$_2$alkylpyrrolidinyl, C$_1$-C$_2$alkylpiperidinyl, C$_1$-C$_2$alkylpiperazinyl, C$_1$-C$_2$morpholinyl, C$_1$-C$_2$tetrahydropyranyl, pyrazolyl, imidazolyl, pyridinyl, pyrimidinyl, pyrazinyl, C$_1$-C$_2$alkylpyrazolyl, C$_1$-C$_2$alkylimidazolyl, C$_1$-C$_2$alkylpyridinyl, C$_1$-C$_2$alkylpyrimidinyl and C$_1$-C$_2$alkylpyrazinyl; each optionally substituted with at least one R$^{10}$ substituent each independently selected from methyl, ethyl, methoxy, ethoxy, —CHF$_2$, —CF$_3$, —OCF$_3$, F, Cl, amino, —NHCH$_3$, —N(CH$_3$)$_2$, —S(O)$_2$CH$_3$, cyano and hydroxy; or R$^5$ and R$^6$ taken together with the nitrogen atom to which they are attached form Ring B which is pyrrolyl, pyrazolyl, pyrrolidinyl, piperidinyl, piperazinyl, morpholinyl or thiomorpholinyl, each optionally substituted with at least one R⁹ substituent selected from methyl, ethyl, F, Cl, cyano, hydroxy, oxo and —CF₃; or Ring B is indolinyl, isoindolinyl, tetrahydroquinolinyl, dihydrobenzooxazinyl or dihydrobenzothiazinyl optionally substituted with at least one oxo; stereoisomers thereof, and pharmaceutically acceptable salts thereof. In another aspect, is a Formula (1-A1) compound wherein R⁰ is H or methyl; R¹ is methyl; R² is H or methyl; R³ is methyl, ethyl or propyl, isopropyl, t-butyl, —CH₂N(CH₃)₂, —CH₂CH₂N(CH₃)₂; or cyclopropyl, cyclobutyl, phenyl, C₁phenyl, piperadinyl, C₁-piperadinyl, piperazinyl, morpholinyl or pyridinyl, each optionally substituted with at least one R⁹ substituent selected from the group consisting of methyl, ethyl, hydroxy, methoxy, ethoxy, F, Cl, cyano, —N(CH₃)₂ and —CF₃; R⁵ is H, methyl, ethyl, propyl or isopropyl; R⁶ is H, methyl, ethyl, propyl, isopropyl, butyl, isobutyl, t-butyl, methoxy, ethoxy, —CH₂CF₃, —CF₃, —OCF₃; —C(O)NRᵃR⁸ wherein Rᵃ is H or methyl and R⁸ is H, methyl, cyclopropyl, phenyl optionally substituted with F, Cl or —CF₃; —(CH₂)S(O)₂R⁸ wherein R⁸ is methyl or phenyl; —CH₂NRᵃRᵇ or —(CH₂)₂NRᵃRᵇ wherein Rᵃ and Rᵇ are each independently H or methyl; —(CH₂)₂OCH₃, —(CH₂)₃OCH₃; or phenyl, C₁alkylphenyl, cyclopropyl, cyclobutyl, cyclopentyl, cyclohexyl, C₁-C₂alkylcyclopropyl, C₁-C₂alkylcyclobutyl, pyrrolidinyl, piperidinyl, piperazinyl, morpholinyl, tetrahydropyranyl, tetrahydrofuranyl, C₁-C₂alkylpyrrolidinyl, C₁-C₂alkylpiperidinyl, C₁-C₂alkylpiperazinyl, C₁-C₂morpholinyl, C₁-C₂tetrahydropyranyl, pyrazolyl, imidazolyl, pyridinyl, pyrimidinyl, pyrazinyl, C₁-C₂alkylpyrazolyl, C₁-C₂alkylimidazolyl, C₁-C₂alkylpyridinyl, C₁-C₂alkylpyrimidinyl or C₁-C₂alkylpyrazinyl; each optionally substituted with at least one R¹⁰ substituent each independently selected from methyl, ethyl, methoxy, ethoxy, —CHF₂, —CF₃, —OCF₃, F, Cl, amino, —NHCH₃, —N(CH₃)₂, —S(O)₂CH₃, cyano and hydroxy; stereoisomers thereof, and pharmaceutically acceptable salts thereof. In another aspect, is a Formula (1-A1) Table H compound, stereoisomers thereof, and pharmaceutically acceptable salts thereof. In another aspect, is a non-antibacterial Formula (1-A1) Table H compound, stereoisomers thereof, and pharmaceutically acceptable salts thereof. In another aspect, is a Formula (1-A1) that is 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea, stereoisomers thereof, and pharmaceutically acceptable salts thereof.

In another aspect, is a composition comprising a Formula (1-A1) compound, stereoisomers thereof, and pharmaceutically acceptable salts thereof. In another aspect, is a composition comprising a Formula (1-A1) Table H compound, stereoisomers thereof, and pharmaceutically acceptable salts thereof. In another aspect, is a composition comprising a non-antibacterial Formula (1-A1) Table H compound, stereoisomers thereof, and pharmaceutically acceptable salts thereof. In another aspect, is a composition comprising a Formula (1-A1) compound that is H-11; 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A1) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A1) Table H compound, stereoisomers thereof, and pharmaceutically acceptable salts thereof. In another aspect, is a method of treating or preventing an inflammatory response in an animal by administering to said animal in need thereof, a therapeutically effective amount of a non-antibacterial Formula (1-A1) Table H compound, stereoisomers thereof, and pharmaceutically acceptable salts thereof. In another aspect, is a method of treating or preventing an inflammatory response in an animal by administering to said animal in need thereof, a therapeutically effective amount Example H-11; 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNF-α and IL-6 in the animal.

In another aspect, is the use of a Formula (1-A1) compound, stereoisomers thereof, and pharmaceutically acceptable salts thereof; to prepare a medicament for treating or preventing an inflammatory response in an animal. In another aspect, is the use of a Formula (1-A1) Table H compound, stereoisomers thereof, and pharmaceutically acceptable salts thereof; to prepare a medicament for treating or preventing an inflammatory response in an animal. In another aspect, is the use of a non-antibacterial Formula (1-A1) Table H compound, stereoisomers thereof, and pharmaceutically acceptable salts thereof; to prepare a medicament for treating or preventing an inflammatory response in an animal. In another aspect, is the use of H-11; 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; stereoisomers thereof, and pharmaceutically acceptable salts thereof; to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1-A1) compound, wherein $R^1$ is methyl and $R^2$ and $R^3$ taken together with the nitrogen atom to which they are attached form Ring A which is optionally substituted by at least one $R^{10}$ substituent, that is a Formula (1-A1b) compound, wherein $R^0$, $R^5$, $R^6$, Ring A, $R^{10}$ and n are as defined

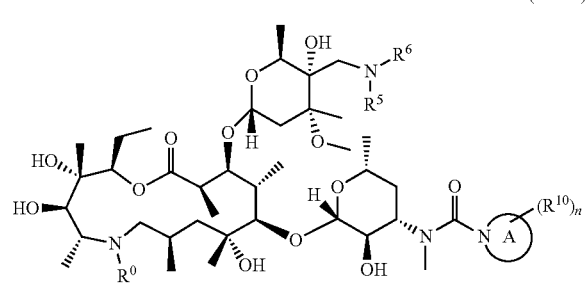

(1-A1a)

herein, stereoisomers thereof, and pharmaceutically acceptable salts thereof. In another aspect, is Formula (1-A1a) compound wherein $R^0$ is H or methyl; and $R^5$, $R^6$, $R^{10}$, Ring A and n are as defined herein, stereoisomers thereof, and pharmaceutically acceptable salts thereof. In another aspect, is Formula (1-A1a) compound wherein $R^0$ is H or methyl; $R^5$ is H, methyl, ethyl, propyl, isopropyl, —CH$_2$morpholinyl, —CH$_2$piperadinyl, —(CH$_2$)$_2$morpholinyl or (CH$_2$)$_2$piperadinyl; $R^6$ is H; $C_1$-$C_6$alkyl or $C_1$-$C_6$alkoxy each optionally substituted with at least one hydroxy; $C_1$-$C_6$haloalkyl, —OCF$_3$, —C(O)NR$^a$R$^8$, —R$^c$S(O)$_p$R$^8$, —R$^c$NR$^a$R$^b$, —R$^c$OR$^a$ or —S(O)$_p$R$^8$; or phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, oxazolidinyl, pyrrolidinyl, piperidinyl, piperazinyl, morpholinyl, tetrahydropyranyl, tetrahydrofuranyl, $C_1$-$C_2$alkyloxazolidinyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, $C_1$-$C_2$tetrahydrofuranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl, each optionally substituted with at least one $R^{10}$ substituent each independently selected from methyl, ethyl, methoxy, ethoxy, —CHF$_2$, —CF$_3$, —OCF$_3$, F, Cl, —NHCH$_3$, —N(CH$_3$)$_2$, —S(O)$_2$CH$_3$, cyano and hydroxy; and Ring A is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, propyl, isopropyl, cyclopropyl, methoxy, F, Cl, Br, CN, —N(CH$_3$)$_2$, hydroxyl, —CHF$_2$, —CF$_3$, —OCHF$_2$, —OCF$_3$ and oxo; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; stereoisomers thereof, and pharmaceutically acceptable salts thereof. In another aspect, is a Formula (1-A1a) compound wherein $R^0$ is H or methyl;

$R^5$ is H, methyl, ethyl, propyl or isopropyl; $R^6$ is H, methyl, ethyl, propyl, isopropyl, butyl, isobutyl, t-butyl, methoxy, ethoxy, —CH$_2$CF$_3$, —CF$_3$, —OCF$_3$; —C(O)NR$^a$R$^8$ wherein R$^a$ is H or methyl and R$^8$ is H, methyl, cyclopropyl, phenyl optionally substituted with F, Cl or —CF$_3$; —(CH$_2$)S(O)$_2$R$^8$ wherein R$^8$ is methyl or phenyl; —CH$_2$NR$^a$R$^b$ or —(CH$_2$)$_2$NR$^a$R$^b$ wherein R$^a$ and R$^b$ are each independently H or methyl; —(CH$_2$)$_2$OCH$_3$, (CH$_2$)$_3$OCH$_3$; or phenyl, $C_1$alkylphenyl, cyclopropyl, cyclobutyl, cyclopentyl, cyclohexyl, $C_1$-$C_2$alkylcyclopropyl, $C_1$-$C_2$alkylcyclobutyl, pyrrolidinyl, piperidinyl, piperazinyl, morpholinyl, tetrahydropyranyl, tetrahydrofuranyl, $C_1$-$C_2$alkylpyrrolidinyl, $C_1$-$C_2$alkylpiperidinyl, $C_1$-$C_2$alkylpiperazinyl, $C_1$-$C_2$morpholinyl, $C_1$-$C_2$tetrahydropyranyl, pyrazolyl, imidazolyl, pyridinyl, pyrimidinyl, pyrazinyl, $C_1$-$C_2$alkylpyrazolyl, $C_1$-$C_2$alkylimidazolyl, $C_1$-$C_2$alkylpyridinyl, $C_1$-$C_2$alkylpyrimidinyl or $C_1$-$C_2$alkylpyrazinyl, each optionally substituted with at least one $R^{10}$ substituent each independently selected from methyl, ethyl, methoxy, ethoxy, —CHF$_2$, —CF$_3$, —OCF$_3$, F, Cl, amino, —NHCH$_3$, —N(CH$_3$)$_2$, —S(O)$_2$CH$_3$, cyano and hydroxy; and Ring A is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, F, Cl, oxo and —CF$_3$; or Ring A is indolinyl, isoindolinyl, tetrahydroquinolinyl, dihydrobenzooxazinyl, or dihydrobenzothiazinyl optionally substituted with at least one oxo; or Ring A is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, F, Cl, oxo and —CF$_3$; stereoisomers thereof, and pharmaceutically acceptable salts thereof. In another aspect, is a Formula (1-A1a) Table I compound, stereoisomers thereof, and pharmaceutically acceptable salts thereof. In another aspect, is a non-antibacterial Formula (1-A1a) Table I compound, stereoisomers thereof, and pharmaceutically acceptable salts thereof.

In another aspect, is a composition comprising a Formula (1-A1a) compound, stereoisomers thereof, and pharmaceutically acceptable salts thereof. In another aspect, is a composition comprising a Formula (1-A1a) Table I compound, stereoisomers thereof, and pharmaceutically acceptable salts thereof. In another aspect, is a composition comprising a non-antibacterial Formula (1-A1a) Table I compound, stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A1a) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A1a) Table I compound, stereoisomers thereof, and pharmaceutically acceptable salts thereof. In another aspect, is a method of treating or preventing an inflammatory response in an animal by administering to said animal in need thereof, a therapeutically effective amount of a non-antibacterial Formula (1-A1a) Table I compound, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNF-α and IL-6 in the animal.

In another aspect, is the use of a Formula (1-A1a) compound, stereoisomers thereof, and pharmaceutically acceptable salts thereof; to prepare a medicament for treating or preventing an inflammatory response in an animal. In another aspect, is the use of a Formula (1-A1a) Table I compound, stereoisomers thereof, and pharmaceutically acceptable salts thereof; to prepare a medicament for treating or preventing an inflammatory response in an animal. In another aspect, is the use of a non-antibacterial Formula (1-A1a) Table I compound, stereoisomers thereof, and pharmaceutically acceptable salts thereof; to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1-A1) compound wherein $R^1$ is methyl, and $R^5$ and $R^6$ taken together with the nitrogen atom to which they are attached form Ring B that is optionally substituted with at least one $R^9$ substituent; that is a Formula (1-A1b) compound; wherein $R^0$, $R^2$, $R^3$, Ring B, $R^9$ and n are as defined herein, (1-A1b)

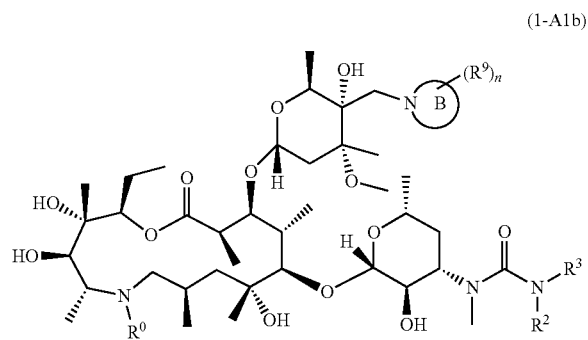

stereoisomers thereof, and pharmaceutically acceptable salts thereof. In another aspect, is a Formula (1-A1b) compound, wherein $R^0$ is H or methyl; and $R^2$, $R^3$, Ring B, $R^9$ and n are as defined herein. In another aspect, is a Formula (1-A1b) compound, wherein $R^0$ is H or methyl; $R^2$ is H, methyl, ethyl, isopropyl, cyclopropyl, —$CF_3$, —$CHF_2$, —$CH_2F$, —$CH_2CF_3$ or phenyl; $R^3$ is H, methyl, ethyl, propyl, isopropyl, t-butyl, —$CH_2N(CH_3)_2$, —$CH_2CH_2N(CH_3)_2$; or cyclopropyl, cyclobutyl, phenyl, $C_1$phenyl, piperadinyl, $C_1$-piperadinyl, $C_2$piperadinyl, piperazinyl, morpholinyl, tetrahydro-2H-pyran, pyrazolyl or pyridinyl, each optionally substituted with at least one $R^9$ substituent selected from the group consisting of methyl, ethyl, hydroxy, methoxy, ethoxy, F, Cl, cyano, amino, —$N(CH_3)_2$ and —$CF_3$; or $R^2$ and $R^3$ taken together with the nitrogen atom to which they are attached form Ring A which is pyrrolyl, pyrazolyl, pyrrolidinyl, piperidinyl, piperazinyl, morpholinyl or thiomorpholinyl, each optionally substituted with at least one $R^{10}$ substituent selected from methyl, ethyl, F, Cl, oxo and —$CF_3$; and wherein each ring is further optionally fused with Y which is phenyl; and $R^5$ and $R^6$ taken together with the nitrogen atom to which they are attached form Ring B which is pyrrolyl, pyrazolyl, pyrrolidinyl, piperidinyl, piperazinyl, morpholinyl or thiomorpholinyl, each optionally substituted with at least one $R^9$ substituent selected from methyl, ethyl, hydroxy, F, Cl, cyano, oxo and —$CF_3$; and wherein each ring is further optionally fused with Y which is phenyl; stereoisomers thereof, and pharmaceutically acceptable salts thereof. In another aspect, is a Formula (1-A1b) compound, wherein $R^0$ is H or methyl; $R^2$ is H or methyl; and $R^3$ is methyl, ethyl, propyl, isopropyl, t-butyl, —$CH_2N(CH_3)_2$, —$CH_2CH_2N(CH_3)_2$; or cyclopropyl, cyclobutyl, phenyl, $C_1$phenyl, piperadinyl, $C_1$-piperadinyl, piperazinyl, morpholinyl or pyridinyl, each optionally substituted with at least one $R^9$ substituent selected from the group consisting of methyl, ethyl, hydroxy, methoxy, ethoxy, F, Cl, cyano, —$N(CH_3)_2$ and —$CF_3$; and Ring B is pyrrolyl, pyrazolyl, pyrrolidinyl, piperidinyl, piperazinyl, morpholinyl or thiomorpholinyl, each optionally substituted with at least one $R^9$ substituent selected from methyl, ethyl, F, Cl, hydroxy, cyano, oxo and —$CF_3$; or Ring A is indolinyl, isoindolinyl, pyrrolopyridinyl, pyrrolopyrimidinyl, dihydropyrrolopyridinyl, dihydropyrrolopyrimidinyl, tetrahydroquinolinyl, tetrahydroisoquinolinyl, tetrahydroquinoxaline, dihydrobenzooxazine or dihydrobenzothiazine optionally substituted with at least one oxo; or Ring B is pyrrolyl, pyrazolyl, pyrrolidinyl, piperidinyl, piperazinyl, morpholinyl or thiomorpholinyl, each optionally substituted with at least one $R^9$ substituent selected from methyl, ethyl, F, Cl, hydroxy, cyano, oxo and —$CF_3$; stereoisomers thereof, and pharmaceutically acceptable salts thereof. In another aspect, is a Formula (1-A1b) Table J compound, stereoisomers thereof, and pharmaceutically acceptable salts thereof. In another aspect, is a non-antibacterial Formula (1-A1b) Table J compound, stereoisomers thereof, and pharmaceutically acceptable salts thereof.

In another aspect, is a composition comprising a Formula (1-A1b) compound, stereoisomers thereof, and pharmaceutically acceptable salts thereof. In another aspect, is a composition comprising a Formula (1-A1b) Table J compound, stereoisomers thereof, and pharmaceutically acceptable salts thereof. In another aspect, is a composition comprising a non-antibacterial Formula (1-A1b) Table J compound, stereoisomers thereof, and pharmaceutically acceptable salts thereof. In another aspect, the composition further comprises a pharmaceutically acceptable carrier.

In another aspect, is a method of treating or preventing an inflammatory response in an animal by administering to said animal in need thereof, a therapeutically effective amount of a Formula (1-A1b) compound, stereoisomers thereof, and pharmaceutically acceptable salts thereof. In another aspect, is a method of treating or preventing an inflammatory response in an animal by administering to said animal in need thereof, a therapeutically effective amount of a Formula (1-A1b) Table J compound, stereoisomers thereof, and pharmaceutically acceptable salts thereof. In another aspect, is a method of treating or preventing an inflammatory response in an animal by administering to said animal in need thereof, a therapeutically effective amount of a non-antibacterial Formula (1-A1b) Table J compound, stereoisomers thereof, and pharmaceutically acceptable salts thereof. In another aspect of the method, the inflammatory response is due to a bacterial, viral, or fungal infection, stress, and/or an environmental factor. In another aspect of the method, the method of treating or preventing an inflammatory response in an animal prevents or mitigates the progression of a respiratory disease or disorder. In another aspect of the method, the animal is livestock. In another aspect of the method, the respiratory disease or disorder is bovine respiratory disease or swine respiratory disease. In another aspect of the method, the method of treating or preventing an inflammatory response in an animal down regulates TNF-α and IL-6 in the animal.

In another aspect, is the use of a Formula (1-A1b) compound, stereoisomers thereof, and pharmaceutically acceptable salts thereof; to prepare a medicament for treating or preventing an inflammatory response in an animal. In another aspect, is the use of a Formula (1-A1b) Table J compound, stereoisomers thereof, and pharmaceutically acceptable salts thereof; to prepare a medicament for treating or preventing an inflammatory response in an animal. In another aspect, is the use of a non-antibacterial Formula (1-A1b) Table J compound, stereoisomers thereof, and pharmaceutically acceptable salts thereof; to prepare a medicament for treating or preventing an inflammatory response in an animal. In another aspect of the use, the inflammatory response is due to a bacterial, viral, or fungal infection, stress, and/or an environmental factor. In another aspect of the use, the use of the medicament for treating or preventing an inflammatory response in the animal prevents or mitigates the progression of a respiratory disease or disorder. In another aspect of the use, the animal is livestock. In another aspect of the use, the respiratory disease or disorder is bovine respiratory disease or swine respiratory disease. In another aspect of the use, the use of administering the medicament to the animal to treat or prevent an inflammatory response in the animal down regulates TNF-α and IL-6 in the animal.

In another aspect of the invention, is a Formula (1) compound, wherein W is Formula (A), and Formula (A) is Formula (A1), R is —C(O)NHR$^d$; R$^0$ and R$^2$ are both H, R$^1$ is methyl, R$^5$ and R$^6$ are joined together with the N atom they share to form Ring B which is 4-methylpiperazine, that is a compound selected from: (2S,3R,4S,6R)-4-(3-(tert-butyl)-1-methylureido)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-3-yl ethylcarbamate; (2S,3R,4S,6R)-4-(3-(tert-butyl)-1-methylureido)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-3-yl tert-butylcarbamate; (2S,3R,4S,6R)-4-(3-(4-(dimethylamino)phenyl)-1-methylureido)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-6-methyltetrahydro-2H-pyran-3-yl (4-(dimethylamino)phenyl)carbamate; and (2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-6-methyl-4-(1-methyl-3-phenylureido)tetrahydro-2H-pyran-3-yl phenylcarbamate. In another aspect of the invention, is a Formula (1) compound, wherein W is Formula (A), and Formula (A) is Formula (A2), R$^0$ and R$^2$ are both H, R$^1$ is methyl, R$^3$ is phenyl, R$^7$ is ethyl, and R is —C(O)NHPhenyl: that is (2S,3R,4S,6R)-2-(((2R,3S,4R,5R,8R,10R,11R,12S,13S,14R)-13-(((2R,4R,5S,6S)-5-(ethoxymethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-6-methyl-4-(1-methyl-3-phenylureido)tetrahydro-2H-pyran-3-yl phenylcarbamate, stereoisomers thereof, and pharmaceutically acceptable salts thereof.

In another aspect of the invention, is a Formula (1) compound, wherein W is Formula (A), and Formula (A) is Formula (A3), R$^0$ and R$^2$ are both H, R$^1$ is methyl, R$^3$ is phenyl, R$^7$ is propyl, and R is —C(O)NHPhenyl: that is (2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylthio)methyl)tetrahydro-2H-pyran-2-yl)oxy)-3,5,8,10,12,14-hexamethyl-15-oxo-1-oxa-6-azacyclopentadecan-11-yl)oxy)-6-methyl-4-(1-methyl-3-phenylureido)tetrahydro-2H-pyran-3-yl phenylcarbamate, stereoisomers thereof, and pharmaceutically acceptable salts thereof. In another aspect of the invention, is a Formula (1) compound wherein W is Formula (A), Formula (A) is Formula (A4), R$^0$ and R$^2$ are both H, R$^1$ is methyl, R$^3$ is phenyl, X is chloro, and R is —C(O)NHPhenyl: that is 2S,3R,4S,6R)-2-(((2R,3S,4R,5R,8R,10R,11R,12S,13S,14R)-13-(((2R,4R,5S,6S)-5-(chloromethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-6-methyl-4-(1-methyl-3-phenylureido)tetrahydro-2H-pyran-3-yl phenylcarbamate, stereoisomers thereof, and pharmaceutically acceptable salts thereof.

In another aspect of the invention, is a Formula (1) compound, wherein W is Formula (A), Formula (A) is Formula (A6), R$^0$ and R$^2$ are both H, R$^1$ is methyl, R$^3$ is phenyl and R is —C(O)NHPhenyl: that is (2S,3R,4S,6R)-2-(((2R,3S,4R,5R,8R,10R,11R,12S,13S,14R)-13-(((2R,4R,5S,6S)-5-(cyanomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-6-methyl-4-(1-methyl-3-phenylureido)tetrahydro-2H-pyran-3-yl phenylcarbamate, stereoisomers thereof, and pharmaceutically acceptable salts thereof. In another aspect, is a composition comprising any one of the Formula (1) phenylcarbamate compounds, and wherein the composition further comprises a pharmaceutically acceptable carrier. In another aspect, is a method of using any one of the Formula (1) phenylcarbamate compounds for treating or preventing an inflammatory response in an animal by administering to said animal in need thereof, a therapeutically effective of a Formula (1) phenylcarbamate compound, stereoisomers thereof, and pharmaceutically acceptable salts thereof. In another aspect, is the use of any one of the Formula (1) phenylcarbamates for preparing a medicament for treating or preventing an inflammatory response in an animal.

In another aspect of the invention, is the combination of a Formula (1) compound, stereoisomers thereof, and pharmaceutically acceptable salts thereof; with at least one additional pharmaceutical agent that can be an antibacterial agent, anti-inflammatory agent, vitamin, mineral, or mixture thereof. The compounds of the invention can be co-administered with the additional pharmaceutical agent(s) simultaneously, separate, or sequentially for treating a bacterial infection and/or preventing an inflammatory and/or immune response in an animal from cascading to the full BRD disease complex.

In another aspect of the invention, is a composition comprising M9, stereoisomers thereof, and pharmaceutically acceptable salts thereof. In yet another aspect, the composition comprising M9 further comprises a pharmaceutically acceptable carrier. In yet another aspect of the invention, is a method of treating or preventing an inflammatory response in an animal by administering to said animal in need thereof, a therapeutically effective amount of M9, stereoisomers thereof, and pharmaceutically acceptable salts thereof. In another aspect, is a method for treating or preventing an inflammatory response in an animal wherein the inflammatory response is due to a bacterial, viral, or fungal infection, stress, and/or an environmental factor. In another aspect, is a method for treating or preventing the inflammatory response in an animal wherein M9 mitigates the progression of a respiratory disease or disorder. In yet another aspect, the animal is livestock. In yet another aspect, the respiratory disease or disorder is bovine respiratory disease or swine respiratory disease.

In another aspect, is a Formula (1) compound that is a non-antibacterial Formula (1.1) Table A compound selected from the group consisting of Example A-1, A-2, A-3, A-4, A-6, A-7, A-9 through A-12, A-14 through A-21 and A-22 through A-26; or a non-antibacterial Formula (1-A0) Table B compound selected from the group consisting of Example B-1a through B-6 and B-8 through B-15; or a non-antibacterial Formula (1-A2) Table C compound selected from the group consisting of Example C-1 and C-3; or a non-antibacterial Formula (1-A3) Table D compound selected from Example C-1 or C-2; or a non-antibacterial Formula (1-A4) Table E compound selected from the group consisting of Example E-1 through E-3; or a non-antibacterial Formula (1-A5) Table F compound that is Example F-1 or F-2; or a non-antibacterial Formula (1-A6) Table G compound selected from the group consisting of Example G-1 through G-3; or a non-antibacterial Formula (1-A1) Table H compound selected from the group consisting of Example H-1, H-2, H-4, H-6, H-8 through H-14, H16, H-17, H-21, H-24, H-25, H-27, H-28, H-29, H-31 through H-35, H-37, H-39 through H-43, H-47, H-48, H49, H-51 through H-57, H-59, H-60, H-62 through H-65, H-77, H-79, H-80, H-82 through H-86, H-88, H-91 through H-97, and H-99 through H-103; or a non-antibacterial Formula (1-A1a) Table I compound selected from the group consisting of Example I-1 and 1-3 through 1-7; or a non-antibacterial Formula (1-A1b) Table J compound selected from the group consisting of Example J-4, J-10, J-12, J-13, J-15, J-16, J-19 through J-24 and J-27 through J-31; stereoisomers thereof, and pharmaceutically acceptable salts thereof; a composition comprising one of these non-antibacterial compounds; a method of using one of these non-antibacterial compounds to treat or prevent an inflammatory response in an animal; or the use of one of these non-antibacterial compounds to prepare a medicament for treating of preventing an inflammatory response in an animal.

DISCUSSION

Description of Figures

FIG. 1. Mechanism of an Immunomodulator in Context of BRD Progression

FIG. 2. Clinical and Genomics Temporal Data Summary

FIG. 3. Plasma Cytokine (IL-6, IL-8, IL-10 and IFN-γ) Levels upon Arrival to the Feedlot for Calves at Risk for BRD FIG. 4. Example H-11 Dose Dependent Cytokines-Whole Blood Assay: IL-6 (A), TNF-α (B) and IL-1β (C)

FIG. 5. IL-36RA Change (%) During the Natural Infection Bovine Studies

FIG. 6. Biomarker Evaluation for M9 and Draxxin Intratracheal Lung Challenge; IL-6 (A) and CD163 Biomarker (B) Results FIG. 7. Biomarker Evaluation for Example H-91 Intratracheal Lung Challenge: IL-6 (A) and CD163 Biomarker (B) Results FIG. 8. Biomarker Evaluation for Example H-11 Intratracheal Lung Challenge: Neutrophils (A), IL-6 (B) and CD163 (C) Results FIG. 9. Intracellular Flow Cytometric Characterization of CD4+ T Helper Cell Subtypes FIG. 10. IL-17 Levels from the Airway of Animals Challenged with *M. haemolytica* Administered Example H-11

It should be understood that this invention is not limited to the particular methodology, protocols, and reagents. etc., defined herein and as such may vary. The terminology used herein is for the purpose of describing embodiments only and is not intended to limit the scope of the present invention, which is defined solely by the claims.

Unless otherwise defined, scientific and technical terms used in connection with the compounds of the invention defined herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry synthesis, macrolides, and immunomodulation defined herein are those that are well known and commonly used in the art.

DEFINITIONS

For purposes of the present invention, as described and claimed herein, the following terms and phrases are defined as follows:

"Additional pharmaceutical agent(s)" as used herein, unless otherwise indicated, refers to other pharmaceutical compounds or products that provide a therapeutically effective amount of said agents that are useful for the treatment of a bacterial infection in an animal and/or modulating an immune response, as defined herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, —OCH(CH$_3$)$_2$, —OC(CH$_3$)$_3$, and the like.

"Alkyl", as used herein, unless otherwise indicated, refers to saturated monovalent hydrocarbon alkane radicals of the general formula C$_n$H$_{2n+1}$. The alkane radical may be straight or branched and may be unsubstituted or substituted. For example, the term "(C$_1$-C$_6$)alkyl" refers to a monovalent, straight or branched aliphatic group containing 1 to 6 carbon atoms; similarly, C$_1$-C$_3$ alkyl refers to a monovalent, straight or branched aliphatic group containing 1 to 3 carbon atoms, etc. Non-exclusive examples of (C$_1$-C$_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as defined herein. Further when used in compound words such as alkylphenyl, said alkyl moiety has the same meaning as herein defined and may be attached to the chemical moiety by any one of the carbon atoms of the aliphatic chain. Non-limiting examples of the compound word, $C_0$-$C_4$alkylphenyl include: $C_0$phenyl (phenyl), $C_1$alkylphenyl (—$CH_2$phenyl), $C_2$alkylphenyl (—$CH_2CH_2$phenyl), and the like.

"Animal(s)", as used herein, unless otherwise indicated, refers to an individual animal that is a mammal. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat and horse. Non-exclusive examples of livestock include: swine, camel, rabbits, goat, sheep, deer, elk, bovine (cattle and μ.

"Antibacterial", as used herein, unless otherwise indicated, refers to a compound with a minimum inhibitory concentration (MIC)≤64 μg/mL for the BRD pathogens, *M. haemolytica* and *P. multocida*. The term "non-antibacterial" as used herein, unless otherwise indicated, refers to a compound with an MIC≥64 μg/mL for the BRD pathogens, *M. haemolytica* and *P. multocida*.

"Aryl", as used herein, unless otherwise indicated, refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Further when used in compound words such as alkylaryl (e.g., alkylphenyl), said alkyl and aryl moiety have the same meaning as herein defined and may be attached to the chemical moiety by any one of the carbon atoms of the aliphatic chain or ring carbon. Examples of $C_0$-$C_3$alkylphenyl, for example: $C_0$alkylphenyl is phenyl; $C_1$-alkylphenyl is —$CH_2$phenyl (benzyl); and $C_2$-alkylphenyl is —$CH_2CH_2$phenyl. The phenyl ring is optionally substituted as defined herein.

"Azalide" as used herein, unless otherwise indicated, refers to a class of macrolides which contain a nitrogen atom in the macrolide ring which imparts different pharmacokinetic properties and is associated with greater stability of the molecule.

"Chiral", as used herein, unless otherwise indicated, refers to the structural characteristic of a molecule that makes it impossible to superimpose it on its mirror image, (e.g., "R" and "S" enantiomers).

"Composition", as used herein, unless otherwise indicated, refers to a compound of the invention that is formulated with at least one pharmaceutically acceptable excipient for dosing administration.

"Compounds of the present invention", "compounds of the invention", as used herein, unless otherwise indicated, includes a Formula (1), (1A), (1.1), (1-A0), (1-A1), (1-A1a), (1-A1b), (1-A2), (1-A3), (1-A4), (1-A5) and (1-A6) compound, stereoisomers thereof, and pharmaceutically acceptable salts thereof. The term(s) also include the respective 13-membered macrolides that are in equilibrium with the 15-membered macrolide ring of the stated Formula's; and includes the class of azalides.

"Cycloalkyl", as used herein, unless otherwise indicated, includes fully saturated or partially saturated carbocyclic alkyl moieties, i.e., a 3- to 6-membered ring containing only carbon atoms and can be monocyclic or part of a fused ring or bridged ring moiety. Examples of saturated carbocyclic (cycloalkyl) rings include, but are not limited to, cyclopropyl, cyclobutyl, cyclopentyl and cyclohexyl. Non-limiting examples of partially saturated cycloalkyls include: cyclopropene, cyclobutene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety have the same meaning as herein defined and may be attached to the chemical moiety by any one of the carbon atoms of the aliphatic chain. Examples of $C_0$-$C_4$alkyl$C_3$-$C_6$cycloalkyl include, for example: $C_0$alkyl$C_3$-$C_6$cycloalkyl is $C_3$-$C_6$cycloalkyl (i.e., cyclopropyl, cyclobutyl, cyclopentyl, cyclohexyl); $C_1$-alkyl$C_3$-$C_6$cycloalkyl is —$CH_2C_3$-$C_6$cycloalkyl (e.g., —$CH_2$-cyclopropyl, —$CH_2$-cyclohexyl, and the like); $C_2$-alkyl$C_3$-$C_6$cycloalkyl is —$CH_2CH_2C_3$-$C_6$cycloalkyl (e.g., —$CH_2CH_2$-cyclopropyl, —$CH_2CH_2$-cyclopentyl) and the like. Cycloalkyl moieties are optionally substituted as defined herein.

"Cytokine", as used herein, unless otherwise indicated, refers to general class of biological molecules which effect/affect all types of cells and influence immunological responses and non-immunological biologic processes. The definition is meant to include, but is not limited to, those biological molecules that act locally or systemically, and which, when used in the compositions or methods of the present invention serve to regulate or modulate an animal's immune response. Exemplary cytokines for use in practicing the invention include but are not limited to interleukins (e.g. among IL-1 to IL-29, in particular, IL-1, IL-1ß, IL-6, IL-9, IL-10 and IL-12), chemokines (e.g. CCL2-5, CCL10, CCL11, CXCL8 (IL-8) and CXCL10), tumor necrosis factors (e.g., TNF-α and TNF-ß), and in particular, NFJ-B, which mediates the induction of pro-inflammatory cytokines, such as TNF-α, IL-1 and IL-6, in monocytes and macrophages.

"Halogen" or "halo", as used herein, unless otherwise indicated, refers to fluorine, chlorine, bromine and iodine. Further, when used in compound words such as "haloalkyl" or "haloalkoxy", said alkyl and alkoxy may be partially or fully substituted with halogen atoms which may be the same or different and said alkyl and alkoxy moiety has the same meaning as above and may be attached to the chemical moiety by any one of the carbon atoms of the aliphatic chain. Examples of "haloalkyl" include $F_3C$—, $ClCH_2$—, $CF_3CH_2$— and $CF_3CCl_2$—, and the like. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O and S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]

pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl (e.g., $C_0$-$C_4$alkylheteroaryl), said alkyl and heteroaryl moiety have the same meaning as herein defined and may be attached to the chemical moiety by any one of the carbon atoms of the aliphatic chain. For example, $C_0$alkylheterocycle is heterocycle (e.g., pyrazolyl, imidazolyl, pyridinyl, piperazinyl, and the like), $C_1$alkylheteroaryl is —$CH_2$heteroaryl (e.g., —$CH_2$imidazolyl, —$CH_2$pyridinyl, and the like), $C_2$alkylheteroaryl is —$CH_2CH_2$heteroaryl (e.g., —$CH_2CH_2$ pyrazolyl, —$CH_2CH_2$oxazolyl, —$CH_2CH_2$pyrimidinyl, and the like), and the like. Heteroaryls are optionally substituted as defined herein.

"Heterocycle", as used herein, unless otherwise indicated, refers to a partially saturated or saturated 4- to 10-membered monocyclic ring, fused ring, or bridged ring structure containing one or more heteroatoms each independently selected from N, O and S, preferably from one to four heteroatoms. Non-exclusive examples of heterocycle include oxetanyl, azetidinyl, thiatanyl, tetrahydrofuryl, pyranyl, pyrazolidinyl, oxazolidinyl, tetrahydrothiophenyl, pyrrolidinyl, tetrahydropyranyl, piperidinyl, piperazinyl, morpholinyl, thiomorpholinyl, oxathianyl, tetrahydropyridinyl, 2H-azirinyl, 2,3-dihydro-azetyl, 3,4-dihydro-2H-pyrrolyl, and the like. The heterocycle group may be attached to the chemical moiety by any one of the carbon atoms or nitrogen heteroatoms within the ring. Further when used in compound words such as alkylheterocycle (e.g., $C_0$-$C_4$alkylheterocycle), said alkyl and heterocycle moiety have the same meaning as herein defined and may be attached to the chemical moiety by any one of the carbon atoms of the aliphatic chain. For example, $C_0$heterocycle is heterocycle (e.g., (piperidinyl, morpholinyl, azetidinyl, and the like); $C_1$alkylheterocycle is —$CH_2$heterocycle (e.g., —$CH_2$morpholinyl, and the like), $C_2$alkylheterocycle is —$CH_2CH_2$heterocycle (e.g., —$CH_2CH_2$pyrrolidinyl, —$CH_2CH_2$thiomorpholinyl, and the like), and the like. Heterocycles are optionally substituted as defined herein.

"Macrolide(s)", as used herein, unless otherwise indicated, refers to compounds characterized by a large lactone ring containing from 12 to 16 carbon atoms to which are attached, via glycosidic bonds, one or more deoxy sugars; and includes the class of azalides.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution. In the case of $R^9$ and $R^{10}$, at least one optional substitution means that the number of substitutions may vary from zero to three (i.e., n is the integer 0, 1, 2 or 3), which also depends on the number of available positions for substitution.

"Pharmaceutically acceptable" as used herein, unless otherwise indicated, indicates that the substance or composition must be compatible chemically and/or toxicologically, with the other ingredients comprising a formulation, composition, and/or the animal being treated therewith. The term "pharmaceutically" or "pharmaceutical" has the same meaning as that recited for "veterinarily" or veterinary.

"Protecting group" or "Pg", as used herein, unless otherwise indicated, refers to a substituent that is commonly employed to block or protect an alcohol on the compound thereby protecting its functionality while allowing for the reaction of other functional groups on the compound. Non-exclusive examples of an alcohol-protecting group include: 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), ethoxyethyl acetal (EE), methoxymethyl acetal (MOM), methoxypropyl acetal (MOP), methyl ether, tetrahydropyranyl acetal (THP), triethylsilyl ether (TES), benzyloxycarbonyl (Cbz), triisopropylsilyl ether (TIPS), trimethylsilyl ether (TMS), tert-butyldimethylsilyl ether (TBS, TBDMS), and tert-butyldiphenylsilyl ether (TBDPS).

"Saturated" or "partially saturated", as used herein, unless otherwise indicated, refers to cycloalkyl rings having 3-6 carbon atoms and heterocyclic rings comprising 2-5 carbon atoms and at least one heteroatom selected from N, O, and S; and wherein each saturated ring contains single bonds between mutually adjacent carbon atoms or carbon heteroatoms; for example: cyclobutane, cyclopentane, cyclohexane, oxirane, oxetane, tetrahydofuran, piperadine, and the like. Partially saturated rings contain at least one double bond between mutually adjacent carbon atoms or carbon heteroatoms; for example: cyclobutene, cyclopentene, cyclohexa-1,3-diene, 2,3-dihydroazete, 2,5-dihydrofuran, 2H-thiopyran, and the like.

"Stereoisomers", as used herein, unless otherwise indicated, refers to the compounds of the invention which have more than one asymmetric carbon atom. In the general Formulas depicted herein, the solid wedge shaped bond indicates that the bond is above the plane of paper and the broken wedge bond indicates that the bond is below the plane of the paper. The compounds of the invention may occur as individual enantiomers or diastereomers, or mixtures thereof, including racemic mixtures. All such isomeric forms are included within the present invention.

"Stress" or "stressful", as used herein, unless otherwise indicated, is a specific or non-specific response that varies in degree. Stressors are particular events, experiences, or environmental stimuli that affect an animal's health, that may be acute, chronic, disruptive, or perceived as uncontrollable. Non-exclusive examples of stressors in animal health include: natural disasters (e.g., floods, fires, and earthquakes), major life events (e.g., relocation/transportation, weaning, maternal and herd separation, comingling of animals from different sources, tail docking, needle teeth extraction, pain, feed and water deprivation and acute or chronic illness), and acute/chronic disruptions (e.g., temperature and humidity variation, confinement, shipping, improper nutrition and hydration, storms, loud noises (e.g., thunder, barking, fireworks, and the like), environmental changes and pollutants, and the like).

"Therapeutically effective amount", as used herein, unless otherwise indicated, refers to an amount of a compound of the invention that (i) treats or prevents the particular disease or disorder, (ii) attenuates, ameliorates, or eliminates one or more symptoms of the particular disease or disorder, or (iii) prevents or delays the onset of one or more symptoms of the particular disease or disorder.

"Treatment", "treating", and the like, as used herein, unless otherwise indicated, refers to control, preventative measures, reversing, alleviating, mitigating, or inhibiting inflammation driven by an environmental, bacterial-, viral-, fungal-, or parasitic-infection, and/or internal disease by moderating an immunological response. As used herein, these terms also encompass, depending on the condition of the animal, preventing the onset of a disorder or condition, or of symptoms associated with a disorder or condition, including reducing the severity of a disorder or condition or symptoms associated therewith. Treatment can also refer to administration of a compound of the invention to an animal that is not at the time of administration afflicted with the infection, immunological episode, or disease disorder or complex. As will be appreciated, it is not always possible to distinguish between "preventing" and "suppressing" a disease or disorder since the ultimate inductive event or events may be unknown or latent.

Other than in operating examples, or where otherwise indicated, all numbers expressing quantities of ingredients or reaction conditions used herein should be understood as modified in all instances by the term "about".

The compounds of the present invention have several asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all steric forms of the compounds of the invention. The present invention includes all stereoisomers of compounds of the invention.

The independent syntheses of the stereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration. If desired, racemic mixtures of the compounds may be separated so that the individual enantiomers or diastereomers are isolated. The separation can be carried out by methods well known in the art, such as the coupling of a racemic mixture of compounds, followed by separation of the individual stereoisomers by standard methods, such as fractional crystallization or chromatography. The coupling reaction is often the formation of salts using an enantiomerically pure acid or base.

The derivatives may then be converted to the pure stereomers by cleavage of the added chiral residue. The racemic mixture of the compounds can also be separated directly by chromatographic methods using chiral stationary phases, which methods are well known in the art. Alternatively, any stereomers of a compound may be obtained by stereoselective synthesis using optically pure starting materials or reagents of known configuration by methods well known in the art.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Syn thesis, John Wiley & Sons, 1991. The protecting groups may be removed at a convenient subsequent stage using methods known from the art.

Macrolide Chemistry

The macrolides are known to have a strong binding affinity to the P-site on the 50S subunit of the bacterial ribosome and to inhibit protein synthesis. Modification of the desosamine group of the macrolide blocks this interaction by either modification of the dimethylamino group to block the salt bridge and/or modification of the neighboring hydroxy group affecting the hydrogen bond formed, thereby removing the antibacterial activity of said compounds of the invention. Although cladinose modifications have a comparatively smaller effect on the bacterial ribosome binding, they have the potential to affect the physicochemical properties, pharmacokinetics and cell permeability of the compound. By modifying macrolide structure therefore sequestering the molecule from entering the bacteria or enhancing efflux from the bacteria reduces or eliminates anti-bacterial activity even with the ability to bind the bacterial ribosome.

Lipophilicity

The lipophilicity of an organic compound can be described by a partition coefficient, log P, which can be defined as the ratio of the concentration of the unionized compound at equilibrium between organic and aqueous phases. Generally speaking, more lipophilic compounds are less soluble in aqueous media. A negative value for log P means the compound has a higher affinity for the aqueous phase (hydrophilic); when log P=0 the compound is equally partitioned between the lipid and aqueous phases; a positive value for log P denotes a higher concentration in the lipid phase (lipophilic). Lipophilicity is a major determining factor in a compound's absorption, distribution in the body, penetration across vital membranes and biological barriers, metabolism and excretion. The compounds of the invention are lipophilic (log P ~0.503 to 5.96) which aid in their transport and absorption into respiratory tissues, e.g., lungs.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying. Pharmaceutical compositions for use in accordance with the present invention may be formulated in conventional manner using one or more pharmaceutically acceptable carriers, which facilitate processing of the active compound into preparations for administration to the animal in need thereof. The formulations of the invention can be designed to be short-acting, fast-releasing, long-acting, and sustained-releasing. Thus, the pharmaceutical formulations can also be formulated for controlled release or for slow release; and are dependent upon the route of administration chosen.

Pharmaceutically acceptable excipients and carriers are generally known to those skilled in the art and are thus included in the instant invention. Such excipients and carriers (including water) are described, for example, in "Remington's Pharmaceutical Sciences" Mack Pub. Co., New Jersey (1991).

For BRD and SRD, pharmaceutical compositions are typically formulated for parenteral administration, e.g., in a liquid carrier or suitable for reconstitution into liquid solution or suspension for parenteral administration. In general, such compositions typically comprise a pharmaceutically acceptable carrier. Pharmaceutical carriers according to the invention can be sterile liquids, such as but not limited to water, saline solutions, aqueous dextrose solutions, aqueous glycerol solutions; and/or oils, including petroleum, animal, vegetable or synthetic origin, such as soybean oil, mineral oil, sesame oil and the like. Suitable pharmaceutical carriers are described in "Remington's Pharmaceutical Sciences" by E. W. Martin, 18th Edition. The pharmaceutical compositions comprising a compound of the invention can be administered orally, topically, parenterally (i.e., intramuscular, subcutaneous, intravenous, and intradermal injection). The pharmaceutical compositions comprising a compound of the invention can also be administered by intramammary and intra-uterine injection.

Pharmaceutical compositions and formulations as defined herein can be prepared by mixing a compound of the invention having the desired degree of purity with one or more pharmaceutically acceptable carrier(s) in the form of lyophilized formulations or aqueous solutions. The term "carrier" refers to a diluent, excipient, or vehicle with which the compound of the invention is administered. Pharmaceutically acceptable carriers are generally nontoxic to recipients at the dosages and concentrations employed, and include, but are not limited to: buffers (e.g., NaOH, KOH, HCl, phosphate, citrate and other organic acids (e.g., for example citric acid, acetic acid, benzoic acid, malic, and the like); antioxidants (e.g., butylated hydroxyanisole (BHA), butylated hydroxytoluene (BHT), sodium metabisulfite, monothioglycerol, propyl gallate, and the like); preservatives (e.g., octadecyldimethylbenzyl ammonium chloride, hexamethonium chloride, benzalkonium chloride, benzethonium chloride, phenol, n-butyl, t-butyl or benzyl alcohol, chlorobutanol, thimerosal's, alkyl parabens such as methyl or propyl paraben, catechol, resorcinol, cyclohexanol, 3-pentanol, m-cresol, and the like); hydrophilic polymers (e.g., polyvinylpyrrolidone (PVP), polyethylene glycol (PEG), polyvinyl alcohol (PVA), polyacrylic acid, polyacrylamides, xanthum gum, and the like); amino acids (e.g., glycine, glutamine, asparagine, histidine, arginine, lysine, and the like); chelating agents such as EDTA; monosaccharides, disaccharides, and other carbohydrates including sugars such as sucrose, mannitol, trehalose or sorbitol, glucose, mannose, or dextrins; and salt-forming counter-ions such as sodium; metal complexes (e.g., Zn-protein complexes). The carrier can be a solvent or reconstitution medium or dispersion medium containing, for example, water, ethanol, polyol (for example, glycerol, propylene glycol, and liquid polyethylene glycol, and the like), and suitable mixtures thereof. For intravenous administration, suitable carriers include physiological saline, bacteriostatic water, water, or phosphate buffered saline (PBS). Prolonged absorption of the injectable compositions can be brought about by including in the composition an agent which delays absorption, for example, aluminum monostearate and gelatin.

Solutions or suspensions used for parenteral application typically include one or more of the following components: a sterile carrier such as water for injection, saline solution, fixed oils, polyethylene glycols, glycerin, propylene glycol, or other synthetic solvents; antibacterial agents such as benzyl alcohol or methyl parabens; antioxidants such as ascorbic acid, BHA, BHT, monothioglycerol or sodium bisulfite; chelating agents such as ethylene-diaminetetraacetic acid; buffers such as acetates, citrates or phosphates; and agents for the adjustment of tonicity such as sodium chloride or dextrose. The pH can be adjusted with acids or bases, such as hydrochloric acid, citric acid or sodium hydroxide. Such preparations may be enclosed in ampoules, disposable syringes or multiple dose vials made of glass or plastic. The formulations to be used for in vivo administration are generally sterile. Sterility may be readily accomplished, e.g., by filtration through sterile filtration membranes, and radiation. The injectable compositions can contain the active component (drug) in the amounts ranging from about 1 to 250 mg/mL, and more preferably, in concentrations ranging from about 1 to 100 mg/mL. Without limiting the scope of the compositional components, an injectable composition comprising a Formula (1) compound (e.g., free base), pharmaceutically acceptable salt thereof, (e.g., acetate) can be prepared by dissolving the compound (e.g., 1 to 25 mg/mL) in a composition comprising citric acid, propylene glycol, water and optionally an antioxidant (e.g., monothioglycerol). As described herein, the composition can contain about 90% (±~6%) of lactone A and 10% lactone B (±~6%) of a Formula (1) compound, and preferably a non-antibacterial Table H compound. Said composition can be administered by injection, (e.g., subcutaneous). The pH of the composition can be adjusted, as needed, with NaOH and/or HCl. Methods for preparation of such formulations will be apparent to those skilled in the art and can be prepared in accordance with procedures described in U.S. Pat. No. 6,514,945.

For oral use, the pharmaceutical compositions of the present invention, may be administered, for example, in the form of tablets or capsules, powders, dispersible granules, or cachets, or as aqueous solutions or suspensions. Oral compositions generally include an inert carrier or an edible carrier. They can be enclosed in gelatin capsules or compressed into tablets. For oral administration, the therapeutic agents can be combined with carriers and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, primogel, sodium starch glycolate, or corn starch; a lubricant such as magnesium stearate or stearates; a glidant such as colloidal silicon dioxide; a sweetening agent such as sucrose or saccharin; or a flavoring agent.

Dosage

Pharmaceutical compositions suitable for use in the present invention include compositions wherein the active ingredients are contained in an amount sufficient to achieve the intended purpose. More specifically, a therapeutically effective amount means an amount of a compound of the invention that is effective to prevent, alleviate or ameliorate symptoms/signs of disease or prolong the survival of the animal being treated. The quantity of active component, which is a compound of the invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 mg/kg to about 10 mg/kg of body weight, preferably about 0.02 mg/kg to about 1 mg/kg of body weight, more preferably about 0.04 mg/kg to about 0.8 mg/kg of body weight, even more preferably about 0.06 mg/kg to about 0.6 mg/kg of body weight. A preferred dosage regimen is parenteral administration of about 0.05 mg/kg to about 0.8 mg/kg of body weight by subcutaneous injection. It is to be understood that the dosages may vary depending upon the requirements of each animal and the severity of the disorders or diseases being treated. The desired dose may conveniently be presented in a single dose or as divided doses administered at appropriate intervals during the course of treatment. The preferred route of administration is parenteral. Parenteral administration includes intravenous, intramuscular, and subcutaneous injection. The preferred route of administration is by subcutaneous injection. The compounds of the invention can be administered to the animal at first signs of stress or bacterial infection, prior to shipment from a farm or ranch, or upon arrival to the feed lot.

A compound of the invention can be administered in a pharmaceutically acceptable form either alone or in combination with one or more additional agents which modulate a mammalian immune system or with anti-inflammatory agents or with one or more antibacterial agents. Additionally, the compounds of the invention can also be co-administered with vitamins and/or minerals. Non limiting examples of anti-inflammatory agents include: ketoprofen, cyclosporin A, rapamycin, FJ-506 (tacrolimus), leflunomide, deoxyspergualin, mycophenolate, azathioprine, daclizumab, aspirin, acetaminophen, ibuprofen, naproxen, piroxicam, and anti-inflammatory steroids (e.g. prednisolone or dexamethasone). Non limiting examples of antibacterial agents include: novobiocin, aminoglycosides (e.g., gentamicin, neomycin, dihydrostreptomycin, spectinomycin, etc.), florfenicol, ceftiofur, cephapirin, ormetoprim, danofloxacin, enrofloxacin, bambermycins, ionophores (e.g., laidlomycin, lasalocid, monensin, narasin, salinomycin, lincomycin, pirlimycin, macrolides (e.g., erythromysin, gamithromycin, tildipirosin, tilmicosin, tulathroymycin, the M9-metabolite of tulathromycin, tylosin, tylvalosin, etc.), avilamycin, penicillins (e.g., amoxicillin, ampicillin, cloxacillin, penicillin, etc), tiamulin, polymyxin B, bacitracin, carbadox, virginiamycin, sulfadimethoxine, sulfamethazine, chlortetracycline, oxytetracycline, and tetracycline. Non-limiting examples of minerals include: calcium, magnesium, phosphorus, potassium, sodium, sulfur, cobalt, sulfur, copper, iodine, iron, manganese, selenium, chromium, and zinc. Non-limiting examples of vitamins include: A, D, E, K, and B vitamins including: thiamin (B1), riboflavin (B2), niacin (B3), pantothenic acid (B5), pyridoxine (B6), biotin (B7) folate (B9), and B12. These additional combination agents may be administered as part of the same or separate dosage forms, via the same or different routes of administration, and on the same or different administration schedules according to standard medical or veterinary practice known to one skilled in the art.

Medical and Veterinary Uses

Methods defined herein are generally performed on an animal in need thereof. An animal in need can be an animal having, diagnosed with, suspected of having, or at risk for developing a disease, disorder, or condition associated with a bacterial infection, viral infection, parasitic infection, inflammation or an immune response. The disease or disorder can include respiratory disease, reproductive diseases like mastitis or metritis, inflammatory bowel disease, bovine viral diarrhea virus (BVDV), infectious bovine thinotracheitis (IBR), bovine respiratory syncytial virus (BRSV), parainfluenza virus, bovine coronavirus, psoriasis, multiple sclerosis, rheumatoid arthritis, allergic autoinflammatory disease, or an autoimmune disease. Generally, a safe and effective amount of a compound of the invention is, for example, that amount that would cause the desired therapeutic effect in an animal while minimizing undesired side effects. In various embodiments, an effective amount of a compound of the invention can substantially mitigate inflammation or an immune response, slow the progress of a disease, disorder, or condition associated with inflammation or an immune response, or limit the development of a disease, disorder, or condition associated with inflammation or an immune response.

Compounds of the invention are macrolide (azalide) analogues that lack antibacterial activity against BRD pathogens and have been shown to have immunomodulatory properties that prevent and/or control the symptoms of BRD in artificially infected cattle. Accordingly, these macrolides are useful therapeutic agents for treating and/or controlling respiratory illnesses that may be provoked by environmental stimuli, stress, and bacterial infection. Some non-limiting macrolides used to treat BRD include: Draxxin© (tulathromycin), Zuprevo© (tildipirosin), and Zactran© (gamithromycin), and the like.

Draxxin©, an injectable solution, is indicated for the treatment of bovine respiratory disease (BRD) associated with *Mannheimia haemolytica, Pasteurella multocida, Histophilus somni*, and *Mycoplasma bovis*; and for the control of respiratory disease in cattle at high risk of developing BRD associated with *Mannheimia haemolytica, Pasteurella multocida, Histophilus somni*, and *Mycoplasma bovis*. Cattle receive a 2.5 mg/kg subcutaneous dose of Draxxin©. In swine, Draxxin© is indicated for the treatment of swine respiratory disease (SRD) associated with *Actinobacillus pleuropneumoniae, Pasteurella multocida, Bordetella bronchiseptica, Haemophilus parasuis*, and *Mycoplasma hyopneumoniae*; and for the control of SRD associated with *Actinobacillus pleuropneumoniae, Pasteurella multocida*, and *Mycoplasma hyopneumoniae* in groups of pigs where SRD has been diagnosed. Swine receive a 2.5 mg/kg intramuscular injection of Draxxin©.

A compound of the invention can treat, reduce, or prevent a disease, disorder, or condition associated with inflammation or an immune response. Inflammation is a critical response to potential danger signals and damage in organs of the body. Commonly referred to as the inflammatory cascade, can be acute or chronic. Acute inflammation, part of the immune response, is the body's immediate response to injury or assault due to physical trauma, infection, stress, or a combination of all three. Acute inflammation helps to prevent further injury and facilitates the healing and recovery process. When inflammation becomes self-perpetuating however, it can result in chronic or long-term inflammation.

Trauma, inflammation, or infection leads to the activation of the inflammatory cascade. Initially, a proinflammatory activation occurs, but almost immediately thereafter a reactive suppressing anti-inflammatory response occurs. This systemic inflammatory response (SIR) usually manifests itself as increased systemic expression of both proinflammatory and anti-inflammatory species. Systemic inflammatory response starts with inflammation as a response to exogenous (microbial, physical, or chemical) agents or endogenous (immunologic or neurologic) factors. The response is initiated when inflammatory cells at the site of inflammation, such as macrophages, are activated and rapidly produce TNF-α and IL-1. These cytokines in turn activate the cytokine cascade resulting in the generation of pro-inflammatory cytokines, IL-6, and IL-8, as well as other chemokines. Inflammatory stimuli also trigger the synthesis of anti-inflammatory cytokines and specific cytokine inhibitors to control the extent of the inflammatory response. Anti-inflammatory cytokines such as IL-4, IL-10, IL-11, and IL-13 inhibit the synthesis of proinflammatory cytokines while the naturally occurring proinflammatory cytokine inhibitors neutralize proinflammatory cytokine activity by binding to pro-inflammatory cytokine receptors, decoy receptor antagonist, and cytokine binding proteins. The interplay among these proinflammatory cytokines, anti-inflammatory cytokines, and naturally occurring cytokine inhibitors determines the inflammatory response and its effectiveness to contain the inflammatory response and bring about resolution of the initiating process. The main known mediators involved in the evolution of SIRS are cytokines, nitric oxide, platelet activating factor (PAF), and eicosanoids. The systemic response to infection is mediated via a macrophage-derived cytokines that target end organ receptors in response to injury or infection. However, production of anti-inflammatory protein and lipid molecules will also take place to attenuate and halt the inflammatory response. These mediators initiate overlapping processes that directly influence the endothelium, cardiovascular, hemodynamic, and coagulation mechanisms. If a balance between pro- and anti-inflammatory substances is not established and homeostasis restored, a massive pro-inflammatory reaction (i.e. SIRS) and multiple organ dysfunction (MODS) may ensue. Thus, after the first pro-inflammatory mediators are released, the body mounts a compensatory anti-inflammatory reaction to the initial inflammatory response. The anti-inflammatory reaction may be as robust and sometimes even more robust than the proinflammatory response. In addition to pro-inflammatory cytokines, other mediators such as NO, PAF, prostaglandins, and leukotrienes are also produced. These molecules are responsible for activating complement, coagulation, and kinin cascades as well.

Diseases associated with inflammation or an immune response can include: for example, but not limited to: bacterial infection; viral infection; fungal infection; parasitic infection; asthma; allergy; age related macular degeneration; dermatitis; pain; mastitis; metritis; autoinflammatory disease; autoimmune disease; inflammatory bowel disease; dermatitis, multiple sclerosis; osteoarthritis; osteoporosis; psoriasis; rheumatoid and osteoarthritis arthritis; synovitis, acne, pustulosis, hyperostosis, airway and respiratory diseases (e.g., equine airway disease and canine infectious respiratory disease); respiratory disease complex (bovine and swine), ischaemia-reperfusion, feline chronic kidney disease, feline and canine degenerative mitral valve disease (inflammatory complex; e.g., pro-inflammatory cytokines in heart failure via up-regulation of valvular and myocardial expression of cytokines, chemokines and adhesion molecules), psoriasis, multiple sclerosis, rheumatoid arthritis autoinflammatory disease, peptic ulcers, tuberculosis, periodontitis, otitis, ulcerative colitis, Crohn's disease, lupus, sinusitis, hepatitis, coeliac disease, pelvic inflammatory disease, glomerulonephritis, transplant rejection, chronic obstructive pulmonary disease, gout, ankylosing spondylitis, myositis, laminitis, gingivitis, scleroderma, vasculitis, malaria, Lyme, babesiosis, ehrlichiosis, anaplasmosis, tularemia, amebiasis, giardiasis, fascioliasis, fasciolopsiasis, elephantitis, cryptosporidiosis, leishmaniasis, microsporidiosis, trypanosomiasis, toxoplasmosis, and the like; and other inflammatory and immune diseases and disorders. A compound of the invention can treat a disease, disorder, or condition associated with inflammation by modulating cytokines, chemokines, and inflammatory markers, for example, IL6, IL-1ß, NFκB, CSP136, LCN, CXCL8 (IL-8), TNFα, and induce TLR4 signaling.

Macrolide Immunomodulation

The chemistry of macrolides provides the basis to understand their immunomodulation effects. Macrolides are defined as cationic amphiphilic drugs; cellular penetration is primarily determined by their lipophilicity and cationic nature at physiological pH. Cellular membrane penetration by macrolides leads to depolarization of phospholipids, resulting in disposition of both drug and phospholipid into the cytosol and lysosomes, ultimately resulting in cellular state of phospholipidosis. Polar association with phospholipids, primarily phosphatidylcholine, within cells inhibits natural degradation by phospholipase enzymes; resulting in a reduction of primary cell signaling components, like arachidonic acid, among others. The decrease in arachidonic acid is postulated to prevent the normal production of the eicosanoid metabolites including prostaglandins, thromboxanes, leukotrienes and lipoxins. Additionally, indirect inhibition of the COX family of inflammatory mediators, NFkB and AP-1 and their resulting pro-inflammatory cytokine production are observed. The reduced ability for cells to signal, both intra and extracellularly is context dependent on the host. In healthy animals, macrolide treatment has been demonstrated to stimulate neutrophil and macrophage response upon disease stimulus. However, in the presence of an acute or chronic inflammation state, an inhibition or reversal of the inflammation is observed.

Modulation of host defense by azithromycin and other macrolide antibiotics occurs through interaction with structural cells, such as epithelial or endothelial cells, smooth muscle cells or fibroblasts, as well as with leukocytes (macrophages, poly-morphonuclear leukocytes or neutrophils, mononuclear leukocytes or monocytes, T cells and dendritic cells). Cellular accumulation of macrolides is a mechanism of passive transport into cells which does not require cellular energy, carrier proteins, and is unsaturable. The mechanism is distinct from ribosome binding associated with antibiotic activity and therefore unrelated. As an example, azithromycin aglycone which demonstrates no antibiotic activity demonstrates a high level of induced phospholipidosis (J. Parnham et al./Pharmacology & Therapeutics 143 (2014) 225-245). Azithromycin penetrates the cell membrane bilayer and stabilizes the membrane, reducing fluidity and neutralizing phospholipid charge on the inner leaflet membrane. This results in reduced fatty acid release and liberation of enzymes bound by electrostatic charge to the membrane, resulting modulation of signaling pathways and inhibition of the activation of transcription factors including AP-1 and NFκB. The signaling pathway most affected is likely dependent on the particular cell, its activation state and the stimulus by which it is activated. Molecules dependent on negatively charged phospholipids are also affected. Azithromycin accumulates in lysosomes, modulating MPR transport of enzymes and lipids and through lipid remodeling in the lysosome membranes. One of the well documented aspects is their ability to moderate inflammatory responses as demonstrated by downregulation of exacerbated cytokine production (IL-1β, TNF-α, IL-6) through the NFκB pathway and effects on granulocytes; and gene expression.

Immunological activity can also be assessed by analyzing CD163. CD163 is a scavenger receptor that binds hemoglobin/haptoglobin and is expressed on macrophages thought to be involved in innate immune sensing that aids in the clearance of activated macrophages thus preventing oxidative damage to tissue.

CD163 also functions as an innate immune sensor for gram-positive and gram-negative bacteria. Accordingly, a high CD163 expression in macrophages is a characteristic of tissues responding to inflammation, considered a highly correlative biomarker of inflammation. The scavenging of the oxidative and proinflammatory hemoglobin leading to stimulation of the heme-oxygenase-1 and production of anti-inflammatory heme metabolites indicates that CD163 thereby indirectly contributes to the anti-inflammatory response (Antioxid Redox Signal., Etzerodt et. al., 2013, 18(17), p. 2352-2363). CD163 may participate in the process leading to lung lesions in BRD. The expression of CD163 may also be correlated to elevated levels of IL-6 as observed in BRD, CD163 surface expression has been experimentally induced by 253+/−4.9% in monocytes and macrophages upon incubation with IL-6 (Journal of Leukocyte Biology; Buechler et al. vol. 67 January 2020; p. 97-103). Alternatively cross-linking of CD163 on alveolar macrophages with monoclonal antibody induced a protein tyrosine kinase-dependent signal that resulted in slow type calcium mobilization, inositol triphosphate production and secretion of IL-6 and GM-CSF (Journal of Leukocyte Biology; Van de Heuvel et al. vol. 66 November 1999; p. 858-866). The anti-inflammatory immune-modulating drug, tacrolimus, was shown to slightly increase the expression of CD163 (PLOS ONE; Kannegleter, et. al., January, 2017; p. 1-19); wherein a later study (HHS Public Access; Motta, et. al., Oral Dis. 2018, 24(4) p. 580-590) reported that therapy did not result in changes in the expression of CD163. Similarly, azithromycin (British Journal of Pharmacology, Vrancic, et. al; 2012, 165; p. 1348-1360) reported enhanced expression of CD163. CD163 expression upregulates glucocorticoids, IL-6, IL-10, and hemoglobin; and downregulates IL-4, IFN-γ, TNF-, CXCL4, and GM-CSF. In contrast, CD163 was suppressed in cattle treated with M9 and H-91 correlating with the proposed mechanism of inflammatory state reduction.

Cytokines are considered to be in a broad and loose category of small proteins (5-20 kDa) that are important in cell signaling. Their release has an effect on the behavior of cells around them. It can be said that cytokines are involved in autocrine signaling, paracrine signaling and endocrine signaling as immunomodulating agents. Cytokines are generally known to include chemokines, interferons, interleukins, lymphokines, and tumor necrosis factors (TNF) but generally not hormones or growth factors. Cytokines can be produced by a broad range of cells, including immune cells like macrophages, neutrophils, B lymphocytes, T lymphocytes and mast cells, as well as epithelial cells, endothelial cells, fibroblasts, and various stromal cells; a given cytokine may be produced by more than one type of cell. Cytokines can act through receptors and are especially important in the immune system. Cytokines can modulate the balance between humoral and cell based immune responses, and they can regulate the maturation, growth, or responsiveness of particular cell populations. Some cytokines can enhance or inhibit the action of other cytokines in complex ways. Cytokines can be important in health and disease, specifically in host responses to infection, immune responses, inflammation, stress, trauma, sepsis, cancer, and reproduction.

Interleukin 6 (IL-6) is a pleitropic cytokine that acts as both a pro-inflammatory cytokine and an anti-inflammatory myokine. IL-6 is produced and secreted by a variety of cells, including B cells, T cells, endothelial cells and macrophages to stimulate an immune response via the classic signaling pathway when it binds to the transmembrane IL-6 receptor (IL-6R) or via the trans-signaling pathway upon binding to the soluble form of IL-6R (sIL-6R); during infection and after tissue trauma leading to inflammation. The trans-signaling is responsible for the pro-inflammatory actions and most of the pathological effects of IL-6. Dysregulation of the IL-6 pathway has been reported to associate with development of several disease states, including a variety of inflammatory disorders. IL-6 is reported to induce vascular endothelial growth factor production, which enhances angiogenesis and increases vascular permeability, a feature of several inflammatory disorders. IL-6 is also implicated in enhancement of neutrophil, monocyte/macrophage recruitment and blockade of anti-inflammatory T-regulatory cells. In chronic inflammation, IL-6 has a detrimental role and leads to mononuclear cell accumulation at the site of injury. This may lead to an increase in serum levels of IL-6 and sIL-6R providing a foundation for the amplification step of chronic inflammatory responses. IL-6 has been implicated in the development of pulmonary neutrophilia by enhancing both neutrophil recruitment from blood and bone marrow and neutrophil survival. IL-6's role as an anti-inflammatory cytokine is mediated through its inhibitory effects on TNF-alpha and IL-1, and activation of IL-1ra and IL-10.

IL-6, like other inflammatory cytokines, has been shown to be elevated in different lung diseases in human and mice. IL-6 was elevated in the bovine BRD (*M. hemolytica*) challenge and was correlated with higher rectal temperature, lung lesions and mortality. The compounds of the invention, M9, and tulathromycin significantly reduced IL-6 levels which also correlated with overall animal survival. Therefore, the immune-modulatory compounds of the invention mitigate the pathologic increase in IL-6 consistent with dose and clinical outcome.

IL-36 is a member of the IL-1 superfamily of cytokines and includes three agonists (IL-36α, IL-36p, and IL-36γ) and an antagonist (IL-36RA). The IL-36 agonists bind to heterodimeric IL-36 receptor (IL-36R) complexes to produce a pro-inflammatory response. The antagonist binds to the IL-36R thereby prohibiting IL-36 signaling. IL-36 signaling occurs through the formation of a heterotrimeric complex IL-36, the IL-36R, and the IL-1AcP (IL-1 accessory protein) and activate the adaptor protein myeloid differentiated protein 88 (MyD88), mitogen-activated protein kinase (MAPK), and nuclear factor-kappa B (NF-κB) signaling pathways and induce inflammatory responses. IL-36RA prevents the interaction between the IL-1AcP and the receptor ligand complex. IL-36 proteins are widely expressed in T cells, keratinocytes, and skin, lung, and gut cells. IL-36 agonists bind to receptors[IL-36R and IL-1 receptor accessory protein (IL-1RAcP)] and then activate. Finally, these pathways initiate the regulation of target genes. Recent evidence suggests that IL-36 regulates the function of both non-immune cells and immune cells; and is involved in immune cell activation, antigen presentation, and pro-inflammatory factor production. IL-36 has attracted great interest because of its dysregulation in inflammatory diseases. For example, serum and tissue IL-36 expression was increased in inflammatory and immune diseases and disorders like psoriasis, rheumatoid arthritis, and inflammatory bowel disease.

Chemokines

Chemokines are a family of small cytokines, or signaling proteins secreted by cells. Their name is derived from their ability to induce directed chemotaxis in nearby responsive cells (i.e., chemotactic cytokines); that stimulate recruitment of leukocytes. The main function of chemokines is to manage the migration of leukocytes (homing) in the respective anatomical locations in inflammatory and homeostatic processes. They are secondary pro-inflammatory mediators that are induced by primary pro-inflammatory mediators such as IL-1 or TNF. There are two major chemokine sub-families based upon the position of cysteine residues, i.e., CXC and CC. All members of the CXC chemokine sub-family have an intervening amino acid between the first two cysteines; members of the CC chemokine sub-family have two adjacent cysteines. As a general rule, members of the CXC chemokines are chemotactic for neutrophils, and CC chemokines are chemotactic for monocytes and a small sub-set of lymphocytes. Some chemokines are considered pro-inflammatory and can be induced during an immune response to recruit cells of the immune system to a site of infection or tissue damage, while others are considered homeostatic and are involved in controlling the migration of cells during normal processes of tissue maintenance or development (e.g., angiogenesis).

Inflammatory chemokines are formed under pathological conditions (on pro-inflammatory stimuli, such as IL-1, TNF-alpha, LPS, or viruses) and actively participate in the inflammatory response attracting immune cells to the site of inflammation and include: CXCL8 (IL-8), CCL2, CCL3, CCL4, CCL5, CCL11, CXCL10. These inflammatory chemokines are produced in high concentrations during infection or injury and determine the migration of inflammatory leukocytes into the damaged area. A typical example is CXCL8, which acts as a chemoattractant for neutrophils. In contrast to the homeostatic chemokine receptors, there is significant promiscuity (redundancy) associated with binding receptor and inflammatory chemokines.

Interleukin-8 (IL-8) is one of the proinflammatory chemokines that attract and activate immune and inflammatory cells. IL-8 mediates an array of biological effects, including several involving neutrophils: inflammatory cell activation and chemotaxis, production of reactive oxygen species, increased expression of the integrin CD11b-CD18, enhancement of cell adhesion to endothelial cells, promotion of angiogenesis, and modulation of histamine release. IL-8 is produced by many cells, including neutrophils, monocytes, macrophages, mast cells, vascular endothelial cells, stromal cells and epithelial cells in response to an innate exogenous/endogenous stimulus. In target cells, IL-8 induces a series of physiological responses required for migration and phagocytosis, such as increases in intracellular $Ca^{2+}$ and exocytosis (e.g. histamine release).

Recruitment of inflammatory cells, such as neutrophils in response to tissue injury such as infection is a normal physiological response to eliminate the infectious agent, remove damaged or dead cells and initiate the healing process. However, excessive recruitment of these cells, the extended residence time and death of cells results in tissue damage. Influx of excessive inflammatory cells is therefore thought to be instrumental in the pathophysiology of pulmonary diseases such as in human inflammatory conditions such as chronic obstructive pulmonary disease (COPD), acute respiratory distress syndrome (ARDS, asthma, pulmonary fibrosis and bacterial pneumonia. This has also been observed in bovine respiratory disease (BRD) and bacterial pneumonia. Control of recruitment and activation of these cells in the lung would be an attractive strategy for therapeutic intervention. In all these conditions, IL-8 appears to be important for the recruitment and activation of neutrophils and T cells into the respiratory tract.

In an experimental cattle challenge study with *M. hemolytica*, one of the major causative agents of BRD, IL-8 levels were up-regulated in serum and tissues. The compounds of the invention were shown to downregulate IL-8 production in this challenge model and this correlated with a mitigated anti-inflammatory response and disease.

Biology of BRD

It has been long believed that the pathobiology of BRD originates from a stress-induced immune suppression leaving calves vulnerable to a myriad of microorganisms they encounter during the transition from cow-calf operation to feedlot. The dogma suggests that stimulation of the innate immune system would have a positive impact on the clinical outcome. However, to date, there has been little success with interventions consistent with this dogma, including the use of a DNA immunostimulant (Zelnate®). With the goal to better understand the progression of BRD, earlier studies suggest that it is the early unresolved heightened inflammatory state rather than immunosuppression that leads to the progression to BRD.

Based on current research driving BRD etiology, a novel understanding of the immunological status has shown that while a heightened pro-inflammatory state is ubiquitous in at-risk cattle, the perpetuation or lack of resolution/mitigation of this state coincides with disease outcome. After shipping on arrival to a feedlot, the pro-inflammatory state is especially characterized by innate immune components such as nasal-mucosal epithelial cell barrier damage and the release of pre-formed mediators such as members of the IL-1 cytokine family. Activation of danger-associated molecule patterns (DAMPs) including pattern recognition receptor (PRR) TLR-4 and inflammasome signaling demonstrate a response by epithelial and resident myeloid cells to the co-localized microbes in the upper airway. As bacterial components such as lipopolysaccharides (LPS; lipoglycans and endotoxins) induce TLR4 signaling, transcription factors such as NF-κB induce the expression of key cytokines involved in perpetuating the inflammatory process such as IL-1β, IL-6 and TNF-α and myeloid-derived granulocytes including macrophages and neutrophils are recruited and activated. These cascades lead to an environment where bacteria normally limited to the upper airway can transgress into the lung and cause disease. Associated with clinical disease are biomarkers of inflammatory processes such as elevated levels of secreted cytokines like IL-6 and acute phase proteins. Also associated with clinical disease are markers of cellular activation, for example expression of the scavenger receptor CD163 on macrophages and neutrophil-associated mediators such as LCN and CXCL8. The compounds of the invention effectively mitigates the heightened pro-inflammatory state in at-risk cattle by equilibrating the immune response and reducing the pathologic inflammatory cascade. This mechanism of an immunomodulator in the context of BRD progression is depicted in FIG. 1.

The compounds of the invention represent a new approach to a highly complex disease and have the potential to significantly reduce the incidence of BRD and the need for antibiotic treatment. They effectively moderate the pathologic innate inflammation occurring during the shipping period enabling the animal to restore homeostasis in a timeframe consistent with clinical disease protection.

Schemes and Experimentals

Within the schemes and experimental procedures presented herein, the following acronyms are defined: benzyloxycarbonyl (Cbz); ON (overnight, 16-24 hours); protecting group (Pg); leaving group (Lg); triethyl amine (TEA); dichloromethane (DCM); cyano (CN); tetrahydrofuran (THF); palladium on carbon (Pd/C); trifluoroacetic acid (TFA); acetic acid (AcOH); tert-butyl alcohol (t-BuOH or TBA); room temperature (RT); ethyl acetate (EtOAc); dimethylformamide (DMF); N-methyl-2-pyrrolidine (NMP); methyl tert-butyl ether (MTBE); N,N-diisopropylethylamine (DIPEA); phenyl (Ph); and copper II acetate (Cu(OAc)$_2$).

Tulathromycin A is a 15-membered (lactone A) closed ring antibacterial macrolide (azalide). The azalide converts to a 13-membered (lactone B) closed ring, tulathromycin B. This conversion is in an equilibrium ratio of about 9:1 (A:B), and is depicted below.

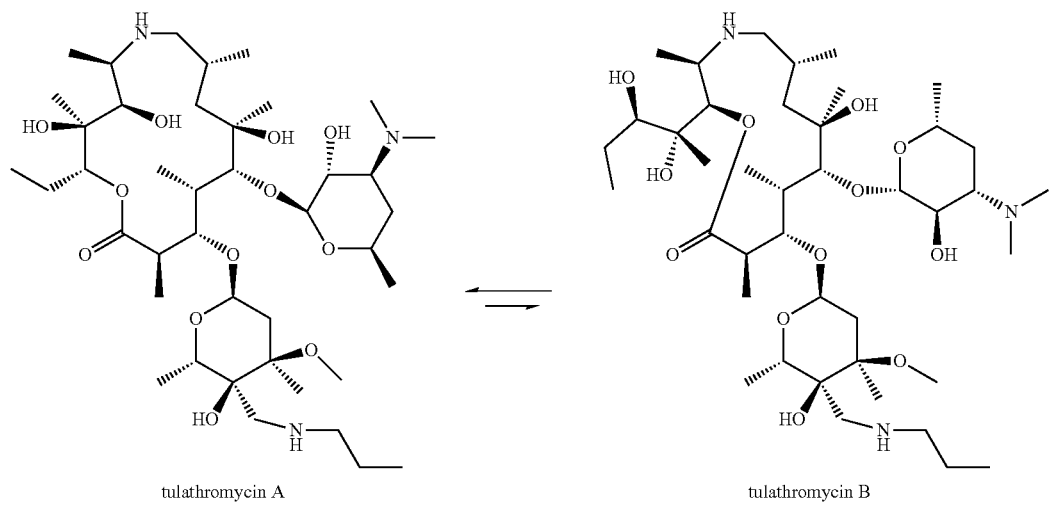 [SMILES: CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@H](C)[C@@H](O)[C@](C)(O)[C@@H](CC)OC(=O)[C@@H]2C)C[C@@]1(C)OC ; CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@H](C)[C@H]([C@](C)(O)[C@H](O)CC)OC(=O)[C@@H]2C)C[C@@]1(C)OC]

tulathromycin A    tulathromycin B

The tulathromycin azalides can also be represented by the following structures:

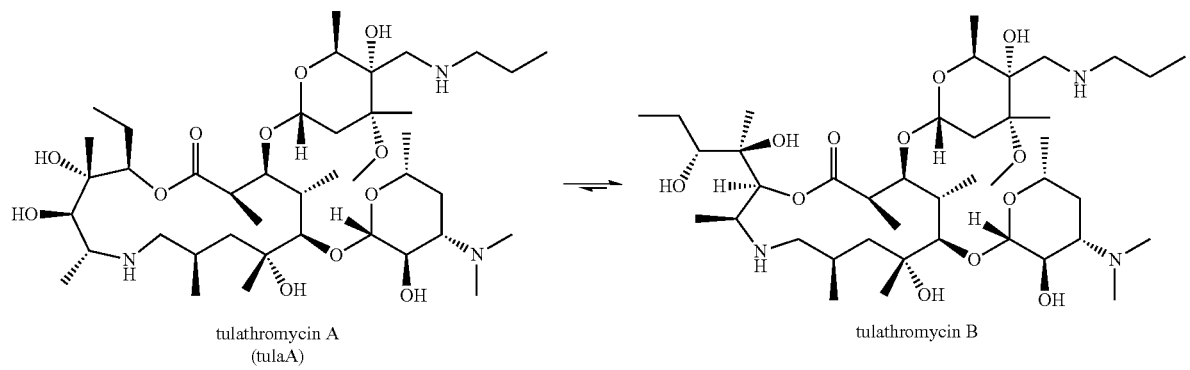 [SMILES: CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@H](C)[C@@H](O)[C@](C)(O)[C@@H](CC)OC(=O)[C@@H]2C)C[C@@]1(C)OC ; CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)C[C@@H](C)CN[C@@H](C)[C@@H]([C@](C)(O)[C@H](O)CC)OC(=O)[C@@H]2C)C[C@@]1(C)OC]

tulathromycin A
(tulaA)

tulathromycin B

Tulathromycin is (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-1-oxa-6-azacyclopentadecan-15-one; and a precursor to tulathromycin, tulathromycin epoxide (tula-epx), is (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one.

In addition to the tulathromycin azalides (tulaA and tulaB) depicted just above, the compound, lactone A and B of Example H-11 is shown below:

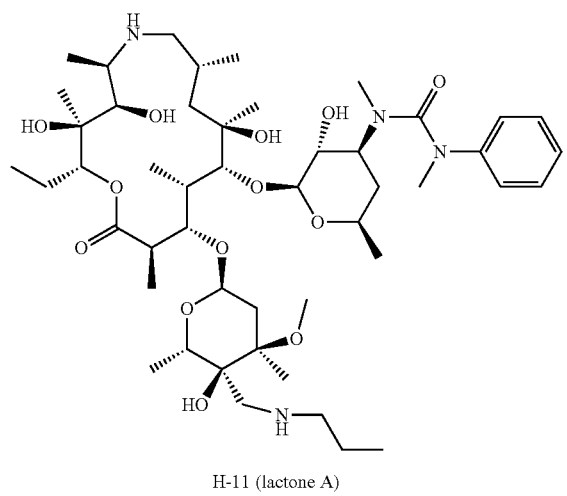

H-11 (lactone A)

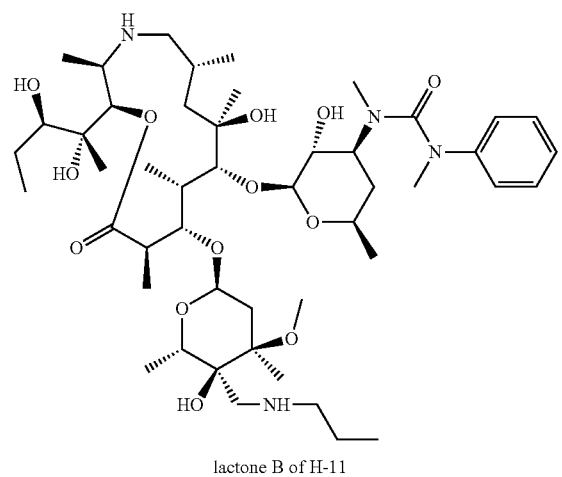

lactone B of H-11

The H-11 lactones were separated by HPLC using an Agilent 1100 quaternary pump and diode array detector (250 nm) with an X-select CSH C18 column (150×4.6 mm, 2.5 µm) at 50° C. using a gradient mobile phase (mp) comprising 0.03% $H_2SO_4$ in water (mpA) and acetonitrile (mpB) over 16 minutes. Lactone A eluted at 5.8 minutes (area % 92.4) and lactone B eluted at 5.2 minutes (area % 7.6).

In an aqueous solution, Example H-11 exists as an equilibrated mixture of two lactone isomers as shown above. The ratio is approximately 9:1 lactone A:B. The rate of equilibration depends on pH and temperature, with neutral pH giving faster equilibration, pH ~5-6 giving much slower equilibration, and higher temperatures resulting in faster equilibration. Equilibration occurs in under 1-hour at pH>6 and temperatures >60° C. H-11 isomerization is a 6 exo-Trig cyclization and is a favored reaction by Baldwin's Rules. The dominant isomer, lactone-A, is a 15-membered macrocyclic lactone, while the minor isomer, lactone-B, is a 13-membered macrocyclic lactone. H-11 exhibits pH dependent aqueous solubility, where it is very soluble at acidic pH under acidic conditions and has a lower solubility as the pH approaches neutral conditions. Due to the pH dependent solubility of H-11, and other compounds of the invention, dissolution of an organic acid (e.g., citric acid) into water prior to adding the active agent (e.g., H-11) may be necessary to ensure complete dissolution, particularly for higher concentration solutions, thereby providing a solution with enough buffering capacity for dissolution.

One of the metabolites of tulathromycin A is the des-methyl azalide, (2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)-tetrahydro-2H-pyran-2-yl)oxy)-11-(((2S,3R,4S,6R)-3-hydroxy-6-methyl-4-(methylamino)tetrahydro-2H-pyran-2-yl)oxy)-3,5,8,10,12,14-hexamethyl-1-oxa-6-azacyclopentadecan-15-one (M9), depicted in the following diagrams below:

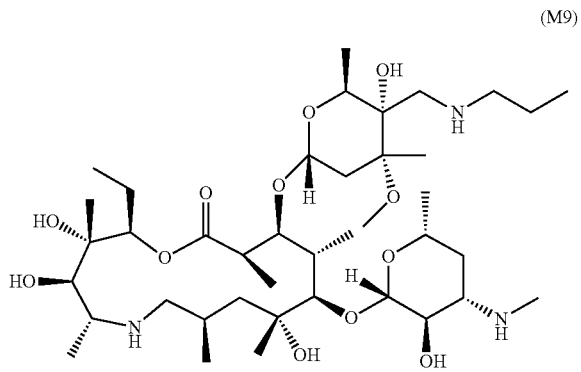
(M9)

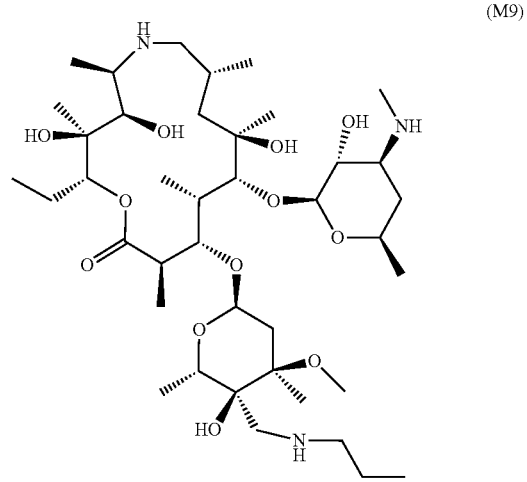
(M9)

Tulathromycin B also metabolizes to the B-des-methyl azalide.

The M9 analogue can be used as a starting material for preparing compounds of the invention. The process to make des-methyl tulathromycin (M9) is a two-step process from tulathromycin A and the intermediate is generally not isolated, but it can be. The first step is an oxidation of the tertiary amine to the N-oxide using any number of oxidizing agents known to oxidize tertiary amines. The second step is a Polonovski-type demethylation which can employ any metal known to effect that type of transformation. It's generally iron, but a copper salt (Cu(II)) can also be used.

To a cold (<0° C.) solution of tulathromycin A (4.0 g, 5.0 mmol) in n-butanol (20 mL), 1.22 g (5.1 mmol) of a commercial 32% peracetic acid solution was added. After 30 minutes, the product was extracted into a 0.25M aqueous solution of disodium ethylenediamine-tetraacetic acid (EDTA, 15 mL). The aqueous solution was basified to pH 9.5 with concentrated aqueous ammonia and extracted with tert-butyl methyl ether (20 mL). The N-oxide product was concentrated to a thick oil but was not isolated, [M+H]$^+$=822. The oil was dissolved in methanol (16 mL). Copper (II) sulfate pentahydrate (1.5 g, 6.1 mmol) and acetic acid (0.28 mL) were added and the reaction was heated to 60° C. for 1-2 hours. The solution was cooled to 25° C. and hydroxylamine hydrochloride (0.75 g, 10 mmol) in water (8 mL) was added. After 2 hours, the product was partitioned between water (28 mL, adjusted to pH 9.5 with aqueous ammonia) and methylene chloride (20 mL). The organics were concentrated to an oil and the product was crystallized from hot acetonitrile (40 mL). The resulting white crystalline powder was dried to provide 3.2 g of M9. LCMS [M+H]$^+$=792.5. HPLC purity >98%. $^1$H NMR (600 MHz, d$_6$-DMSO): N-Me (3H, 2.42 ppm, S) compared to tulathromycin NMe$_2$ (6H, 2.26 ppm).

Alternatively, M9 can be prepared by mixing a 20° C. solution of tulathromycin A (4.0 g, 5.0 mmol) in n-butanol (10 mL) and then add hexafluoroacetone trihydrate (0.27 g, 1.2 mmol) followed by 30% aqueous hydrogen peroxide (0.62 g, 5.5 mmol). After 4 hours, acetic acid (0.31 g, 5.5 mmol) was added followed by methyl tert-butyl ether (6 mL) and water (25 mL). The upper organic layer was discarded. Methyl tert-butyl ether (8 mL) was added and the pH of the aqueous layer was adjusted to 9.8 with aqueous ammonia. The lower aqueous layer was discarded. The N-oxide product was concentrated to a thick oil but was not isolated. [M+H]$^+$=822. The oil was dissolved in methanol (12 mL). Anhydrous copper(II) sulfate (0.97 g, 6.1 mmol) and acetic acid (0.28 mL) were added and the reaction was heated to 60° C. for 1 hour. The solution was cooled to 25° C. and hydroxylamine hydrochloride (0.75 g, 10 mmol) in water (8 mL) was added. After 2 hours, the product was partitioned between water (28 mL, adjusted to pH 9.5 with aqueous ammonia) and methylene chloride (20 mL). The organics were concentrated to an oil and the product was crystallized from hot acetonitrile (40 mL). The resulting white crystalline powder was dried to provide 3.2 g of product; LCMS [M+H]$^+$=792.5. HPLC purity >98%. 1H NMR (600 MHz, d6-DMSO): N-Me (3H, 2.42 ppm, S) compared to tulathromycin NMe$_2$ (6H, 2.26 ppm).

Alternatively, M9 can be prepared by mixing a solution of an epoxide precursor of Tulathromycin A, (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx), (20.0 g, 27 mmol) in methanol (40 mL) and then add acetic acid (1.6 mL, 30 mmol), hexafluoroacetone trihydrate (0.38 mL, 3 mmol) and then 30% aqueous hydrogen peroxide (0.62 g, 30 mmol).

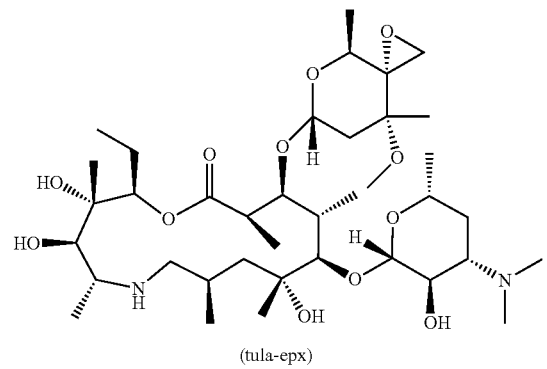 [SMILES: CC[C@H]1OC(=O)[C@H](C)[C@@H](O[C@H]2C[C@@](C)(OC)[C@]3(CO3)[C@H](C)O2)[C@H](C)[C@@H](O[C@@H]2O[C@H](C)C[C@H](N(C)C)[C@H]2O)[C@](C)(O)C[C@@H](C)CN[C@H](C)[C@@H](O)[C@]1(C)O]

(tula-epx)

After 4 hours at 35° C., the reaction was cooled to 20° C. and anhydrous copper(II) sulfate (4.5 g, 29 mmol) was added and the reaction was heated to 60° C. for 1 hour. After cooling to 20° C., added 60 mL methylene chloride and 80 mL water. Basified the mixture to approximately pH 9.8 with concentrated aqueous ammonia. Concentrated the organics under vacuum to a solid and then added 2-propanol (40 mL) and n-propylamine (40 mL). Heated to 65° C. and stirred for 15 hours. Concentrated under vacuum to remove solvents. Added acetonitrile (120 mL) and heated to 78° C. Cooled to 10° C. and isolated product by filtration. The resulting white crystalline powder was dried to provide 12 g of product; LCMS [M+H]$^+$=792.5. HPLC purity >98%. 1H NMR (600 MHz, d6-DMSO): N-Me (3H, 2.42 ppm, S) compared to tulathromycin NMe$_2$ (6H, 2.26 ppm).

Azithromycin (depicted below), an azalide similar to tulathromycin, except the core ring N is substituted with a methyl group (1') and the cladinose sugar is not further substituted with methylpropanamine (2'); depicted below.

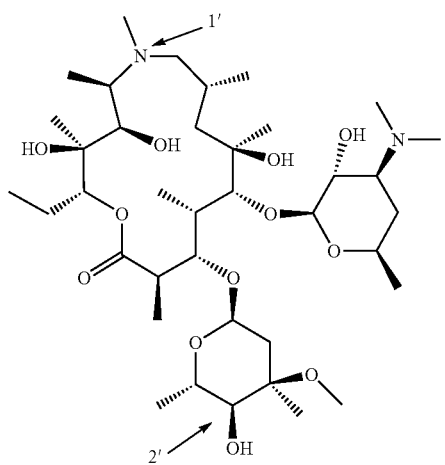 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(O)C[C@@H](C)CN(C)[C@H](C)[C@@H](O)[C@]1(C)O]

Azithromycin can be derivatized to prepare a des-methyl analogue, similar to M9. Further derivatizations can be conducted in accordance with the schemes and experimentals defined herein to prepare immune-modulating azithromycin derivatives that are not active (i.e., non-antibacterial) against BRD bacterial pathogens. In addition to azithromycin, other macrolides, for example, erythromycin, tilmicosin, clarithromycin, gamithromycin, fidaxomicin, roxithromycin, telithromycin, dirithromycin, josamycin, midecamycin, oleandomycin, roxithromycin, and others, can be modified in a similar manner as M9 to prepare immune-modulating analogues that lack antibacterial properties against BRD and other bacterial pathogens in animals, including humans.

For illustrative purposes, the reaction schemes depicted below demonstrate potential routes for synthesizing key intermediates and compounds of the invention. For a more detailed description of the individual reaction steps, see the Examples section below. Those skilled in the art will appreciate that other suitable starting materials, reagents, and synthetic routes may be used to synthesize the intermediates and compounds of the invention and a variety of derivatives thereof. Further, many of the compounds prepared by the methods described below can be prepared and/or modified using conventional chemistry.

The compounds of the invention may be used in its native form or as a salt. In cases where forming a stable nontoxic acid salt is desired, administration of the compound as a pharmaceutically acceptable salt may be appropriate. For the purpose of the present invention, the term "pharmaceutically acceptable salt" refers to those salts which are, within the scope of sound medical evaluation, suitable for use in contact with the tissues and organs of animals without displaying toxicity, irritation, allergic response and the like and are commensurate with a reasonable benefit/risk ratio. Further, the compounds of the invention have a secondary or tertiary amine group, which has basic character and thus can form acid addition salts, which may be pharmaceutically acceptable acids. Therefore, pharmaceutically acceptable salts according to the present invention include those pharmaceutically acceptable acid addition salts formed with organic and inorganic acids and those pharmaceutically acceptable salts formed with optically active acids. Representative acid addition salts include, but are not limited to, acetate, adipate, alginate, ascorbate, citrate, aspartate, benzoate, benzenesulfonate, besylate, bicarbonate/carbonate, bisulfate/sulfate, borate, butyrate, camphorate, camphorsulfonate, camsylate, citrate, digluconate, edisylate, etoglutarate, esylate, formate, fumarate, gluceptate, gluconate, glucuronate, glutamate, glycerophosphate, hemisulfate, heptanoate, hexafluorophosphate, hexanoate, hibenzate, fumarate, hydrochloride, hydrobromide, hydroiodide, 2-hydroxyethansulfonate, isethionate, lactate, malate, maleate, malonate, mesylate, methylsulphate, naphthylate, 2-napsylate, nicotinate, nitrate, orotate, oxalate, palmitate, pamoate, pectinate, persulfate, phosphate/hydrogen phosphate/dihydrogen phosphate, picrate, pivalate, proprionate, saccharate, stearate, succinate, tartrate, thiocyanate, tosylate and trifluoroacetate salts.

In the following Schemes, the demethylation or Polonovski reaction occurs when an amine oxide reacts with an acylating agent. The accepted mechanism involves proton removal to give a nitrogen ylide which loses acetate (using acetic anhydride) which attacks the carbon adjacent to the nitrogen atom giving an α-acetoxyamine. The central feature of the Polonovski reaction is the transformation of an N-oxide to an iminium ion intermediate. Depending on the structure of the substrate and the acid anhydride or other activating reagent employed, iminium ion formation can occur through loss of an α hydrogen, or through fragmentation of a Cα-carbon bond. Again, depending on conditions, the reaction will either stop at this stage and iminium ions become the Polonovski products, or proceed to give enamines or tertiary amides and/or secondary amines and aldehydes.

In principle, any reagent capable of activating the N-oxide oxygen towards iminium ion formation thus triggering the Polonovski reaction can be used. However, three major types of activating agents, acid anhydrides and chlorides (including chloroformate esters), iron or copper salts and complexes, and sulfur dioxide, can be employed.

In the following Schemes and preparations, the following acronyms include: methanol (MeOH), ethanol (EtOH), dichloromethane (DCM), trifluoroacetic acid (TFA), hydrogen peroxide ($H_2O_2$), potassium cyanide (KCN), triethylamine (TEA), triethylamine trihydrofluoride (TEA·3HF), dimethylformamide (DMF), potassium cyanide (KCN), N,N-diisopropylethylamine (DIPEA), dichloroethane (DCE), isopropyl alcohol (IPA), ethylenediaminetetraacetic acid (EDTA), acetic acid (AcOH), ammonium hydroxide ($NH_4OH$), acetonitrile (MeCN or Acn), sodium triacetoxyborohydride (STAB), sodium methoxide (MeONa), cerium (III) chloride ($CeCl_3$), sodium azide ($NaN_3$), sodium bicarbonate ($NaHCO_3$), ammonium chloride ($NH_4Cl$), magnesium sulfate ($MgSO_4$), bromine ($Br^2$), sodium sulfate ($Na_2SO_4$), ammonium sulfate (($NH_4)_2SO_4$), copper sulfate ($CuSO_4$), sodium cyanoborohydride ($NaBH_3CN$), 1-butanol (N-BuOH), hexafluoroacetone (($CF_3)_2CO$—$H_2O$), methoxy (OMe), ethoxy (OEt), room temperature (RT), overnight (ON) and water ($H_2O$).

Scheme 1a. Preparation of Formula (1) Urea Compounds (1-A1) through (1-A6)

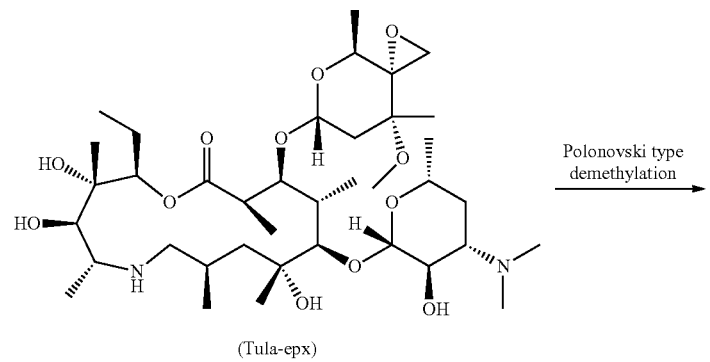

(Tula-epx) → Polonovski type demethylation

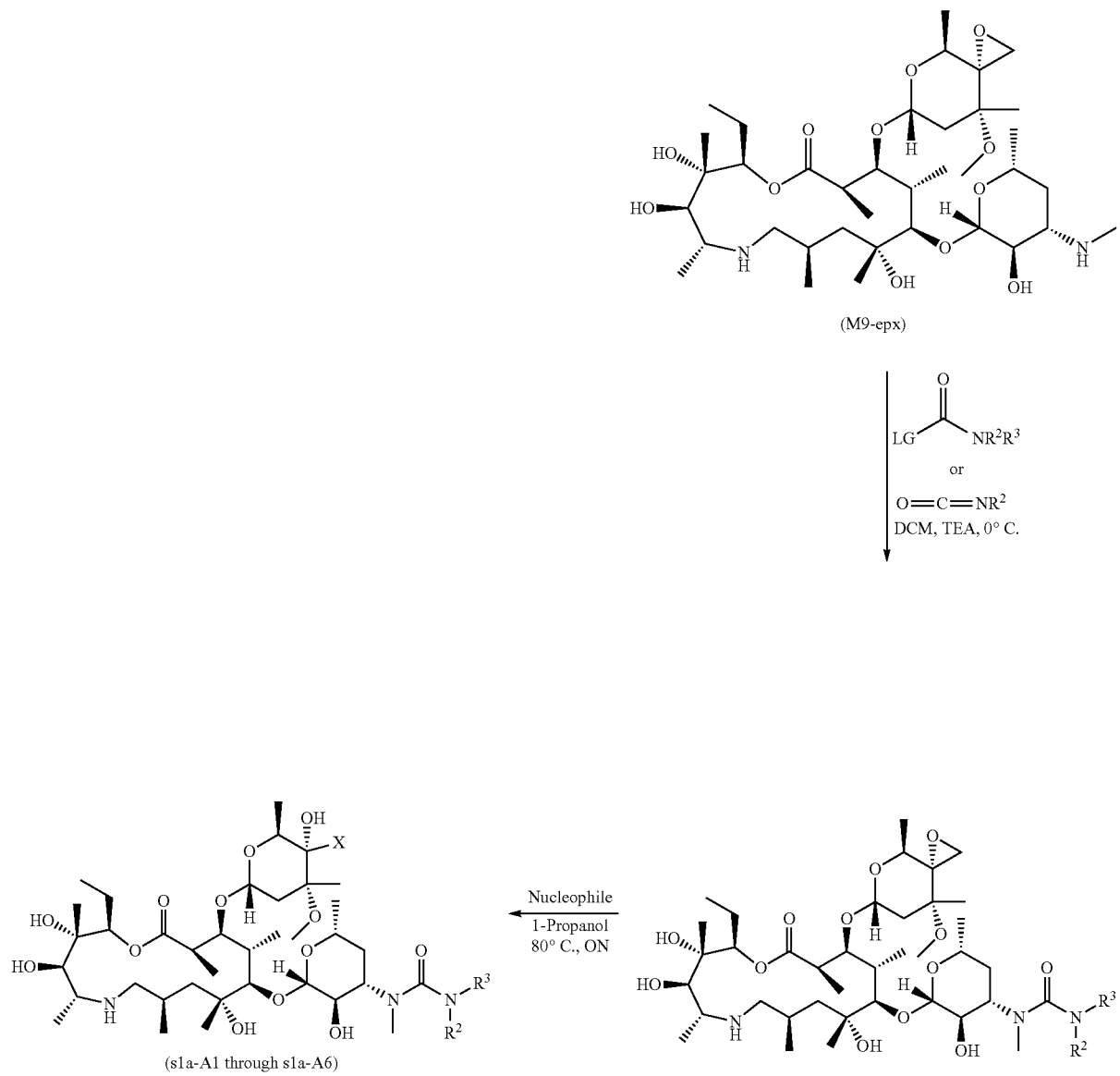

The urea analogs can be prepared following the 3-step procedure outlined in Scheme 1a above. First, the commercially available tulathromycin epoxide (tula-epx) can be demethylated under but not limited to the Polonovski reaction to give M9 epoxide (M9-epx). The N-oxide can be formed using different oxidizing agents such as iodine, N-iodosuccinimide, peracetic acid or hydrogen peroxide. The demethylation of the N-oxide can be triggered with iron or copper salts. The secondary amine thus formed can be transformed into variousureas using urea forming reagents such as isocyanates; activated carbamoyl-chlorides, -imidazoles, —N-methyl imidazoles; p-$NO_2$ phenol esters and others. Mild bases such as TEA or DIPEA can be sometimes used to facilitate the urea formation reaction. Non-limiting examples of leaving groups (LG) include chlorine, imidazole, methyl-imidazole, p-$NO_2$-phenol, and the like. In the last step, the epoxide functional group can be opened to give the final urea analogs using different nucleophiles such as primary and secondary amines, alcohols, thiols, cyanide, azide or halogen anions and others at higher temperature in alcoholic solvents such as but not limited to 1-propanol, 1-butanol or 2-propanol. This reaction can be completed overnight. Mild bases such as $NaHCO_3$ or salts such as $NH_4Cl$ or $(NH_4)_2SO_4$ can sometimes accelerate the epoxide opening reaction. For any of the Schemes presented herein, the "nucleophile" of the epoxide opening step on the cladinose ring, can be one of the following but not limited to the following: $HNR^5R^6$, $HOR^7$, $HS(O)_pR^7$, $NaN_3$, $CeCl_3$, TEA·3HF, and KCN, wherein $R^5$, $R^6$, $R^7$ and p are as defined herein.

Scheme 1b: Details for Scheme 1a Step 3 (Nucleophilic Epoxide Opening)
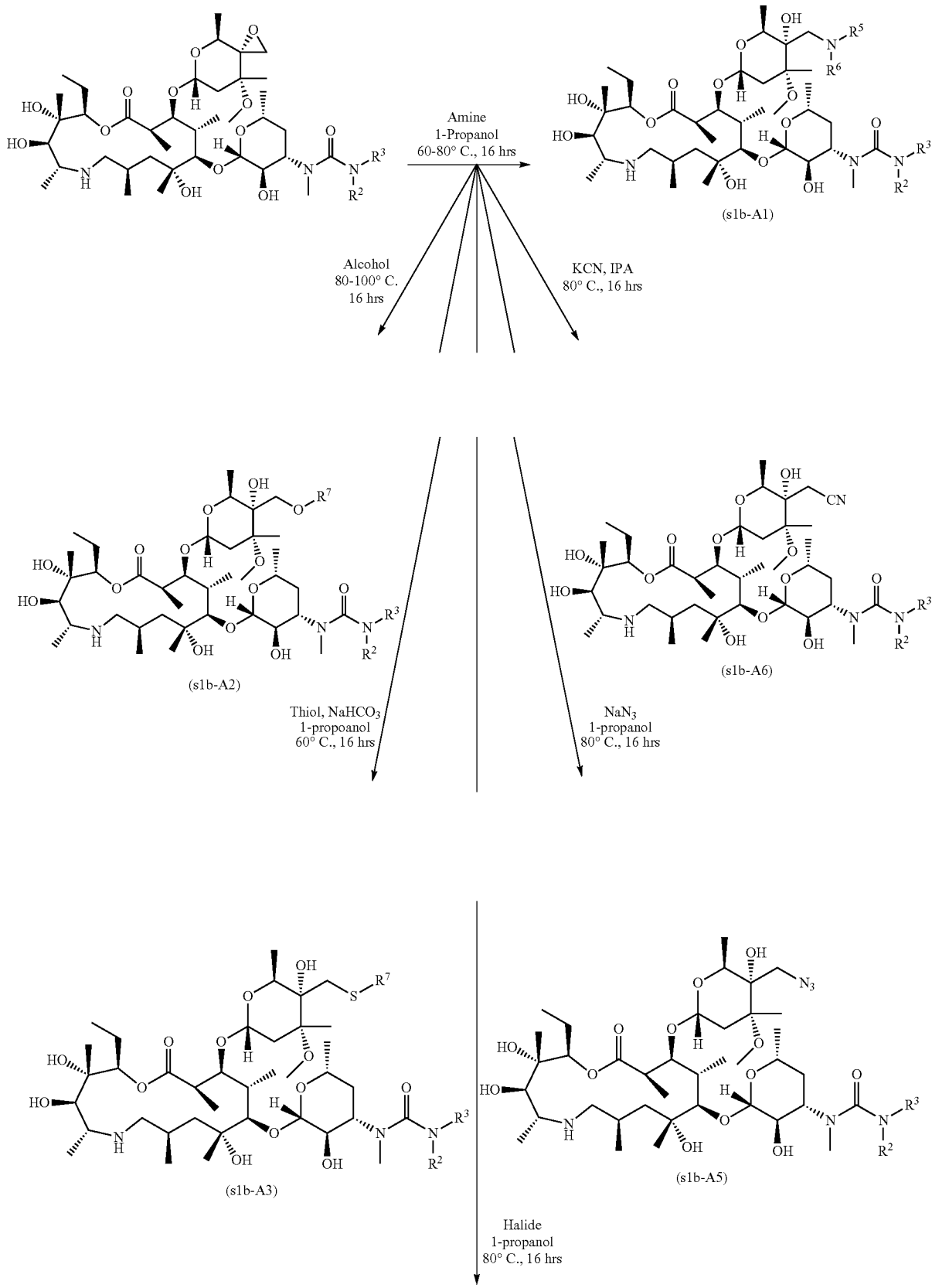

-continued

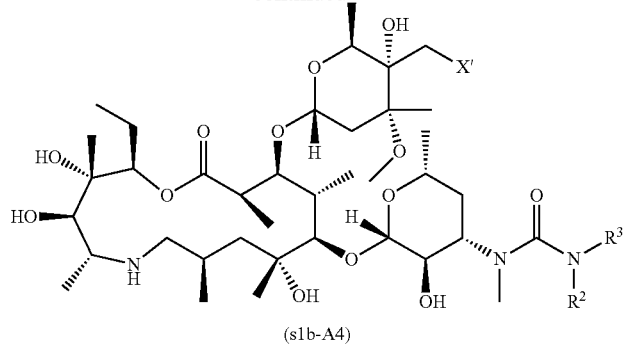

(s1b-A4)

For the (s1b-A1) analogs, the epoxide functional group can be opened to give the final urea analogs using different primary or secondary amines in alcoholic solvents such as but not limited to methanol, ethanol, 1-proponaol and others. For the (s1b-A2) analogs, the epoxide functional group can be opened to give the final urea analogs using different alcohols used as solvents such as but not limited to methanol, ethanol, 1-proponaol and others. Mild bases such as $NaHCO_3$ or salts such as $NH_4Cl$ or $(NH_4)_2SO_4$ can sometimes accelerate the epoxide opening reaction. For the (s1b-A3) analogs, the epoxide functional group can be opened to give the final urea analogs using different thiols such as but not limited to ethanethiol, propanethiol, isopropyl mercaptan and others in alcoholic solvents such as but not limited to ethanol or 1-propanol. Mild bases such as $NaHCO_3$ but not limited to are used to accelerate the epoxide opening reaction. For the (s1b-A4) analogs, the epoxide functional group can be opened to give the final urea analogs using different halides from reagents such as but not limited to $CeCl_3$ or $Br_2$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction. For the (s1b-A5) analogs, the epoxide functional group can be opened to give the final urea analogs using different sources of the azide anion such as but not limited to $NaN_3$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction. For the (s1b-A6) analogs, the epoxide functional group can be opened to give the final urea analogs using different sources of the cyanide anion such as but not limited to KCN in alcoholic solvents such as but not limited to IPA or 1-propanol. Mild bases such as $NaHCO_3$ or salts such as $NH_4Cl$ or $(NH_4)_2SO_4$ can sometimes accelerate the epoxide opening reaction.

Scheme 2a. Preparation of Formula (1) Urea Compounds (1-A1) through (1-A6)

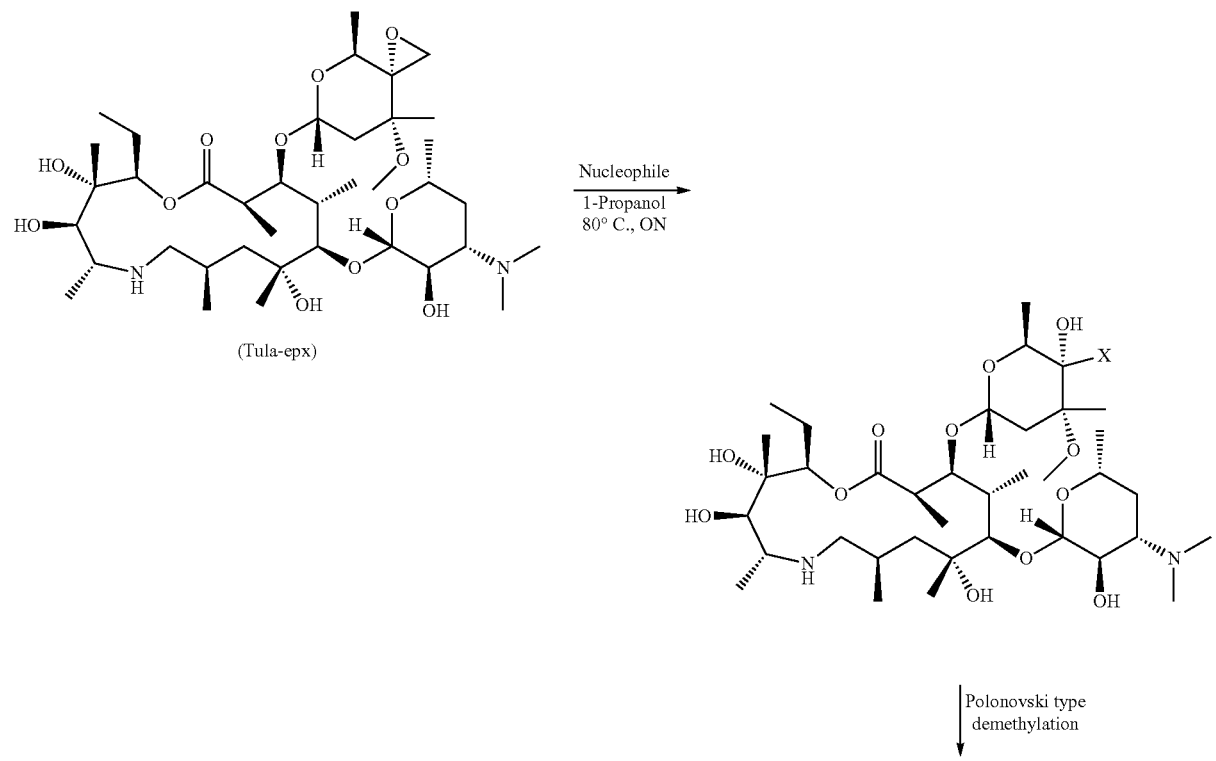

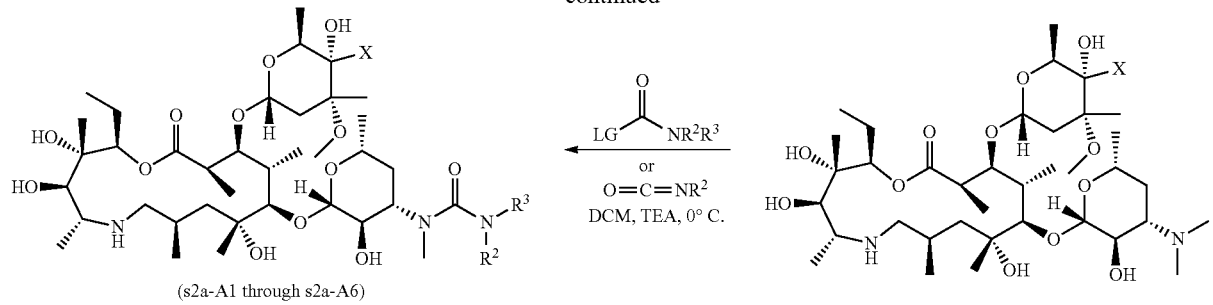

Alternatively, the urea analogs can be prepared according to Scheme 2a. In the first step, the commercially available tulathromycin epoxide intermediate is treated with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol. This reaction can occur overnight. Mild bases such as $NaHCO_3$ or salts such as $NH_4Cl$ or $(NH_4)_2SO_4$ can sometimes accelerate the epoxide opening reaction. In the second step, the tertiary dimethyl amine on the desosamine sugar can be demethylated using Polonovski type conditions as described above. The final urea analogs can be prepared by reacting the secondary methyl amine moiety with urea forming reagents such as but not limited to isocyanates; activated carbamoyl-chlorides, -imidazoles, —N-methyl imidazoles; p-$NO_2$ phenol esters, and the like.

Scheme 2b: Details for Scheme 2a Step 1 (Nucleophilic Expoxide Opening)

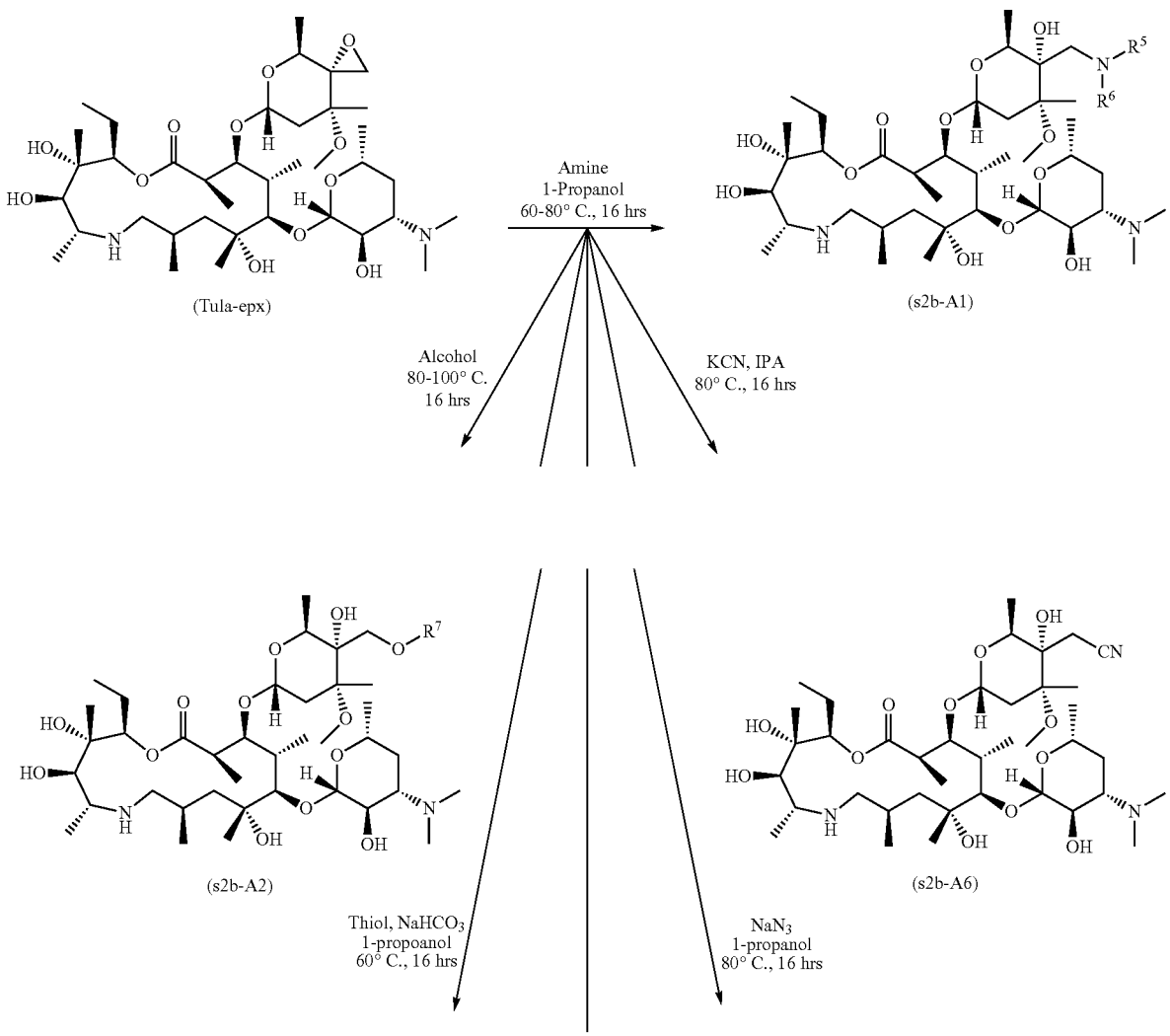

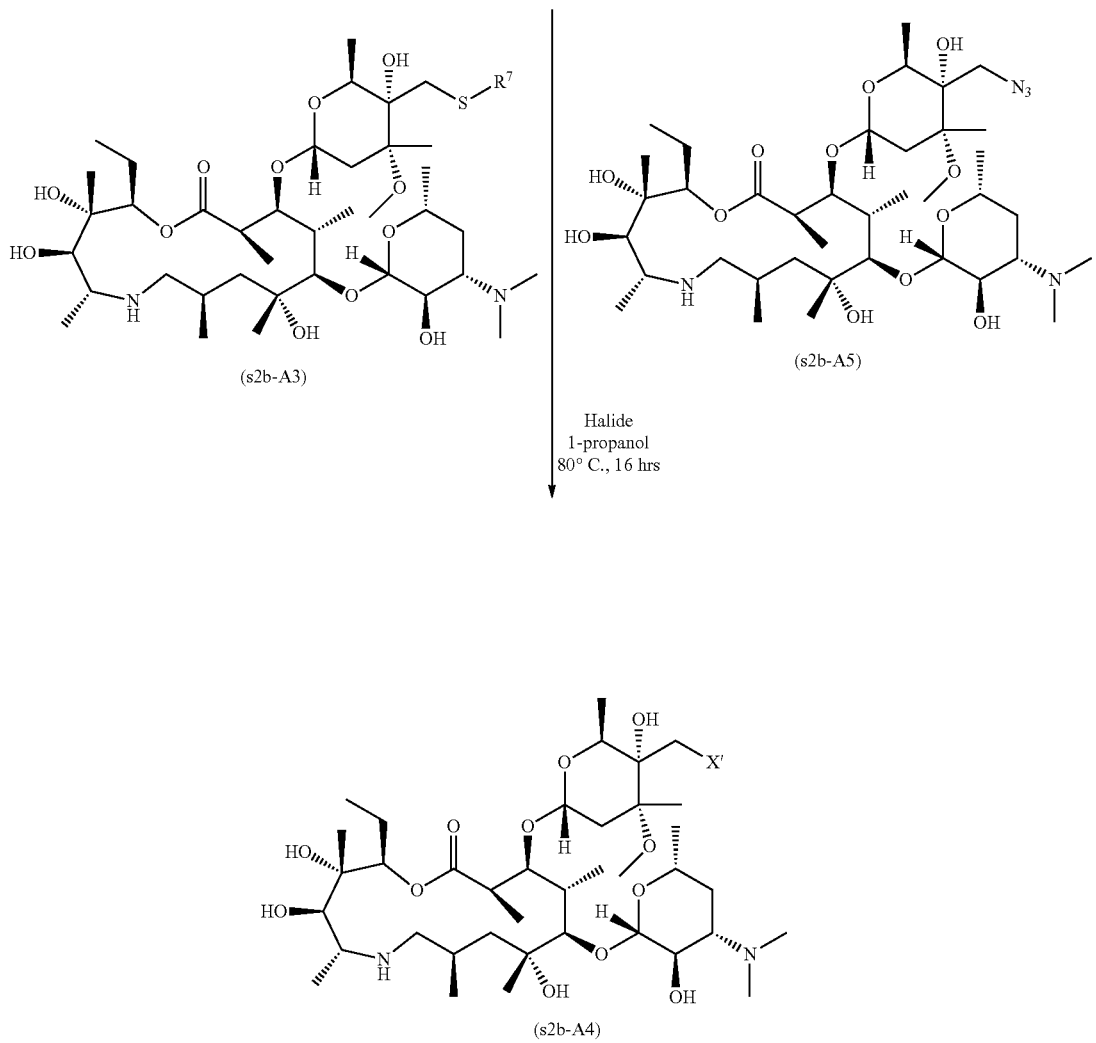

For the (s2b-A1) compounds, the epoxide functional group can be opened using different primary or secondary amines in alcoholic solvents such as but not limited to methanol, ethanol, 1-proponaol and others. For the (s2b-A2) compounds, the epoxide functional group can be opened using different alcohols used as solvents such as but not limited to methanol, ethanol, 1-proponaol and others. Mild bases such as NaHCO$_3$ or salts such as NH$_4$Cl or (NH$_4$)$_2$SO$_4$ can sometimes accelerate the epoxide opening reaction. For the (s2b-A3) compounds, the epoxide functional group can be opened using different thiols such as but not limited to ethanethiol, propanethiol, isopropyl mercaptan and others in alcoholic solvents such as but not limited to ethanol or 1-propanol. Mild bases such as NaHCO$_3$ but not limited to are used to accelerate the epoxide opening reaction. For the (s2b-A4) compounds, the epoxide functional group can be opened using different halides from reagents such as but not limited to CeCl$_3$ or Br$_2$ in alcoholic solvents such as but not limited to ethanol or 1-propanol. Mild bases such as NaHCO$_3$ or salts such as NH$_4$Cl or (NH$_4$)$_2$SO$_4$ can sometimes accelerate the epoxide opening reaction. For the (s2b-A5) compounds, the epoxide functional group can be opened by the azide ion using different sources of the azide anion such as but not limited to NaN$_3$ in alcoholic solvents such as but not limited to ethanol or 1-propanol. Mild bases such as NaHCO$_3$ or salts such as NH$_4$Cl or (NH$_4$)$_2$SO$_4$ can sometimes accelerate the epoxide opening reaction. For the (s2b-A6) compounds, the epoxide functional group can be opened by the cyanide ion using different sources of the cyanide anion such as but not limited to KCN in alcoholic solvents such as but not limited to IPA or 1-propanol. Mild bases such as NaHCO$_3$ or salts such as NH$_4$Cl or (NH$_4$)$_2$SO$_4$ can sometimes accelerate the epoxide opening reaction.

Scheme 2c: Details for Scheme 2a Step 2 (Demethylation)
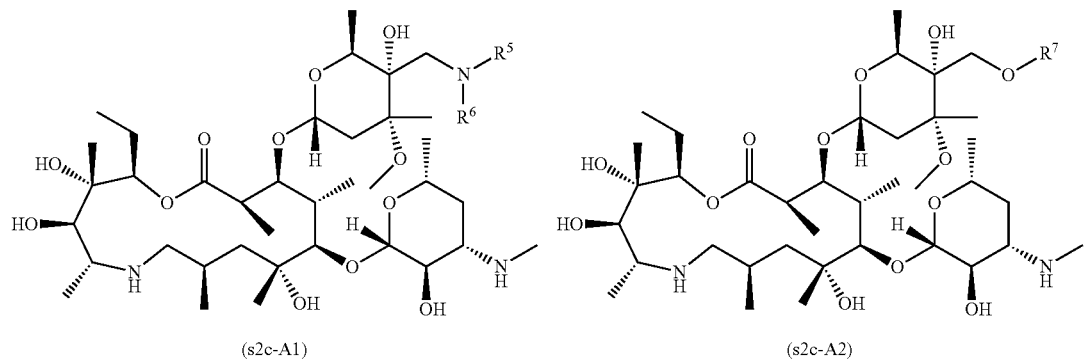
(s2c-A1)  (s2c-A2)
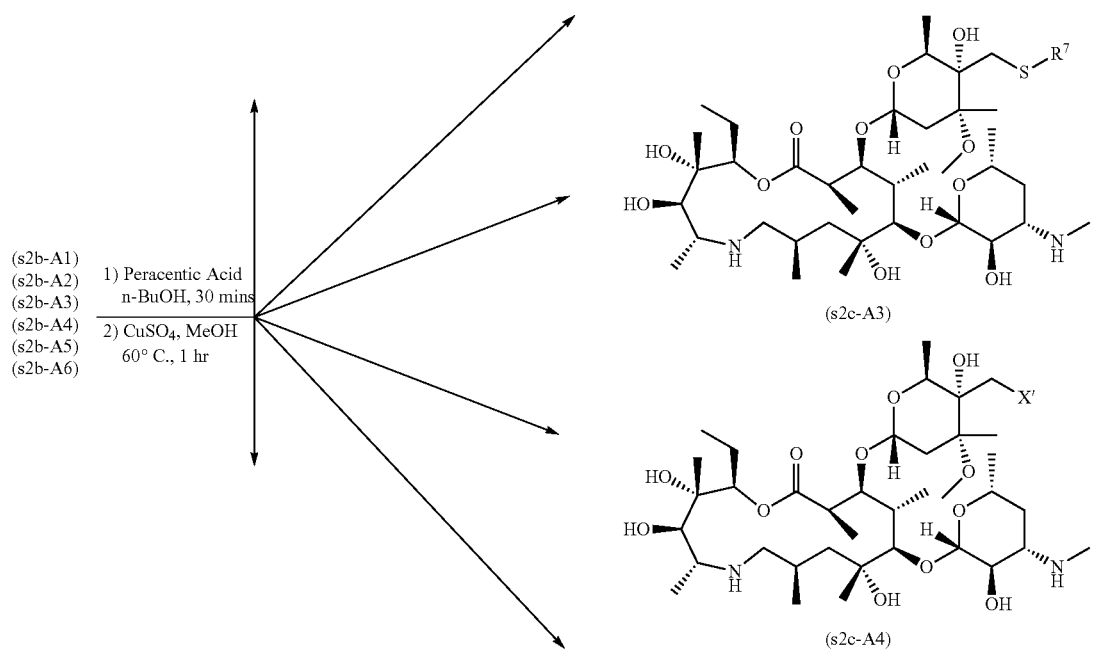
(s2b-A1)
(s2b-A2)
(s2b-A3)
(s2b-A4)
(s2b-A5)
(s2b-A6)
1) Peracentic Acid
   n-BuOH, 30 mins
2) CuSO$_4$, MeOH
   60° C., 1 hr
(s2c-A3)
(s2c-A4)
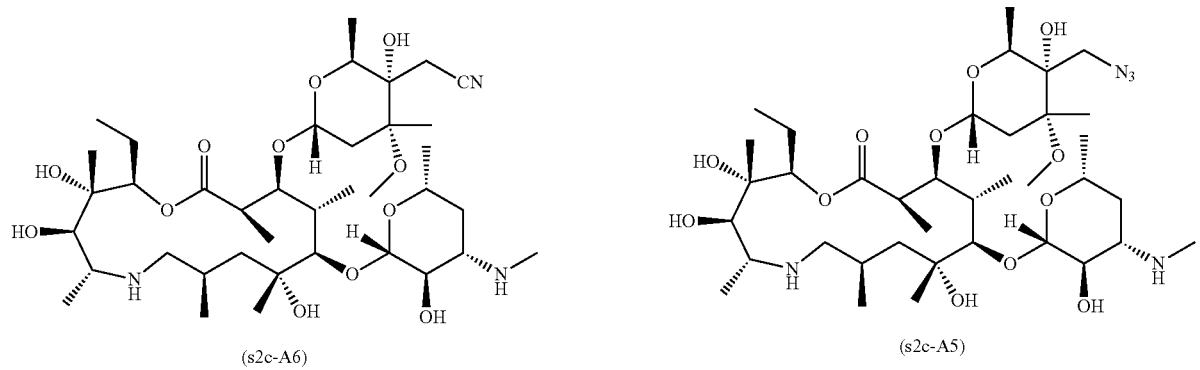
(s2c-A6)  (s2c-A5)

All compounds (s2b-A1) through (s2b-A6) can undergo a Polonovski type demethylation as described above, to give the corresponding compounds (s2c-A1) through (s2c-A6). The N-oxide can be formed using different oxidizing agents such as iodine, NIS, peracetic acid or hydrogen peroxide. The demethylation of the N-oxide can be triggered by such reagents as iron or copper salts.

Scheme 2d: Details for Scheme 2a Step 3 (Urea formation)

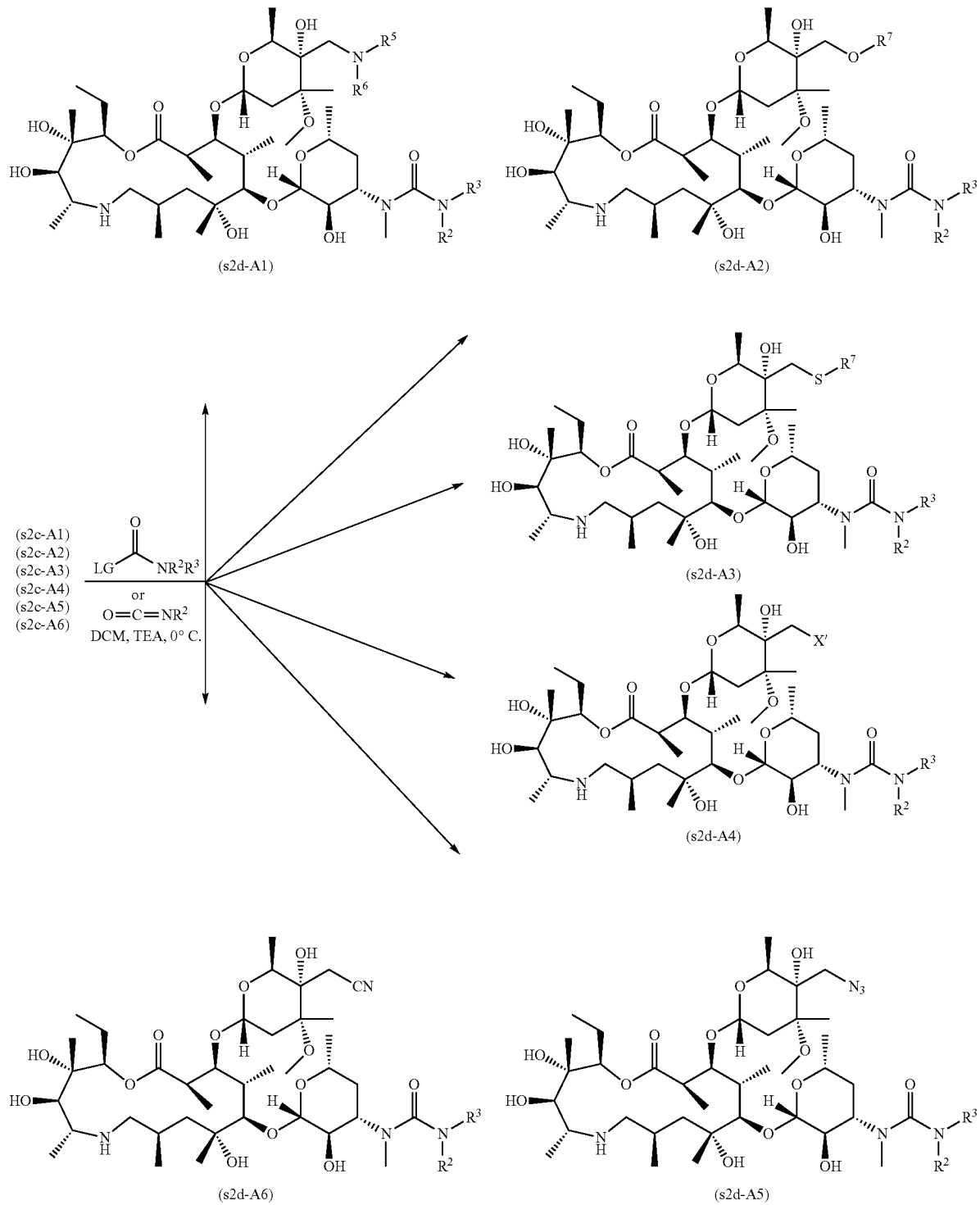

In the last step of the sequence the final analogs can be prepared by reacting the Polonovski reaction product (s2c-A #) with urea forming reagents such as but not limited to isocyanates; activated carbamoyl-chlorides, -imidazoles, —N-methyl imidazoles; p-NO₂ phenol esters, and the like. Details of this last transformation are shown in Scheme 2d above.

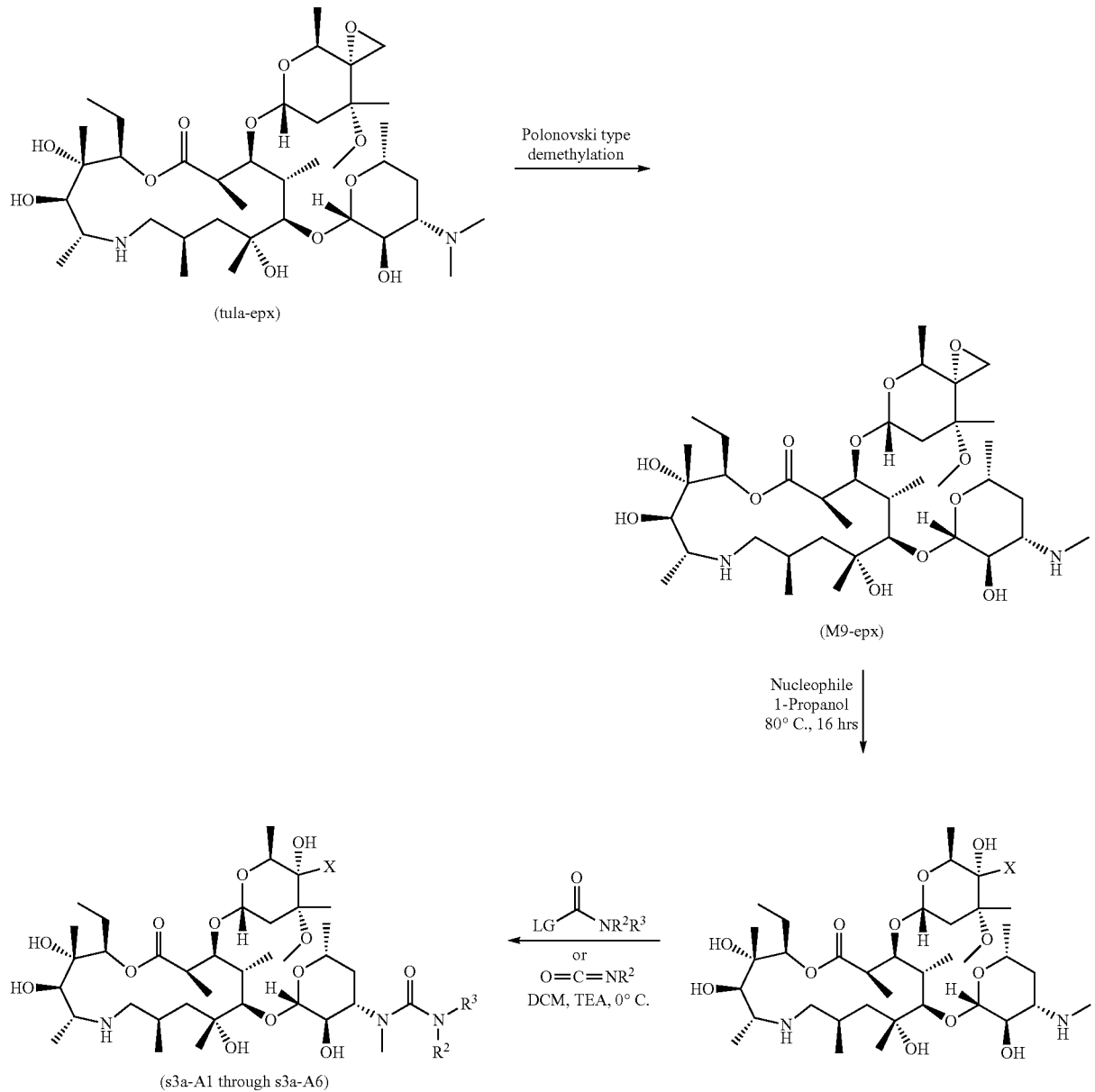

Alternatively, the analogs can be prepared as depicted in Scheme 3a. In the first step, the commercially available tulathromycin epoxide can be demethylated under but not limited to the Polonovski reaction as described above. M9-epoxide thus formed can be reacted with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol to open up the epoxide moiety. Mild bases such as NaHCO₃ or salts such as NH₄Cl or (NH₄)₂SO₄ can sometimes accelerate the epoxide opening reaction. The details of this second step are shown below in Scheme 3b. In the last step, The final urea analogs can be prepared by reacting the secondary methyl amine moiety with urea forming reagents such as but not limited to isocyanates; activated carbamoyl-chlorides, -imidazoles, —N-methyl imidazoles; p-NO₂ phenol esters, and the like. Details of this last transformation are shown in Scheme 3c below.

Scheme 3b: Details for Scheme 3a Step 2 (Nucleophilic Epoxide Opening)
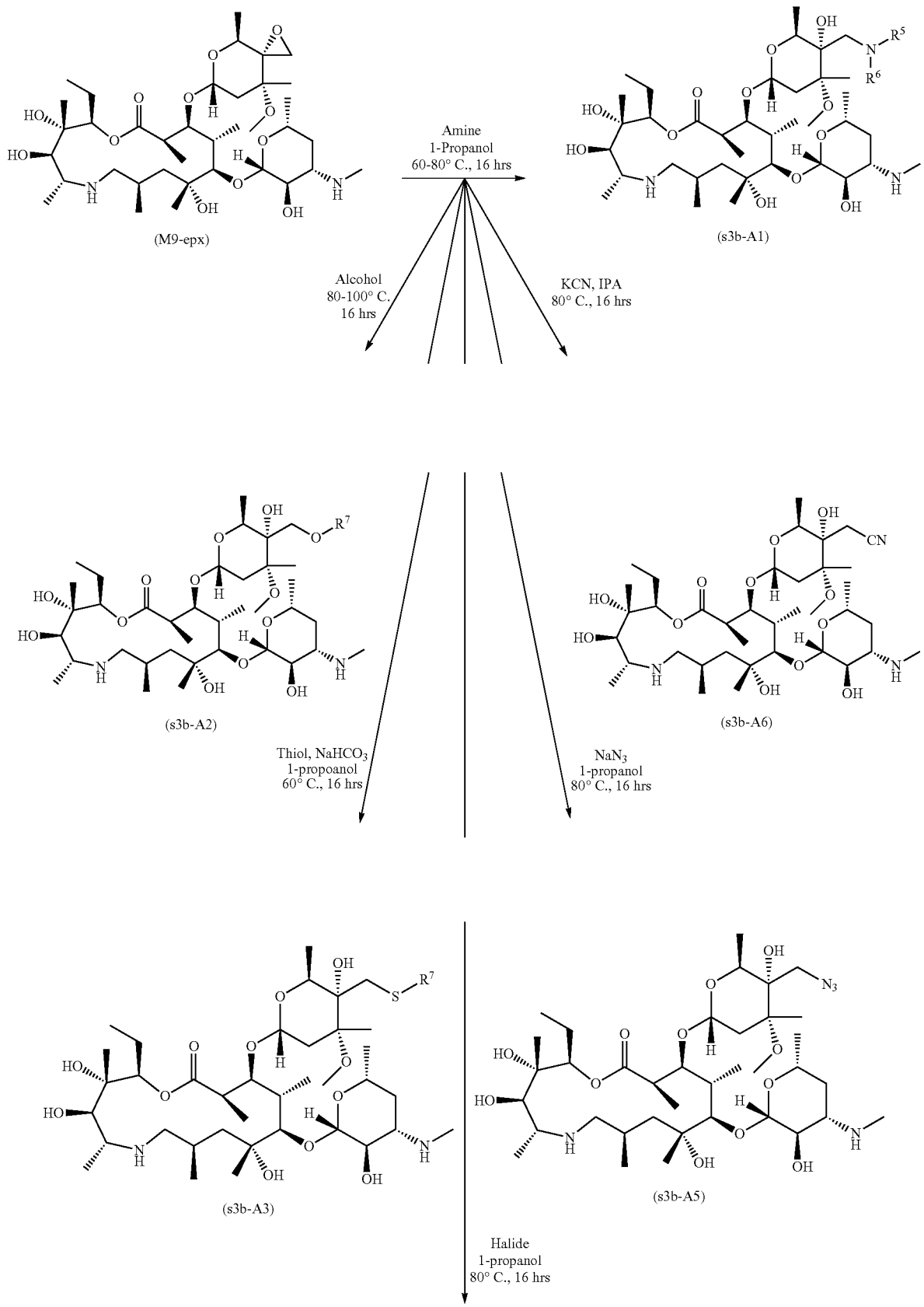

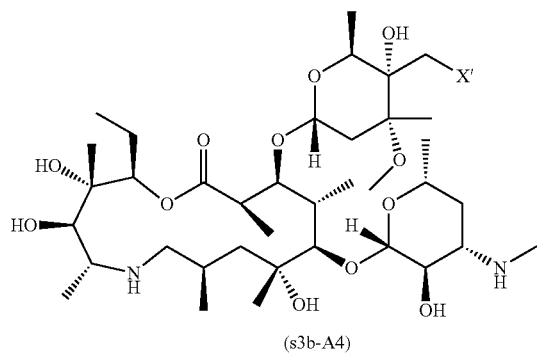

(s3b-A4)

M9-epoxide formed from the demethylation of the commercially available tulathromycin epoxide (Scheme 3a) can be reacted to give the following compounds with Formula: (s3b-A1)—with various primary or secondary amines in alcoholic solvents such as but not limited to methanol, ethanol or 1-propanol; (s3b-A2)—with various alcohols used as solvent such as but not limited to methanol, ethanol or 1-propanol. Mild bases such as NaHCO$_3$ or salts such as NH$_4$Cl or (NH$_4$)$_2$SO$_4$ can sometimes accelerate the epoxide opening reaction; (s3b-A3)—with various thiols such as but not limited to ethanethiol, propanethiol, isopropyl mercaptan and others in alcoholic solvents such as but not limited to ethanol or 1-propanol. Mild bases such as but not limited to NaHCO$_3$ are used to accelerate the epoxide opening reaction; (s3b-A4)—with halides from reagents such as but not limited to CeCl$_3$ or Br$_2$ in alcoholic solvents such as but not limited to ethanol or 1-propanol. Mild bases such as NaHCO$_3$ or salts such as NH$_4$Cl or (NH$_4$)$_2$SO$_4$ can sometimes accelerate the epoxide opening reaction; (s3b-A5)—with the azide anion from sources such as but not limited to NaN$_3$ in alcoholic solvents such as but not limited to ethanol or 1-propanol. Mild bases such as NaHCO$_3$ or salts such as NH$_4$Cl or (NH$_4$)$_2$SO$_4$ can sometimes accelerate the epoxide opening reaction; and (s3b-A6)—with the cyanide anion from sources such as but not limited to KCN in alcoholic solvents such as but not limited to IPA or 1-propanol. Mild bases such as NaHCO$_3$ or salts such as NH$_4$Cl or (NH$_4$)$_2$SO$_4$ can sometimes accelerate the epoxide opening reaction.

Scheme 3c: Details for Scheme 3a Step 3 (Urea formation)

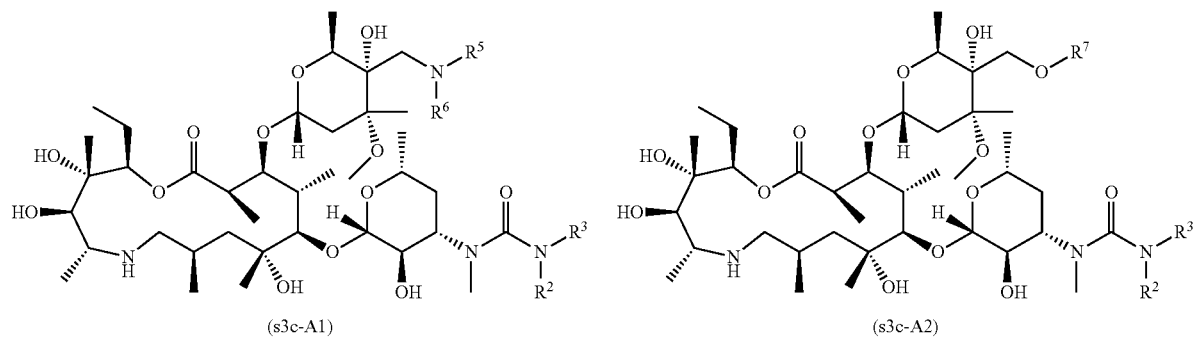

(s3c-A1)       (s3c-A2)

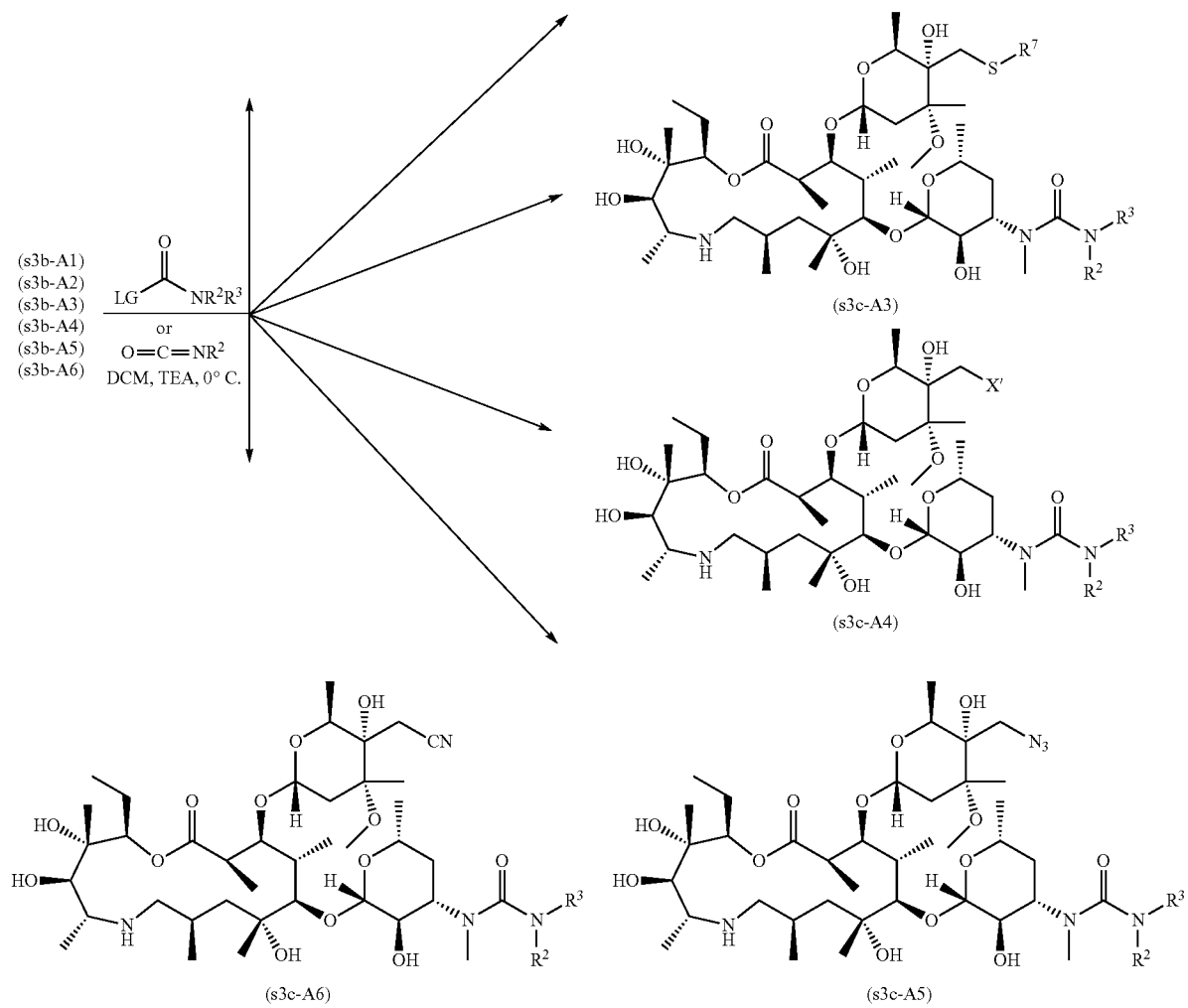

In the last step of the sequence, the final analogs of Formula (s3c-A1) through (s3c-A6) can be prepared by reacting the respective (s3b-A #) analogs with urea forming reagents such as but not limited to isocyanates; activated carbamoyl-chlorides, -imidazoles, —N— methyl imidazoles; p-NO$_2$ phenol esters, and the like in aprotic solvents such as DCM and mild bases such as but not limited to TEA or DIPEA.

Scheme 4a. Preparation of Urea Compounds (1-A1) through (1-A6)

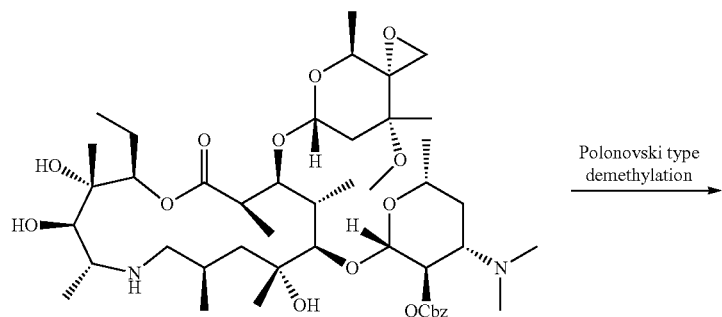

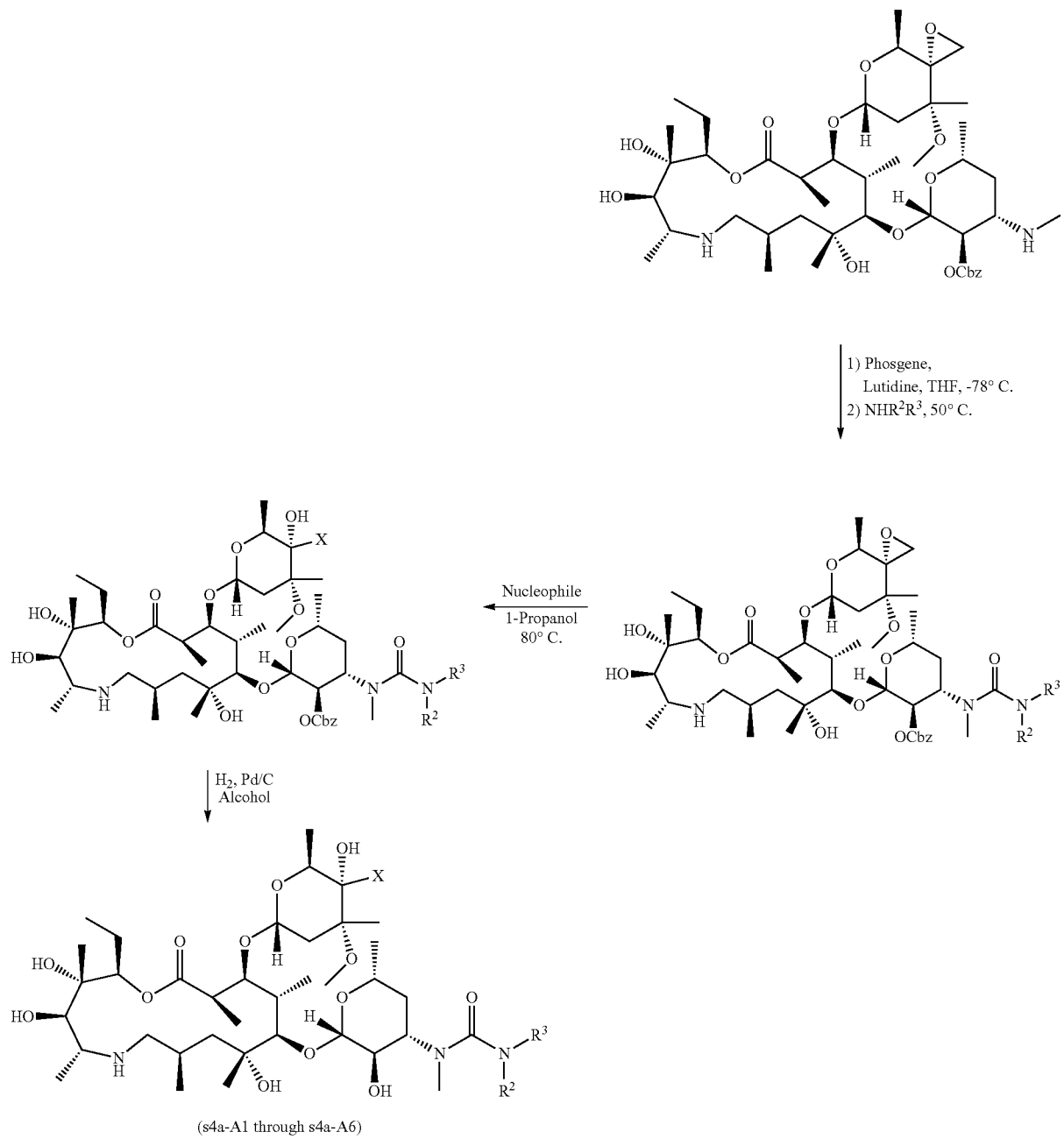

(s4a-A1 through s4a-A6)

Alternatively, the ureas can be prepared according to Scheme 4a. This 4-step synthesis starts with the commercially available benzyloxycarbonyl (Cbz) protected tulathromycin epoxide. In the first step, the dimethylamine moiety on the desosamine sugar is demethylated using Polonovski type conditions defined herein. In the second step, the secondary methyl amine is activated with phosgene in the presence of a mild base such as lutidine and quenched in situ with the desired amines to form the urea functional group. In the subsequent step, the epoxide moiety is opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol. This reaction can be completed overnight. Mild bases such as $NaHCO_3$ or salts such as $NH_4Cl$ or $(NH_4)_2SO_4$ can sometimes accelerate the epoxide opening reaction. The details of this third step are presented in the scheme 4b below. The final analogs are revealed by removing the Cbz protecting group under catalytic Pd/C mediated hydrogenolysis with $H_2$ gas in an alcoholic solvent such as ethanol, methanol, or trifluoroethanol. The details of this last step are shown in the Scheme 4c below.

Scheme 4b: Details for Scheme 4a Step 3 (Nucleophilic Expoxide Opening)
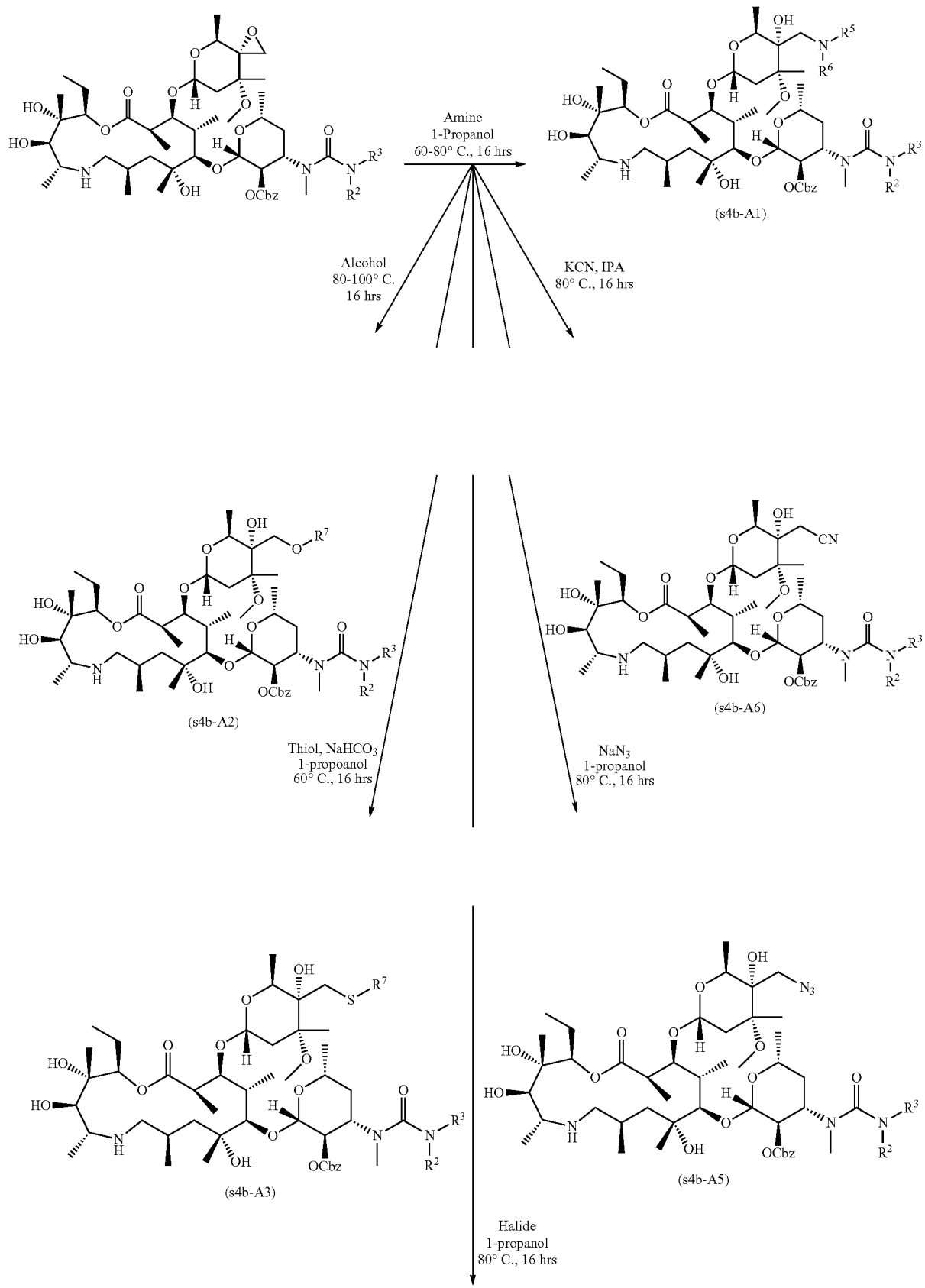

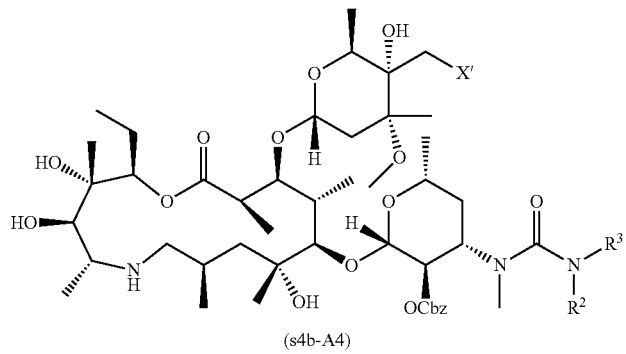

(s4b-A4)

OCbz urea epoxide can be reacted to give the following compounds with Formula: (s4b-A1)—with various primary or secondary amines in alcoholic solvents such as but not limited to methanol, ethanol or 1-propanol; (s4b-A2)—with various alcohols used as solvent such as but not limited to methanol, ethanol or 1-propanol. Mild bases such as $NaHCO_3$ or salts such as $NH_4Cl$ or $(NH_4)_2SO_4$ can sometimes accelerate the epoxide opening reaction; (s4b-A3)—with various thiols such as but not limited to ethanethiol, propanethiol, isopropyl mercaptan and others in alcoholic solvents such as but not limited to ethanol or 1-propanol. Mild bases such as but not limited to $NaHCO_3$ are used to accelerate the epoxide opening reaction; (s4b-A4)—with halides from reagents such as but not limited to $CeCl_3$ or $Br_2$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction; (s4b-A5)—with the azide anion from sources such as but not limited to $NaN_3$ in alcoholic solvents such as but not limited to ethanol or 1-propanol. Mild bases such as $NaHCO_3$ or salts such as $NH_4Cl$ or $(NH_4)_2SO_4$ can sometimes accelerate the epoxide opening reaction; and (s4b-A6)—with the cyanide anion from sources such as but not limited to KCN in alcoholic solvents such as but not limited to IPA or 1-propanol. Mild bases such as $NaHCO_3$ or salts such as $NH_4Cl$ or $(NH_4)_2SO_4$ can sometimes accelerate the epoxide opening reaction.

Scheme 4c: Details for Scheme 3a Step 4 (Deprotection)

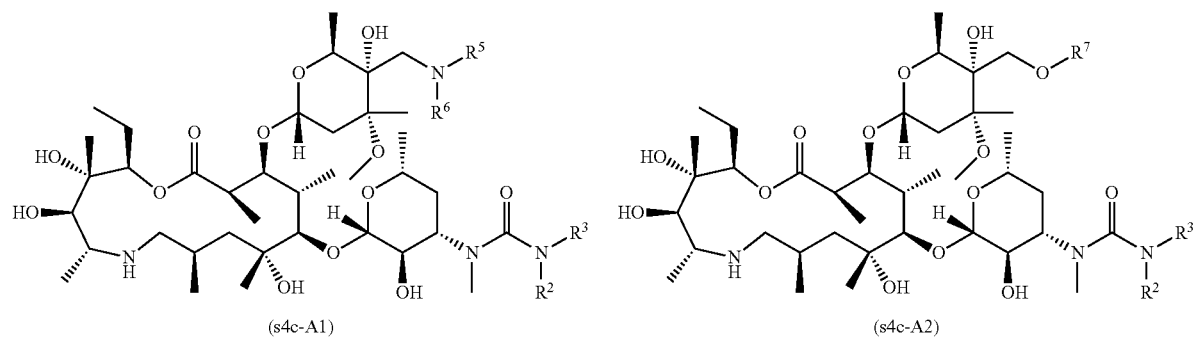

(s4c-A1)            (s4c-A2)

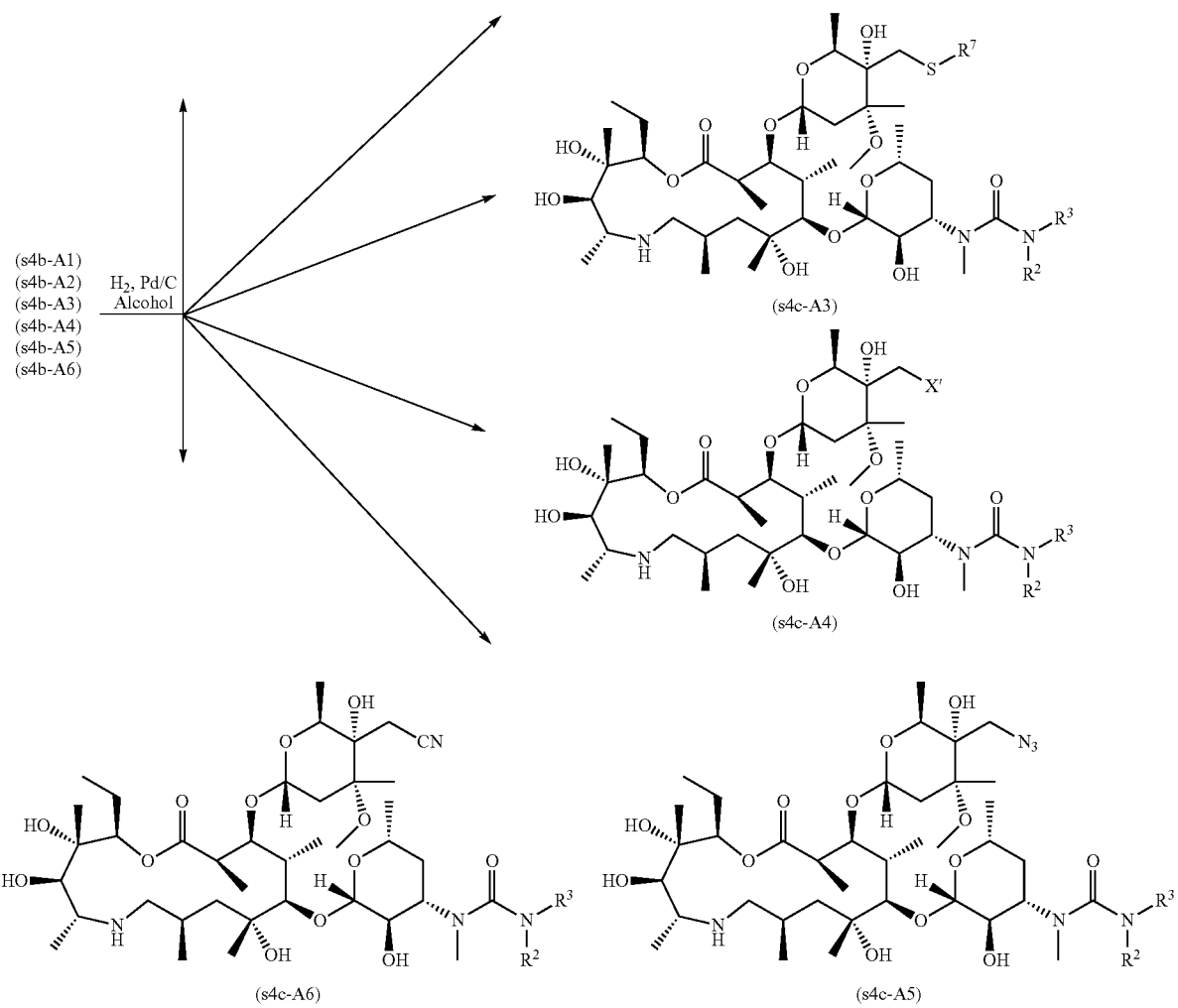
In the last step of the sequence, the final analogs of Formula (s4c-A1) through (s4c-A6) can be prepared by deprotecting the Cbz protecting groups on the respective (s4b-A #) analogs under hydrogenation conditions with catalytic amounts of Pd/C in alcoholic solvents.
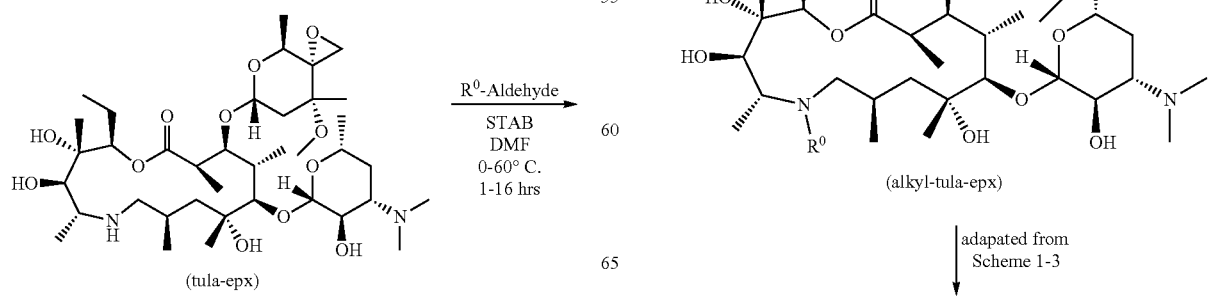

95
-continued

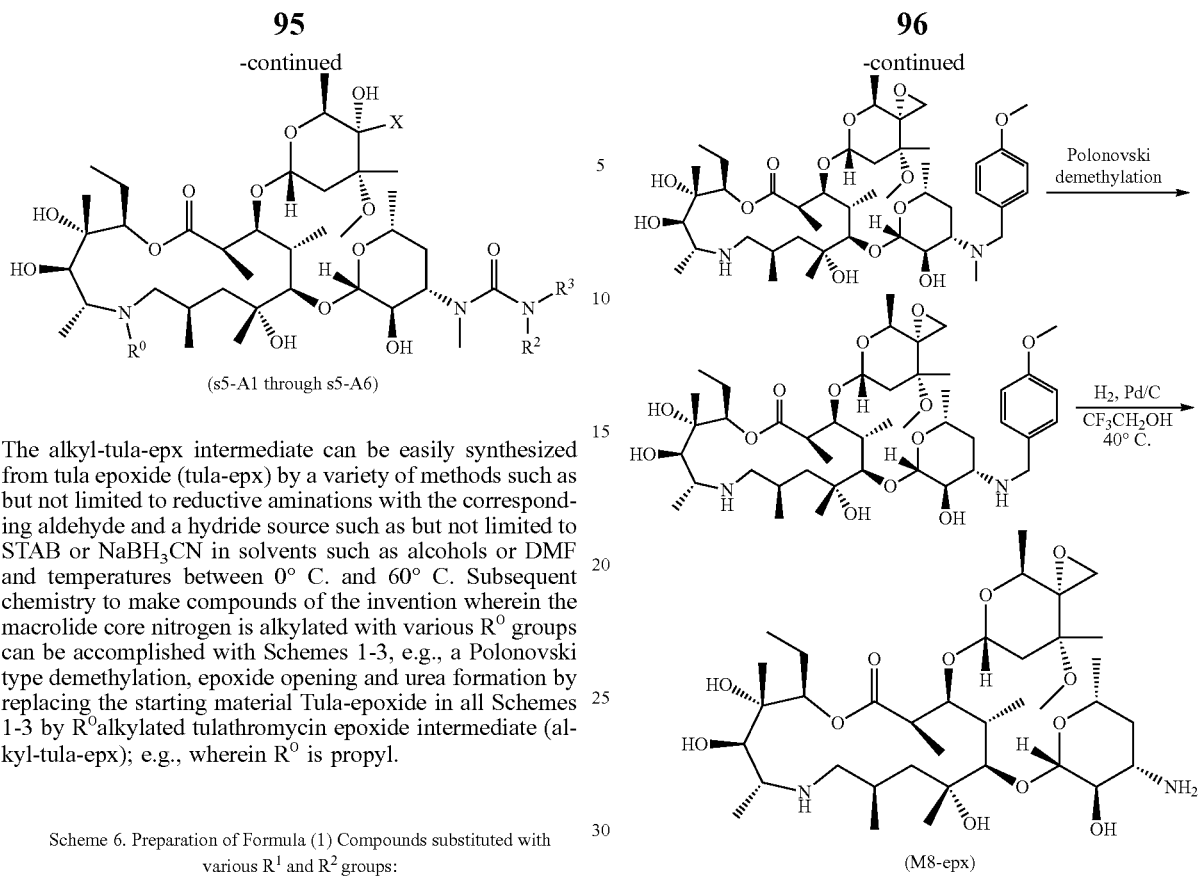

(s5-A1 through s5-A6)

The alkyl-tula-epx intermediate can be easily synthesized from tula epoxide (tula-epx) by a variety of methods such as but not limited to reductive aminations with the corresponding aldehyde and a hydride source such as but not limited to STAB or $NaBH_3CN$ in solvents such as alcohols or DMF and temperatures between 0° C. and 60° C. Subsequent chemistry to make compounds of the invention wherein the macrolide core nitrogen is alkylated with various $R^0$ groups can be accomplished with Schemes 1-3, e.g., a Polonovski type demethylation, epoxide opening and urea formation by replacing the starting material Tula-epoxide in all Schemes 1-3 by $R^0$alkylated tulathromycin epoxide intermediate (alkyl-tula-epx); e.g., wherein $R^0$ is propyl.

Scheme 6. Preparation of Formula (1) Compounds substituted with various $R^1$ and $R^2$ groups:
Preparation of a common intermediate M8 epoxide (M8-epx)

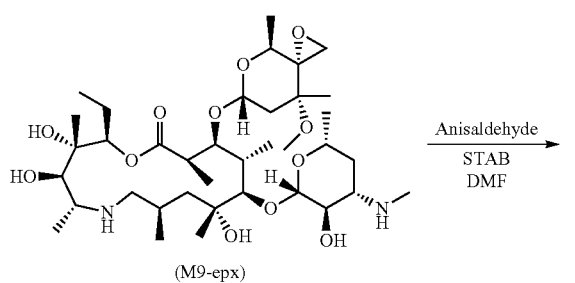

(M9-epx)

96
-continued

The (M8-epx) intermediate can be easily synthesized from M9 epoxide by a variety of methods such as a second demethylation with 12 and NaOMe or a triple sequence where M9 epoxide is first protected with a 4-OMe benzyl group and then demethylated using a Polonovski demethylation. M8 epoxide is revealed by removing the protecting group under hydrogenolysis conditions using Pd/C and $H_2$ gas in alcoholic solvents such as but not limited to methanol, ethanol or trifluoroethanol. M8 epoxide can be used in various ways to prepare compounds of the invention as shown in the Scheme 7 below.

Scheme 7. Preparation of Formula (1) Compounds substituted with various $R^1$ groups from M8 epoxide (M8-epx)

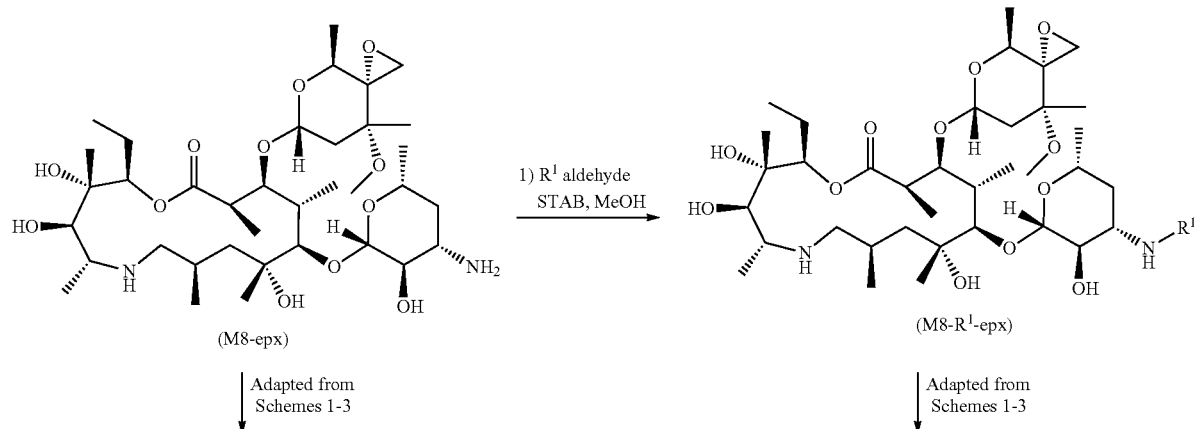

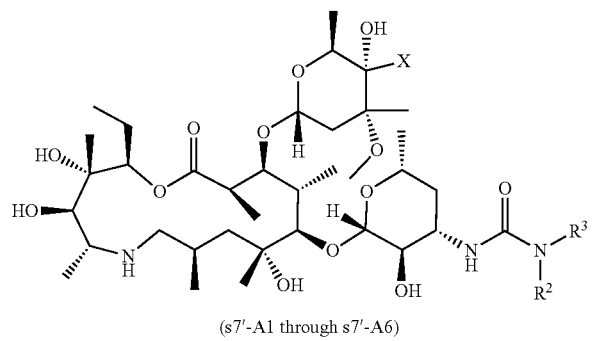

(s7'-A1 through s7'-A6)

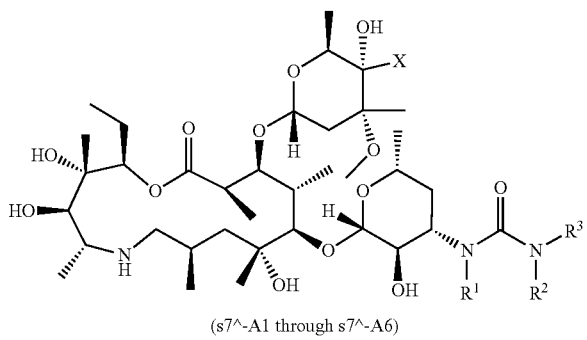

(s7^-A1 through s7^-A6)

M8 epoxide can be reacted with urea forming reagents such as but not limited to isocyanates; activated carbamoyl-chlorides, -imidazoles, —N-methyl imidazoles; p-NO₂ phenol esters, and the like in aprotic solvents such as DCM and mild bases such as but not limited to TEA or DIPEA as shown on Scheme 7 to give compounds of the invention (s7'-A1) through (s7'-A6) after the opening of the epoxide. This chemistry is an adaptation of the chemistries described in Schemes 1-3.

M8 epoxide can also undergo a reductive amination with the corresponding $R^1$ aldehyde and a hydride source such as but not limited to STAB or NaBH₃CN in solvents such as alcohols, DMF, DCM or DCE and temperatures between 0° C. and 60° C. Subsequent chemistry to make compounds of the invention wherein $R^1$ is not CH₃ as in the tulathromycin derived analogs can be accomplished by adapting the chemistry from schemes 1-3 shown herein, to form the urea on the desosamine Nitrogen and open the cladinose epoxide with various nucleophiles. The urea functional group can be installed by using different urea forming reagents such as but not limited to isocyanates; activated carbamoyl-chlorides, -imidazoles, —N-methyl imidazoles; p-NO₂ phenol esters, and the like in aprotic solvents such as DCM and mild bases such as but not limited to TEA or DIPEA whereas the epoxide can be opened up using different nucleophiles such as primary and secondary amines, alcohols, thiols, cyanide, azide or halogen anions and others at higher temperature in alcoholic solvents such as but not limited to 1-propanol, 1-butanol or 2-propanol as shown on Scheme 7 to give compounds of the invention (s7^-A1) through (s7^-A6).

Scheme 8. Preparation of Formula (1-A0)
Compounds of Formula (1) by Reductive Amination from Azithromycin

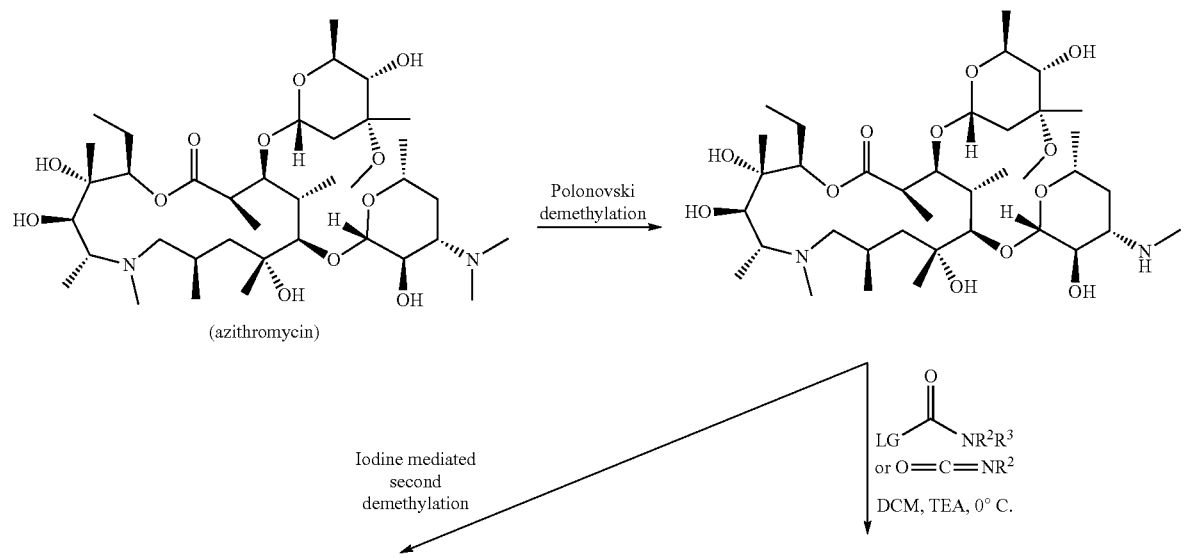

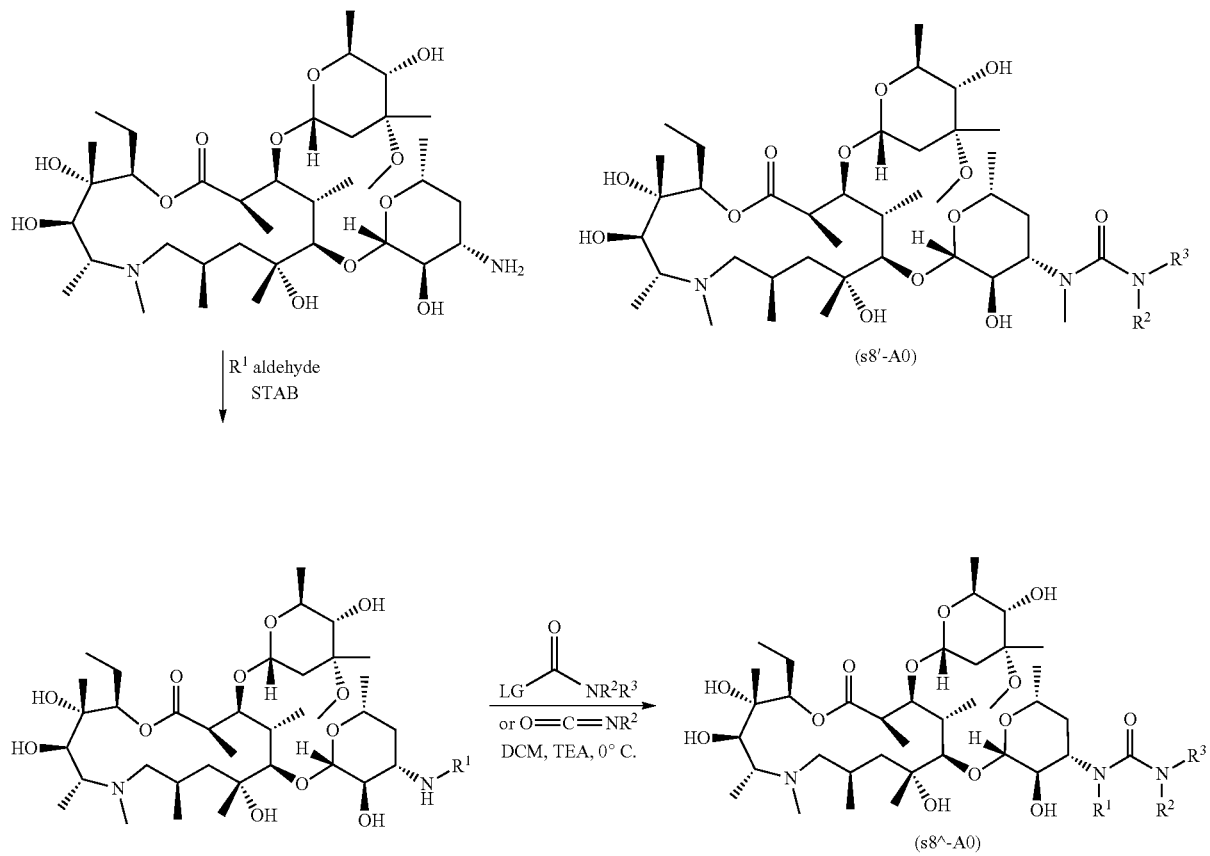

Azithromycin can be used as a starting material for the synthesis of Formula (1) compounds of the invention as shown in Scheme 8. Azithromycin can undergo a demethylation reaction similar to tulathromycin under similar conditions such as but not limited to the Polonovski reaction defined herein. Demethylated azithromycin can be reacted with urea forming reagents such as but not limited to isocyanates; activated carbamoyl-chlorides, -imidazoles, —N-methyl imidazoles; p-NO$_2$ phenol esters, and the like in aprotic solvents such as DCM and mild bases such as but not limited to TEA or DIPEA as shown on Scheme 8 to give compounds of the invention (s8'-A0). Moreover, des-methyl azithromycin can undergo a second demethylation as described above using I$_2$ and NaOMe followed by reductive amination with R$^1$ corresponding aldehydes. Compounds of the invention (s8^-A0) can be synthesized by reacting the double demethylated azithromycin with urea forming reagents such as but not limited to isocyanates; activated carbamoyl-chlorides, -imidazoles, —N-methyl imidazoles; p-NO$_2$ phenol esters, and the like in aprotic solvents such as DCM and mild bases such as but not limited to TEA or DIPEA as shown on Scheme 8.

Scheme 9. Preparation of Formula (1.1) Des-cladinose Compounds

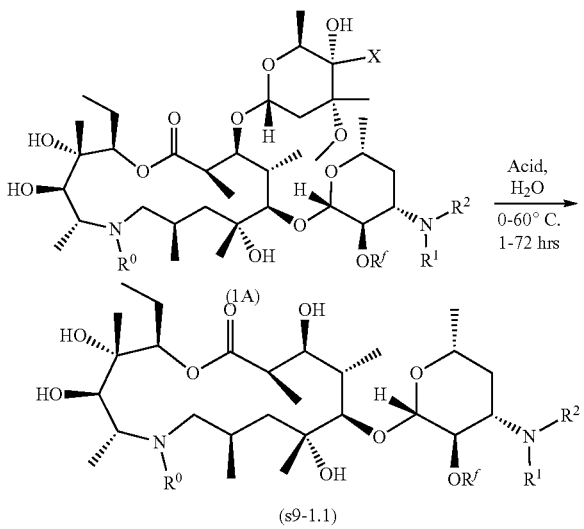

Des-cladinose compounds of Formula (1.1) can be easily synthesized from Formula (1A) compounds, by stirring said compound in aqueous acetic acid or hydrochloric acid at temperatures between 0° C. and 60° C. in solvents such as but not limited to THF, MeCN or H$_2$O for 1 to 72 hours as shown in Scheme 9.

Scheme 10. Preparation of Formula (1.1) Des-cladinose Compounds

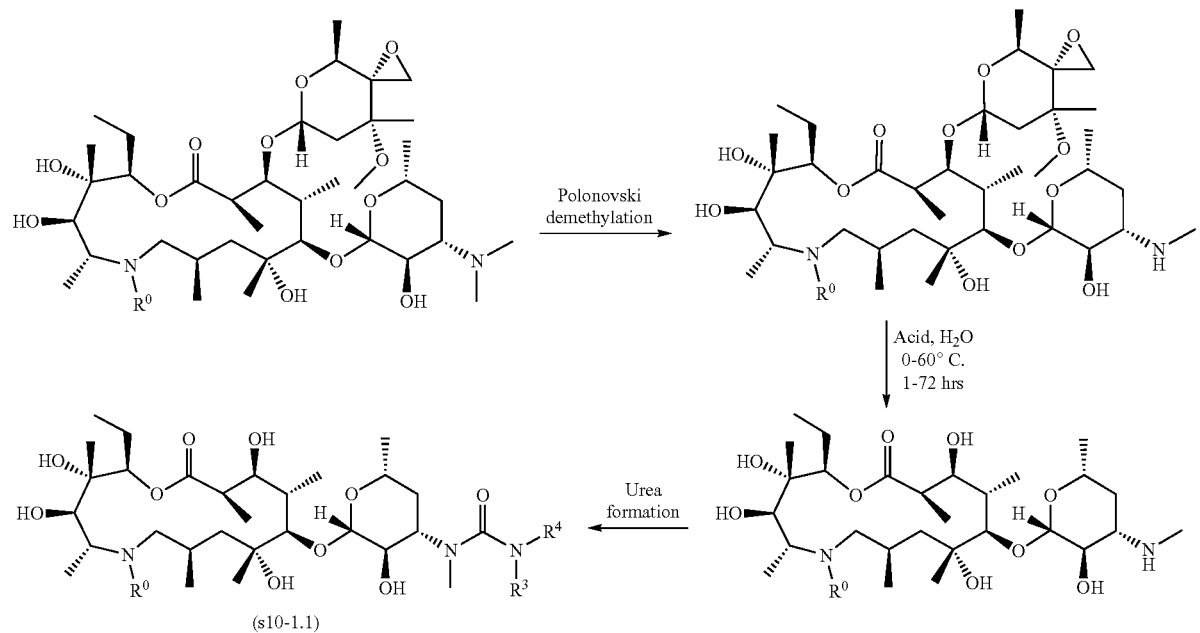

(s10-1.1)

Des-cladinose urea compounds of Formula (1.1) can also be synthesized according to the sequence shown in Scheme 10. Tulathromycin epoxide (tula epx) or N-core substituted Tula epoxide (alkyl tula epoxide synthesized as shown in Scheme 5) can be demethylated according to the Polonovski demethylation conditions described herein. The cladinose sugar of des-methyl product can be cleaved off under aqueous acidic conditions with acids such as acetic or hydrochloric and others in solvents such as THF or acetonitrile. The urea functionality can be installed using urea forming reagents such as but not limited to isocyanates; activated carbamoyl-chlorides, -imidazoles, —N-methyl imidazoles; p-$NO_2$ phenol esters, and the like in aprotic solvents such as DCM and mild bases such as but not limited to TEA or DIPEA as shown on Scheme 10 to give the desired des-cladinose urea compounds of the invention (s10-1.1).

EXAMPLES

Preparation of des-cladinose Example A-13 of Formula (1.1)

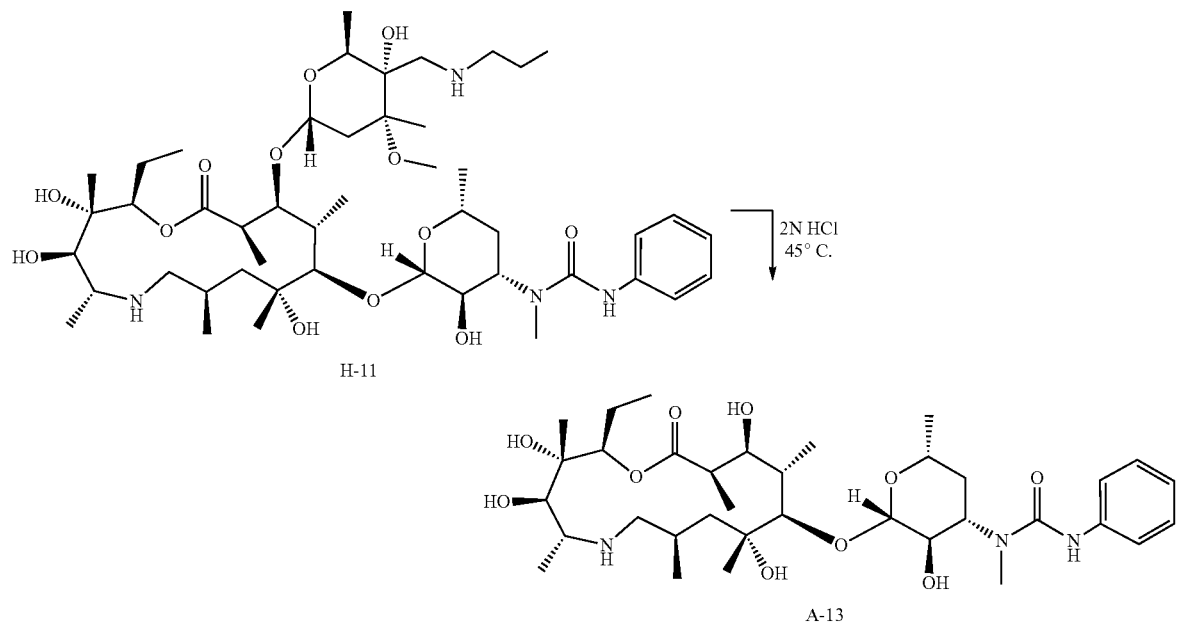

To crude example H-11 (600.0 mg) was added 2N HCl (10.0 mL) and the resulting mixture was heated at 45° C. for 2 hours before being cooled to room temperature. The crude reaction mixture was poured into an ice cooled solution of NH$_4$OH (pH>7), stirred for 5 minutes, then concentrated and lyophilized. The crude material was purified by Prep HPLC using ammonium acetate as a buffer and the purified material was passed through an SCX column to afford the product as the free base.

Formula (1.1) compounds can be made similarly to that shown above for Example A-13 under similar conditions but for the Formula (1-A1) starting materials.

Preparation of Example B-6 of Formula (1-A0); that is an Application of Scheme 8

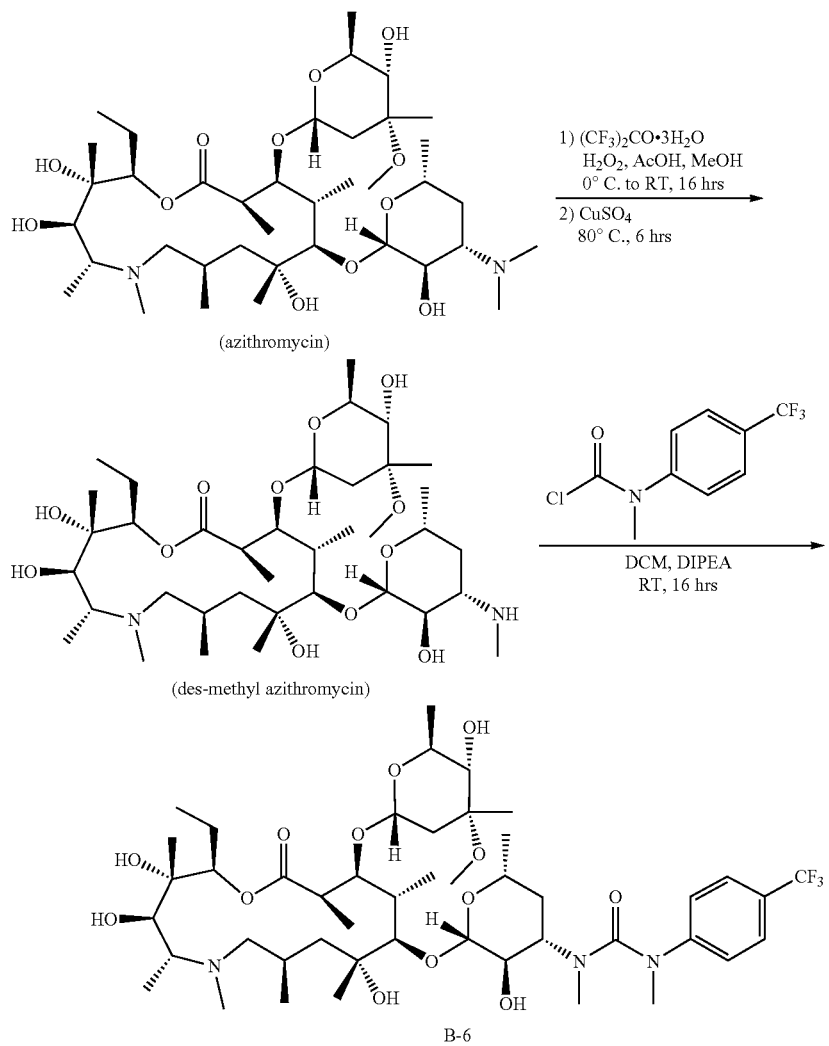

condenser and the reaction mixture was stirred at 80° C. for 6 h under N$_2$ atmosphere. The reaction mixture was then cooled to room temperature, concentrated to remove MeOH and diluted with DCM (300 mL). The solution was filtered through celite and the filtrate was basified to pH 10 using aqueous ammonia solution. The organic phase was separated, washed with water and brine, dried over anhydrous Na$_2$SO$_4$ and concentrated to obtain the crude material. The crude material was triturated with pentane-diethyl ether (2:1) solution to obtain the desired demethylated azithromycin as an off-white solid (13 g, 66.2%).

Step 2: To a stirred solution of des-methyl azithromycin (300 mg, 0.408 mmol, 1 eq) in dry DCM (5 mL) was added N-methyl-N-[4-(trifluoromethyl)phenyl]carbamoyl chloride (107 mg, 0.449 mmol, 1.1 eq) and Et$_3$N (0.083 mL, 0.82

Step 1: To a 500 mL round bottom flask was added azithromycin (20 g, 26.77 mmol, 1 eq) in MeOH (40 mL) and glacial acetic acid (3.4 mL, 53.54 mmol, 2.2 eq), hexafluoroacetone (1.9 mL, 13.38 mmol, 0.5 eq) and H$_2$O$_2$ (30% w/w in H$_2$O, 5 mL) sequentially at 0° C. under a N$_2$ atmosphere. The reaction mixture was stirred at RT (25° C.) for 16 h before anhydrous CuSO$_4$ (6.4 g, 40.15 mmol, 1.5 eq) was added. The round bottom was equipped with a reflux condenser and the reaction mixture was stirred at 80° C. for mmol, 2 eq) at RT. The reaction mixture was stirred at RT for 12 hours after which the LCMS analysis showed full conversion of the starting material. The mixture was concentrated under reduced pressure, and the crude was purified on C$_{18}$ silica using reverse flash chromatography with 1.0% AcOH as the modifier (0 to 100% MeCN in H$_2$O). The desired fractions were lyophilized to give the desired urea product as a white solid acetate salt (260 mg, 64%).

Formula (1-A0) compounds can be made similarly to that shown above (B-6) under similar conditions by either varying the urea forming reagent or the starting material and using tulathromycin epoxide instead of azithromycin.

Preparation of Example C-1 of Formula (1-A2)

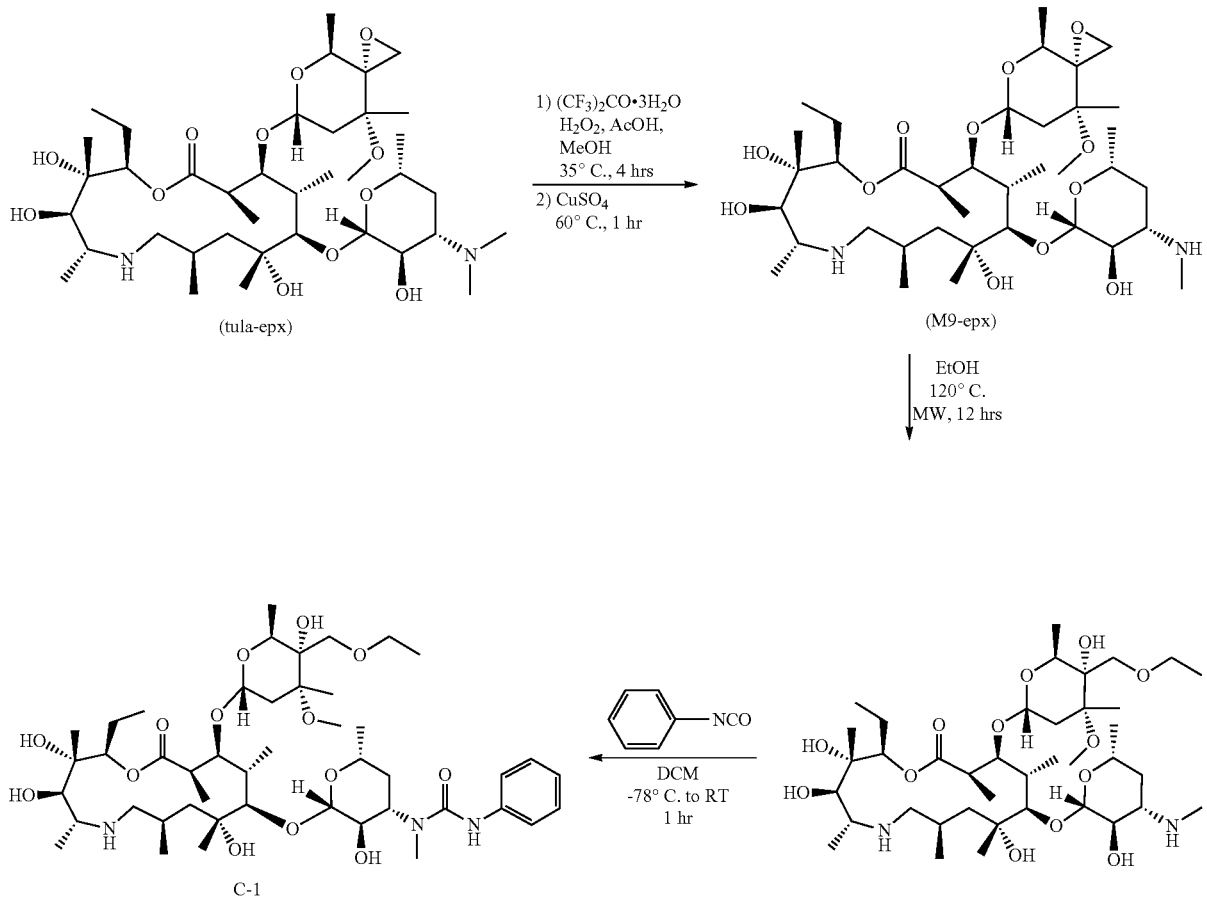

Step 1: A solution of tula-epx (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL H₂O were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: M9 epoxide (M9-epx; 1.00 g, 1.36 mmol, 1.0 eq) was dissolved in 10 mL dry EtOH in a pressure MW vial. The resulting solution was heated to 120° C. in a microwave reactor for 12 hours. The volatiles were then removed under reduced pressure and the crude was purified on $C_{18}$ silica using reverse flash chromatography with 1.0% AcOH as the modifier (0 to 100% MeCN in H₂O The fractions containing the desired product were combined, the pH was adjusted to pH~12 with NH₄OH and extracted 3 times with 50 mL DCM to give the desired product as a free base (220 mg, 20%).

Step 3: The product from Step 2 (0.14 mmol, 110 mg, 1.00 eq) was dissolved in DCM (5 ml) and cooled to −78° C. followed by the addiction of phenyl isocyanate (1.0 eq, 16 uL, 0.14 mmol) and the reaction was left to warm up to RT under stirring over 60 minutes. After completion of the reaction as judged by LCMS analysis, the volatiles were removed under a stream of N₂ and the crude purified by $C_{18}$ reverse flash chromatography with 0.5% AcOH as modifier (0 to 100% MeCN in H₂O). The fractions containing the desired product were lyophilized to give the desired product as the acetate salt (15 mg, 11%).

Preparation of Example D-2 of Formula (1-A3)

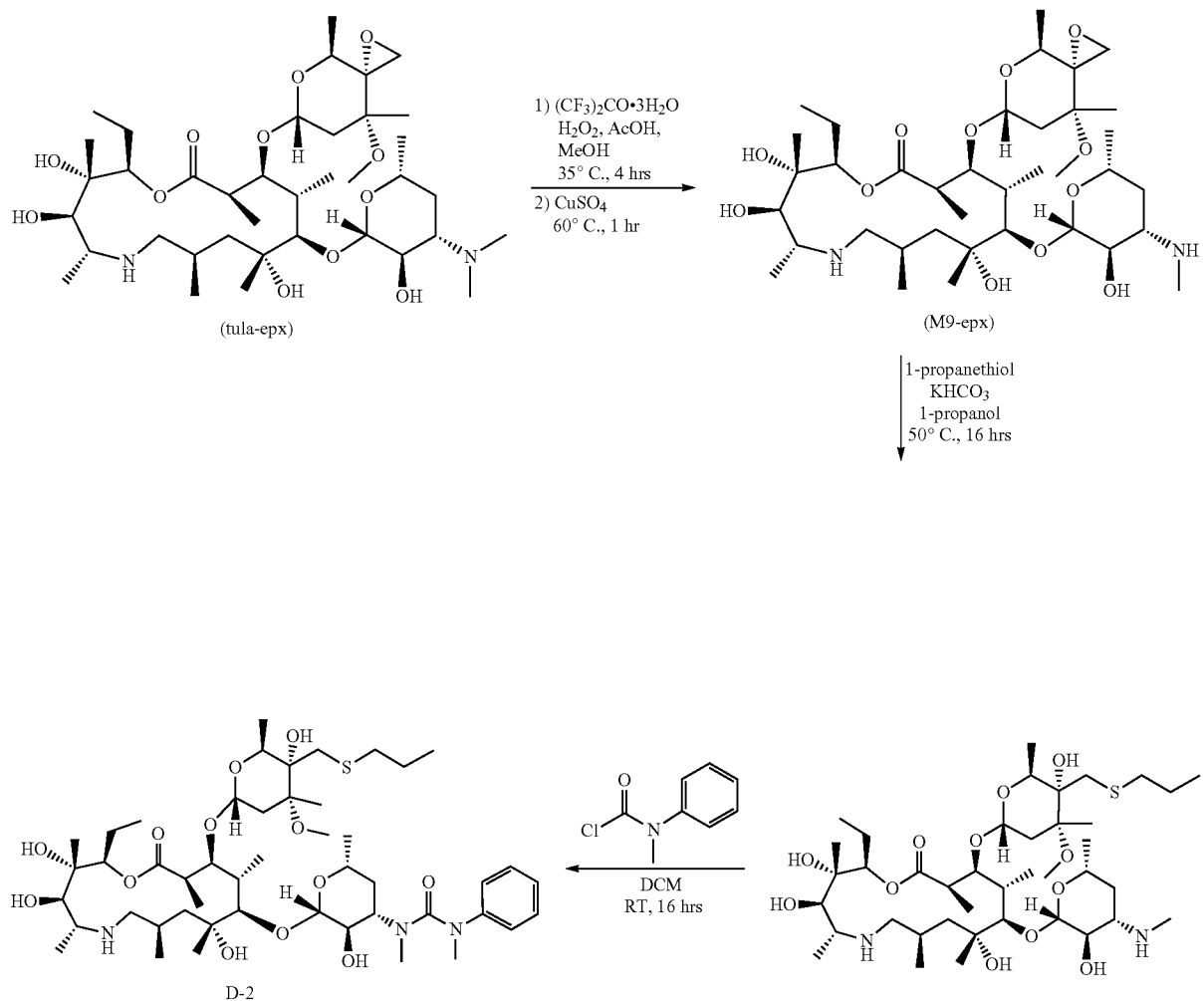

Step 1: A solution of tula-epx (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: M9 epoxide (M9-epx 1.00 g, 1.36 mmol, 1.0 eq) was dissolved in 10 mL dry 1-propanol in a 25 mL round bottom flask. Potassium bicarbonate (3.0 eq, 4.1 mmol, 410 mg) was added followed by 1-propanethiol (5.0 eq, 6.8 mmol, 640 ul) and the resulting solution was heated to 50° C. overnight after which the LCMS analysis showed consumption of the starting material. The reaction mixture was diluted with 20 mL DCM and $H_2O$ and the pH was adjusted to pH~12 with $NH_4OH$ and extracted 3 times with 30 mL DCM to give the desired product as a free base (1053 mg, 95%) and used as is in the following step.

Step 3: The product from Step 2 (0.25 mmol, 200 mg, 1.0 eq) was dissolved in DCM (5 ml) and TEA (2.0 eq, 70 μL, 0.49 mmol) followed by N-methyl-N-phenyl-carbamoyl chloride (1.0 eq, 42 mg, 0.25 mmol) were added and the resulting solution was stirred at RT overnight. After completion of the reaction as judged by LCMS analysis, the volatiles were removed under a stream of $N_2$ and the crude purified by $C_{18}$ reverse flash chromatography with 0.5% AcOH as modifier (0 to 100% MeCN in $H_2O$). The fractions containing the desired product were lyophilized to give the desired product as the acetate salt (135 mg, 55%).

Preparation of Example E-3 of Formula (1-A4)

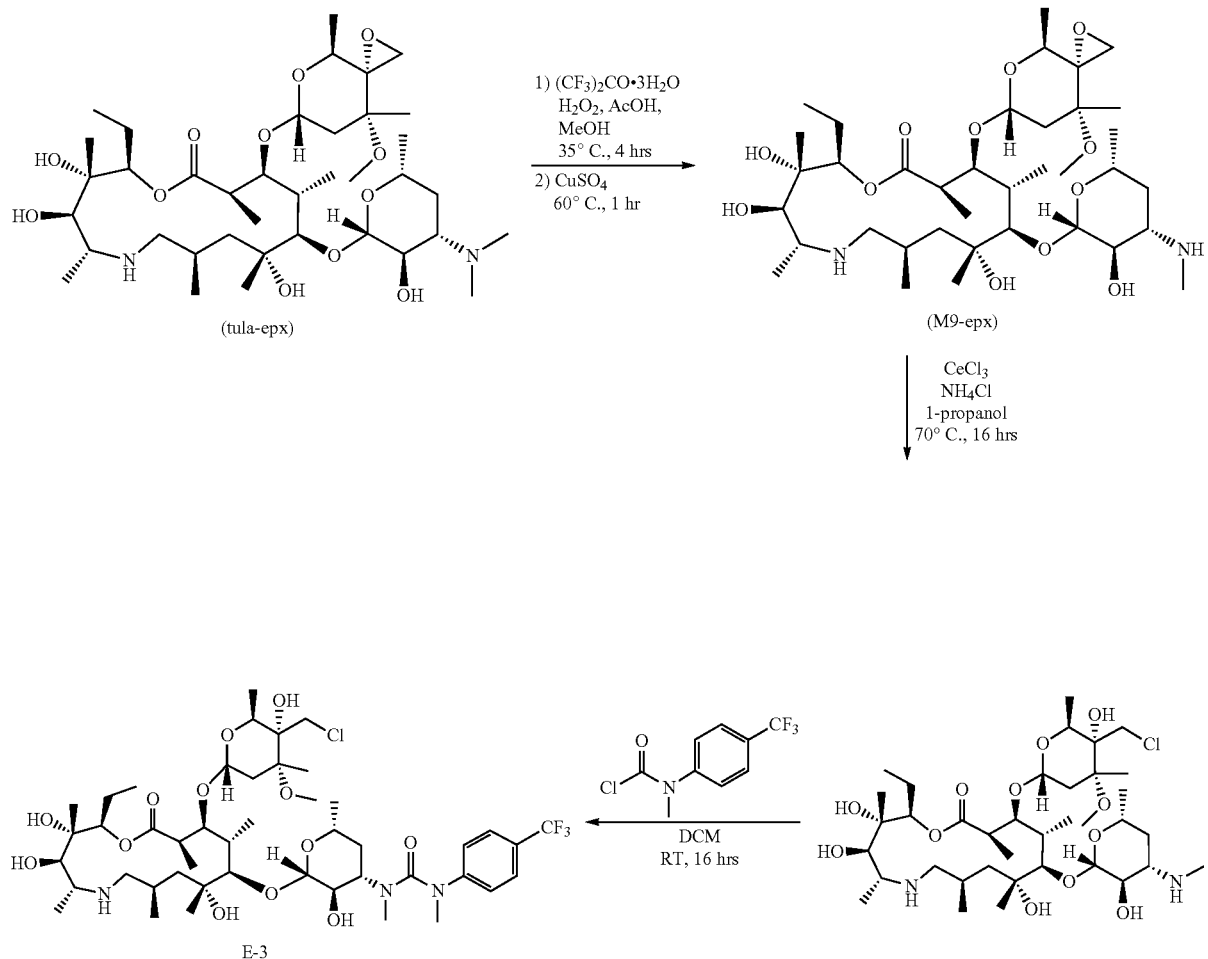

Step 1: A solution of tula-epx (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: M9 epoxide (M9-epx 5.00 g, 6.82 mmol, 1.0 eq) was dissolved in 100 mL dry 1-propanol in a 250 mL round bottom flask. Ammonium chloride (3.0 eq, 20.5 mmol, 1.1 g) was added followed by cerium chloride (3.0 eq, 20.5 mmol, 5.1 g) and the resulting solution was heated to 70° C. overnight after which the LCMS analysis showed consumption of the starting material. The reaction mixture was diluted with 100 mL DCM and $H_2O$ and the pH was adjusted to pH~12 with $NH_4OH$ and extracted 3 times with 100 mL DCM to give the desired product as a free base (5091 mg, 97%) and used as is in the following step.

Step 3: The product from Step 2 (0.26 mmol, 200 mg, 1.0 eq) was dissolved in DCM (5 ml) and TEA (2.0 eq, 73 μL, 0.52 mmol) followed by N-methyl-N-[4-(trifluoromethyl)phenyl]carbamoyl chloride (1.0 eq, 62 mg, 0.26 mmol) were added and the resulting solution was stirred at RT overnight. After completion of the reaction as judged by LCMS analysis, the volatiles were removed under a stream of $N_2$ and the crude purified by $C_{18}$ reverse flash chromatography with 0.5% AcOH as modifier (0 to 100% MeCN in $H_2O$). The fractions containing the desired product were lyophilized to give the desired product as the acetate salt (119 mg, 44%)

Preparation of Example F-2 of Formula (1-A5)

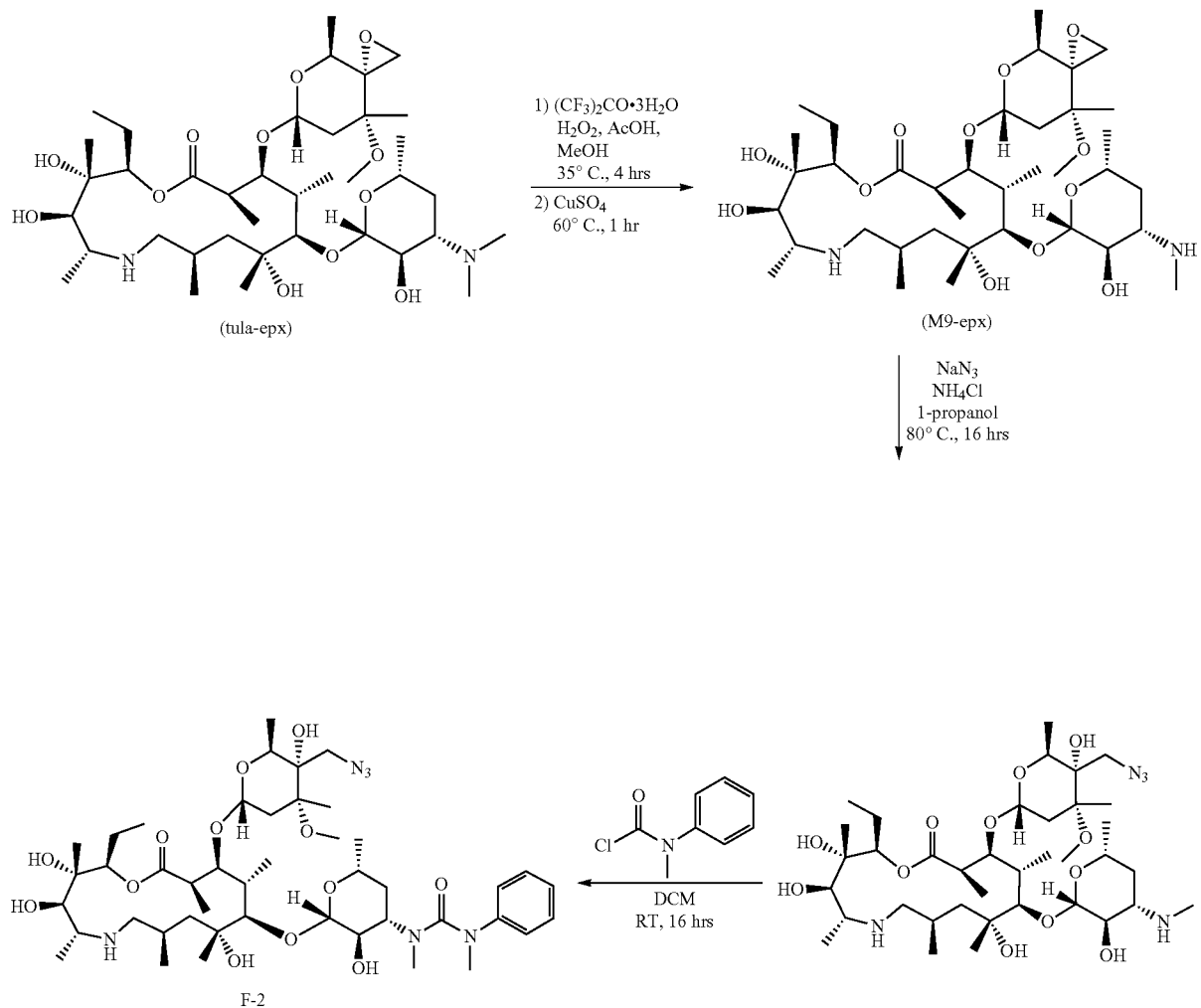

Step 1: A solution of tula-epx (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: M9 epoxide (M9-epx 6.00 g, 8.19 mmol, 1.0 eq) was dissolved in 100 mL dry 1-propanol in a 250 mL round bottom flask. Ammonium chloride (3.0 eq, 24.6 mmol, 1.31 g) was added followed by sodium azide (3.0 eq, 24.6 mmol, 1.6 g) and the resulting solution was heated to 80° C. overnight after which the LCMS analysis showed consumption of the starting material. The reaction mixture was diluted with 100 mL DCM and $H_2O$ and the pH was adjusted to pH~12 with $NH_4OH$ and extracted 3 times with 100 mL DCM to give the desired product as a free base (5981 mg, 94%) and used as is in the following step.

Step 3: The product from Step 2 (0.36 mmol, 282 mg, 1.0 eq) was dissolved in DCM (5 ml) and TEA (2.0 eq, 102 µL, 0.73 mmol) followed by N-methyl-N-phenyl-carbamoyl chloride (1.0 eq, 62 mg, 0.36 mmol) were added and the resulting solution was stirred at RT overnight. After completion of the reaction as judged by LCMS analysis, the volatiles were removed under a stream of $N_2$ and the crude purified by $C_{18}$ reverse flash chromatography with 0.5% AcOH as modifier (0 to 100% MeCN in $H_2O$). The fractions containing the desired product were lyophilized to give the desired product as the acetate salt (180 mg, 51%).

Preparation of Example G-3 of Formula (1-A6)

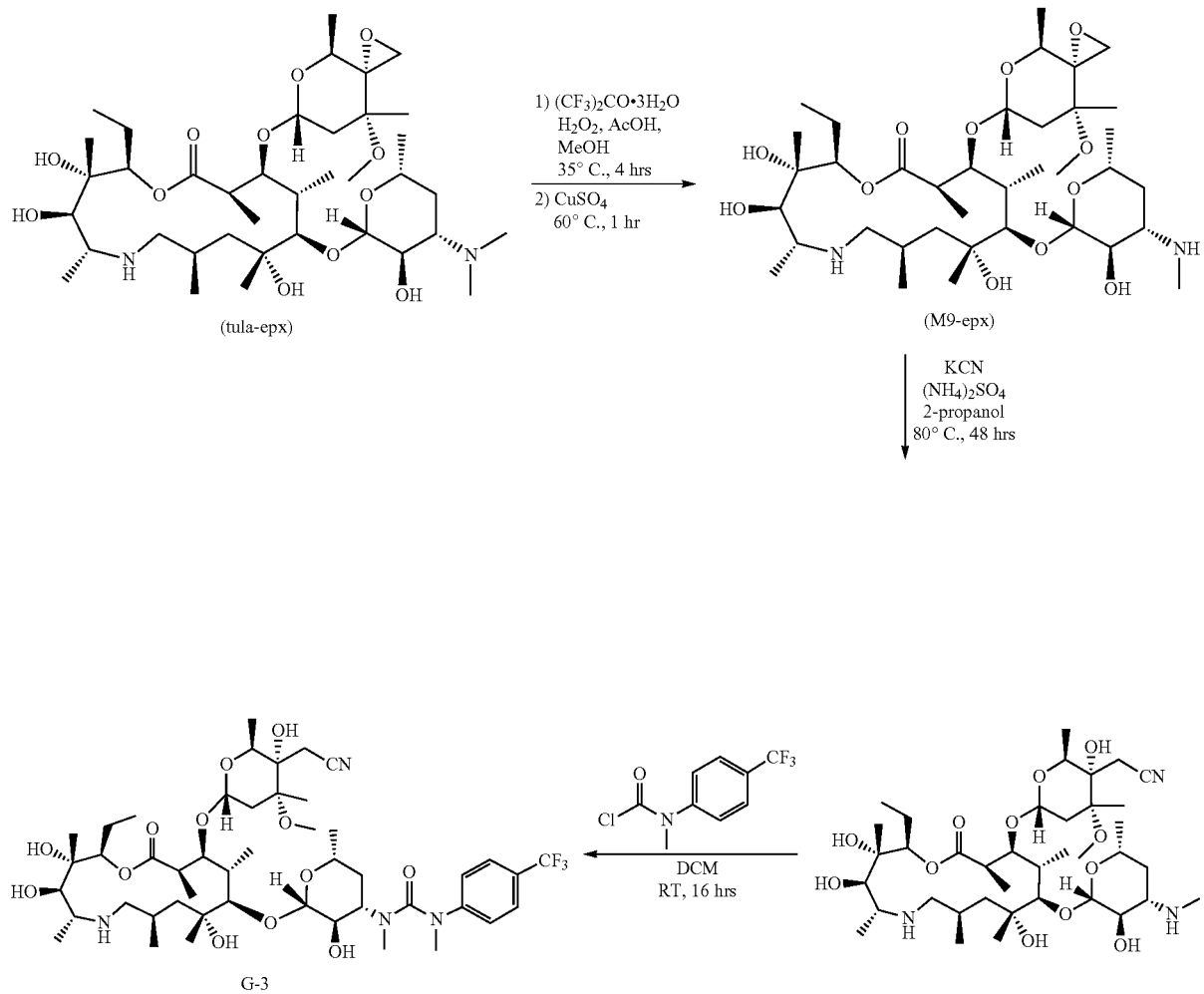

Step 1: A solution of tula-epx (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: M9 epoxide (M9-epx 3.00 g, 4.09 mmol, 1.0 eq) was dissolved in 50 mL dry 2-propanol in a 100 mL round bottom flask. Ammonium sulfate (3.0 eq, 12.3 mmol, 1.6 g) was added followed by potassium cyanide (6.0 eq, 24.6 mmol, 1.6 g) and the resulting solution was heated to 80° C. for 48 hours after which the LCMS analysis showed consumption of the starting material. The reaction mixture was diluted with 100 mL DCM and $H_2O$ and the pH was adjusted to pH~12 with $NH_4OH$ and extracted 3 times with 30 mL DCM to give the desired product as a free base (2922 mg, 94%) and used as is in the following step.

Step 3: The product from Step 2 (0.13 mmol, 100 mg, 1.0 eq) was dissolved in DCM (5 ml) and TEA (2.0 eq, 37 µL, 0.26 mmol) followed by N-methyl-N-phenyl-carbamoyl chloride (1.0 eq, 22 mg, 0.13 mmol) were added and the resulting solution was stirred at RT overnight. After completion of the reaction as judged by LCMS analysis, the volatiles were removed under a stream of $N_2$ and the crude purified by $C_{18}$ reverse flash chromatography with 0.5% AcOH as modifier (0 to 100% MeCN in $H_2O$). The fractions containing the desired product were lyophilized to give the desired product as the acetate salt (58 mg, 46%).

Formula (1-A2 through 1-A6) compounds can be made similarly to that shown above (Examples C-1, D-2, E-3, F-2 and G-3) under similar conditions by either varying the urea forming reagent or the starting material and using (alkyl-tula-epx) as the starting material instead of tulathromycin epoxide as shown in Scheme 5.

Preparation of Example H-11 of Formula (1-A1)

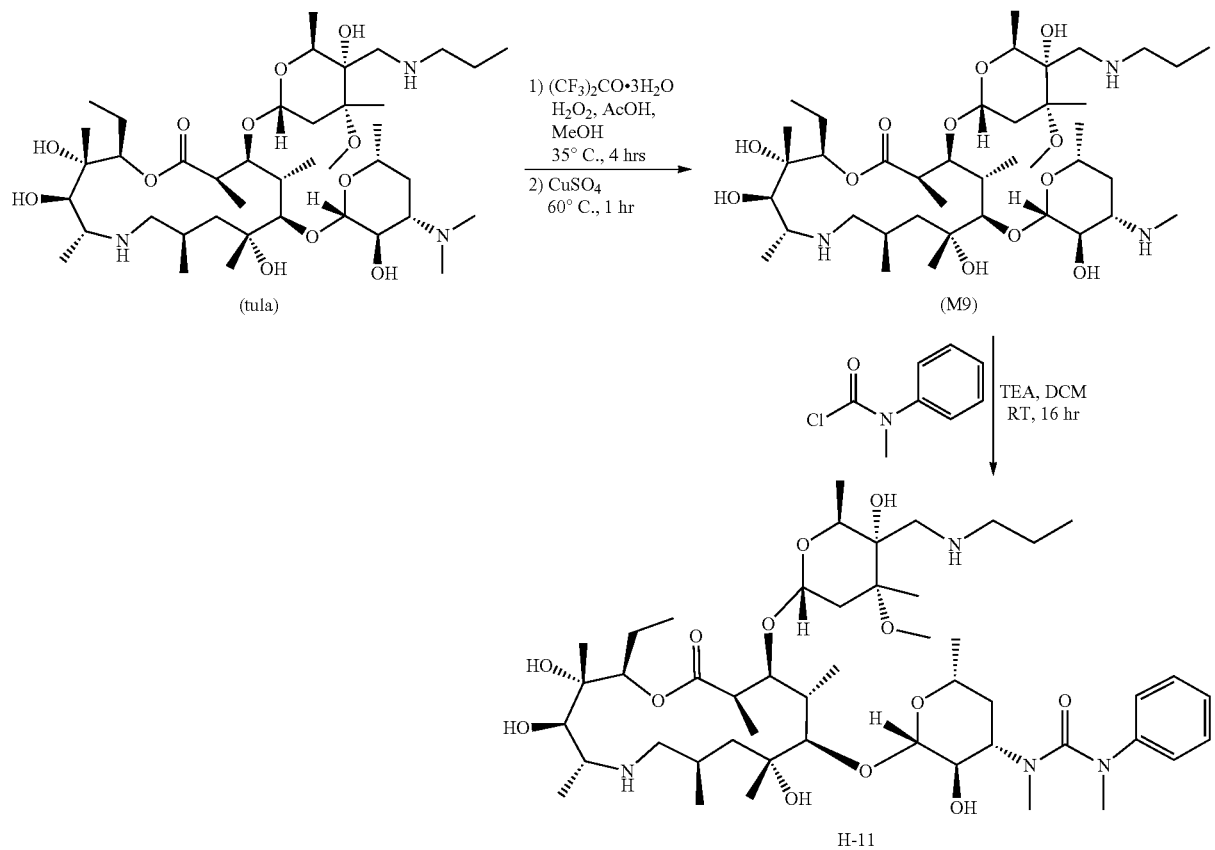

Step 1: To a solution of tulathromycin (tula) (20.0 g, 24.8 mmol) in methanol (40 mL) and acetic acid (1.6 mL, 28 mmol), hexafluoroacetone trihydrate (0.62 g, 2.8 mmol) and then 30% aqueous hydrogen peroxide (2.88 ml, 28 mmol) were added together and stirred for 4 hours at 35° C. After consumption of the starting material as judged by LCMS, the reaction was cooled to 20° C. and anhydrous copper(II) sulfate (4.35 g, 28 mmol) was added and the reaction was heated to 60° C. for 2 hours. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 14.2 g of a white crystalline product (M9-epx) that was >95% pure by LCMS and used as is in the next step.

Step 2: M9 from Step 1 (0.25 mmol, 200 mg, 1.0 eq) was dissolved in DCM (5 ml) and TEA (2.0 eq, 70 uL, 0.49 mmol) followed by (N-methyl-N-phenyl-carbamoyl chloride (1.0 eq, 42 mg, 0.25 mmol) were added and the resulting solution was stirred at RT overnight. After completion of the reaction as judged by LCMS analysis, the volatiles were removed under a stream of $N_2$ and the crude purified by $C_{18}$ reverse flash chromatography with 0.5% AcOH as modifier (0 to 100% MeCN in $H_2O$). The fractions containing the desired product were lyophilized to give the desired product as the acetate salt (175 mg, 71%).

Formula (1-A1; Table H) and Formula (1-A1a; Table 1) compounds wherein $R^5$ is H and $R^6$ is propyl can be made similarly to that shown above for Example (H-11) under similar conditions by either varying the urea forming reagent or the starting material and using (alkyl-tula-epx) as the starting material instead of tulathromycin epoxide as shown in Scheme 5. The following (1-A1) compounds follow the procedure of Example (H-11) and only the last, urea forming step is shown.

Preparation of Example H-8. To a solution of M9 (200 mg, 0.2525 mmol) in DCM (3 mL, 46.80 mmol) was added isocyanato(trimethyl)silane (1.5 equiv., 0.3788 mmol) and the reaction was stirred at room temperature for 16 hours. The reactants were evaporated, MeOH (10 mL) was added and then evaporated. The residue was purified by prep HPLC to give a white solid as a TFA salt (79 mg).

Preparation of Example H-72: To a dry round bottom flask, M9 (400 mg, 0.505 mmol) and 3-aminopyridine (47.53 mg, 0.505 mmol) were added to DCM (5 mL). The reaction mixture was cooled to −78° C. and triphosgene (44.962 mg, 0.152 mmol) was added followed 10 minutes later by triethylamine (0.141 ml, 1.01 mmol). The mixture was stirred at −78° C. for 1 hour. The mixture was then concentrated and purified by Prep HPLC using ammonium acetate as a buffer. Like fractions were combined, concentrated, and lyophilized. The lyophilized material was passed through an SCX/PL-HCO$_3$ resin column to make the free base. The free base was then dissolved in 1 N AcOH solution, stirred for 30 minutes at room temperature, concentrated, and dissolved in t-BuOH and lyophilized to provide the product as an acetate salt.

Preparation of Example H-91: To a solution of M9 (21.0 gm, 27 mmol) in methylene chloride (200 mL) at 0° C. was slowly added phenylisocyanate (3.76 gm, 31.6 mmol). After 15 minutes, a solution of acetic acid (3.19 gm, 53.0 mmol) in water (200 mL) was added and the product was extracted into the aqueous layer. The organics were discarded. To the aqueous solution was added methyl tert-butyl ether (175 mL) and the aqueous layer was basified to pH 7.9 with 2N aqueous sodium hydroxide. The product-containing organic layer was concentrated to a solid. The solids were dissolved in methyl tert-butyl ether (80 mL) at 55° C. and acetic acid (1.7 gm, 28 mmol) was added. The resulting slurry was cooled to 5° C. and the product acetate salt was isolated by filtration. The solids were dried under vacuum to afford 11.0 g of a white solid.

Preparation of Example I-4. To a solution of M9 (500 mg, 0.63 mmol) and TEA (114 µL, 1.3 equiv., 0.82 mmol) in DCM (5 mL) was added indoline-1-carbonyl chloride (126 mg, 0.69 mmol) and 4-dimethylaminopyridine (4 mg, 0.05 eq., 0.032 mmol). The mixture was stirred at room temperature for 3 hours. The mixture was quenched with NaHCO$_3$ (sat. aq. soln.), separated, and the solvent was evaporated. The crude mixture was purified by Prep SFC (2PIC column) 25% MeOH with NH$_3$ to give a white solid.

Preparation of Example I-6: A solution of 3,4-dihydro-2H-1λ6,4-benzothiazine 1,1-dioxide (183 mg, 0.99874 mmol) and pyridine (2 equiv. 1.9975 mmol) in DCM (5 mL, 78.00 mmol) was added dropwise to a solution of triphosgene (0.4 equiv., 0.39950 mmol) in DCM (5 mL, 78.00 mmol) at −20° C. under N$_2$. The reaction mixture was allowed to warm to room temperature over 30 minutes and then stirred for 2 hours at room temperature. The reaction was quenched with a 2M aqueous solution of hydrogen chloride, separated and added to a solution of M9 (700 mg, 0.8838 mmol) and TEA (1.3 equiv., 1.149 mmol) and 4-dimethylaminopyridine (0.05 equiv., 0.04419 mmol) in DCM (5 mL, 78.00 mmol). The mixture was stirred at room temperature overnight. The mixture was quenched with NaHCO$_3$ (sat. aq. soln.), separated, and the solvent was evaporated. The crude mixture was purified by prep SFC (BiP column, eluting with 26% MeOH with NH$_3$ (aq) to give a white solid.

Preparation of Example H-27 of Formula (1-A1)

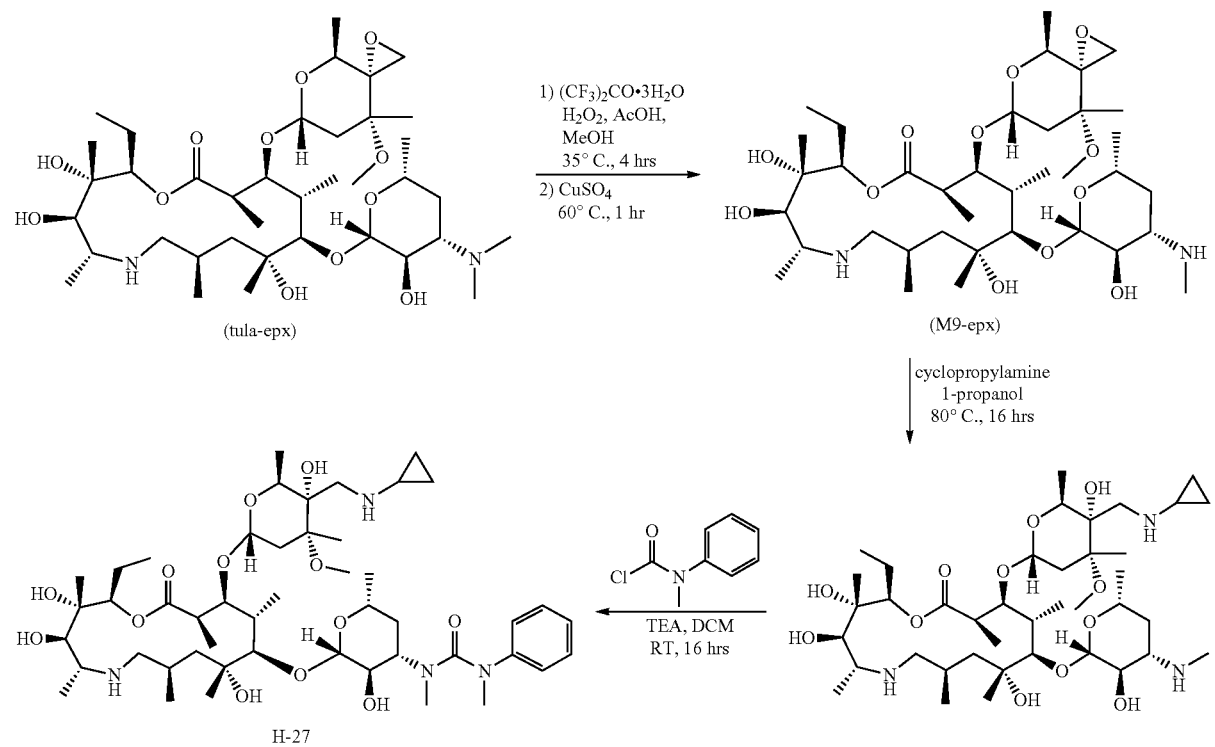

Step 1: A solution of (2R,3S,4R,5R,8R,10R,11R,12S,13S,14R)-11-(((2S,3R,4S,6R)-4-(dimethylamino)-3-hydroxy-6-methyltetrahydro-2H-pyran-2-yl)oxy)-2-ethyl-3,4,10-trihydroxy-13-(((3S,4S,6R,8R)-8-methoxy-4,8-dimethyl-1,5-dioxaspiro[2.5]octan-6-yl)oxy)-3,5,8,10,12,14-hexamethyl-1-oxa-6-azacyclopentadecan-15-one (tula-epx) (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL H$_2$O were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: A solution of 10 g (13.14 mmol) M9-epx from Step 1 and 9.12 mL cyclopropylamine (10.0 eq, 131.4 mmol) in 100 mL 1-propanol was heated to 80° C. for 16 hours. After completion of the reaction as judged by LCMS analysis, the volatiles were removed under reduced pressure, then dissolved in 100 ml DCM and H$_2$O and the pH was adjusted to ~9.8 with NH$_4$OH. The aqueous layer was extracted 3 times with DCM and the organic layers combined, dried over anhydrous magnesium sulfate. The volatiles were removed under reduced pressure to give the crude material that was purified on C$_{18}$ silica using reverse flash chromatography with 1.0% AcOH as the modifier (0 to 100% MeCN in H$_2$O). The desired fractions were combined, the pH adjusted to ~9.8 with NH$_4$OH and extracted 3 times with DCM. The organic layers were combined, dried over anhydrous magnesium sulfate and the volatiles removed under reduced pressure to give the desired material as an off-white amorphous solid (8.2 g).

Step 3: The product from Step 2 (0.39 mmol, 300 mg, 1.00 eq) was dissolved in DCM (5 ml) followed by the addiction N-methyl-N-phenyl-carbamoyl chloride (1.0 eq, 63 mg, 0.39 mmol) and the resulting solution was stirred at RT overnight. After completion of the reaction as judged by LCMS analysis, the volatiles were removed under a stream of N$_2$ and the crude purified by C$_{18}$ reverse flash chromatography with 0.5% AcOH as modifier (0 to 100% MeCN in H$_2$O). The fractions containing the desired product were lyophilized to give the desired compound as the acetate salt (212 mg).

Formula (1-A1) and Formula (1-A1a) compounds shown in Tables H and I can be made similarly to that shown above for Example (H-27) under similar conditions by either varying the amine used in the second step to open the epoxide functional group or the urea forming reagent or the starting material and using (alkyl-tula-epx) as the starting material instead of tulathromycin epoxide as shown in Scheme 5.

Preparation of Example J-7 of Formula (1-A1b)

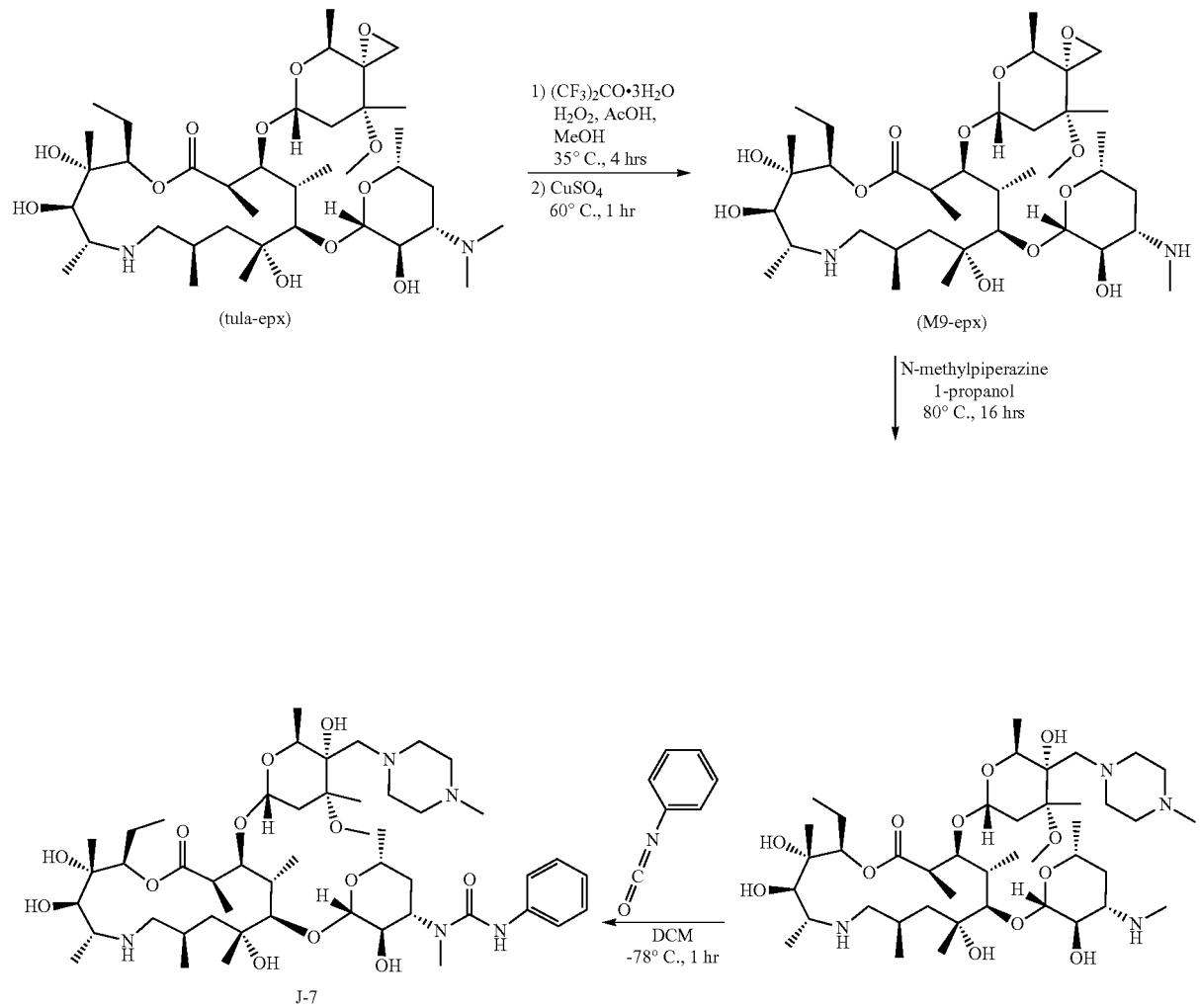

Step 1: A solution of tula-epx (20.0 g, 27 mmol) in methanol (40 mL) and acetic acid (1.6 mL, 30 mmol), hexafluoroacetone trihydrate (0.38 mL, 3 mmol) and then 30% aqueous hydrogen peroxide (0.62 g, 30 mmol) were mixed together and stirred for 4 hours at 35° C. After consumption of the starting material as judged by LCMS, the reaction was cooled to 20° C. and anhydrous copper(II) sulfate (4.5 g, 29 mmol) was added and the reaction was heated to 60° C. for 1 hour. After completion of the reaction as judged by LCMS, the reaction mixture was cooled to 20° C. and 60 mL DCM and 80 mL $H_2O$ were added. The mixture was basified to approximately pH 9.8 with concentrated aqueous ammonia. The mixture was concentrated under vacuum to a solid and recrystallized from acetone/water to give 60 g of a white crystalline product (M9-epx) that was 95% pure by LCMS and used as is in the next step.

Step 2: A solution of 10 g (13.14 mmol) M9-epx from Step 1 and 14.7 mL 1-methylpiperazine (10.0 eq, 131.4 mmol) in 100 mL 1-propanol was heated to 80° C. for 16 hours. After completion of the reaction as judged by LCMS analysis, the volatiles were removed under reduced pressure, then dissolved in 100 ml DCM and $H_2O$ and the pH was adjusted to ~9.8 with $NH_4OH$. The aqueous layer was extracted 3 times with DCM and the organic layers combined, dried over anhydrous magnesium sulfate. The volatiles were removed under reduced pressure to give the crude material that was purified on $C_{18}$ silica using reverse flash chromatography with 1.0% AcOH as the modifier (0 to 100% MeCN in $H_2O$). The desired fractions were combined, the pH adjusted to ~9.8 with $NH_4OH$ and extracted 3 times with DCM. The organic layers were combined, dried over anhydrous magnesium sulfate and the volatiles removed under reduced pressure to give the desired material as an off-white amorphous solid.

Step 3: The product from Step 2 (0.390 mmol, 300 mg, 1.00 eq) was dissolved in DCM (5 ml) and cooled to −78° C. followed by the addiction of phenyl isocyanate (1.0 eq, 44 uL mg) and the reaction was stirred for 60 minutes while the temperature was slowly brought to room temperature. After completion of the reaction as judged by LCMS analysis, the volatiles were removed under a stream of $N_2$ and the crude purified by $C_{18}$ reverse flash chromatography with 0.5% AcOH as modifier (0 to 100% MeCN in $H_2O$). The fractions containing the desired product were lyophilized to give the desired compound as the acetate salt (184 mg).

Formula (1-A1b) compounds shown in Table J can be made similarly to that shown above for Example (J-7) under similar conditions by either varying the amine used in the second step to open the epoxide functional group or the urea forming reagent or the starting material and using (alkyl-tula-epx) as the starting material instead of tulathromycin epoxide as shown in Scheme 5.

Example H-69 of Formula (1-A1) was prepared using a modification of Scheme 7 wherein the nucleophile used in the last step to open the epoxide is N-propylamine and such that $R^1$ is propyl from a reductive amination reaction with propionaldehyde.

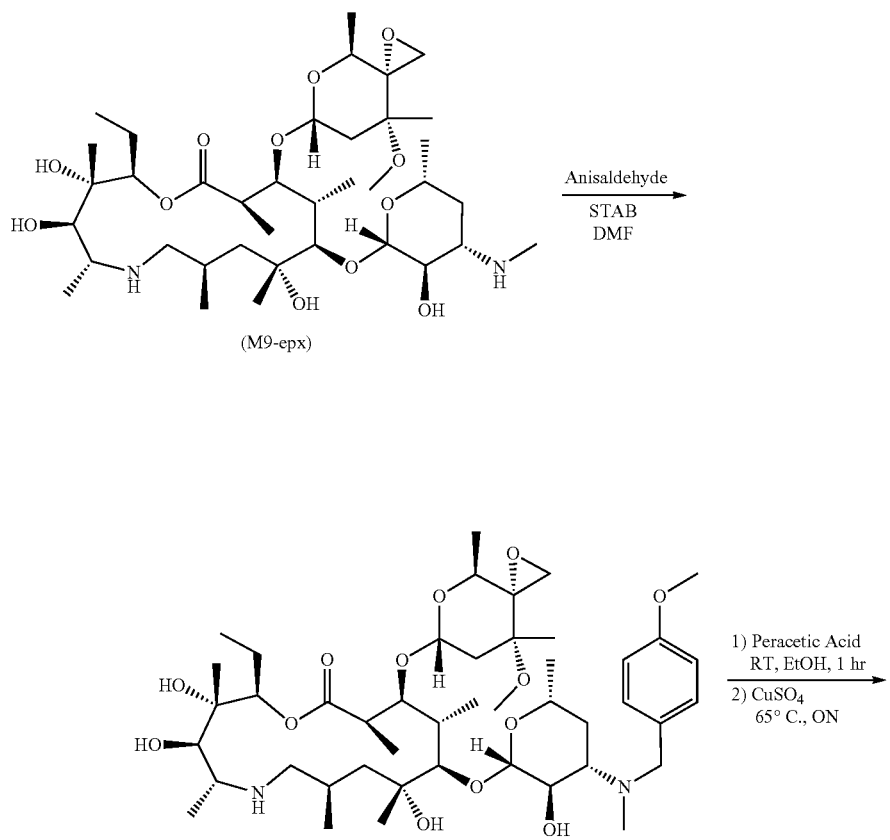

-continued
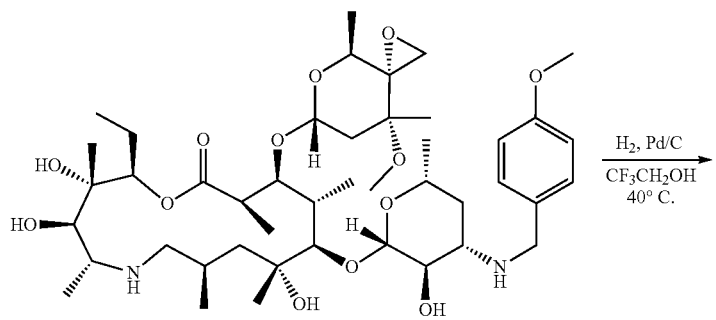
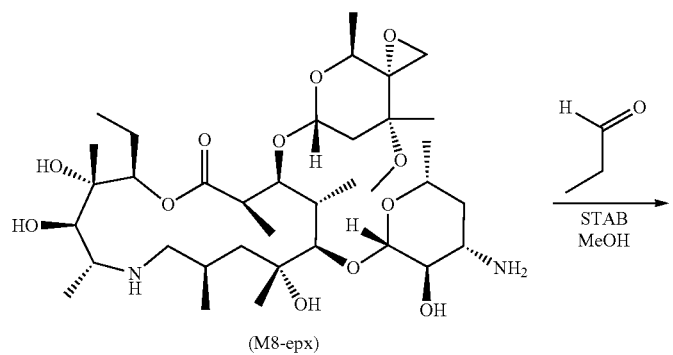
(M8-epx)
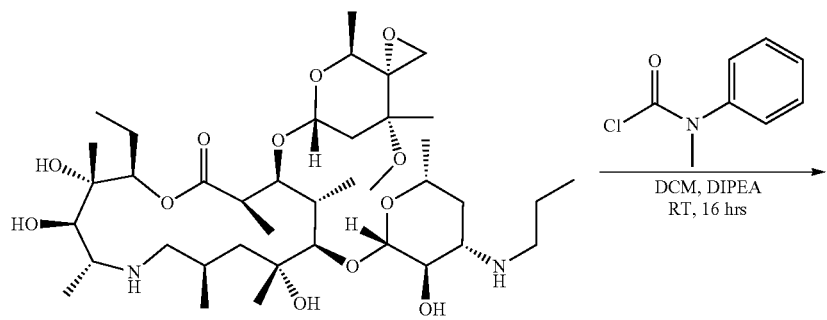
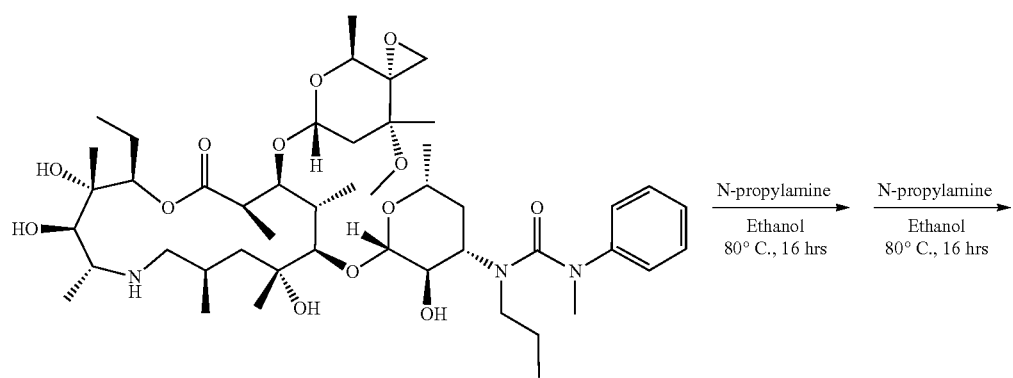

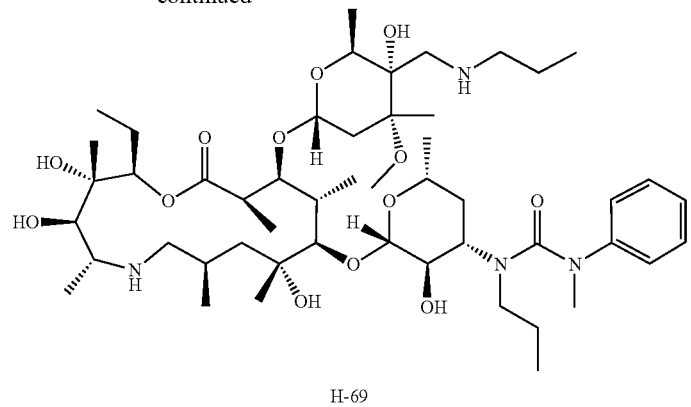

H-69

Step 1: 1.0 g (1.36 mmol, 1.00 eq) of M9 Epoxide was dissolved in 10 mL dry DMF in a 50 mL round bottom flask and 2.0 eq p-Anisaldehyde was added (0.332 mL, 2.73 mmol) followed by 1.17 g sodium triacetoxyborohydride (STAB, 4.0 eq, 5.5 mmol). The resulting solution was heated at 40° C. for 2 hours. An additional 0.6 g, (2.7 mmol, 2.0 eq) STAB was added and the resulting solution was heated at 40° C. overnight after which the LCMS analysis showed full consumption of the starting material. The reaction mixture was then cooled to 0° C. and 5 mL of a saturated solution of $NH_4Cl$ was added and the solution stirred for 5 minutes. The reaction mixture was then diluted with DCM (30 mL and $H_2O$) and transferred to a separatory funnel. The pH was adjusted to pH~12 with $NH_4OH$ and extracted 3 times with 20 mL DCM. The organics were combined and dried over $MgSO_4$ and removed under reduced pressure to afford the crude material that was purified by reverse phase chromatography on a C18 column eluting with a gradient of 1% AcOH in MeCN and $H_2O$. The fractions containing the desired product were combined, the pH was adjusted to pH~12 with $NH_4OH$ and extracted 3 times with 50 mL DCM to give the desired product as a free base (1008 mg, 87%).

Step 2: 1008 mg of product from Step 1 (1.18 mmol, 1.00 eq) was dissolved in 10 mL dry EtOH and peracetic acid was added (32% dilute solution in acetic acid; 1.5 eq 304 ul). The resulting solution was stirred at RT for 45 minutes after which the LCMS showed a full conversion to the corresponding N-oxide. After that copper sulfate (II) anhydrous was added (3.0 eq; 566 mg) and the solution was stirred at 65° C. for 4 hours after which the LCMS showed a complete reaction with 41% debenzylated product and 44% demethylated product. The reaction mixture was diluted with 20 mL DCM and $H_2O$ and the pH adjusted to ~12 with $NH_4OH$. The crude material was extracted 3 times with DCM and the organics were combined, dried over $MgSO_4$ and the volatiles removed under reduced pressure. The crude was purified by reverse phase chromatography on a C18 column with a gradient of 1% AcOH in MeCN and $H_2O$. The fractions containing the desired product were combined, the pH was adjusted to pH~12 with $NH_4OH$ and extracted 3 times with 50 mL DCM to give the desired product as a free base (250 mgs 25% yield)

Step 3: The product from Step 2 (250 mg, 0.30 mmol, 1.0 eq) was dissolved in 10 mL $CF_3CH_2OH$. 5% Pd/C (25 mgs) was added and the resulting slurry was hydrogenated under balloon pressure $H_2$ at 40° C. overnight after which the LCMS showed complete reaction. The Pd/C was filtered off on Celite and the volatiles removed under reduced pressure to give the desired product (M8 epoxide; M8-epx) as a white powder (195 mgs, 91%).

Step 4: The product from step 3 (M8-epx, 250 mgs, 1.0 eq, 0.35 mmol) was dissolved in 5 mL dry MeOH in a 25 mL round bottom flask and the solution was cooled to 0° C. Propionaldehyde (1.2 eq, 30 ul) was added followed by a portion wise addition of sodium triacetoxyborohydride (5 eq, 369 mg). The solution was stirred at 0° C. to RT for 2 hours after which the LCMS showed a full conversion to the desired product. The reaction mixture was then cooled to 0° C. and 1 mL of a saturated solution of $NH_4Cl$ was added and the solution stirred for 5 minutes. The reaction mixture was then diluted with DCM (30 mL and $H_2O$) and transferred to a separatory funnel. The pH was adjusted to pH~12 with $NH_4OH$ and extracted 3 times with 20 mL DCM. The organics were combined and dried over $MgSO_4$ and removed under reduced pressure to afford the desired product (250 mg) as a white solid material with ~80% LCMS purity that was used as is in subsequent epoxide opening.

Step 5: The material from Step 4 (200 mg, 0.32 mmol, 1.0 eq) was dissolved in dry DCM (5 ml) in a dry round bottom flask and DIPEA (0.141 mL, 2.5 eq.) was added followed by N-methyl-N-phenyl-carbamoyl chloride (66 mg, 1.2 eq, 0.39 mmol. The mixture was stirred overnight after which the LCMS analysis indicated all starting material being consumed. The volatiles were removed under a stream of $N_2$ and the crude material was purified by reverse phase chromatography on a C18 column with a gradient of 1% AcOH in MeCN and $H_2O$. The fractions containing the desired product were combined, the pH was adjusted to pH~12 with $NH_4OH$ and extracted 3 times with 50 mL DCM to give the desired product as a free base (93 mgs 32% yield).

Step 6: To a pressure vial was added the product from step 2 (93 mg, 0.10 mmol, 1 eq) and EtOH (2 mL) followed by N-propylamine (103 ul, 1.25 mmol, 12 eq). The reaction mixture was stirred at 80° C. for 16 hours. The reaction mixture was then concentrated under vacuum and the crude product was purified by reverse phase chromatography on a C18 column with a gradient of 1% AcOH in MeCN and $H_2O$. The fractions containing the desired product were lyophilized to give the desired product as the acetate salt as a white solid (35 mg, 33% yield).

Following this example, the alkyl group $R^1$ on the desosamine nitrogen can be varied by replacing propionaldehyde in the fourth step of the sequence by any other alkyl aldehyde such as but not limited to acetaldehyde or isobutylaldehyde or carbaldehydes such as benzaldehyde, or 2-pyridyl carbaldehyde and others. Similarly to other examples shown herein, the epoxide can be opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol in the last step.

Preparation of Example H-102 of Formula (1-A1) using a modification of Scheme 5 wherein the aldehyde used in the first step is propionaldehyde and the nucleophile used in the last step to open the epoxide is 1-propylamine:

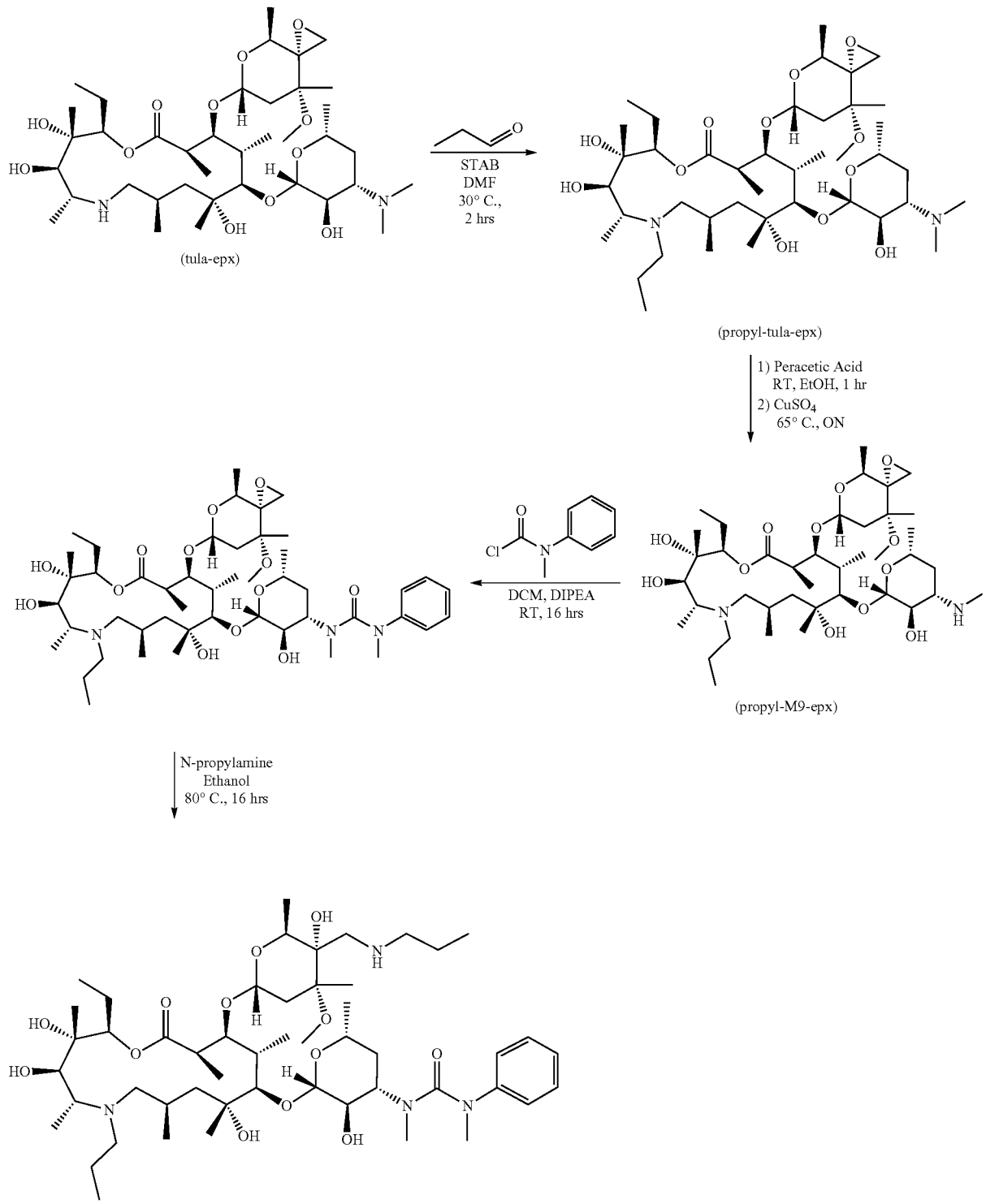

Step 1: To a solution of tula-epx (1.0 g, 1.34 mmol) in dry DMF (10 mL) was added STAB and the resulting solution was stirred for 4 hours at 35° C. After consumption of the starting material as judged by LCMS, the reaction was cooled to 0° C. and 2 mL of a saturated solution of $NH_4Cl$ was added and the solution stirred for 5 minutes. The reaction mixture was then diluted with DCM (30 mL and $H_2O$) and transferred to a separatory funnel. The pH was adjusted to pH~12 with $NH_4OH$ and extracted 3 times with 20 mL DCM. The organics were combined and dried over $MgSO_4$ and removed under reduced pressure to afford the crude material that was purified by reverse phase chromatography on a C18 column with a gradient of 1% AcOH in MeCN and $H_2O$. The fractions containing the desired product were combined, the pH was adjusted to pH~12 with $NH_4OH$ and extracted 3 times with 50 mL DCM to give the desired product as a free base (600 mgs, 57% yield).

Step 2: 600 mg of product from step 1 (0.76 mmol, 1.00 eq) was dissolved in 10 mL dry EtOH and peracetic acid was added (32% dilute solution in acetic acid; 1.2 eq 192 ul). The resulting solution was stirred at RT for 45 minutes after which the LCMS showed a full conversion to the corresponding N-oxide. The reaction mixture was then diluted with DCM (30 mL and $H_2O$) and transferred to a separatory funnel. The pH was adjusted to pH~12 with $NH_4OH$ and extracted 3 times with 20 mL DCM. The organics were combined and dried over $MgSO_4$ and removed under reduced pressure to afford the crude N-oxide. The crude N-oxide (0.76 mmol, 1.0 eq) was dissolved in 10 mL dry ethanol and copper sulfate (II) pentahydrate was added (5.0 eq; 950 mg) and the solution was stirred at 65° C. for 16 hours after which the LCMS showed a complete reaction. The reaction mixture was diluted with 20 mL DCM and $H_2O$ and the pH adjusted to ~12 with $NH_4OH$. The crude material was extracted 3 times with DCM and the organics were combined, dried over $MgSO_4$ and the volatiles removed under reduced pressure to give the crude desired product with LCMS purity >90% that was used as is in the following step.

Step 3: The material from Step 2 (250 mg, 0.32 mmol, 1.0 eq) was dissolved in dry DCM (5 ml) in a dry round bottom flask and DIPEA (0.141 mL, 2.5 eq.) was added followed by N-methyl-N-phenyl-carbamoyl chloride (66, 1.2 eq, 0.39 mmol). The reaction was stirred for 16 hrs at RT after which the LCMS analysis indicated all starting material being consumed. The volatiles were removed under a stream of $N_2$ and the crude material was purified by reverse phase chromatography on a C18 column with a gradient of 1% AcOH in MeCN and $H_2O$. The fractions containing the desired product were combined, the pH was adjusted to pH~12 with $NH_4OH$ and extracted 3 times with 50 mL DCM to give the desired product as a free base (150 mgs 51% yield).

Step 4: To a pressure vial was added the product from step 3 (150 mg, 0.17 mmol, 1 eq) and N-propanol (5 mL) followed by the addition N-propylamine (117 ul, 2.0 mmol, 12 eq). The reaction mixture was stirred at 70° C. for 16 hours. The reaction mixture was then concentrated under vacuum and the crude product was purified by reverse phase chromatography using a C18 column with a gradient of 1% AcOH in MeCN and $H_2O$. The fractions containing the desired product were lyophilized to give the desired product as an acetate salt (90 mg, 53% yield).

Following this example, the alkyl group $R^2$ on the core nitrogen can be varied by replacing propionaldehyde in the first step of the sequence by any other alkyl aldehyde such as but not limited to formaldehyde or acetaldehyde and others. Similarly to other examples shown herein, the epoxide can be opened with various nucleophiles such as but not limited to primary and secondary amines, alcohols, thiols, cyanide, azide or halogen anions and others at higher temperature in alcoholic solvents such as but not limited to 1-propanol, 1-butanol or 2-propanol in the last step.

NMR data for the tabulated Examples are provided below each of the respective Example Tables/Names.

EXAMPLES

Formula (1) compounds were prepared in accordance with the Schemes and procedures defined herein and that which is known in the art.

The following Formula (1.1) compounds were prepared as defined herein; wherein $R^0$ is H and $R^1$ is methyl; are shown in Table A. The respective compound names are provided below the table.

(1.1)

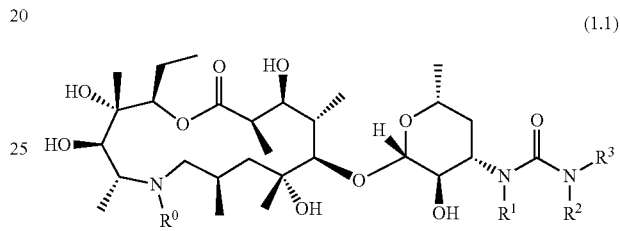

TABLE A

| Ex # | R2 | R3 | Mass [M + H]+ |
|---|---|---|---|
| A-1 | H | ![pyrimidin-2-yl structure] | 685 |
| A-2 | H | ![pyrazin-2-yl structure] | 685 |
| A-3 | H | pyridin-2yl | 684 |
| A-4 | H | pyridin-3yl | 684 |
| A-5 | H | pyridin-4yl | 684 |
| A-6 | H | ![1-methylpyrazol-4-yl structure] | 687 |
| A-7 | H | ![1,5-dimethylpyrazol-4-yl structure] | 701 |
| A-8 | H | 2-methoxyphenyl | 712 |
| A-9 | H | 4-cyanophenyl | 707 |
| A-10 | H | 3-trifluoromethylphenyl | 750 |
| A-11 | H | 3-cyanophenyl | 707 |
| A-12 | H | 2-chlorophenyl | 716 |
| A-13 | H | phenyl | 682 |
| A-14 | H | 2-methylphenyl | 696 |
| A-15 | H | 4-trifluoromethylphenyl | 750 |
| A-16 | H | 2-trifluoromethylphenyl | 750 |
| A-17 | H | 2-fluorophenyl | 700 |
| A-18 | H | 4-fluorophenyl | 700 |
| A-19 | H | 4-chlorophenyl | 716 |

TABLE A-continued

Formula (1.1) Compounds

| Ex # | R2 | R3 | Mass [M + H]+ |
|---|---|---|---|
| A-20 | H | 3-fluorophenyl | 700 |
| A-21 | H | 3-methoxyphenyl | 712 |
| A-22 | H | 4-methoxyphenyl | 712 |
| A-23 | H | 3-chlorophenyl | 716 |
| A-24 | H | 4-methylphenyl | 696 |
| A-25 | H | 3-methylphenyl | 695 |
| A-26 | methyl | phenyl | 696 |

Table A Example Names:

A-1. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyrimidin-2-yl)urea;

A-2. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyrazin-2-yl)urea;

A-3. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-2-yl)urea;

A-4. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-3-yl)urea;

A-5. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-4-yl)urea;

A-6. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(1-methyl-1H-pyrazol-4-yl)urea;

A-7. 3-(1,5-dimethyl-1H-pyrazol-3-yl)-1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

A-8. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(2-methoxyphenyl)-1-methylurea;

A-9. 3-(4-cyanophenyl)-1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

A-10. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(3-(trifluoromethyl)phenyl)urea;

A-11. 3-(3-cyanophenyl)-1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

A-12. 3-(2-chlorophenyl)-1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

A-13. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

A-14. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(o-tolyl)urea;

A-15. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(4-(trifluoromethyl)phenyl)urea;

A-16. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(2-(trifluoromethyl)phenyl)urea;

A-17. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(2-fluorophenyl)-1-methylurea;

A-18. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-fluorophenyl)-1-methylurea;

A-19. 3-(4-chlorophenyl)-1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

A-20. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(3-fluorophenyl)-1-methylurea;

A-21. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(3-methoxyphenyl)-1-methylurea;

A-22. 1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-methoxyphenyl)-1-methylurea;

A-23. 3-(3-chlorophenyl)-1-((2S,3R,4S,6R)-2-(((2R,3S,4R,5R,8R,10R,11R,12S,13S,14R)-2-ethyl-3,4,10,13-tetrahydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

A-24. 1-((2S,3R,4S,6R)-2-(((2R,3S,4R,5R,8R,10R,11R, 12S,13S,14R)-2-ethyl-3,4,10,13-tetrahydroxy-3,5,8, 10,12,14-hexamethyl-15-oxo-1-oxa-6-azacyclopenta-decan-11-yl)oxy)-3-hydroxy-6-methyltetrahydro-2H-pyran-4-yl)-1-methyl-3-(p-tolyl)urea;

A-25. 1-((2S,3R,4S,6R)-2-(((2R,3S,4R,5R,8R,10R,11R, 12S,13S,14R)-2-ethyl-3,4,10,13-tetrahydroxy-3,5,8, 10,12,14-hexamethyl-15-oxo-1-oxa-6-azacyclopenta-decan-11-yl)oxy)-3-hydroxy-6-methyltetrahydro-2H-pyran-4-yl)-1-methyl-3-(m-tolyl)urea; and A-26. 1-((2S,3R,4S,6R)-2-(((2R,3S,4R,5R,8R,10R,11R, 12S,13S,14R)-2-ethyl-3,4,10,13-tetrahydroxy-3,5,8, 10,12,14-hexamethyl-15-oxo-1-oxa-6-azacyclopenta-decan-11-yl)oxy)-3-hydroxy-6-methyltetrahydro-2H-pyran-4-yl)-1,3-dimethyl-3-phenylurea.

TABLE A

Example NMR's
$^1$H NMR (400 MHz, DMSO-d6) (unless described otherwise) δ ppm

| | |
|---|---|
| A-1 | 0.5-1.5 (m, 31H), 1.5-2.3 (m, 4H), 2.4-3.0 (m, 6H), 3.22 (t, 1H), 3.31-3.34 (m, 2H), 3.47 (s, 1H), 3.52 (brs, 1H), 3.99 (d, 1H), 4.09 (s, 1H), 4.24 (s, 1H), 4.67 (d, 1H), 4.96 (d, 1H), 5.20 (brs, 2H), 7.00 (t, 1H), 8.52 (d, 2H), 9.14 (brs, 1H). |
| A-2 | 0.5-1.5 (m, 32H), 1.5-2.3 (m, 4H), 2.4-2.9 (m, 6H), 3.0 (brd, 1H), 3.47 (s, 1H), 3.57 (brs, 1H), 4.09 (brs, 2H), 4.16 (brs, 2H), 4.68 (d, 1H), 4.97 (d, 1H), 5.1 (brs, 2H), 8.18 (s, 1H), 8.27 (s, 1H), 9.01 (s, 1H), 9.17 (s, 1H). |
| A-3 | 0.5-1.5 (m, 32H), 1.5-2.3 (m, 4H), 2.4-3.0 (m, 6H), 3.21 (brs, 1H), 3.31 (brs, 1H), 3.47 (s, 1H), 3.56 (brs, 1H), 4.07 (br d, 2H), 4.24 (d, 1H), 4.67 (d, 1H), 4.96 (d, 1H), 5.10 (brs, 1H), 5.20 (d, 1H), 6.94 (t, 1H), 7.66 (t, 1H), 7.75 (d, 1H), 8.20 (s, 1H), 8.74 (s, 1H). |
| A-4 | 0.5-1.5 (m, 32H), 1.5-2.3 (m, 4H), 2.4-3.0 (m, 6H), 3.24 (brt, 1H), 3.33 (d, 1H), 3.38 (t, 1H), 3.51 (s, 1H), 3.56 (t, 1H), 4.13 (brs, 1H), 4.37 (brs, 1H), 4.67 (d, 1H), 4.85 (d, 1H), 5.01 (d, 1H), 5.22 (d, 1H), 7.23-7.26 (m, 1H), 7.86 (d, 1H), 8.13 (brs, 1H), 8.40 (s, 1H), 8.64 (s, 1H). |
| A-5 | 0.5-1.5 (m, 33H), 1.5-2.3 (m, 4H), 2.4-3.0 (m, 6H), 3.22 (t, 1H), 3.32-3.38 (m, 1H), 3.46 (s, 1H), 3.56 (brs, 1H), 4.11 (brs, 2H), 4.25 (brs, 1H), 4.66 (d, 1H), 4.96 (d, 1H), 5.25 (d, 1H), 7.49 (d, 2H), 8.28 (d, 2H), 8.68 (s, 1H). |
| A-6 | 0.5-1.5 (m, 33H), 1.5-2.3 (m, 4H), 2.4-3.0 (m, 6H), 3.21 (brs, 1H), 3.31 (brs, 1H), 3.49 (s, 1H), 3.56 (brs, 1H), 3.73 (s, 3H), 4.08 (brs, 1H), 4.30 (brs, 1H), 4.64 (d, 1H), 4.75 (d, 1H), 4.96 (d, 1H), 5.19 (d, 1H), 7.33 (s, 1H), 7.62 (s, 1H), 8.20 (s, 1H). |
| A-7 | 0.5-1.5 (m, 32H), 1.5-2.3 (m, 4H), 2.4-3.0 (m, 9H), 3.23 (brs, 1H), 3.31 (brs, 1H), 3.35-3.42 (m, 3H), 3.55 (s, 3H), 4.09 (s, 1H), 4.24 (d, 1H), 4.63 (d, 1H), 4.85 (s, 1H), 4.96 (d, 1H), 5.19 (d, 1H), 6.07 (s, 1H), 8.47 (s, 1H). |
| A-8 | 0.5-1.5 (m, 32H), 1.5-2.3 (m, 4H), 2.4-3.0 (m, 6H), 3.22 (brs, 1H), 3.32-3.35 (m, 1H), 3.47 (s, 1H), 3.55 (brs, 1H), 3.81 (s, 3H), 3.99 (brs, 1H), 4.10 (brs, 1H), 4.26 (brs, 1H), 4.69 (d, 1H), 4.97 (d, 1H), 5.23 (brs, 2H), 6.82-6.86 (m, 1H), 6.89-6.97 (m, 2H), 7.79 (d, 1H), 7.87 (brs, 1H). |
| A-9 | 0.5-1.5 (m, 32H), 1.5-2.3 (m, 4H), 2.4-3.0 (m, 6H), 3.24 (brs, 1H), 3.31 (brs, 1H), 3.46 (s, 1H), 3.56 (br t, 1H), 4.09 (brs, 2H), 4.24 (d, 1H), 4.66 (d, 1H), 4.89 (brs, 1H), 4.96 (d, 1H), 5.19 (d, 1H), 7.66 (s, 4H), 8.71 (s, 1H). |
| A-10 | 0.5-1.5 (m, 32H), 1.5-2.3 (m, 4H), 2.4-3.0 (m, 6H), 3.22 (brs, 1H), 3.32 (brs, 1H), 3.47 (s, 1H), 3.57 (brs, 1H), 4.12 (brs, 2H), 4.26 (brs, 1H), 4.66 (d, 1H), 4.89 (brs, 1H), 4.96 (d, 1H), 5.23 (brs, 1H), 7.24 (d, 1H), 7.44 (t, 1H), 7.74 (d, 1H), 7.93 (s, 1H), 8.59 (s, 1H). |
| A-11 | 0.5-1.5 (m, 32H), 1.5-2.3 (m, 4H), 2.4-3.0 (m, 6H), 3.24 (d, 1H), 3.32 (brs, 1H), 3.39 (s, 1H), 3.47 (brs, 1H), 4.11 (brs, 2H), 4.25 (d, 1H), 4.66 (d, 1H), 4.87 (d, 1H), 4.96 (d, 1H), 5.20 (d, 1H), 7.35 (d, 1H), 7.43 (t, 1H), 7.76 (d, 1H), 7.93 (s, 1H), 8.56 (s, 1H). |
| A-12 | 0.5-1.5 (m, 33H), 1.5-2.3 (m, 4H), 2.4-3.0 (m, 7H), 3.22 (brs, 1H), 3.32 (brs, 1H), 3.47 (s, 1H), 3.54 (brs, 1H), 4.01 (brs, 1H), 4.10 (s, 1H), 4.25 (d, 1H), 4.69 (d, 1H), 4.96 (d, 1H), 5.21 (d, 1H), 7.24 (t, 1H), 7.41 (d, 1H), 7.68 (d, 1H), 8.02 (d, 1H). |
| A-13 | 0.5-1.5 (m, 32H), 1.5-2.3 (m, 4H), 2.4-3.0 (m, 6H), 3.21 (brs, 1H), 3.46 (s, 1H), 3.6 (brs, 1H), 4.10 (brs, 2H), 4.25 (d, 1H), 4.65 (d, 1H), 4.87 (brs, 1H), 4.96 (d, 1H), 5.21 (d, 1H), 6.45 (brs, 1H), 6.92-6.90 (m, 1H), 7.21 (t, 2H), 7.44 (d, 2H), 8.20 (s, 1H). |

TABLE A-continued

Example NMR's
$^1$H NMR (400 MHz, DMSO-d6) (unless described otherwise) δ ppm

| | |
|---|---|
| A-14 | 0.5-1.5 (m, 31H), 1.5-2.3 (m, 4H), 2.4-3.0 (m, 9H), 3.20-3.23 (m, 1H), 3.25-3.31 (m, 2H), 3.47 (s, 1H), 3.53-3.54 (m, 1H), 4.06-4.08 (m, 2H), 4.26 (brs, 1H), 4.67 (d, 1H), 4.95 (d, 1H), 4.98 (brs, 2H), 6.96 (t, 1H), 7.07-7.15 (m, 2H), 7.26 (d, 1H), 7.84 (s, 1H). |
| A-15 | 0.5-1.5 (m, 32H), 1.5-2.3 (m, 4H), 2.4-3.0 (m, 6H), 3.31 (brs, 1H), 3.47 (s, 2H), 3.56 (brs, 1H), 4.11 (brs, 2H), 4.25 (d, 1H), 4.66 (d, 1H), 4.89 (brs, 1H), 4.96 (d, 1H), 4.20 (d, 1H), 7.57 (d, 2H), 7.68 (d, 2H), 8.61 (s, 1H). |
| A-16 | 0.5-1.5 (m, 32H), 1.5-2.3 (m, 4H), 2.4-3.0 (m, 6H), 3.22 (brs, 1H), 3.32 (brs, 1H), 3.4 (s, 1H), 3.52 (brs, 1H), 4.0 (brs, 1H), 4.10 (s, 1H), 4.26 (d, 1H), 4.66 (d, 1H), 4.97 (d, 1H), 5.19 (d, 2H), 7.28 (t, 1H), 7.52-7.64 (m, 3H), 8.05 (s, 1H). |
| A-17 | 0.5-1.5 (m, 32H), 1.5-2.3 (m, 4H), 2.4-3.0 (m, 6H), 3.24 (brs, 1H), 3.31 (brs, 1H), 3.47 (s, 1H), 3.55 (br t, 1H), 4.06 (br d, 2H), 4.23 (d, 1H), 4.66 (d, 1H), 4.96 (d, 1H), 5.06 (brs, 1H), 5.19 (d, 1H), 7.03-7.48 (m, 3H), 7.50-7.52 (m, 1H), 8.07 (s, 1H). |
| A-18 | 0.5-1.5 (m, 32H), 1.5-2.3 (m, 4H), 2.4-3.0 (m, 6H), 3.22 (brs, 1H), 3.39 (brs, 1H), 3.50 (s, 1H), 3.6 (brs, 2H), 4.1 (brs, 2H), 4.66 (d, 1H), 4.83 (d, 1H), 5.0 (d, 1H), 5.23 (d, 1H), 7.05 (t, 2H), 7.43-7.46 (m, 2H), 8.24 (s, 1H). |
| A-19 | 0.5-1.5 (m, 32H), 1.5-2.3 (m, 4H), 2.4-3.0 (m, 6H), 3.20 (brs, 1H), 3.31 (brs, 1H), 3.47 (s, 1H), 3.55 (brs, 1H), 4.12 (brs, 2H), 4.26 (d, 1H), 4.65 (d, 1H), 4.85 (s, 1H), 4.96 (d, 1H), 5.19 (d, 1H), 7.26 (d, 2H), 7.49 (d, 2H), 8.3 (s, 1H). |
| A-20 | 0.5-1.5 (m, 32H), 1.5-2.3 (m, 4H), 2.4-3.0 (m, 6H), 3.21 (brs, 1H), 3.31-3.35 (m, 1H), 3.47 (s, 1H), 3.56 (brs, 1H), 4.1 (brs, 2H), 4.24 (d, 1H), 4.65 (d, 1H), 4.85 (brs, 1H), 4.96 (d, 1H), 4.19 (d, 1H), 6.69-6.71 (m, 1H), 7.23 (d, 2H), 7.44 (d, 1H), 8.40 (s, 1H). |
| A-21 | 0.5-1.5 (m, 32H), 1.5-2.3 (m, 4H), 2.4-3.0 (m, 6H), 3.19 (brs, 1H), 3.35 (brs, 1H), 3.36-3.38 (m, 1H), 3.51 (s, 1H), 3.58 (brs, 1H), 3.68 (s, 3H), 4.11 (brs, 1H), 4.4 (brs, 1H), 4.66 (d, 1H), 4.85 (d, 1H), 5.01 (d, 1H), 5.24 (d, 1H), ), 6.49 (d, 1H), 7.03 (d, 1H), 7.08-7.12 (m, 1H), 7.17 (s, 1H), 8.18 (s, 1H). |
| A-22 | 0.5-1.5 (m, 32H), 1.5-2.3 (m, 4H), 2.4-3.0 (m, 6H), 3.20 (brs, 1H), 3.32-3.35 (m, 1H), 3.46 (s, 1H), 3.54 (brs, 1H), 3.69 (s, 3H), 4.41 (brs, 2H), 4.25 (d, 1H), 4.64 (d, 1H), 4.83 (brs, 1H), 4.96 (d, 1H), 5.20 (d, 1H), 6.80 (d, 2H), 7.32 (d, 2H), 8.04 (s, 1H). |
| A-23 | 0.5-1.5 (m, 30H), 1.5-2.3 (m, 4H), 2.4-3.0 (m, 6H), 3.18-3.20 (m, 2H), 3.31 (d, 2H), 3.44 (t, 1H), 3.47 (brs, 2H), 4.10 (brs, 1H), 4.50 (d, 1H), 4.67 (d, 1H), 4.85 (d, 1H), 4.94 (brs, 1H), 5.03 (d, 1H), 5.26 (d, 1H), 7.23 (t, 1H), 7.41 (d, 1H), 7.63 (s, 1H), 8.41 (s, 1H). |
| A-24 | 0.5-1.5 (m, 32H), 1.5-2.3 (m, 4H), 2.4-3.0 (m, 9H), 3.22 (brs, 1H), 3.32 (brs, 1H), 3.46 (s, 1H), 3.55 (brs, 1H), 4.11 (br t, 2H), 4.28 (brs, 1H), 4.64 (d, 1H), 4.83 (d, 1H), 4.96 (d, 1H), 5.19 (d, 1H), 7.01 (d, 2H), 7.32 (d, 2H), 8.09 (s, 1H). |
| A-25 | 0.5-1.5 (m, 32H), 1.5-2.3 (m, 4H), 2.4-3.0 (m, 9H), 3.18-3.21 (m, 1H), 3.31-3.35 (m, 1H), 3.37 (s, 1H), 3.6 (brs, 1H), 4.11 (brs, 2H), 4.26 (d, 1H), 4.65 (d, 1H), 4.84 (d, 1H), 4.96 (d, 1H), 5.19 (d, 1H), 6.73 (d, 1H), 7.06 (t, 1H), 7.26-7.23 (m, 2H), 8.11 (s, 1H). |
| A-26 | METHANOL-d4) δ ppm 0.9-1.5 (28H), 1.61 (m, 1H), 1.77 (d, 1H), 1.90 (m, 1H), 2.05 (br, 1H), 2.18 (q, 1H), 2.51 (s, 3H), 2.63 (t, 1H), 2.75 (m, 1H), 3.20 (s, 3H), 3.29 (m, 1H), 3.40 (m, 1H), 3.5-3.6 (mm, 2H), 3.63 (d, 1H), 3.74 (s, 1H), 4.03 (dt, 1H), 4.72 (d, 1H), 4.98 (d, 1H), 7.15 (t, 1H), 7.24 (d, 2H), 7.37 (t, 2H) |

The following Formula (1-A0) compounds were prepared in accordance with the Schemes and procedures defined herein, and wherein $R^1$ is methyl; are shown in Table B. The respective compound names are provided below the table. Examples B-1a, B-2a, B-3a and B-13a are stereoisomers of B-1, B-2, B-3 and B-13, respectively, (i.e., hydroxyl diastereomers at the $R^a$ alpha carbon (5R in lieu of 5S))

(1-A0)

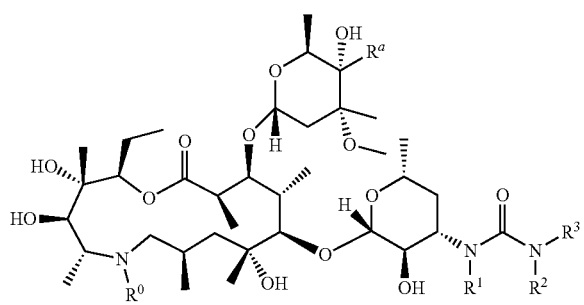

TABLE B

Formula (1-A0) Compounds

| Ex# | R⁰ | Rᵃ | R² | R³ | Mass [M + H]⁺ |
|---|---|---|---|---|---|
| B-1* | H | methyl | methyl | phenyl | 869 |
| B-1a | H | methyl | methyl | phenyl | 869 |
| B-2 | H | H | methyl | 4-trifluoromethyl-phenyl | 922 |
| B-2a | H | H | methyl | 4-trifluoromethyl-phenyl | 922 |
| B-3 | H | H | methyl | phenyl | 854 |
| B-3a | H | H | methyl | phenyl | 854 |
| B-4 | methyl | H | H | phenyl | 854 |
| B-5 | methyl | H | methyl | phenyl | 868 |
| B-6 | methyl | H | methyl | 4-trifluoromethyl-phenyl | 936 |
| B-7* | methyl | H | H | 4-dimethylamino-phenyl | 897 |
| B-8 | methyl | H | H | 4-trifluoromethyl-phenyl | 922 |
| B-9 | methyl | H | H | 4-fluorophenyl | 872 |
| B-10 | methyl | H | H | cyclohexyl | 860 |
| B-11 | methyl | H | H | t-butyl | 834 |
| B-12 | methyl | H | H | 4-cyanophenyl | 879 |
| B-13 | H | methyl | methyl | 4-trifluoromethyl-phenyl | 936 |
| B-13a | H | methyl | methyl | 4-trifluoromethyl-phenyl | 936 |
| B-14 | propyl | H | methyl | 4-trifluoromethyl-phenyl | |
| B-15 | propyl | H | methyl | phenyl | |

*MIC ≤ 64 µg/mL for at least one BRD bacterial strain

Table B Example Names:
B-1. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,5,6-trimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

B-1a. 1-((2S,3R,4S,6R)-2-(((2R,3S,4R,5R,8R,10R,11R,12S,13S,14R)-2-ethyl-3,4,10-trihydroxy-13-(((2R,4R,5R,6S)-5-hydroxy-4-methoxy-4,5,6-trimethyltetrahydro-2H-pyran-2-yl)oxy)-3,5,8,10,12,14-hexamethyl-11S-oxo-1-oxa-6-azacyclopentadecan-11-yl)oxy)-3-hydroxy-6-methyltetrahydro-2H-pyran-4-yl)-1,3-dimethyl-3-phenylurea;

B-2. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

B-2a. 1-((2S,3R,4S,6R)-2-(((2R,3S,4R,5R,8R,10R,11R,12S,13S,14R)-2-ethyl-3,4,10-trihydroxy-13-(((2R,4R,5R,6S)-5-hydroxy-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

B-3. 1-((2S,3R,4S,6R)-2-(((2R,3S,4R,5R,8R,10R,11R,12S,13S,14R)-2-ethyl-3,4,10-trihydroxy-13-(((2R,4R,5R,6S)-5-hydroxy-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

B-3a. 1-((2S,3R,4S,6R)-2-(((2R,3S,4R,5R,8R,10R,11R,12S,13S,14R)-2-ethyl-3,4,10-trihydroxy-13-(((2R,4R,5R,6S)-5-hydroxy-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

B-4. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1-methyl-3-phenylurea;

B-5. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

B-6. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

B-7. 3-(4-(dimethylamino)phenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1-methylurea;

B-8. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1-methyl-3-(4-(trifluoromethyl)phenyl)urea;

B-9. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-3-(4-fluorophenyl)-1-methylurea;

B-10. 3-cyclohexyl-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14- heptamethyl-15-oxo-1-oxa-6-azacyclopentadecan-11-yl)oxy)-3-hydroxy-6-methyltetrahydro-2H-pyran-4-yl)-1-methylurea;

B-11. 3-(tert-butyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1-methylurea;

B-12. 3-(4-cyanophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1-methylurea;

B-13. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,5,6-trimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

B-13a. 1-((2S,3R,4S,6R)-2-(((2R,3S,4R,5R,8R,10R,11R,12S,13S,14R)-2-ethyl-3,4,10-trihydroxy-13-(((2R,4R,5R,6S)-5-hydroxy-4-methoxy-4,5,6-trimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

B-4. 1-((2S,3R,4S,6R)-2-(((2R,3S,4R,5R,8R,1R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea (964); and B-5. 1-((2S,3R,4S,6R)-2-(((2R,3S,4R,5R,8R,1R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-1,3-dimethyl-3-phenylurea (896).

TABLE B

| Example | NMR's<br>$^1$H NMR: 400 MHz, DMSO-d6 (unless otherwise specified) δ ppm |
|---|---|
| B-1^ | 0.74-1.18 (m, 32 H), 1.19 (br s, 6 H), 1.60-1.90 (m, 4 H), 1.90 (s, 1 H), 1.91-1.98 (m, 2 H), 2.43 (s, 3 H), 2.60-2.71 (m, 2 H), 2.81-2.89 (m, 1 H), 2.90-3.00 (m, 1 H), 3.05 (s, 3 H), 3.08-3.16 (m, 1 H), 3.31-3.33 (m, 5 H), 3.34 (br s, 1 H), 3.37-3.45 (m, 1 H), 3.48 (br d, 1 H), 3.68-3.80 (m, 1 H), 3.87 (td, 1 H), 4.16 (br s, 1 H), 4.20 (s, 1 H), 4.22-4.29 (m, 1 H), 4.29-4.35 (m, 1 H), 4.84 (dd, 1 H), 4.90 (t, 2 H), 7.05 (t, 1 H), 7.11-7.18 (m, 2 H), 7.25-7.33 (m, 2 H) |
| B-1a^ | 0.72-1.20 (m, 32 H), 1.20-1.86 (m, 9 H), 1.89 (s, 2 H), 1.92 (br d, 1 H), 2.20 (br d, 1 H), 2.41-2.47 (m, 4 H), 2.52-2.59 (m, 1 H), 2.61-2.70 (m, 1 H), 2.79-2.86 (m, 1 H), 3.02 (br d, 1 H), 3.05 (s, 3 H), 3.09-3.17 (m, 2 H), 3.36 (br s, 6 H), 3.38 (s, 3 H), 3.46 (br d, 1 H), 3.67-3.78 (m, 1 H), 3.81-3.90 (m, 1 H), 4.13 (br s, 1 H), 4.30 (q, 1 H), 4.35 (br d, 1 H), 4.83 (br dd, 1 H), 4.89 (br d, 1 H), 7.06 (t, 1 H), 7.14 (d, 2 H), 7.27-7.33 (m, 2 H) |
| B-2^ | 0.70-1.21 (m, 32 H), 1.22-1.88 (m, 11 H), 1.90 (s, 1 H), 1.91-1.96 (m, 1 H), 2.27 (br d, 1 H), 2.52 (br s, 3 H), 2.58 (br d, 1 H), 2.62-2.71 (m, 1 H), 2.85 (br d, 1 H), 2.94 (dd, 1 H), 3.12 (s, 3 H), 3.14-3.21 (m, 1 H), 3.24 (s, 3 H), 3.53 (br d, 1 H), 3.77 (br dd, 2 H), 3.95-4.05 (m, 1 H), 4.07-4.11 (m, 1 H), 4.12 (br s, 1 H), 4.27 (br d, 1 H), 4.45 (d, 1 H), 4.83 (dd, 1 H), 4.88 (d, 1 H), 5.02 (d, 1 H), 7.30 (d, 2 H), 7.60 (d, 2 H) |
| B-2a^ | 0.67-1.21 (m, 32 H), 1.22-1.55 (m, 7 H), 1.57-1.86 (m, 4 H), 1.89 (s, 2 H), 1.91 (br s, 1 H), 2.27 (br d, 1 H), 2.51 (br s, 3 H), 2.53-2.58 (m, 1 H), 2.66 (dt, 1 H), 2.84 (br d, 1 H), 2.94 (br dd, 1 H), 3.12 (s, 3 H), 3.14-3.20 (m, 1 H), 3.24 (s, 3 H), 3.53 (br d, 1 H), 3.72-3.82 (m, 2 H), 3.95-4.04 (m, 1 H), 4.07-4.11 (m, 1 H), 4.12 (br s, 1 H), 4.28 (br d, 1 H), 4.44 (br d, 1 H), 4.83 (br dd, 1 H), 4.88 (br d, 1 H), 5.03 (d, 1 H), 7.30 (br d, 2 H), 7.60 (br d, 2 H) |
| B-3^ | 0.70-1.20 (m, 32 H), 1.21-1.84 (m, 12 H), 1.89 (br s, 2 H), 2.28 (br dd, 1 H), 2.41 (br d, 3 H), 2.54 (br d, 2 H), 2.65 (br d, 1 H), 2.83 (br dd, 1 H), 2.91-2.97 (m, 1 H), 3.04 (br d, 3 H), 3.07-3.17 (m, 2 H), 3.50 (br s, 1 H), 3.62-3.70 (m, 1 H), 3.77 (br s, 1 H), 3.88-3.98 (m, 1 H), 4.03-4.16 (m, 3 H), 4.20-4.31 (m, 1 H), 4.38-4.45 (m, 1 H), 4.75-4.85 (m, 2 H), 4.88 (br s, 1 H), 7.00-7.08 (m, 1 H), 7.11-7.21 (m, 2 H), 7.30 (br d, 2 H) |
| B-3a^ | $^1$H NMR (400 MHz, DMSO-d$_6$) δ ppm 0.72-1.27 (m, 32 H), 1.27-1.88 (m, 10 H), 1.91 (br s, 2 H, AcOH), 1.98 (br s, 1 H), 2.25-2.35 (m, 1 H), 2.42 (br d, 3 H), 2.53-2.60 (m, 2 H), 2.67 (br s, 1 H), 2.84 (br dd, 1 H), 2.92-3.01 (m, 1 H), 3.06 (br d, 3 H), 3.10-3.16 (m, 1 H), 3.31 (br s, 3 H), 3.51 (br d, 1 H), 3.62-3.72 (m, 1 H), 3.76-3.86 (m, 1 H), 3.93 (br dd, 1 H), 4.05-4.21 (m, 3 H), 4.43 (br d, 1 H), 4.83 (br d, 2 H), 4.89 (br s, 1 H), 7.01-7.10(m, 1 H), 7.16 (br d, 2 H), 7.31 (br d, 2 H) |
| B-4 | CHLOROFORM-d 0.78-1.05 (m, 14H), 1.12-1.27 (m, 16H), 1.36-2.03 (m, 14H), 2.18-2.35 (m, 5H), 2.43-2.52 (m, 4H), 2.54-2.89 (m, 1H), 2.74-2.82 (m, 1H), 2.85 (s, 1H), 2.81-2.89 (m, 1H), 2.91-3.04 (m, 1H), 3.25 (s, 3H), 3.32-3.42 (m, 1H), 3.53-3.64 (m, 3H), 3.93-4.06 (m, 1H), 4.08-4.22 (m, 2H), 4.13-4.21 (m, 2H), 4.42-4.52 (m, 1H), 4.57-4.68 (m, 1H), 4.96-5.05 (m, 1H), 6.93 (s, 1H), 7.18-7.25 (m, 4H) |
| B-5 | 0.5-1.5 (m, 37H), 1.5-2.3 (m, 10H), 2.4-3.0 (m, 6H), 3.04 (s, 3H), 3.11 (brs, 1H), 3.29 (s, 3H), 3.47 (br d, 2H), 3.66 (brs, 1H), 3.93 (brs, 1H), 4.08 (br t, 1H), 4.16 (d, 2H), 4.29 (brs, 1H), 4.42 (d, 1H), 4.75 (brs, 1H), 4.84 (brs, 2H), 7.04 (t, 1H), 7.15 (d, 2H), 7.30 (t, 2H). |
| B-6^ | 0.5-1.5 (m, 37H), 1.5-2.3 (m, 13H), 2.4-3.0 (m, 6H), 3.11 (s, 3H), 3.2 (brs, 1H), 3.3 (s, 3H), 3.44 (d, 1H), 3.52 (d, 1H), 4.08 (brs, 1H), 4.14 (br t, 1H), 4.31 (brs, 1H), 4.45 (d, 3H), 4.72 (d, 1H), 4.74 (d, 1H), 4.84 (d, 1H), 5.01 (d, 1H), 7.29 (d, 2H), 7.60 (d, 2H). |
| B-7 | 0.5-1.5 (m, 37H), 1.5-2.3 (m, 10H), 2.4-3.0 (m, 12H), 3.24 (s, 3H), 3.44 (d, 1H), 3.52 (d, 1H), 3.7 (brs, 1H), 4.09 (brs, 2H), 4.18 (brs, 2H), 4.29 (brs, 2H), 4.46 (d, 1H), 4.73 (d, 1H), 4.83 (br t, 1H), 6.63 (d, 2H), 7.20 (d, 2H), 7.92 (s, 1H). |
| B-8 | 0.5-1.6 (m, 37H), 1.7-2.3 (m, 10H), 2.4-3.0 (m, 7H), 3.24 (s, 3H), 3.45 (brs, 1H), 3.52 (d, 1H), 3.8 (brs, 1H), 4.0-4.2 (m, 4H), 4.35 (brs, 2H), 4.5 (d, 1H), 4.75 (d, 1H), 4.8-5.0 (pm, 1H), 7.56 (d, 2H), 7.65 (d, 2H), 8.7 (s, 1H). |
| B-9 | 0.5-1.6 (m, 36H), 1.7-2.3 (m, 10H), 2.4-3.0 (m, 7H), 3.1-3.4 (m, 5H), 3.55 (d, 1H), 3.8 (brs, 1H), 4.0-4.3 (m, 5H), 4.45 (d, 1H), 4.75 (d, 1H), 4.85 (brs, 1H), 7.05 (t, 2H), 7.41-7.70 (m, 3H), 8.3 (s, 1H). |
| B-10 | 0.5-1.4 (m, 40H), 1.5-2.4 (m, 17H), 2.6-2.7 (m, 4H), 2.85-2.95 (m, 1H), 3.05-3.15 (m, 1H), 3.2 (s, 3H), 3.45-3.55 (m, 2H), 3.8 (brs, 1H), 3.9-4.3 (m, 5H), 4.45 (d, 1H), 4.45 (d, 1H), 4.65-4.85 (m, 3H), 5.75 (d, 1H), 7.55 (brs, 1H) |
| B-11 | 0.5-1.4 (m, 42H), 1.5-2.4 (m, 15H), 2.6-2.7 (m, 5H), 2.85-2.95 (m, 1H), 3.05-3.15 (m, 1H), 3.45 (d, 1H), 3.55 (d, 1H), 3.75 (brs, 1H), 3.8-3.85 (m, 1H), 4.05-4.2 (m, 3H), 4.25-4.35 (m, 2H), 4.45 (d, 1H), 4.75 (d, 1H), 4.85 (s, 2H), 5.45 (s, 1H), 7.45 (brs, 1H) |
| B-12 | 0.5-1.2 (m, 34H), 1.5-2.3 (m, 13H), 2.65-2.95 (m, 6H), 3.2 (s, 3H), 3.45-3.55 (m, 2H), 3.8 (brs, 1H), 4.0-4.2 (m, 4H), 4.25-4.45 (m, 2H), 4.45 (d, 1H), 4.75-4.95 (m, 3H), 7.6-7.7 (m, 4H), 8.8 (s, 1H). |
| B-13^ | 1.09 (br s, 32 H), 1.22-1.87 (m, 10 H), 1.90 (s, 2 H), 1.93 (br d, 1 H), 2.18 (br d, 1 H), 2.53 (s, 3 H), 2.57 (br d, 1 H), 2.62-2.70 (m, 1 H), 2.83 (br d, 1 H), 3.09-3.15 (m, 4 H), 3.16-3.24 (m, 2 H), 3.30 (br s, 6 H), 3.50 (br d, 1 H), 3.56-3.63 (m, 1 H), 3.70-3.78 (m, 1 H), 3.92-4.03 (m, 1 H), 4.15 (br s, 1 H), 4.32 (q, 1 H), 4.39 (d, 1 H), 4.83 (dd, 1 H), 4.89 (d, 1 H), 5.08 (br d, 1 H), 7.29 (br d, 2 H), 7.60 (br d, 2 H) |

TABLE B-continued

Example NMR's
¹H NMR: 400 MHz, DMSO-d6 (unless otherwise specified) δ ppm

| | |
|---|---|
| B-13a^ | 0.72-1.19 (m, 32 H), 1.20-1.88 (m, 11 H), 1.89 (s, 2 H), 1.90-1.97 (m, 1 H), 2.53 (s, 3 H), 2.56 (br s, 1 H), 2.60-2.70 (m, 1 H), 2.83 (br d, 1 H), 3.10-3.14 (m, 3 H), 3.15-3.20 (m, 1 H), 3.22-3.27 (m, 3 H), 3.44-3.56 (m, 2 H), 3.63-3.69 (m, 1 H), 3.70-3.77 (m, 1 H), 3.85-3.94 (m, 1 H), 3.94-4.03 (m, 1 H), 4.07-4.14 (m, 1 H), 4.15-4.21 (m, 1 H), 4.21-4.29 (m, 1 H), 4.33 (br d, 1 H), 4.60-4.70 (m, 1 H), 4.83 (dd, 1 H), 4.89 (br d, 1 H), 4.94-5.02 (m, 1 H), 5.09 (d, 1 H), 7.24-7.33 (m, 2 H), 7.55-7.64 (m, 2 H) |

^acetate salt

The following Formula (1-A2) compounds were prepared in accordance with the Schemes and procedures defined herein; and wherein $R^0$ is H, $R^1$ is methyl and $R^7$ is ethyl; are provided in Table C. Respective compound names are provided below the table.

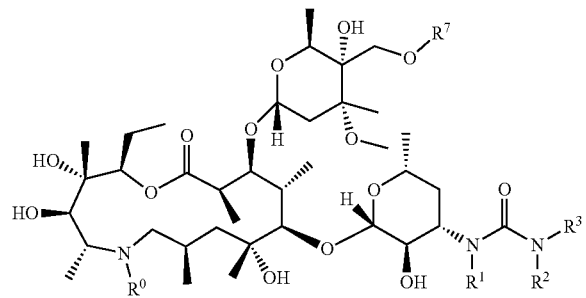

(1-A2)

TABLE C

Formula (1-A2) Compounds

| Ex # | $R^2$ | $R^3$ | Mass [M + H]⁺ |
|---|---|---|---|
| C-1 | H | phenyl | 898 |
| C-2 | methyl | phenyl | 912 |
| C-3 | methyl | ![4-CF3-phenyl] | 980 |

Table C Example Names:
C-1. 1-((2S,3R,4S,6R)-2-(((2R,3S,4R,5R,8R,10R,11R,12S,13S,14R)-13-(((2R,4R,5S,6S)-5-(ethoxymethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

C-2. 1-((2S,3R,4S,6R)-2-(((2R,3S,4R,5R,8R,10R,11R,12S,13S,14R)-13-(((2R,4R,5S,6S)-5-(ethoxymethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; and C-3. 1-((2S,3R,4S,6R)-2-(((2R,3S,4R,5R,8R,10R,11R,12S,13S,14R)-13-(((2R,4R,5S,6S)-5-(ethoxymethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea.

TABLE C

Example NMR's

| | |
|---|---|
| C-1^ | ¹H NMR (600 MHz, DMSO-d₆) δ ppm 0.91 (s, 32 H), 1.21-1.53 (m, 5 H), 1.61-1.74 (m, 3 H), 1.79 (br dd, 1 H), 1.88 (s, 1 H, AcOH), 2.07-2.09 (m, 1 H), 2.14 (td, 1 H), 2.24 (br d, 1 H), 2.34-2.40 (m, 1 H), 2.60-2.66 (m, 2 H), 2.70-2.74 (m, 2 H), 2.83 (s, 3 H), 2.84-2.89 (m, 1 H), 3.17 (br d, 1 H), 3.21 (s, 3 H), 3.25-3.30 (m, 2 H), 3.40-3.42 (m, 2 H), 3.49 (br d, 1 H), 3.59-3.65 (m, 1 H), 3.98-4.17 (m, 4 H), 4.42 (d, 1 H), 4.65 (d, 1 H), 4.73 (br s, 1 H), 4.76 (q, 1 H), 5.10 (br s, 2 H), 6.87-6.93 (m, 1 H), 7.17-7.24 (m, 2 H), 7.41 (br d, 2 H), 8.24 (s, 1 H) |
| C-2^ | ¹H NMR (400 MHz, DMSO-d₆) δ ppm 0.69-1.44 (m, 37 H), 1.63-1.84 (m, 3 H), 1.89 (s, 2 H, AcOH), 2.08-2.18 (m, 1 H), 2.27 (br d, 1 H), 2.36 (br dd, 1 H), 2.44 (s, 3 H), 2.63 (br dd, 1 H), 2.67 (br d, 1 H), 2.69-2.75 (m, 1 H), 2.77 (br d, 1 H), 2.82-2.91 (m, 1 H), 3.04 (s, 3 H), 3.13-3.23 (m, 2 H), 3.25 (s, 3 H), 3.31 (br s, 6 H), 3.38-3.48 (m, 3 H), 3.84-3.95 (m, 1 H), 3.98-4.13 (m, 3 H), 4.38 (br d, 1 H), 4.69 (br d, 1 H), 4.78 (q, 1 H), 5.02 (br s, 1 H), 7.06 (t, 1 H), 7.14 (d, 2 H), 7.27-7.35 (m, 2 H) |
| C-3^ | ¹H NMR (400 MHz, DMSO-d₆) δ ppm 0.73-1.23 (m, 32 H), 1.23-1.84 (m, 8 H), 1.87 (s, 1 H, AcOH), 2.10-2.20 (m, 1 H), 2.26 (br d, 1 H), 2.36 (br dd, 1 H), 2.54 (s, 3 H), 2.60-2.68 (m, 2 H), 2.70-2.77 (m, 2 H), 2.87 (br d, 1 H), 3.12 (s, 3 H), 3.17 (br d, 1 H), 3.21 (s, 3 H), 3.26 (br d, 2 H), 3.28-3.39 (m, 5 H), 3.41 (br d, 1 H), 3.47 (br s, 1 H), 3.49-3.58 (m, 1 H), 3.90-4.14 (m, 4 H), 4.41 (br d, 1 H), 4.67 (br d, 1 H), 4.77 (q, 1 H), 5.16-5.31 (m, 1 H), 7.28 (br d, 2 H), 7.60 (br d, 2 H) |

^acetate salt

The following Formula (1-A3) compounds were prepared in accordance with the Schemes and procedures defined herein; wherein $R^0$ is H, $R^1$ is methyl and $R^7$ is propyl; are shown in Table D. Respective compound names are provided below the Table.

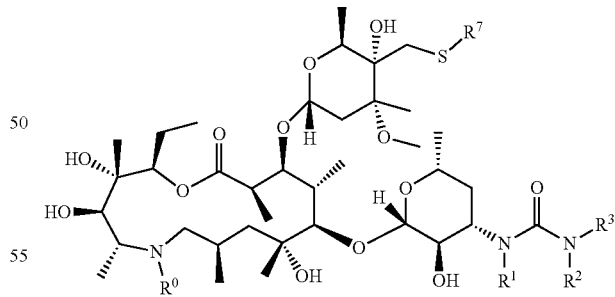

(1-A3)

TABLE D

Formula (1-A3) Compounds

| Example # | $R^2$ | $R^3$ | Mass [M + H]⁺ |
|---|---|---|---|
| D-1 | H | phenyl | 928 |
| D-2 | methyl | phenyl | 942 |

TABLE D-continued

Formula (1-A3) Compounds

| Example # | R² | R³ | Mass [M + H]⁺ |
|---|---|---|---|
| D-3* | methyl | ⁂—⟨C₆H₄⟩—CF₃ | 1010 |

*MIC ≤ 64 μg/mL for at least one BRD bacterial strain

Table D Example Names:
- D-1. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylthio)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;
- D-2. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylthio)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; and
- D-3. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylthio)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea.

TABLE D

Example NMR's

| | |
|---|---|
| D-1^ | ¹H NMR (400 MHz, DMSO-d₆) δ ppm 0.69-1.22 (m, 32 H), 1.23-1.85 (m, 11 H), 1.89 (s, 2 H), 1.91 (br s, 1 H), 2.15 (br d, 1 H), 2.45-2.48 (m, 2 H), 2.55 (br d, 1 H), 2.60-2.68 (m, 1 H), 2.74 (br d, 2 H), 2.78 (s, 3 H), 2.83 (br d, 1 H), 3.15-3.24 (m, 1 H), 3.26 (s, 3 H), 3.32 (br s, 5 H), 3.45 (br d, 1 H), 3.71 (br s, 3 H), 3.96-4.07 (m, 1 H), 4.09 (br s, 1 H), 4.37-4.47 (m, 2 H), 4.80-4.89 (m, 2 H), 4.94 (br d, 1 H), 6.89 (t, 1 H), 7.21 (t, 2 H), 7.44 (d, 2 H), 8.33 (s, 1 H) |
| D-2^ | ¹H NMR (400 MHz, DMSO-d₆) δ ppm 0.72-1.22 (m, 32 H), 1.22-1.85 (m, 10 H), 1.90 (s, 2 H), 1.91-1.99 (m, 2 H), 2.19 (br d, 1 H), 2.43 (s, 3 H), 2.45-2.49 (m, 2 H), 2.59 (br d, 1 H), 2.63-2.70 (m, 1 H), 2.75 (s, 2 H), 2.83 (br d, 1 H), 3.06 (s, 3 H), 3.09-3.19 (m, 1 H), 3.33 (br d, 6 H), 3.36 (s, 3 H), 3.41-3.52 (m, 2 H), 3.71-3.81 (m, 1 H), 3.82-3.94 (m, 1 H), 4.10 (br s, 1 H), 4.31-4.40 (m, 2 H), 4.84 (br d, 1 H), 4.88 (br d, 2 H), 7.06 (t, 1 H), 7.14 (br d, 2 H), 7.26-7.35 (m, 2 H) |
| D-3^ | ¹H NMR (400 MHz, DMSO-d₆) δ ppm 0.72-1.22 (m, 32 H), 1.22-1.87 (m, 11 H), 1.89 (s, 2 H), 1.90-1.96 (m, 2 H), 2.16 (br d, 1 H), 2.44-2.48 (m, 2 H), 2.53 (s, 3 H), 2.56 (br d, 1 H), 2.61-2.69 (m, 1 H), 2.74 (s, 2 H), 2.83 (br d, 1 H), 3.13 (s, 3 H), 3.19 (br t, 2 H), 3.29 (s, 3 H), 3.32 (br s, 3 H), 3.43 (s, 1 H), 3.47 (br d, 1 H), 3.63 (br d, 1 H), 3.76 (br dd, 1 H), 3.92-4.03 (m, 1 H), 4.12 (br s, 1 H), 4.34-4.42 (m, 2 H), 4.80-4.89 (m, 1 H), 4.87 (br d, 1 H), 5.08 (br d, 1 H), 7.29 (br d, 2 H), 7.60 (d, 2 H) |

^acetate salt

The following Formula (1-A4) compounds were prepared in accordance with the Schemes and procedures defined herein; wherein R⁰ is H, R¹ is methyl and X' is chloro; are shown in Table E. Respective compound names are provided below the table.

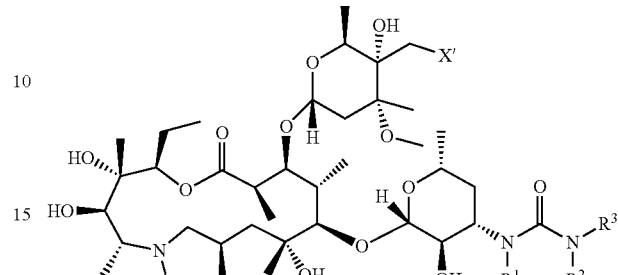

(1-A4)

TABLE E

Formula (1-A4) Compounds

| Example # | R² | R³ | Mass [M + H]⁺ |
|---|---|---|---|
| E-1 | H | phenyl | 889 |
| E-2 | methyl | phenyl | 903 |
| E-3 | methyl | ⁂—⟨C₆H₄⟩—CF₃ | 971 |

Table E Example Names:
- E-1. 1-((2S,3R,4S,6R)-2-(((2R,3S,4R,5R,8R,10R,11R,12S,13S,14R)-13-(((2R,4R,5S,6S)-5-(chloromethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;
- E-2. 1-((2S,3R,4S,6R)-2-(((2R,3S,4R,5R,8R,10R,11R,12S,13S,14R)-13-(((2R,4R,5S,6S)-5-(chloromethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; and
- E-3. 1-((2S,3R,4S,6R)-2-(((2R,3S,4R,5R,8R,10R,11R,12S,13S,14R)-13-(((2R,4R,5S,6S)-5-(chloromethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(4-(trifluoromethyl)phenyl)urea.

TABLE E

Example NMR's

| | |
|---|---|
| E-1^ | ¹H NMR (400 MHz, DMSO-d₆) δ ppm 0.69-1.27 (m, 30 H), 1.45 (br s, 4 H), 1.57-1.81 (m, 3 H), 1.83-1.89 (m, 2 H), 1.89 (s, 2 H), 1.91-1.97 (m, 1 H), 2.18 (br d, 1 H), 2.54-2.61 (m, 1 H), 2.62-2.70 (m, 1 H), 2.79 (s, 3 H), 2.83 (br d, 1 H), |

TABLE E-continued

Example NMR's

| | |
|---|---|
| | 3.17-3.24 (m, 2 H), 3.26 (s, 3 H), 3.32 (br s, 3 H), 3.45 (br d, 1 H), 3.65-3.79 (m, 3 H), 3.80-3.87 (m, 1 H), 4.00-4.07 (m, 1 H), 4.10 (br s, 1 H), 4.12 (s, 1 H), 4.44 (br d, 1 H), 4.50 (q, 1 H), 4.81-4.87 (m, 1 H), 4.90 (br d, 1 H), 4.95 (br s, 1 H), 6.90 (t, 1 H), 7.21 (t, 2 H), 7.43 (d, 2 H), 8.30 (s, 1 H) |
| E-2^ | $^1$H NMR (400 MHz, DMSO-$d_6$) δ ppm 0.71-1.25 (m, 32 H), 1.25-1.49 (m, 6 H), 1.65 (br d, 1 H), 1.71-1.88 (m, 3 H), 1.89 (s, 1 H), 1.90-1.97 (m, 2 H), 2.20 (br d, 1 H), 2.42 (s, 3 H), 2.56 (br d, 1 H), 2.66 (br dd, 1 H), 2.82 (br d, 1 H), 3.06 (s, 3 H), 3.10-3.19 (m, 1 H), 3.35 (s, 3 H), 3.45 (br d, 1 H), 3.53 (br dd, 1 H), 3.71-3.86 (m, 4 H), 3.92 (br d, 1 H), 4.12 (br s, 1 H), 4.36 (br d, 1 H), 4.46 (br d, 1 H), 4.84 (br d, 1 H), 4.88 (br d, 1 H), 4.91 (br d, 1 H), 7.06 (t, 1 H), 7.15 (br d, 2 H), 7.27-7.34 (m, 2 H) |
| E-3^ | $^1$H NMR (400 MHz, DMSO-$d_6$) δ ppm 0.71-1.26 (m, 32 H), 1.27-1.88 (m, 10 H), 1.89 (s, 2 H), 1.90-1.99 (m, 1 H), 2.18 (br d, 1 H), 2.52 (br s, 3 H), 2.56 (br d, 1 H), 2.66 (br dd, 1 H), 2.83 (br d, 1 H), 3.13 (s, 3 H), 3.16-3.24 (m, 2 H), 3.28 (s, 3 H), 3.48 (br d, 1 H), 3.64-3.78 (m, 3 H), 3.80-3.86 (m, 1 H), 3.97 (s, 1 H), 3.98-4.07 (m, 1 H), 4.12 (br s, 1 H), 4.40 (br d, 1 H), 4.47 (q, 1 H), 4.81-4.87 (m, 1 H), 4.91 (br d, 1 H), 5.08 (d, 1 H), 7.29 (br d, 2 H), 7.60 (d, 2 H) |

^acetate salt

The following Formula (1-A5) compounds were prepared in accordance with the Schemes and procedures defined herein; wherein $R^0$ is H and $R^1$ is methyl; are shown in Table F. Respective compound names are provided below the table.

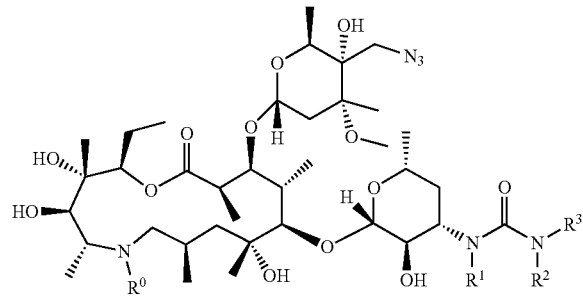

(1-A5)

TABLE F

Formula (1-A5) Compounds

| Example # | $R^2$ | $R^3$ | Mass [M + H]$^+$ |
|---|---|---|---|
| F-1 | H | phenyl | 895 |
| F-2 | methyl | phenyl | 909 |
| F-3* | methyl | ⸺⟨C$_6$H$_4$⟩-CF$_3$ | 977 |

*MIC ≤ 64 μg/mL for at least one BRD bacterial strain

Table F Example Names:

F-1. 1-((2S,3R,4S,6R)-2-(((2R,3S,4R,5R,8R,10R,11R,12S,13S,14R)-13-(((2R,4R,5S,6S)-5-(azidomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

F-2. 1-((2S,3R,4S,6R)-2-(((2R,3S,4R,5R,8R,10R,11R,12S,13S,14R)-13-(((2R,4R,5S,6S)-5-(azidomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; and F-3. 1-((2S,3R,4S,6R)-2-(((2R,3S,4R,5R,8R,10R,11R,12S,13S,14R)-13-(((2R,4R,5S,6S)-5-(azidomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea.

TABLE F

Example NMR's

| | |
|---|---|
| F-1^ | $^1$H NMR (400 MHz, DMSO-$d_6$) δ ppm 0.73-1.26 (m, 31 H), 1.27-1.52 (m, 4 H), 1.60-1.80 (m, 4 H), 1.86 (br s, 1 H), 1.89 (s, 3 H), 1.91-1.97 (m, 1 H), 2.16 (br d, 1 H), 2.52-2.60 (m, 1 H), 2.60-2.69 (m, 1 H), 2.77 (s, 3 H), 2.83 (br d, 1 H), 3.18-3.22 (m, 1 H), 3.25 (s, 3 H), 3.27-3.30 (m, 1 H), 3.36 (br s, 1 H), 3.37-3.42 (m, 3 H), 3.42-3.46 (m, 1 H), 3.63-3.82 (m, 2 H), 3.95-4.05 (m, 1 H), 4.08 (br s, 1 H), 4.20 (s, 1 H), 4.45 (br d, 1 H), 4.47-4.55 (m, 1 H), 4.83 (br d, 1 H), 4.87 (br d, 1 H), 4.97 (br s, 1 H), 6.89 (t, 1 H), 7.21 (t, 2 H), 7.45 (d, 2 H), 8.35 (s, 1 H) |
| F-2^ | $^1$H NMR (400 MHz, DMSO-$d_6$) δ ppm 0.69-1.23 (m, 32 H), 1.29-1.49 (m, 5 H), 1.59-1.86 (m, 4 H), 1.90 (s, 2 H), 1.91-1.95 (m, 1 H), 2.19 (br d, 1 H), 2.43 (s, 3 H), 2.52-2.60 (m, 1 H), 2.62-2.70 (m, 1 H), 2.82 (br d, 1 H), 3.07 (s, 3 H), 3.11-3.19 (m, 1 H), 3.25 (br d, 1 H), 3.36 (s, 3 H), 3.38 (br s, 1 H), 3.42 (br s, 2 H), 3.43-3.46 (m, 1 H), 3.49-3.57 (m, 1 H), 3.75 (br d, 1 H), 3.78 (s, 1 H), 3.87-3.96 (m, 1 H), 4.13 (br s, 1 H), 4.35 (br d, 1 H), 4.44 (q, 1 H), 4.83 (br d, 1 H), 4.90 (br d, 2 H), 7.05 (t, 1 H), 7.15 (d, 2 H), 7.27-7.34 (m, 2 H) |
| F-3^ | $^1$H NMR (400 MHz, DMSO-$d_6$) δ ppm 0.73-1.27 (m, 32 H), 1.27-1.87 (m, 10 H), 1.89 (s, 1 H), 1.90-1.98 (m, 1 H), 2.17 (br d, 1 H), 2.53 (br s, 3 H), 2.57 (br s, 1 H), 2.66 (br dd, 1 H), 2.83 (br d, 1 H), 3.14 (s, 3 H), 3.21 (br dd, 1 H), 3.29 (br s, 3 H), 3.40 (br s, 2 H), 3.43-3.50 (m, 2 H), 3.61-3.71 (m, 1 H), 3.75 (br dd, 1 H), 3.91 (br s, 1 H), 3.96-4.07 (m, 1 H), 4.13 (br s, 1 H), 4.38 (br d, 1 H), 4.42-4.50 (m, 1 H), 4.83 (br d, 1 H), 4.89 (br d, 1 H), 5.10 (br d, 1 H), 7.29 (br d, 2 H), 7.60 (br d, 2 H) |

The following Formula (1-A6) compounds were prepared in accordance with the Schemes and procedures defined herein; wherein $R^0$ is H and $R^1$ is methyl; are shown in Table G. Respective compound names are provided below the table.

(1-A6)

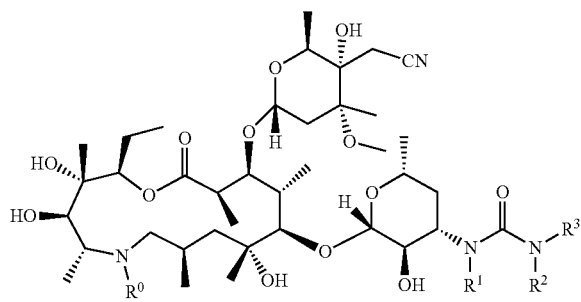

TABLE G

| | Formula (1-A6) Compounds | | |
|---|---|---|---|
| Example # | $R^2$ | $R^3$ | Mass $[M + H]^+$ |
| G-1 | H | phenyl | 879 |
| G-2 | methyl | phenyl | 893 |
| G-3 | methyl | ⸺⟨phenyl⟩-CF₃ | 961 |

Table G Example Names:
 G-1. 1-((2S,3R,4S,6R)-2-(((2R,3S,4R,5R,8R,10R,11R,12S,13S,14R)-13-(((2R,4R,5S,6S)-5-(cyanomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;
 G-2. 1-((2S,3R,4S,6R)-2-(((2R,3S,4R,5R,8R,10R,11R,12S,13S,14R)-13-(((2R,4R,5S,6S)-5-(cyanomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; and
 G-3. 1-((2S,3R,4S,6R)-2-(((2R,3S,4R,5R,8R,10R,11R,12S,13S,14R)-13-(((2R,4R,5S,6S)-5-(cyanomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea.

TABLE G

| Example NMR's | |
|---|---|
| G-1 | ¹H NMR (400 MHz, DMSO-d₆) δ ppm 0.68-1.22 (m, 32 H), 1.22-1.95 (m, 12 H), 2.13-2.23 (m, 1 H), 2.55 (br d, 1 H), 2.65 (br dd, 1 H), 2.78 (s, 4 H), 2.82 (br d, 1 H), 3.16-3.23 (m, 1 H), 3.26 (s, 3 H), 3.39-3.44 (m, 1 H), 3.70 (br s, 2 H), 3.95-4.07 (m, 1 H), 4.11 (br s, 1 H), 4.18 (s, 1 H), 4.37 (s, 1 H), 4.42 (br d, 1 H), 4.48 (q, 1 H), 4.83 (br d, 1 H), 4.88 (br d, 1 H), 5.00 (br d, 1 H), 6.90 (t, 1 H), 7.21 (t, 2 H), 7.43 (br d, 2 H), 8.32 (s, 1 H) |
| G-2^ | ¹H NMR (400 MHz, DMSO-d₆) δ ppm 0.67-1.24 (m, 32 H), 1.25-1.86 (m, 10 H), 1.88 (s, 1 H), 1.92 (br s, 1 H), 2.21 (br d, 1 H), 2.37-2.46 (m, 3 H), 2.56 (br d, 1 H), 2.65 (br d, 1 H), 2.70-2.86 (m, 3 H), 3.07 (s, 3 H), 3.11-3.19 (m, 1 H), 3.26 (br s, 1 H), 3.36 (s, 3 H), 3.40-3.45 (m, 1 H), 3.48-3.58 (m, 1 H), 3.75 (br s, 1 H), 3.87-3.98 (m, 1 H), 4.07 (br s, 1 H), 4.15 (br s, 1 H), 4.33 (br d, 1 H), 4.40-4.50 (m, 1 H), 4.83 (br d, 1 H), 4.91 (br t, 2 H), 7.06 (br t, 1 H), 7.15 (br d, 2 H), 7.24-7.36 (m, 2 H) |
| G-3^ | ¹H NMR (400 MHz, DMSO-d₆) δ ppm 0.68-1.26 (m, 32 H), 1.26-1.88 (m, 10 H), 1.89 (s, 2 H), 1.91-1.98 (m, 1 H), 2.14-2.24 (m, 1 H), 2.52 (s, 3 H), 2.54-2.60 (m, 1 H), 2.61-2.69 (m, 1 H), 2.77 (d, 2 H), 2.79-2.87 (m, 1 H), 3.14 (s, 3 H), 3.16-3.25 (m, 2 H), 3.30 (s, 3 H), 3.42-3.48 (m, 1 H), 3.61-3.71 (m, 1 H), 3.71-3.81 (m, 1 H), 3.97-4.08 (m, 1 H), 4.16 (br s, 1 H), 4.23 (s, 1 H), 4.33-4.39 (m, 1 H), 4.41-4.48 (m, 1 H), 4.80-4.86 (m, 1 H), 4.88-4.93 (m, 1 H), 5.09-5.15 (m, 1 H), 7.29 (d, 2 H), 7.60 (d, 2 H) |

^acetate salt

The following Formula (1-A1) compounds were prepared using the Schemes and procedures defined herein; $R^0$ is H, methyl or propyl, as defined in Table H. The respective compound names (mass [M+H]⁺) are provided below the table.

(1-A1)

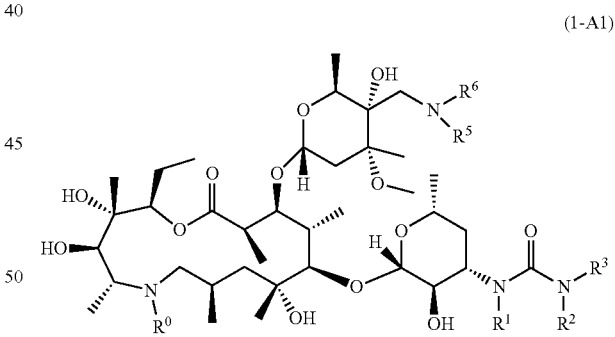

TABLE H

| | Formula (1-1) Compounds | | | | |
|---|---|---|---|---|---|
| Ex # | $R^1$ | $R^2$ | $R^3$ | $R^5$ | $R^6$ |
| | | | $R^0$ is H | | |
| H-1 | methyl | H | cyclopropyl | 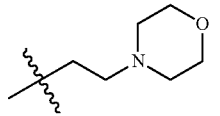 [SMILES: *CCN1CCOCC1] | 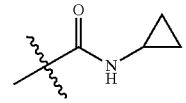 [SMILES: *C(=O)NC1CC1] |

TABLE H-continued

Formula (1-1) Compounds

| Ex # | R¹ | R² | R³ | R⁵ | R⁶ |
|---|---|---|---|---|---|
| H-2 | methyl | H | phenyl | methyl | methyl |
| H-3 | methyl | H | phenyl | H | —(CH$_2$)$_2$N(CH$_3$)$_2$ |
| H-4 | methyl | H | phenyl | ethyl | ethyl |
| H-5* | methyl | H | propyl | H | —(CH$_2$)$_2$N(CH$_3$)$_2$ |
| H-6 | methyl | H | —(CH$_2$)$_2$N(CH$_3$)$_2$ | H | propyl |
| H-7* | methyl | H | 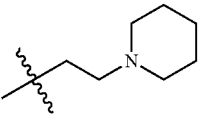 [SMILES: *CCN1CCCCC1] | H | propyl |
| H-8 | propyl | methyl | 4-CF$_3$-phenyl | H | propyl |
| H-9 | methyl | H | H | propyl | —(CH$_2$)$_2$N(CH$_3$)$_2$ |
| H-10 | methyl | H | 4-F-phenyl | propyl | 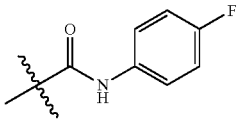 [SMILES: *C(=O)Nc1ccc(F)cc1] |
| H-11 | methyl | methyl | phenyl | H | propyl |
| H-12 | methyl | H | 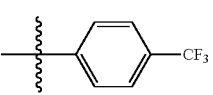 | propyl | 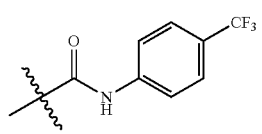 [SMILES: *C(=O)Nc1ccc(C(F)(F)F)cc1] |
| H-13 | methyl | methyl | 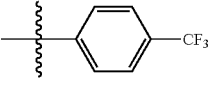 | H | propyl |
| H-14 | methyl | 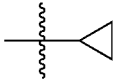 | phenyl | H | propyl |
| H-15* | methyl | H | pyridin-yl | H | propyl |
| H-16 | methyl | ethyl | phenyl | H | propyl |
| H-17 | methyl | isopropyl | phenyl | H | propyl |
| H-18* | methyl | methyl | phenyl | H | —(CH$_2$)$_2$OCH$_3$ |
| H-19* | methyl | methyl | phenyl | H | —(CH$_2$)$_3$OCH$_3$ |
| H-20 | methyl | methyl | phenyl | methyl | —(CH$_2$)$_2$N(CH$_3$)$_2$ |
| H-21 | methyl | methyl | phenyl | H | —(CH$_2$)$_2$S(O)$_2$CH$_3$ |
| H-22 | methyl | H | H | propyl | —C(O)NH$_2$ |
| H-23* | methyl | methyl | phenyl | H | ethyl |
| H-24 | methyl | methyl | phenyl | H | —CH$_2$CH(CH$_3$)$_2$ |
| H-25 | methyl | methyl | phenyl | H | 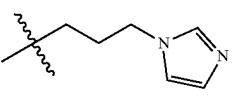 [SMILES: *CCCn1ccnc1] |
| H-26 | methyl | methyl | phenyl | H | methyl |
| H-27 | methyl | methyl | phenyl | H | 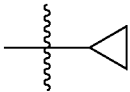 [SMILES: *C1CC1] |
| H-28 | methyl | methyl | phenyl | H | butyl |
| H-29 | methyl | methyl | phenyl | H | isopentyl |
| H-30 | methyl | methyl | phenyl | H | 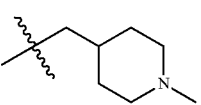 [SMILES: *CC1CCN(C)CC1] |

TABLE H-continued

Formula (1-1) Compounds

| Ex # | R¹ | R² | R³ | R⁵ | R⁶ |
|---|---|---|---|---|---|
| H-31 | methyl | methyl | phenyl | H | N-acetylpiperidin-4-ylmethyl |
| H-32 | methyl | methyl | phenyl | H | phenyl |
| H-33 | methyl | methyl | phenyl | H | (tetrahydro-2H-pyran-4-yl)methyl |
| H-34 | methyl | methyl | phenyl | H | cyclopropylmethyl |
| H-35 | methyl | methyl | phenyl | H | 3-(2-oxopyrrolidin-1-yl)propyl |
| H-36* | methyl | methyl | phenyl | H | biphenyl-4-ylmethyl |
| H-37 | methyl | methyl | phenyl | methyl | cyclobutyl |
| H-38 | methyl | methyl | phenyl | H | 3-(piperidin-1-yl)propyl |
| H-39 | methyl | phenyl | phenyl | H | propyl |
| H-40 | methyl | phenyl | benzyl | H | propyl |
| H-41 | methyl | methyl | phenyl | H | cyclopropylmethyl |
| H-42 | methyl | methyl | phenyl | H | 2-(morpholin-4-yl)ethyl |
| H-43 | methyl | methyl | phenyl | H | 2-(phenylsulfonyl)ethyl |
| H-44* | methyl | methyl | phenyl | H | 4-(trifluoromethyl)phenethyl |
| H-45 | methyl | methyl | pyridin-yl | H | propyl |
| H-46 | methyl | methyl | pyrazin-2-yl | H | propyl |
| H-47 | methyl | methyl | phenyl | H | 3-(2-oxo-2H-pyridin-1-yl)propyl |

TABLE H-continued

Formula (1-1) Compounds

| Ex # | R¹ | R² | R³ | R⁵ | R⁶ |
|---|---|---|---|---|---|
| H-48 | methyl | methyl | pyridazin-3-yl | H | propyl |
| H-49 | methyl | methyl | pyrimidin-2-yl | H | propyl |
| H-50 | methyl | methyl | pyrimidin-5-yl | H | propyl |
| H-51 | methyl | methyl | 5-chloropyrimidin-2-yl | H | propyl |
| H-52 | methyl | methyl | 5-cyclopropylpyrimidin-2-yl | H | propyl |
| H-53 | methyl | methyl | pyridin-yl | H | propyl |
| H-54 | methyl | —CH₂CF₃ | phenyl | H | propyl |
| H-55 | methyl | phenyl | tetrahydropyran-4-yl | H | propyl |
| H-56 | methyl | methyl | 1,2,4-triazin-3-yl | H | propyl |
| H-57 | methyl | methyl | 2,6-dimethylpyrimidin-4-yl | H | propyl |
| H-58 | methyl | methyl | 1-methyl-1H-pyrazol-4-yl | H | propyl |
| H-59 | methyl | methyl | pyridin-4-yl | H | propyl |
| H-60 | 4-methoxybenzyl | methyl | phenyl | H | propyl |
| H-61* | methyl | methyl | thiazol-2-yl | H | propyl |

TABLE H-continued

Formula (1-1) Compounds

| Ex # | R¹ | R² | R³ | R⁵ | R⁶ |
|---|---|---|---|---|---|
| H-62 | methyl | methyl | 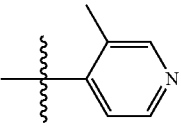 | H | propyl |
| H-63 | methyl | methyl | phenyl | propyl | 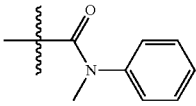 [SMILES: *C(=O)N(C)c1ccccc1] |
| H-64 | 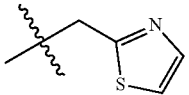 [SMILES: *Cc1nccs1] | methyl | phenyl | H | propyl |
| H-65 | benzyl | methyl | phenyl | H | propyl |
| H-66 | methyl | methyl | phenyl | H | H |
| H-67 | methyl | methyl | 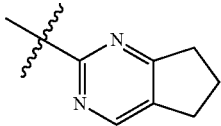 [SMILES: *c1ncc2c(n1)CCC2] | H | propyl |
| H-68 | methyl | methyl | 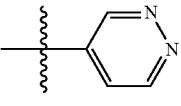 | H | propyl |
| H-69 | propyl | methyl | phenyl | H | propyl |
| H-70 | isobutyl | methyl | phenyl | H | propyl |
| H-71 | 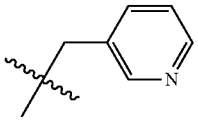 [SMILES: *Cc1cccnc1] | methyl | phenyl | H | propyl |
| H-72 | methyl | H | pyridin-yl | H | propyl |
| H-73 | methyl | H | pyridin-yl | H | propyl |
| H-74 | methyl | H | 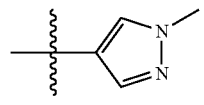 | H | propyl |
| H-75* | methyl | H | 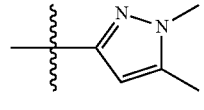 | H | propyl |
| H-76* | methyl | H | 2-ethoxyphenyl | H | propyl |
| H-77 | methyl | H | 4-yanophenyl | H | propyl |
| H-78* | methyl | H | 3-CF₃-phenyl | H | propyl |
| H-79 | methyl | H | 3-cyanophenyl | H | propyl |
| H-80 | methyl | H | 2-chlorophenyl | H | propyl |
| H-81 | methyl | H | 2-methylphenyl | H | propyl |
| H-82 | methyl | H | 2-fluorophenyl | H | propyl |
| H-83 | methyl | H | 4-fluorophenyl | H | propyl |
| H-84 | methyl | H | 4-chlorophenyl | H | propyl |
| H-85 | methyl | H | 3-fluorophenyl | H | propyl |
| H-86 | methyl | H | 3-OMe-phenyl | H | propyl |
| H-87* | methyl | H | 4-OMe-phenyl | H | propyl |
| H-88 | methyl | H | 3-chlorophenyl | H | propyl |
| H-89* | methyl | H | 4-methylphenyl | H | propyl |
| H-90* | methyl | H | 3-methylphenyl | H | propyl |
| H-91 | methyl | H | phenyl | H | propyl |
| H-92 | methyl | H | methyl | H | propyl |

TABLE H-continued

Formula (1-1) Compounds

| Ex # | R¹ | R² | R³ | R⁵ | R⁶ |
|---|---|---|---|---|---|
| H-93 | methyl | H | cyclopropyl | H | propyl |
| H-94 | methyl | H | cyclobutyl | H | propyl |
| H-95 | methyl | H | 4-CF₃-phenyl | H | propyl |
| H-96 | methyl | H | H | H | propyl |
| H-97 | methyl | H | —(CH₂)₂N(CH₃)₂ | H | propyl |
| H-98* | methyl | H | 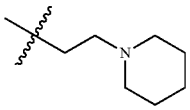 [SMILES: *CCN1CCCCC1] | H | propyl |
| H-99 | methyl | methyl | 4-OHphenyl<br>R⁰ is methyl | H | propyl |
| H-100 | methyl | methyl | 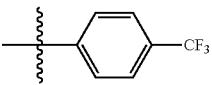 | H | propyl |
| H-101 | methyl | methyl | phenyl<br>R⁰ is propyl | H | propyl |
| H-102 | methyl | methyl | phenyl | H | propyl |
| H-103 | methyl | methyl | 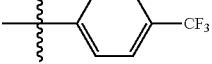 | H | propyl |

*MIC ≤ 64 μg/mL for at least one BRD bacterial strain

Table H Example Names:
H-1. 3-cyclopropyl-1-((2S,3R,4S,6R)-2-(((2R,3S,4R,5R,8R,10R,11R,12S,13S,14R)-13-(((2R,4R,5S,6S)-5-((3-cyclopropyl-1-(2-morpholinoethyl)ureido)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (1029);

H-2. 1-((2S,3R,4S,6R)-2-(((2R,3S,4R,5R,8R,10R,11R,12S,13S,14R)-13-(((2R,4R,5S,6S)-5-((dimethylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea (897);

H-3. 1-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea (940);

H-4. 1-((2S,3R,4S,6R)-2-(((2R,3S,4R,5R,8R,10R,11R,12S,13S,14R)-13-(((2R,4R,5S,6S)-5-((diethylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea (925);

H-5. 1-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea (906);

H-6. 3-(2-(dimethylamino)ethyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (906);

H-7. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(2-(piperidin-1-yl)ethyl)urea (946);

H-8. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-propyl-3-(4-(trifluoromethyl)phenyl)urea (1021);

H-9. 1-((2S,3R,4S,6R)-2-(((2R,3S,4R,5R,8R,10R,11R,12S,13S,14R)-13-(((2R,4R,5S,6S)-5-(((2-(dimethylamino)ethyl)(propyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl- 15-oxo-1-oxa-6-azacyclopentadecan-11-yl)oxy)-3-hydroxy-6-methyltetrahydro-2H-pyran-4-yl)-1-methylurea (878);

H-10. 1-((2S,3R,4S,6R)-2-(((2R,3S,4R,5R,8R,10R,11R,12S,13S,14R)-2-ethyl-13-(((2R,4R,5S,6S)-5-((3-(4-fluorophenyl)-1-propylureido)methyl)-5-hydroxy-4-methoxy-4,6-dimethyltetrahydro-2H-pyran-2-yl)oxy)-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-fluorophenyl)-1-methylurea (1066);

H-11. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (925);

H-12. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((1-propyl-3-(4-(trifluoromethyl)phenyl)ureido)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(4-(trifluoromethyl)phenyl)urea (1166);

H-13. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea (993);

H-14. 1-cyclopropyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-phenylurea (951);

H-15. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-2-yl)urea (913);

H-16. 1-ethyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-phenylurea (939);

H-17. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-isopropyl-1-methyl-3-phenylurea (953);

H-18. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-5-(((2-methoxyethyl)amino)methyl)-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (941);

H-19. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-5-(((3-methoxypropyl)amino)methyl)-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (955);

H-20. 1-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (968);

H-21. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(methylsulfonyl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (989);

H-22. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((1-propylureido)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (878);

H-23. 1-((2S,3R,4S,6R)-2-(((2R,3S,4R,5R,8R,10R,11R,12S,13S,14R)-2-ethyl-13-(((2R,4R,5S,6S)-5-((ethylamino)methyl)-5-hydroxy-4-methoxy-4,6-dimethyltetrahydro-2H-pyran-2-yl)oxy)-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (911);

H-24. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-5-((isobutylamino)methyl)-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (939);

H-25. 1-((2S,3R,4S,6R)-2-(((2R,3S,4R,5R,8R,10R,11R,12S,13S,14R)-13-(((2R,4R,5S,6S)-5-(((3-(1H-imidazol-1-yl)propyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (991);

H-26. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((methylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (897);

H-27. 1-((2S,3R,4S,6R)-2-(((2R,3S,4R,5R,8R,10R,11R,12S,13S,14R)-13-(((2R,4R,5S,6S)-5-((cyclopropylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (923);

H-28. 1-((2S,3R,4S,6R)-2-(((2R,3S,4R,5R,8R,10R,11R,12S,13S,14R)-13-(((2R,4R,5S,6S)-5-((butylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (939);

H-29. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-5-((isopentylamino)methyl)-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (953);

H-30. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((((1-methylpiperidin-4-yl)methyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (994);

H-31. 1-((2S,3R,4S,6R)-2-(((2R,3S,4R,5R,8R,10R,11R,12S,13S,14R)-13-(((2R,4R,5S,6S)-5-((((1-acetylpiperidin-4-yl)methyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1022);

H-32. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((phenylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (959);

H-33. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(tetrahydro-2H-pyran-4-yl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (995);

H-34. 1-((2S,3R,4S,6R)-2-(((2R,3S,4R,5R,8R,10R,11R,12S,13S,14R)-13-(((2R,4R,5S,6S)-5-(((2-cyclopropylethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (951);

H-35. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((3-(2-oxopyrrolidin-1-yl)propyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1008);

H-36. 1-((2S,3R,4S,6R)-2-(((2R,3S,4R,5R,8R,10R,11R,12S,13S,14R)-13-(((2R,4R,5S,6S)-5-((([1,1'-biphenyl]-4-ylmethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1049);

H-37. 1-((2S,3R,4S,6R)-2-(((2R,3S,4R,5R,8R,10R,11R,12S,13S,14R)-13-(((2R,4R,5S,6S)-5-((cyclobutyl(methyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (951);

H-38. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((3-(piperidin-1-yl)propyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1008);

H-39. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3,3-diphenylurea (987);

H-40. 1-benzyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea (939);

H-41. 1-((2S,3R,4S,6R)-2-(((2R,3S,4R,5R,8R,10R,11R,12S,13S,14R)-13-(((2R,4R,5S,6S)-5-(((cyclopropylmethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (937);

H-42. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-morpholinoethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (996);

H-43. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(phenylsulfonyl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1051);

H-44. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((4-(trifluoromethyl)phenethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1055);

H-45. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-2-yl)urea (926);

H-46. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrazin-2-yl)urea (927);

H-47. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((3-(2-oxopyridin-1(2H)-yl)propyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1018);

H-48. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridazin-3-yl)urea (927);

H-49. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrimidin-2-yl)urea (927);

H-50. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrimidin-5-yl)urea (927);

H-51. 1-(5-chloropyrimidin-2-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea (962);

H-52. 1-(5-cyclopropylpyrimidin-2-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea (967);

H-53. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-3-yl)urea (926);

H-54. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenyl-3-(2,2,2-trifluoroethyl)urea (993);

H-55. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenyl-3-(tetrahydro-2H-pyran-4-yl)urea (995);

H-56. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(1,2,4-triazin-3-yl)urea (928);

H-57. 1-(2,6-dimethylpyrimidin-4-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea (955);

H-58. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(1-methyl-1H-pyrazol-4-yl)urea (929);

H-59. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8, azacyclopentadecan-11-yl)oxy)-3-hydroxy-6-methyltetrahydro-2H-pyran-4-yl)-1,3-dimethyl-3-(pyridin-4-yl)urea (926);

H-60. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-(4-methoxybenzyl)-3-methyl-3-phenylurea (1031);

H-61. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(thiazol-2-yl)urea (932);

H-62. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(3-methylpyridin-4-yl)urea (940);

H-63. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((3-methyl-3-phenyl-1-propylureido)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (1058);

H-64. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenyl-1-(thiazol-2-ylmethyl)urea (1008);

H-65. 1-benzyl-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenylurea (1001);

H-66. 1-((2S,3R,4S,6R)-2-(((2R,3S,4R,5R,8R,10R,11R,12S,13S,14R)-13-(((2R,4R,5S,6S)-5-(aminomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea (883);

H-67. 1-(6,7-dihydro-5H-cyclopenta[d]pyrimidin-2-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea (967);

H-68. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridazin-4-yl)urea (927);

H-69. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenyl-1-propylurea (953);

H-70. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-isobutyl-3-methyl-3-phenylurea (967)

H-71. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenyl-1-(pyridin-3-ylmethyl)urea (1002);

H-72. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-3-yl)urea (913);

H-73. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-4-yl)urea (913);

H-74. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(1-methyl-1H-pyrazol-4-yl)urea (916);

H-75. 3-(1,5-dimethyl-1H-pyrazol-3-yl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (930);

H-76. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-3-(2-methoxyphenyl)-1-methylurea (942);

H-77. 3-(4-cyanophenyl)-1-((2S,3R,4S,6R)-2-(((2R,3S, 4R,5R,8R,10R,11R,12S,13S,14R)-2-ethyl-3,4,10-trihydroxy-13-(((2R,4R,5S,6S)-5-hydroxy-4-methoxy-4, 6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (937);

H-78. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1-methyl-3-(3-(trifluoromethyl)phenyl)urea (980);

H-79. 3-(3-cyanophenyl)-1-((2S,3R,4S,6R)-2-(((2R,3S, 4R,5R,8R,10R,11R,12S,13S,14R)-2-ethyl-3,4,10-trihydroxy-13-(((2R,4R,5S,6S)-5-hydroxy-4-methoxy-4, 6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (937);

H-80. 3-(2-chlorophenyl)-1-((2S,3R,4S,6R)-2-(((2R,3S, 4R,5R,8R,10R,11R,12S,13S,14R)-2-ethyl-3,4,10-trihydroxy-13-(((2R,4R,5S,6S)-5-hydroxy-4-methoxy-4, 6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (946);

H-81. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1-methyl-3-(o-tolyl)urea (926);

H-82. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-3-(2-fluorophenyl)-1-methylurea (930);

H-83. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-3-(4-fluorophenyl)-1-methylurea (930);

H-84. 3-(4-chlorophenyl)-1-((2S,3R,4S,6R)-2-(((2R,3S, 4R,5R,8R,10R,11R,12S,13S,14R)-2-ethyl-3,4,10-trihydroxy-13-(((2R,4R,5S,6S)-5-hydroxy-4-methoxy-4, 6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (946);

H-85. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-3-(3-fluorophenyl)-1-methylurea (930);

H-86. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-3-(3-methoxyphenyl)-1-methylurea (942);

H-87. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-3-(4-methoxyphenyl)-1-methylurea (942);

H-88. 3-(3-chlorophenyl)-1-((2S,3R,4S,6R)-2-(((2R,3S, 4R,5R,8R,10R,11R,12S,13S,14R)-2-ethyl-3,4,10-trihydroxy-13-(((2R,4R,5S,6S)-5-hydroxy-4-methoxy-4, 6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (946);

H-89. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1-methyl-3-(p-tolyl)urea (925);

H-90. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1-methyl-3-(m-tolyl)urea (926);

H-91. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea (911);

H-92. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1,3-dimethylurea (849);

H-93. 1-((2S,3R,4S,6R)-2-(((2R,3S,4R,5R,8R,10R,11R, 12S,13S,14R)-13-(((2R,4R,5S,6S)-5-((cyclopropylamino)methyl)-5-hydroxy-4-methoxy-4,6-dimethyl-tetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea (875);

H-94. 1-((2S,3R,4S,6R)-2-(((2R,3S,4R,5R,8R,10R,11R,12S,13S,14R)-13-(((2R,4R,5S,6S)-5-((cyclobutylamino)methyl)-5-hydroxy-4-methoxy-4,6-dimethyl-tetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea (889);

H-95. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((4-(trifluoromethyl)phenyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea (979);

H-96. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (835);

H-97. 3-(2-(dimethylamino)ethyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea (906);

H-98. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(2-(piperidin-1-yl)ethyl)urea (946);

H-99. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-hydroxyphenyl)-1,3-dimethylurea (941);

H-100. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea (1007);

H-101. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1,3-dimethyl-3-phenylurea (939);

H-102. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-1,3-dimethyl-3-phenylurea (967); and H-103. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea (1035).

TABLE H

Example NMR's
$^1$H NMR 400 MHz, DMSO-d6 (unless otherwise specified) δ ppm

| | |
|---|---|
| H-1 | 0.17-2.24 (m, 47 H) 2.30-2.73 (m, 19 H) 2.75-2.91 (m, 1 H) 3.04-4.21 (m, 24 H) 4.21-5.03 (m, 7 H) 6.16-6.40 (m, 1 H) 7.06-7.26 (m, 1 H) |
| H-2 | 0.64-2.43 (m, 44 H) 2.61-3.12(m, 6 H) 3.12-3.55 (m, 11 H) 3.60-4.16 (m, 4 H) 4.26-4.63 (m, 3 H) 4.74-5.09 (m, 3 H) 5.87-6.08 (m, 1 H) 6.76-6.95 (m, 1 H) 7.09-7.27 (m, 2 H) 7.33-7.58 (m, 2 H) 8.12-8.42 (m, 2 H) |
| H-3 | 0.67-1.83 (m, 33 H) 1.83-2.04 (m, 9 H) 2.04-2.22 (m, 7 H) 2.25-2.41 (m, 2 H) 2.54-2.74 (m, 5 H) 2.74-2.95 (m, 4 H) 3.10-3.40 (m, 6 H) 3.40-3.56 (m, 2 H) 3.64-3.86 (m, 2 H) 3.95-4.19 (m, 3 H) 4.29-4.57 (m, 3 H) 4.75-5.05 (m, 3 H) 6.79-6.97 (m, 1 H) 7.12-7.30 (m, 2 H) 7.37-7.53 (m, 2 H) 8.18-8.40 (m, 1 H) |
| H-4 | 0.71-1.85 (m, 42 H) 1.85-2.02 (m, 6 H) 2.07-2.21 (m, 1 H) 2.54-2.73 (m, 7 H) 2.73-2.91 (m, 4 H) 3.13-3.52 (m, 13 H) 3.69-3.91 (m, 2 H) 3.97-4.24 (m, 2 H) 4.43-4.65 (m, 2 H) 4.77-5.00 (m, 3 H) 6.83-7.01 (m, 1 H) 7.11-7.30 (m, 2 H) 7.33-7.58 (m, 2 H) 8.10-8.43 (m, 1 H) |
| H-5^ | 0.64-1.25 (m, 39 H), 1.26-1.52 (m, 8 H), 1.65-1.81 (m, 2 H), 1.88 (s, 9 H), 1.92 (br s, 1 H), 1.94-2.03 (m, 1 H), 2.04-2.13 (m, 2 H), 2.15 (s, 6 H), 2.16-2.19 (m, 1 H), 2.28-2.38 (m, 2 H), 2.59 (br t, 2 H), 2.64 (s, 3 H), 2.64-2.73 (m, 4 H), 2.83 (br d, 1 H), 3.12 (br dd, 1 H), 3.31 (s, 3 H), 3.34 (s, 1 H), 3.47 (br d, 1 H), 3.60-3.72 (m, 1 H), 3.94-4.06 (m, 1 H), 4.12 (br s, 1 H), 4.35-4.44 (m, 2 H), 4.66 (br d, 1 H), 4.80-4.88 (m, 2 H), 6.13 (br t, 1 H) |
| H-6^ | 0.68-1.43 (m, 38 H), 1.44-1.88 (m, 6 H), 1.91 (s, 3 H), 2.00 (br d, 1 H), 2.13 (br d, 1 H), 2.44 (br s, 4 H), 2.51 (br s, 3 H), 2.61-2.80 (m, 6 H), 2.80-2.95 (m, 3 H), 2.96-3.09 (m, 2 H), 3.16-3.23 (m, 2 H), 3.25 (s, 3 H), 3.27-3.35 (m, 3 H), 3.35-3.42 (m, 2 H), 3.42-3.49 (m, 2 H), 3.62-3.73 (m, 2 H), 3.94 (br d, 1 H), 4.18 (br d, 1 H), 4.31-4.38 (m, 1 H), 4.41 (br d, 1 H), 4.72 (br s, 1 H), 4.90 (br d, 1 H), 5.02-5.10 (m, 1 H), 6.09 (br s, 1 H) |
| H-7^ | 0.74-1.27 (m, 35 H), 1.28-1.56 (m, 13 H), 1.71-1.83 (m, 2 H), 1.91 (s, 6 H), 1.92-2.03 (m, 2 H), 2.17 (br d, 1 H), 2.27-2.45 (m, 7 H), 2.53-2.61 (m, 2 H), 2.64 (s, 3 H), 2.66-2.73 (m, 1 H), 2.76 (br d, 1 H), 2.90 (br d, 1 H), 2.93-3.00 (m, 1 H), 3.02-3.22 (m, 5 H), 3.27 (br s, 1 H), 3.33 (s, 3 H), 3.38 (br s, 2 H), 3.44 (br d, 1 H), 3.68 (br dd, 1 H), 4.04 (m, 1 H), 4.06 (br s, 1 H), 4.38 (br d, 1 H), 4.43 (br d, 3.93-1 H), 4.74 (br s, 1 H), 4.86 (br dd, 1 H), 4.89 (br d, 1 H), 6.13 (br s, 1 H) |
| H-8 | 0.64-1.19 (m, 37 H), 1.19-1.88 (m, 15 H), 1.90 (s, 2 H), 1.92 (br d, 1 H), 2.02 (br dd, 1 H), 2.09-2.17 (m, 1 H), 2.39-2.46 (m, 1 H), 2.50-2.51 (m, 3 H), 2.52-2.70 (m, 5 H), 2.76-2.86 (m, 2 H), 3.07 (s, 3 H), 3.18-3.21 (m, 1 H), 3.23 (s, 3 H), 3.43 (br d, 1 H), 3.48-3.57 (m, 1 H), 3.62-3.79 (m, 2 H), 4.07 (br s, 1 H), 4.32-4.41 (m, 2 H), 4.78-4.87 (m, 2 H), 4.99 (br d, 1 H), 7.27 (br d, 2 H), 7.60 (br d, 2 H) |

TABLE H-continued

Example NMR's
¹H NMR 400 MHz, DMSO-d6 (unless otherwise specified) δ ppm

| | |
|---|---|
| H-10^ | 0.71-1.26 (m, 33 H), 1.27-1.84 (m, 10 H), 1.89 (s, 3 H), 1.90-1.98 (m, 1 H), 2.01-2.09 (m, 1 H), 2.15-2.22 (m, 1 H), 2.54-2.63 (m, 1 H), 2.67 (br dd, 1 H), 2.80 (s, 3 H), 2.84 (br s, 1 H), 3.19-3.26 (m, 2 H), 3.30 (s, 3 H), 3.34 (br s, 3 H), 3.37-3.40 (m, 1 H), 3.44 (br d, 1 H), 3.47-3.58 (m, 2 H), 3.65-3.80 (m, 2 H), 4.05-4.15 (m, 1 H), 4.18 (br s, 1 H), 4.42 (br d, 1 H), 4.52-4.62 (m, 2 H), 4.87 (br d, 1 H), 4.96 (br s, 1 H), 5.03 (br d, 1 H), 7.06 (td, 4 H), 7.42 (ddd, 4 H), 8.33 (s, 1 H), 8.83-9.11 (m, 1 H) |
| H-11 | 0.5-1.5 (m, 42H), 1.5-2.3 (m, 8H), 2.4-3.0 (m, 10H), 3.05 (s, 3 H), 3.07 (s, 1 H), 3.09-3.15 (m, 1 H), 3.27-3.33 (m, 1 H), 3.35 (s, 3 H), 3.44 (br d, 1 H), 3.47-3.57 (m, 1 H), 3.63 (br s, 1 H), 3.81 (br s, 1 H), 3.88 (br t, 1 H), 4.10 (br s, 1 H), 4.36 (d, 1 H), 4.39 (br d, 1 H), 4.44 (dd, 1 H), 4.87 (d, 1 H), 4.90 (d, 1 H), 7.06 (t, 1 H), 7.15 (dd, 2 H), 7.24-7.36 (m, 2 H) |
| H-12^ | 0.42-0.52 (m, 2 H), 0.72-1.34 (m, 55 H), 1.35-1.89 (m, 11 H), 1.92 (s, 1 H), 1.93-2.00 (m, 1 H), 2.01-2.12 (m, 2 H), 2.16-2.26 (m, 1 H), 2.55-2.63 (m, 1 H), 2.65-2.73 (m, 1 H), 2.84 (br s, 3 H), 2.90 (br s, 1 H), 3.18-3.25 (m, 1 H), 3.29 (br s, 3 H), 3.45 (br d, 2 H), 3.56-3.66 (m, 1 H), 3.68-3.79 (m, 2 H), 4.05-4.15 (m, 1 H), 4.19 (br s, 1 H), 4.29 (br d, 1 H), 4.41-4.49 (m, 1 H), 4.56-4.66 (m, 1 H), 4.72 (br s, 1 H), 4.84-4.93 (m, 1 H), 5.01-5.13 (m, 2 H), 5.24 (br s, 1 H), 7.59-7.75 (m, 7 H), 8.84 (br s, 1 H) |
| H-13^ | 0.74-1.26 (m, 33 H), 1.28-1.54 (m, 7 H), 1.61-1.84 (m, 2 H), 1.90 (s, 3 H), 1.94 (br d, 2 H), 1.99-2.07 (m, 1 H), 2.12-2.19 (m, 1 H), 2.41-2.49 (m, 2 H), 2.52 (s, 3 H), 2.53-2.57 (m, 1 H), 2.58-2.72 (m, 4 H), 2.84 (br d, 1 H), 3.13 (s, 3 H), 3.14-3.22 (m, 2 H), 3.27-3.28 (m, 1 H), 3.28 (s, 3 H), 3.33 (br s, 3 H), 3.47 (br d, 1 H), 3.67 (br s, 1 H), 3.77 (br d, 1 H), 3.98 (br dd, 1 H), 4.10 (br s, 1 H), 4.41 (br d, 2 H), 4.83 (br d, 1 H), 4.87 (br d, 1 H), 5.06 (br d, 1 H), 7.30 (br d, 2 H), 7.60 (br d, 2 H) |
| H-14^ | 0.47-0.57 (m, 1H), 0.60-0.68 (m, 1H) 1.5 (m, 46H), 1.6-1.71 (m, 1H), 1.72-1.82 (m, 1H), 1.87 (s, 1.5H) 1.88-1.98 (m, 2H), 1.99-2.09 (m, 1H), 2.13-2.23 (m, 1H), 2.37-2.78 (m, 12H), 2.79-2.89 (m, 1H), 3.08-3.18 (m, 1H), 3.25-3.37 (s, 4 H), 3.38-3.46 (m, 1 H), 3.47-3.55 (m, 1H), 3.85-3.40 (br s, 1 H), 4.01-4.10(m, 1 H), 4.29-4.47 (m, 2 H), 4.77-4.95 (m, 2 H), 7.04 (t, 1 H), 7.16 (br d, 2 H), 7.25-7.36 (m, 2 H) |
| H-15^ | 0.5-1.5 (m, 40H), 1.5-2.3 (m, 11H), 2.4-3.0 (m, 10H), 3.19-3.31 (m, 3H), 3.44 (d, 1H), 3.7 (brs, 1H), 4.08 (brs, 3H), 4.16 (s, 1H), 4.45 (dd, 4H), 4.85 (br d, 3H), 5.3 (brs, 2H), 6.91-6.94 (m, 1H), 7.64-7.68 (m, 2H), 8.16-8.3 (m, 1H), 8.18-8.33 (brs, 1H). |
| H-16 | METHANOL-d₄ δ ppm 0.78-1.09 (m, 20 H) 1.09-1.60 (m, 22 H) 1.71-1.84 (m, 5 H) 1.87-1.98 (m, 2 H) 2.19-2.31 (m, 2 H) 2.31-2.38 (m, 3 H) 2.58-2.68 (m, 2 H) 2.73-2.82 (m, 2 H) 2.87-3.05 (m, 3 H) 3.11-3.19 (m, 1 H) 3.35-3.42 (m, 4 H) 3.46-3.66 (m, 4 H) 3.89-3.98 (m, 1 H) 4.03-4.10 (m, 1 H) 4.40-4.48 (m, 2 H) 4.84-4.90 (m, 1 H) 4.90-4.96 (m, 1 H) 7.00-7.07 (m, 1 H) 7.07-7.14 (m, 2 H) 7.22-7.31 (m, 2 H) |
| H-17 | METHANOL-d₄ δ ppm 0.78-1.35 (m, 41 H) 1.36-1.97 (m, 15 H) 2.25-2.33 (m, 4 H) 2.44-2.52 (m, 1 H) 2.78-2.89 (m, 3 H) 2.97-3.19 (m, 5 H) 3.38-3.54 (m, 6 H) 3.86-3.96 (m, 1 H) 4.00-4.07 (m, 1 H) 4.17-4.29 (m, 1 H) 4.37-4.43 (m, 1 H) 4.43-4.52 (m, 1 H) 4.85-4.92 (m, 1 H) 4.92-4.97 (m, 1 H) 7.03-7.15 (m, 3 H) 7.23-7.33 (m, 2 H) |
| H-18^ | 0.5-1.5 (m, 36H), 1.7-2.3 (m, 12H), 2.4-2.8 (m, 10H), 3.0-3.4 (m, 14H), 3.5-3.9 (m, 3H), 4.1-4.4 (m, 4H), 4.82-4.87 (m, 3H), 7.05 (t, 1H, J = 8 Hz), 7.14 (d, 2H, J = 8 Hz), 7.30 (t, 2H, J = 8 Hz) |
| H-19^ | ¹H NMR (400 MHz, DMSO-d₆) δ ppm 0.5-1.5 (m, 36H), 1.7-2.3 (m, 12H), 2.4-2.8 (m, 12H), 3.0-3.4 (m, 14H), 3.5-3.9 (m, 3H), 4.1-4.5 (m, 4H), 4.85-4.86 (m, 3H), 7.05 (t, 1H, J = 8 Hz), 7.14 (d, 2H, J = 8 Hz), 7.30 (t, 2H, J = 8 Hz) |
| H-20^ | 0.5-1.5 (m, 36H), 1.7-2.3 (m, 20H), 2.4-2.8 (m, 10H), 3.0-3.4 (m, 14H), 3.5-3.9 (m, 3H), 4.1-4.5 (m, 4H), 4.81-4.84 (m, 3H), 7.05 (t, 1H, J = 8 Hz), 7.16 (d, 2H, J = 8 Hz), 7.30 (t, 2H, J = 8 Hz) |
| H-21 | ppm 0.5-1.5 (m, 36H), 1.7-2.3 (m, 9H), 2.4-2.8 (m, 10H), 3.0-3.4 (m, 14H), 3.5-3.9 (m, 3H), 4.1-4.5 (m, 4H), 4.81-4.88 (m, 3H), 7.05 (t, 1H, J = 8 Hz), 7.14 (d, 2H, J = 8 Hz), 7.29 (t, 2H, J = 8 Hz) |
| H-22 | 0.77-0.93 (m, 10 H), 0.93-1.11 (m, 20 H), 1.12-1.22 (m, 7 H), 1.25-1.40 (m, 4 H), 1.40-1.56 (m, 5 H), 1.61-1.76 (m, 2 H), 1.76-1.85 (m, 2 H), 1.88 (s, 5 H), 1.96-2.06 (m, 1 H), 2.06-2.19 (m, 1 H), 2.54-2.58 (m, 1 H), 2.64 (s, 4 H), 2.82 (br d, 1 H), 3.41-3.47 (d, 1 H), 3.60-3.70 (m, 1 H), 3.74 (br s, 2 H), 3.90 (bs, 1 H), 4.13 (br s, 1 H), 4.38 (br d, 1 H), 4.49 (br d, 1 H), 4.67 (br s, 1 H), 4.83 (br d, 2 H), 4.93 (br d, 1 H), 5.68 (s, 2 H), 6.00 (br s, 2 H) |
| H-23^ | 0.5-1.5 (m, 44H), 1.7-2.3 (m, 12H), 2.4-2.8 (m, 8H), 3.0-3.4 (m, 9H), 3.5-3.9 (m, 4H), 4.1-4.5 (m, 4H), 4.81-4.87 (m, 3H), 7.05 (t, 1H, J = 8 Hz), 7.14 (d, 2H, J = 8 Hz), 7.29 (t, 2H, J = 8 Hz) |
| H-24^ | 0.5-1.5 (m, 37H), 1.7-2.3 (m, 14H), 2.4-2.8 (m, 8H), 3.0-3.4 (m, 8H), 3.5-3.9 (m, 3H), 4.1-4.5 (m, 7H), 4.82-4.88 (m, 3H), 6.87 (brs, 1H), 7.05 (t, 1H, J = 8 Hz), 7.13-7.15 (m, 3H), 7.28 (t, 2H, J = 8 Hz), 7.59 (s, 1H) |
| H-25^ | 0.5-1.5 (m, 36H), 1.7-2.3 (m, 20H), 2.4-2.8 (m, 10H), 3.0-3.4 (m, 14H), 3.5-3.9 (m, 3H), 4.1-4.5 (m, 4H), 4.81-4.84 (m, 3H), 7.05 (t, 1H, J = 8 Hz), 7.16 (d, 2H, J = 8 Hz), 7.30 (t, 2H, J = 8 Hz) |
| H-26^ | 0.5-1.5 (m, 37H), 1.7-2.3 (m, 14H), 2.4-2.8 (m, 8H), 3.0-3.4 (m, 8H), 3.5-3.9 (m, 4H), 4.1-4.5 (m, 4H), 4.81-4.87 (m, 3H), 7.05 (t, 1H, J = 8 Hz), 7.14 (d, 2H, J = 8 Hz), 7.29 (t, 2H, J = 8 Hz) |
| H-27 | 0.2-1.5 (m, 41H), 1.7-2.3 (m, 9H), 2.4-2.8 (m, 8H), 3.0-3.4 (m, 8H), 3.5-3.9 (m, 4H), 4.1-4.5 (m, 4H), 4.81-4.87 (m, 3H), 7.06 (t, 1H, J = 8 Hz), 7.14 (d, 2H, J = 8 Hz), 7.29 (t, 2H, J = 8 Hz) |
| H-28 | ppm 0.5-1.5 (m, 43H), 1.7-2.3 (m, 8H), 2.4-2.8 (m, 8H), 3.0-3.4 (m, 8H), 3.5-3.9 (m, 7H), 4.1-4.5 (m, 4H), 4.81-4.87 (m, 3H), 7.05 (t, 1H, J = 8 Hz), 7.14 (d, 2H, J = 8 Hz), 7.29 (t, 2H, J = 8 Hz) |
| H-29 | 0.5-1.5 (m, 45H), 1.7-2.3 (m, 8H), 2.4-2.8 (m, 8H), 3.0-3.4 (m, 8H), 3.5-3.9 (m, 7H), 4.1-4.4 (m, 4H), 4.81-4.86 (m, 3H), 7.05 (t, 1H, J = 8 Hz), 7.14 (d, 2H, J = 8 Hz), 7.29 (t, 2H, J = 8 Hz) |
| H-30 | 0.5-1.5 (m, 41 H), 1.7-2.3 (m, 12H), 2.4-2.8 (m, 15H), 3.0-3.4 (m, 8H), 3.5-3.9 (m, 3H), 4.1-4.4 (m, 4H), 4.81-4.87 (m, 3H), 7.07 (t, 1H, J = 8 Hz), 7.15 (d, 2H, J = 8 Hz), 7.29 (t, 2H, J = 8 Hz) |
| H-31^ | 0.5-1.5 (m, 42H), 1.7-2.3 (m, 14H), 2.4-2.8 (m, 10H), 3.0-3.4 (m, 10H), 3.5-3.9 (m, 4H), 4.1-4.4 (m, 6H), 4.81-4.88 (m, 3H), 7.06 (t, 1H, J = 8 Hz), 7.14 (d, 2H, J = 8 Hz), 7.29 (t, 2H, J = 8 Hz) |
| H-32^ | 0.5-1.5 (m, 36H), 1.7-2.3 (m, 12H), 2.4-2.9 (m, 8H), 3.0-3.4 (m, 8H), 3.5-3.9 (m, 4H), 4.1-4.4 (m, 4H), 4.83-5.0 (m, 3H), 6.55 (t, 1H, J = 7 Hz), 6.66 (d, 2H, J = 8 Hz), 7.06-7.15 (m, 5H), 7.31 (t, 2H, J = 8 Hz) |
| H-33^ | 0.5-1.5 (m,41 H), 1.6-2.3 (m, 12H), 2.4-2.9 (m, 10H), 3.0-3.4 (m, 14H), 3.5-3.9 (m, 5H), 4.1-4.4 (m, 3H), 4.84-4.88 (m, 3H), 7.05 (t, 1H, J = 8 Hz), 7.14 (d, 2H, J = 8 Hz), 7.30 (t, 2H, J = 8 Hz) |
| H-35 | 0.5-1.5 (m, 39H), 1.7-2.3 (m, 12H), 2.4-2.9 (m, 12H), 3.0-3.4 (m, 10H), 3.5-3.9 (m, 4H), 4.1-4.4 (m, 4H), 4.84-4.87 (m, 3H), 7.05 (t, 1H, J = 8 Hz), 7.14 (d, 2H, J = 8 Hz), 7.30 (t, 2H, J = 8 Hz) |
| H-36^ | 0.5-1.5 (m, 38H), 1.7-2.3 (m, 12H), 2.4-2.9 (m, 8H), 3.0-3.4 (m, 8H), 3.5-3.9 (m, 4H), 4.1-4.4 (m, 4H), 4.81-4.90 (m, 3H), 7.05 (t, 1H, J = 8 Hz), 7.13 (d, 2H, J = 8 Hz), 7.27-7.36 (m, 3H), 7.42-7.47 (m, 4H), 7.63-7.67 (m, 4H) |
| H-37^ | 0.5-1.5 (m, 39H), 1.7-2.3 (m, 12H), 2.4-2.9 (m, 10H), 3.0-3.4 (m, 10H), 3.5-3.9 (m, 4H), 4.1-4.4 (m, 4H), 4.81-4.88 (m, 3H), 7.05 (t, 1H, J = 8 Hz), 7.14 (d, 2H, J = 8 Hz), 7.29 (t, 2H, J = 8 Hz) |
| H-38^ | 0.5-1.5 (m, 45H), 1.7-2.3 (m, 16H), 2.4-2.9 (m, 10H), 3.0-3.4 (m, 9H), 3.5-3.9 (m, 4H), 4.1-4.4 (m, 4H), 4.84-4.87 (m, 3H), 7.05 (t, 1H, J = 8 Hz), 7.14 (d, 2H, J = 8 Hz), 7.30 (t, 2H, J = 8 Hz) |
| H-39 | METHANOL-d₄ δ ppm 0.78-1.15 (m, 36 H) 1.29-1.47 (m, 5 H) 1.65-2.14 (m, 11 H) 2.40-2.84 (m, 8 H) 3.10-3.38 (m, 9 H) 3.92-4.39 (m, 2 H) 4.33-4.39 (m, 2 H) 4.84 (m, 2 H) 5.09 (m, 1 H) 6.00 (m 4 H) 7.09 t (t, 2 H) 7.29 (t, 4 H) |

TABLE H-continued

Example NMR's
¹H NMR 400 MHz, DMSO-d6 (unless otherwise specified) δ ppm

| | |
|---|---|
| H-40 | METHANOL-d₄ δ ppm 0.88-1.71 (36H, m), 1.79-2.27 (8H, m), 2.69-2.99 (12H, m), 3.22-3.74 (8H, m), 3.97-4.58 (6H, m), 4.99 (2H, m), 7.26-7.37 (5H, m) |
| H-41^ | 0.09-1.5 (m, 41H), 1.7-2.3 (m, 12H), 2.4-2.9 (m, 9H), 3.0-3.4 (m, 10H), 3.5-3.9 (m, 4H), 4.1-4.4 (m, 3H), 4.84-4.87 (m, 3H), 7.05 (t, 1H, J = 8 Hz), 7.15 (d, 2H, J = 8 Hz), 7.29 (t, 2H, J = 8 Hz) |
| H-42^ | 0.5-1.5 (m, 36H), 1.6-2.3 (m, 12H), 2.4-2.9 (m, 16H), 3.0-3.4 (m, 9H), 3.5-3.9 (m, 8H), 4.1-4.4 (m, 3H), 4.79-4.86 (m, 3H), 7.05 (t, 1H, J = 8 Hz), 7.14 (d, 2H, J = 8 Hz), 7.29 (t, 2H, J = 8 Hz) |
| H-43^ | 0.5-1.5 (m, 38H), 1.6-2.3 (m, 12H), 2.4-2.9 (m, 9H), 3.0-3.5 (m, 10H), 3.6-3.9 (m, 4H), 4.1-4.4 (m, 3H), 4.82-4.86 (m, 3H), 7.05 (t, 1H, J = 8 Hz), 7.13 (d, 2H, J = 8 Hz), 7.29 (t, 2H, J = 8 Hz), 7.66 (t, 2H, J = 8 Hz), 7.73 (t, 1H, J = 7 Hz), 7.90 (d, 2H, J = 8 Hz) |
| H-44^ | 0.8-1.5 (m, 37H), 1.6-2.3 (m, 12H), 2.4-2.9 (m, 12H), 3.0-3.5 (m, 8H), 3.6-3.9 (m, 4H), 4.1-4.4 (m, 3H), 4.84-4.86 (m, 3H), 7.05 (t, 1H, J = 8 Hz), 7.13 (d, 2H, J = 8 Hz), 7.29 (t, 2H, J = 8 Hz), 7.45 (d, 2H, J = 8 Hz), 7.62 (d, 2H, J = 8 Hz) |
| H-45 | 0.5-1.5 (m, 43H), 1.7-2.3 (m, 9H), 2.4-2.9 (m, 9H), 3.0-3.4 (m, 9H), 3.5-3.9 (m, 3H), 4.1-4.4 (m, 3H), 4.78-4.83 (m, 2H), 5.07 (d, 1H, J = 4 Hz), 6.86 (t, 1H, J = 7 Hz), 7.03 (d, 1H, J = 8 Hz), 7.58 (t, 1H, J = 8 Hz), 8.19 (d, 1H, J = 4 Hz) |
| H-46^ | 0.5-1.5 (m, 43H), 1.7-2.3 (m, 19H), 2.4-2.9 (m, 10H), 3.0-3.4 (m, 9H), 3.7-3.9 (m, 3H), 4.1-4.4 (m, 3H), 4.81-4.83 (m, 2H), 5.2 (s, 1H), 8.04 (d, 1H, J = 3 Hz), 8.24 (s, 1H), 8.36 (s, 1H) |
| H-47 | 0.8-1.5 (m, 37H), 1.6-2.3 (m, 9H), 2.4-2.9 (m, 10H), 3.0-3.5 (m, 8H), 3.6-3.9 (m, 5H), 4.1-4.4 (m, 4H), 4.79-4.86 (m, 3H), 6.17 (t, 1H, J = 8 Hz), 6.33 (d, 1H, J = 8 Hz), 7.02 (t, 1H, J = 8 Hz), 7.11 (d, 2H, J = 8 Hz), 7.25-7.35 (m, 3H), 7.61 (d, 1H, J = 7 Hz) |
| H-48 | 0.5-1.5 (m, 42H), 1.7-2.3 (m, 9H), 2.4-2.9 (m, 9H), 3.0-3.4 (m, 9H), 3.5-3.9 (m, 3H), 4.1-4.4 (m, 4H), 4.8-4.9 (m, 2H), 5.17 (d, 1H, J = 5 Hz), 7.34 (d, 1H, J = 9 Hz), 7.44-7.48 (m, 1H), 8.75 (d, 1H, J = 4 Hz) |
| H-49^ | 0.5-1.5 (m, 42H), 1.7-2.3 (m, 16H), 2.4-2.9 (m, 9H), 3.0-3.4 (m, 9H), 3.7 (brs, 2H), 4.1-4.5 (m, 5H), 4.81-4.82 (m, 2H), 5.0 (brs, 1H), 6.87 (brs, 1H), 8.45 (d, 2H, J = 4 Hz) |
| H-50^ | 0.5-1.5 (m, 42H), 1.7-2.3 (m, 13H), 2.4-2.9 (m, 9H), 3.0-3.4 (m, 9H), 3.7-3.9 (m, 3H), 4.1-4.5 (m, 3H), 4.8-4.9 (m, 2H), 5.08 (s, 1H), 8.60 (s, 2H), 8.78 (s, 1H) |
| H-51^ | 0.5-1.5 (m, 43H), 1.7-2.3 (m, 20H), 2.4-2.9 (m, 9H), 3.0-3.4 (m, 9H), 4.1-4.5 (m, 5H), 4.81-4.83 (m, 2H), 8.53 (s, 2H) |
| H-52 | 0.5-1.5 (m, 47H), 1.7-2.3 (m, 10H), 2.4-2.9 (m, 9H), 3.0-3.4 (m, 9H), 3.65 (brs, 1H), 4.08-4.34 (m, 4H), 4.8-4.9 (m, 3H), 8.27 (s, 1H) |
| H-53 | 0.5-1.5 (m, 43H), 1.7-2.3 (m, 9H), 2.4-2.9 (m, 9H), 3.0-3.4 (m, 9H), 3.5-3.9 (m, 3H), 4.1-4.4 (m, 4H), 4.8-4.9 (m, 2H), 5.17 (d, 1H, J = 5 Hz), 7.34 (d, 1H, J = 9 Hz), 7.44-7.48 (m, 1H), 8.75 (d, 1H, J = 6 Hz) |
| H-54 | METHANOL-d₄ δ ppm 0.92-1.70 (40H, m), 1.86-2.05 (6H, m), 2.30-2.37 (2H, m), 2.91 (3H, s), 2.73-3.15 (7H, m), 3.49 (3H, m), 3.63-3.75 (2H, m), 4.02-4.20 (3H, m), 4.53-4.71 (2H, m), 4.97-5.05 (2H, m), 7.17-7.41 (5H, m) |
| H-55 | METHANOL-d₄ δ ppm 0.90-1.42 (36H, m), 1.52-1.74 (6H, m), 1.78-2.05 (11H, m), 2.37-2.54 (5H, m), 2.78-3.25 (8H, m), 3.42-3.60 (8H, m), 3.93-4.03 (3H, m), 4.14-4.18 (2H, m), 4.51-4.60 (2H, m), 4.98-5.06 (2H, m), 7.18-7.44 (5H, m) |
| H-56^ | 0.5-1.5 (m, 43H), 1.7-2.3 (m, 14H), 2.4-2.9 (m, 10H), 3.0-3.6 (m, 10H), 4.1-4.5 (m, 5H), 4.8-5.0 (m, 3H), 8.48 (s, 1H), 8.86 (s, 1H) |
| H-57^ | 0.5-1.5 (m, 43H), 1.7-2.3 (m, 17H), 2.4-2.9 (m, 12H), 3.0-3.4 (m, 6H), 3.5-3.7 (m, 4H), 4.1-4.5 (m, 3H), 4.81-4.84 (m, 2H), 5.2 (brs, 1H), 6.61 (s, 1H) |
| H-58^ | 0.5-1.5 (m, 43H), 1.7-2.3 (m, 12H), 2.4-2.9 (m, 12H), 3.0-3.5 (m, 6H), 3.6-3.8 (m, 6H), 4.1-4.5 (m, 3H), 4.84-4.89 (m, 3H), 7.30 (s, 1H), 7.63 (s, 1H) |
| H-59^ | 0.5-1.5 (m, 43H), 1.7-2.3 (m, 16H), 2.4-2.9 (m, 9H), 3.0-3.4 (m, 9H), 3.7-3.9 (m, 3H), 4.1-4.5 (m, 3H), 4.81-4.86 (m, 2H), 5.2 (brs, 1H), 6.97 (d, 2H, J = 5 Hz), 8.27 (d, 2H, J = 6 Hz) |
| H-60 | CHLOROFORM-d 0.77-1.51 (m, 38H), 1.60-1.66 (m, 1H), 1.77-2.20 (m, 10H), 2.46-2.59 (m, 2H), 2.64-2.76 (m, 3H), 2.86-2.91 (m, 3H), 3.06-3.13 (m, 1H), 3.25-3.31 (m, 1H), 3.37 (s, 3H), 3.41-3.57 (m, 4H), 3.70-3.73 (m, 3H), 3.93-4.09 (m, 3H), 4.31-4.38 (m, 1H), 4.42-4.45 (m, 1H), 4.79-4.84 (m, 1H), 4.87-4.90 (m, 1H), 6.71-6.77 (m, 2H), 6.82-6.88 (m, 2H), 6.93-6.98 (m, 2H), 7.01-7.08 (m, 1H), 7.19-7.25 (m, 2H) |
| H-61^ | 0.5-1.5 (m, 42H), 1.7-2.3 (m, 12H), 2.4-2.9 (m, 9H), 3.0-3.5 (m, 9H), 3.7-3.8 (m, 3H), 4.1-4.4 (m, 3H), 4.81-4.83 (m, 2H), 5.03 (brs, 1H), 7.08 (d, 1H, J = 4 Hz), 7.34-7.35 (d, 1H, J = 4 Hz), 8.46 (s, 1H) |
| H-62^ | 0.5-1.5 (m, 43H), 1.7-2.3 (m, 20H), 2.4-2.9 (m, 10H), 3.0-3.4 (m, 6H), 3.7-3.9 (m, 3H), 4.1-4.4 (m, 3H), 4.81-4.87 (m, 2H), 7.14 (d, 1H, J = 5 Hz), 8.31-8.35 (m, 2H) |
| H-63 | 0.6-1.5 (mm, 44H), 1.65 (m, 1H), 1.7-1.9 (mm, 3 H), 1.93 (m, 1H), 2.07 (s, 1H), 2.18 (d, 1H), 2.44 (s, 3H), 2.55 (br, 1H), 2.66 (m, 1H), 2.83 (br d, 1H), 2.95 (m, 1H), 3.02 (m, 1H), 3.07 (s, 3H), 3.10 (m, 3H), 3.16 (m, 1H), 3.36 (m, 3H), 3.37 (s, 1H), 3.44 (d, 1H), 3.50 (br m, 1H), 3.58 (d, 1H), 3.71 (br, 1H), 3.90 (m, 1H), 4.12 (m, 1H), 4.38 (m, 2H), 4.85 (dd, 1H), 4.88 (d, 1H), 4.91 (d, 1H), 7.04 (t, 1H), 7.10 (t, 1H), 7.16 (d, 2H), 7.23 (2, 2H). 7.30 (q, 4H) |
| H-64 | CHLOROFORM-d 0.78-1.03 (m, 20H), 1.12-1.22 (m, 13H), 1.25-1.30 (m, 3H), 1.37-1.50 (m, 4H), 1.57-1.66 (m, 1H), 1.75-2.01 (m, 8H), 2.12-2.18 (m, 2H), 2.42-2.59 (m, 2H), 2.61-2.79 (m, 4H), 2.99 (s, 3H), 3.07-3.13 (m, 1H), 3.21-3.34 (m, 2H), 3.35-3.46 (m, 4H), 3.47-3.54 (m, 1H), 3.88-3.99 (m, 1H), 4.06-4.14 (m, 1H), 4.19-4.35 (m, 4H), 4.38-4.45 (m, 2H), 4.78-4.83 (m, 1H), 4.87-4.91 (m, 1H), 7.01-7.10 (m, 3H), 7.16-7.18 (m, 1H), 7.20-7.28 (m, 2H), 7.57-7.61 (m, 1H) |
| H-65 | CHLOROFORM-d 0.79-1.08 (m, 17H), 1.09-1.65 (m, 22H), 1.77-1.97 (m, 5H), 2.05-2.20 (m, 2H), 2.54-2.82 (m, 8H), 2.84-2.87 (m, 3H), 3.03-3.10 (m, 2H), 3.25-3.33 (m, 2H), 3.33-3.37 (m, 3H), 3.38-3.68 (m, 7H), 4.00-4.14 (m, 3H), 4.32-4.39 (m, 1H), 4.42-4.47 (m, 1H), 4.73-4.79 (m, 1H), 4.89-4.94 (m, 1H), 6.81-6.88 (m, 2H), 6.97-7.09 (m, 3H), 7.12-7.17 (m, 1H), 7.19-7.25 (m, 4H) |
| H-66^ | 0.99 (s, 29 H), 1.18-1.87 (m, 11 H), 1.89 (s, 2 H), 1.92 (br d, 1 H), 2.17 (br d, 1 H), 2.38-2.46 (m, 3 H), 2.53-2.58 (m, 1 H), 2.62-2.70 (m, 2 H), 2.76-2.86 (m, 2 H), 3.05 (s, 3 H), 3.09-3.16 (m, 2 H), 3.23-3.32 (m, 1 H), 3.32 (br s, 2 H), 3.34 (s, 3 H), 3.46 (br d, 2 H), 3.57-3.66 (m, 2 H), 3.67-3.76 (m, 1 H), 3.88-3.98 (m, 1 H), 4.10 (br s, 1 H), 4.21-4.30 (m, 1 H), 4.41 (br d, 1 H), 4.43-4.48 (m, 1 H), 4.83 (br d, 1 H), 4.85-4.88 (m, 1 H), 7.06 (br t, 1 H), 7.16 (br d, 2 H), 7.26-7.38 (m, 2 H) |
| H-67^ | 0.5-1.5 (m, 45H), 1.7-2.3 (m, 20H), 2.4-2.9 (m, 10H), 3.0-3.4 (m, 10H), 4.1-4.3 (m, 3H), 4.80-4.83 (m, 2H), 4.97 (s, 1H), 8.26 (s, 1H) |
| H-68^ | .5-1.5 (m, 43H), 1.7-2.3 (m, 14H), 2.4-2.9 (m, 9H), 3.0-3.5 (m, 9H), 4.1-4.5 (m, 4H), 4.8-4.9 (m, 2H), 5.3 (s, 1H), 7.09-7.11 (m, 1H), 8.82 (d, 1H, J = 6 Hz), 8.95 (s, 1H) |
| H-69^ | 0.63-1.19 (m, 37 H), 1.19-1.89 (m, 13 H), 1.90 (s, 2 H), 1.92 (br s, 1 H), 2.09-2.22 (m, 2 H), 2.39-2.48 (m, 2 H), 2.50-2.51 (m, 3 H), 2.52-2.64 (m, 3 H), 2.66 (s, 2 H), 2.82 (br d, 1 H), 3.00 (s, 3 H), 3.05-3.21 (m, 3 H), 3.26-3.29 (m, 1 H), 3.36 (s, 3 H), 3.40 (br d, 1 H), 3.59-3.71 (m, 2 H), 4.07 (br s, 1 H), 4.31 (br d, 1 H), 4.33-4.40 (m, 1 H), 4.80 (br d, 2 H), 4.85 (br dd, 1 H), 7.09 (t, 1 H), 7.15 (br d, 2 H), 7.26-7.34 (m, 2 H) |
| H-70 | METHANOL-d4 δ ppm 0.66-0.75 (m, 6 H) 0.79-0.86 (m, 3 H) 0.90-1.11 (m, 16 H) 1.11-1.35 (m, 18 H) 1.38-1.98 (m, 12 H) 2.24-2.37 (m, 2 H) 2.49-2.58 (m, 1 H) 2.74-2.86 (m, 2 H) 2.90-3.01 (m, 2 H) 3.02-3.13 (m, 5 H) 3.23-3.29 (m, 2 H) 3.32-3.46 (m, 6 H) 3.71-3.83 (m, 1 H) 3.99-4.05 (m, 1 H) 4.32-4.39 (m, 1 H) 4.41-4.51 (m, 1 H) 4.86-4.91 (m, 1 H) 4.92-4.97 (m, 1 H) 7.01-7.09 (m, 1 H) 7.13-7.20 (m, 2 H) 7.22-7.32 (m, 2 H) |
| H-71 | CHLOROFORM-d 0.77-1.47 (m, 36H), 1.55-1.94 (m, 6H), 2.11-2.26 (m, 2H), 2.35-2.60 (m, 4H), 2.65-2.75 (m, 3H), 2.79-2.84 (m, 3H), 2.95-3.03 (m, 3H), 3.26-3.45 (m, 6H), 3.50-3.57 (m, 1H), 3.90-3.99 (m, 1H), 4.05-4.17 (m, 2H), 4.18-4.24 (m, 1H), 4.28-4.40 (m, 1H), 4.43-4.53 (m, 1H), |

TABLE H-continued

Example NMR's
¹H NMR 400 MHz, DMSO-d6 (unless otherwise specified) δ ppm

| | |
|---|---|
| | 4.66-4.76 (m, 1H), 4.89-4.98 (m, 1H), 5.95-6.09 (m, 1H), 6.85-6.93 (m, 2H), 6.93-7.05 (m, 2H), 7.05-7.11 (m, 1H), 7.18-7.24 (m, 2H), 7.49-7.61 (m, 1H), 8.32-8.49(m, 1H) |
| H-72 | 0.5-1.5 (m, 43H), 1.5-2.3 (m, 11H), 2.4-3.0 (m, 10H), 3.2-3.35 (m, 5H), 3.5 (d, 1H), 3.6 (brs, 1H), 4.15 (brs, 3H), 4.43 (d, 2H), 4.82-4.90 (m, 3H), 7.22-7.25 (m, 1H), 7.87 (d, 1H), 8.11-8.12 (s, 1H), 8.49 (s, 1H), 8.60-8.61 (m, 1H). |
| H-73 | 0.5-1.5 (m, 40H), 1.5-2.3 (m, 11H), 2.4-3.0 (m, 10H), 3.1-3.2 (m, 2H), 3.49-3.5 (m, 4H), 3.75 (brs, 2H), 4.09-4.1 (m, 4H), 4.42 (s, 2H), 4.81-4.86 (m, 4H), 7.44 (s, 2H), 8.28 (d, 2H), 8.78 (brs, 1H). |
| H-74 | 0.5-1.5 (m, 41H), 1.5-2.3 (m, 14H), 2.4-3.0 (m, 13H), 3.14-3.16 (brt, 1H), 3.25 (s, 1H), 3.33 (d, 3H), 3.46 (d, 1H), 3.73 (s, 4H), 4.08 (brs, 2H), 4.42 (t, 2H), 4.82-4.88 (m, 3H), 7.29 (s, 1H), 7.63 (s, 1H), 8.2 (s, 1H). |
| H-75 | 0.5-1.5 (m, 40H), 1.5-2.3 (m, 12H), 2.4-3.0 (m, 13H), 3.13-3.25 (brs, 1H), 3.29 (brs, 3H), 3.56 (d, 2H), 3.68 (s, 3H), 3.7 (brs, 2H), 4.12 (br t, 1H), 4.22 (brs, 2H), 4.41 (d, 2H), 4.81-4.87 (m, 4H) 6.05 (s, 1H), 8.46 (s, 1H). |
| H-76 | 0.5-1.5 (m, 41H), 1.5-2.3 (m, 8H), 2.4-3.0 (m, 16H), 3.19-3.20 (m, 3H), 3.28-3.33 (m, 4H), 3.47 (d, 2H), 3.72 (s, 4H), 4.11 (d, 3H), 4.42 (d, 2H), 4.82-4.87 (m, 2H), 6.80-6.85 (m, 2H), 6.87-6.93 (m, 1H), 7.77 (d, 1H), 8.1 (brs, 1H). |
| H-77 | 0.5-1.5 (m, 43H), 1.5-2.3 (m, 8H), 2.4-3.0 (m, 13H), 3.19-3.21 (m, 3H), 3.44 (d, 2H), 3.48 (brs, 2H), 4.07 (brs, 3H), 4.40 (m, 2H), 4.78-4.83 (m, 3H), 7.62 (s, 4H), 8.83 (s, 1H). |
| H-78 | 0.5-1.5 (m, 40H), 1.5-2.3 (m, 8H), 2.4-3.0 (m, 13H), 3.22-3.25 (m, 5H), 3.46 (d, 3H), 3.60 (brs, 3H), 4.10 (brs, 2H), 4.42 (d, 2H), 4.81-4.86 (m, 3H), 7.22 (d, 1H), 7.44 (t, 1H), 7.76 (d, 1H), 7.88 (s, 1H), 8.68 (s, 1H). |
| H-79 | 0.5-1.5 (m, 43H), 1.5-2.3 (m, 10H), 2.4-3.0 (m, 10H), 3.25 (s, 4H), 3.43 (d, 1H), 3.73 (brs, 1H), 4.04 (brs, 2H), 4.43 (d, 2H), 4.82-4.92 (m, 3H), 7.33-7.35 (m, 1H), 7.41-7.45 (m, 1H), 7.74-7.76 (m, 1H), 7.91 (s, 1H), 8.68 (brs, 1H). |
| H-80 | 0.5-1.5 (m, 44H), 1.5-2.3 (m, 10H), 2.4-3.0 (m, 16H), 3.17-3.26 (m, 4H), 3.46 (d, 1H), 3.61 (brs, 1H), 4.04-4.10 (m, 2H), 4.42 (d, 2H), 4.81-4.86 (m, 2H), 6.97 (t, 1H), 7.23 (t, 1H), 7.38 (d, 1H), 7.72 (t, 1H), 8.3 (brs, 1H). |
| H-81 | 0.5-1.5 (m, 44H), 1.5-2.3 (m, 11H), 2.4-3.0 (m, 11H), 3.2-3.31 (m, 6H), 3.5 (d, 2H), 3.7 (brs, 2H), 4.03 (brs, 1H), 4.12 (brs, 1H), 4.39-4.44 (m, 2H), 4.81-4.85 (m, 2H), 6.92-6.96 (m, 1H), 7.07-7.13 (m, 2H), 7.29 (d, 1H), 7.91 (brs, 1H). |
| H-82 | 0.5-1.5 (m, 40H), 1.5-2.3 (m, 8H), 2.4-3.0 (m, 10H), 3.21 (brd, 2H), 3.26-3.38 (m, 4H), 3.46 (d, 2H), 3.71 (brs, 2H), 4.0-4.10 (m, 3H), 4.42 (d, 2H), 4.81-4.86 (m, 3H), 6.69 (m, 1H), 7.22-7.23 (m, 2H), 7.42 (d, 1H), 8.54 (s, 1H). |
| H-83 | 0.5-1.5 (m, 40H), 1.5-2.3 (m, 11H), 2.4-3.0 (m, 10H), 3.21 (br d, 2H), 3.26-3.38 (m, 4H), 3.46 (d, 2H), 3.71 (brs, 2H), 4.0-4.10 (m, 3H), 4.42 (d, 2H), 4.81-4.86 (m, 3H), 6.69 (m, 1H), 7.22-7.23 (m, 2H), 7.42 (d, 1H), 8.54 (s, 1H). |
| H-84 | 0.5-1.5 (m, 44H), 1.5-2.3 (m, 10H), 2.4-3.0 (m, 10H), 3.17-3.26 (m, 4H), 3.46 (d, 1H), 3.61 (brs, 1H), 4.04-4.10 (m, 2H), 4.42 (d, 2H), 4.81-4.86 (m, 2H), 7.25 (d, 2H), 7.47 (d, 2H), 8.42 (s, 1H). |
| H-85 | 0.5-1.5 (m, 40H), 1.5-2.3 (m, 14H), 2.4-3.0 (m, 10H), 3.21 (br d, 2H), 3.26-3.38 (m, 4H), 3.46 (d, 2H), 3.71 (brs, 2H), 4.0-4.10 (m, 3H), 4.42 (d, 2H), 4.81-4.86 (m, 3H), 6.69 (m, 1H), 7.22-7.23 (m, 2H), 7.42 (d, 1H), 8.54 (s, 1H). |
| H-86 | 0.5-1.5 (m, 40H), 1.5-2.3 (m, 8H), 2.4-3.0 (m, 10H), 3.19-3.20 (m, 3H), 3.28-3.33 (m, 4H), 3.47 (d, 2H), 3.69 (s, 4H), 4.11 (d, 3H), 4.42 (d, 2H), 4.82-4.87 (m, 2H), 6.48 (d, 1H), 7.00 (d, 1H), 7.07-7.14 (m, 2H), 8.27 (s, 1H). |
| H-87 | 0.5-1.5 (m, 41H), 1.5-2.3 (m, 8H), 2.4-3.0 (m, 13H), 3.19-3.20 (m, 3H), 3.28-3.33 (m, 4H), 3.47 (d, 2H), 3.69 (s, 4H), 4.11 (d, 3H), 4.42 (d, 2H), 4.82-4.87 (m, 2H), 6.80 (d, 2H), 7.31 (d, 2H), 8.11 (s, 1H). |
| H-88 | 0.5-1.5 (m, 44H), 1.5-2.3 (m, 10H), 2.4-3.0 (m, 13H), 3.17-3.26 (m, 4H), 3.46 (d, 1H), 3.61 (brs, 1H), 4.04-4.10 (m, 2H), 4.42 (d, 2H), 4.81-4.86 (m, 2H), 6.93 (d, 1H), 7.22 (t, 1H), 7.39 (d, 1H), 7.63 (s, 1H), 8.56 (s, 1H). |
| H-89 | 0.5-1.5 (m, 40H), 1.5-2.3 (m, 8H), 2.4-3.0 (m, 13H), 3.19-3.23 (brs, 2H), 3.28-3.31 (brs, 3H), 3.47-3.48 (d, 2H), 3.85 (brd, 3H), 4.11 (brs, 2H), 4.42 (brs, 1H), 4.44 (d, 2H), 4.86-4.87 (m, 3H), 7.01 (d, 2H), 7.30 (d, 2H), 8.17 (s, 1H). |
| H-90 | 0.5-1.5 (m, 44H), 1.5-2.3 (m, 11H), 2.4-3.0 (m, 11H), 3.2-3.31 (m, 6H), 3.5 (d, 2H), 3.7 (brs, 2H), 4.03 (brs, 1H), 4.12 (brs, 1H), 4.39-4.44 (m, 2H), 4.81-4.85 (m, 2H), 6.92-6.96 (m, 1H), 7.07-7.13 (m, 2H), 7.29 (d, 1H), 7.91 (brs, 1H). |
| H-91 | 0.5-1.5 (m, 42H), 1.5-2.3 (m, 11H), 2.4-3.0 (m, 11H), 3.1-3.3 (m, 5H), 3.48 (d, 1H), 3.72 (br s, 1H), 4.1 (m, 3H), 4.44 (br, 3H), 4.87 (d, 4H), 6.90 (dd, 1H), 7.21 (dd, 2H), 7.43 (d, 2H), 8.29 (s, 1H) |
| H-92 | 0.88-1.54 (m, 38 H) 1.57-2.11 (m, 12 H) 2.59-2.85 (m, 8 H) 2.87-2.97 (m, 1 H) 2.99-3.10 (m, 2 H) 3.13-3.23 (m, 2 H) 3.27-3.38 (m, 5 H) 3.43-3.72 (m, 5 H) 3.73-3.91 (m, 2 H) 4.09-4.17 (m, 1 H) 4.24-4.37 (m, 1 H) 4.55-4.68 (m, 1 H) 4.72-4.80 (m, 1 H) 4.95-5.03 (m, 1 H) 5.03-5.10 (m, 1 H) |
| H-93 | 0.88-1.54 (m, 38 H) 1.57-2.11 (m, 12 H) 2.59-2.85 (m, 8 H) 2.87-2.97 (m, 1 H) 2.99-3.10 (m, 2 H) 3.13-3.23 (m, 2 H) 3.27-3.38 (m, 5 H) 3.43-3.72 (m, 5 H) 3.73-3.91 (m, 2 H) 4.09-4.17 (m, 1 H) 4.24-4.37 (m, 1 H) 4.55-4.68 (m, 1 H) 4.72-4.80 (m, 1 H) 4.95-5.03 (m, 1 H) 5.03-5.10 (m, 1 H) |
| H-94 | 0.88-1.54 (m, 40 H) 1.57-2.11 (m, 12 H) 2.59-2.85 (m, 8 H) 2.87-2.97 (m, 1 H) 2.99-3.10 (m, 2 H) 3.13-3.23 (m, 2 H) 3.27-3.38 (m, 5 H) 3.43-3.72 (m, 5 H) 3.73-3.91 (m, 2 H) 4.09-4.17 (m, 1 H) 4.24-4.37 (m, 1 H) 4.55-4.68 (m, 1 H) 4.72-4.80 (m, 1 H) 4.95-5.03 (m, 1 H) 5.03-5.10 (m, 1 H) |
| H-95^ | 0.70-1.27 (m, 33 H), 1.27-1.53 (m, 6 H), 1.58-1.82 (m, 3 H), 1.89 (s, 3 H), 1.90-1.95 (m, 1 H), 2.04-2.18 (m, 2 H), 2.38-2.48 (m, 1 H), 2.52-2.64 (m, 2 H), 2.66 (s, 2 H), 2.81 (s, 3 H), 2.83-2.87 (m, 1 H), 3.17-3.24 (m, 3 H), 3.26 (s, 4 H), 3.31-3.35 (m, 3 H), 3.44-3.49 (m, 3 H), 3.68-3.79 (m, 2 H), 4.01-4.07 (m, 1 H), 4.08-4.15 (m, 2 H), 4.38-4.48 (m, 2 H), 4.80-4.85 (m, 1 H), 4.87 (br d, 1 H), 4.95 (br d, 1 H), 7.56 (d, 2 H), 7.63-7.70 (m, 2 H), 8.73 (br s, 1 H) |
| H-96 | 0.65-1.55 (m, 42H), 1.61-1.86 (m, 2 H), 1.88 (s, 7 H) 1.97-2.22 (m, 2 H), 2.35-2.45 (m, 1H), 2.58-2.70 (m, 7 H), 2.82 (br d, 1 H), 3.03-3.22 (m, 2 H), 3.38-3.57 (m, 2 H), 3.57-3.79 (m, 3 H), 3.94 (br s, 3 H), 4.13 (br s, 2 H), 4.39 (br dd, 2 H), 4.68 (br s, 1 H), 4.75-5.03 (m, 3 H), 5.70 (s, 2 H) |
| H-100 | CHLOROFORM-d 0.68-1.51 (m, 36 H) 1.55-2.44 (m, 22 H) 2.47-3.08 (m, 6 H) 3.13-3.47 (m, 6 H) 3.64-3.89 (m, 2 H) 3.90-4.19 (m, 4 H) 4.20-4.38 (m, 1 H) 4.45-4.57 (m, 1 H) 4.62-4.81 (m, 1 H) 4.79-4.94 (m, 1 H) 4.92-5.21 (m, 4 H) 7.15-7.24 (m, 2 H) 7.44-7.52 (m, 2 H) |
| H-101 | CHLOROFORM-d 0.66-1.75 (m, 40 H)1.76-2.38 (m, 14 H) 2.42-3.04 (m, 10 H) 3.09-3.67 (m, 7 H) 3.70-3.93 (m, 1 H) 4.00-4.22 (m, 3 H) 4.34-4.46 (m, 1 H) 4.46-4.61 (m, 1 H) 4.63-4.86 (m, 2 H) 4.91-5.12 (m, 1 H) 6.97-6.97 (m, 1 H) 7.02-7.09 (m, 2 H) 7.14-7.36 (m, 2 H) |
| H-102^ | 0.69-1.22 (m, 37 H), 1.22-1.58 (m, 9 H), 1.72-1.81 (m, 1 H), 1.91 (s, 4 H), 1.94-2.01 (m, 1 H), 2.02-2.12 (m, 2 H), 2.14-2.21 (m, 1 H), 2.36-2.42 (m, 1 H), 2.43 (s, 3 H), 2.44-2.48 (m, 1 H), 2.53-2.81 (m, 7 H), 3.05 (s, 3 H), 3.09-3.17 (m, 1 H), 3.26 (br d, 3 H), 3.34 (br s, 3 H), 3.48 (br dd, 2 H), 3.52-3.59 (m, 1 H), 3.91 (br d, 2 H), 3.99 (br d, 1 H), 4.31 (br s, 1 H), 4.38 (br d, 1 H), 4.41 (br d, 1 H), 4.79 (br d, 1 H), 4.83-4.90 (m, 2 H), 7.06 (t, 1 H), 7.15 (d, 2 H), 7.26-7.35 (m, 2 H) |
| H-103^ | 0.63-1.26 (m, 37 H), 1.28-1.56 (m, 10 H), 1.69-1.83 (m, 2 H), 1.90 (s, 3 H), 1.94-2.19 (m, 5 H), 2.40-2.46 (m, 2 H), 2.53 (br s, 3 H), 2.55-2.61 (m, 2 H), 2.69 (br s, 5 H), 3.12 (s, 3 H), 3.14-3.22 (m, 2 H), 3.22-3.25 (m, 1 H), 3.26 (s, 3 H), 3.46-3.53 (m, 2 H), 3.64-3.72 (m, 1 H), 3.88-3.95 (m, 1 H), 3.95-4.02 (m, 2 H), 4.31 (br s, 1 H), 4.34-4.42 (m, 1 H), 4.45 (br d, 1 H), 4.78 (br d, 1 H), 4.83-4.90 (m, 1 H), 5.05 (br d, 1 H), 7.29 (br d, 2 H), 7.60 (br d, 2 H) |

The following Formula (1-A1a) compounds were prepared using the Schemes and procedures defined herein; and wherein $R^c$ is H and $R^5$ is H; are shown in Table 1. The respective compound names are provided below the table.

(1-A1a)

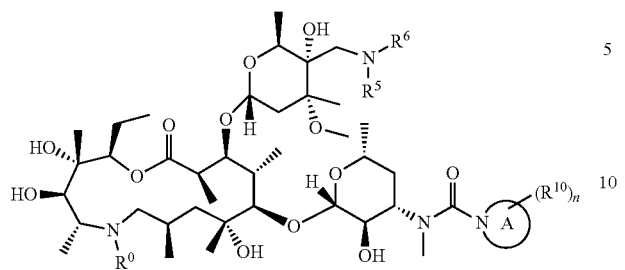

TABLE I

Formula (1-A1a) Compounds

| Ex # | Ring A ± (R¹⁰)ₙ | R⁶ | Mass [M + H]⁺ |
|---|---|---|---|
| I-1 | -N(piperazine)N-ethyl | methyl | 904 |
| I-2* | -N(piperazine)N-ethyl | propyl | 932 |
| I-3 | indoline | propyl | 937 |
| I-4 | tetrahydroquinoline | propyl | 951 |
| I-5 | 2,3-dihydrobenzothiazine 1,1-dioxide | propyl | 1001 |
| I-6 | 2,3-dihydrobenzoxazine | propyl | 953 |
| I-7 | isoindoline | propyl | 937 |

*MIC ≤ 64 µg/mL for at least one BRD bacterial strain

Table I Example Names:

I-1. 4-ethyl-N-((2S,3R,4S,6R)-2-(((2R,3S,4R,5R,8R, 10R,11R,12S,13S,14R)-2-ethyl-3,4,10-trihydroxy-13-(((2R,4R,5S,6S)-5-hydroxy-4-methoxy-4,6-dimethyl-5-((methylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylpiperazine-1-carboxamide;

I-2. 4-ethyl-N-((2S,3R,4S,6R)-2-(((2R,3S,4R,5R,8R, 10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-N-methylpiperazine-1-carboxamide;

I-3. N-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-N-methylindoline-1-carboxamide;

I-4. N-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-N-methyl-3,4-dihydroquinoline-1(2H)-carboxamide;

I-5. N-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-N-methyl-2,3-dihydro-4H-benzo[b][1,4]thiazine-4-carboxamide 1,1-dioxide;

I-6. N-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-N-methyl-2,3-dihydro-4H-benzo[b][1,4]oxazine-4-carboxamide;

I-7. N-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-N-methylisoindoline-2-carboxamide

TABLE I

Example NMR's.
¹H NMR 400 MHz, DMSO-d6 (or otherwise specified) δ ppm

I-2  0.86-1.48 (m, 37 H) 1.80-2.37 (18 H) 2.55-3.10 (m, 11 H) 3.18 (m, 1 H) 3.21 (m, 1 H) 3.33 (s, 3 H) 3.42 (m, 1 H) 3.42 (m, 1 H) 3.48 (m, 1 H) 3.53 (m, 1 H) 3.77 (m, 1 H) 3.80 (m, 1 H) 3.81 (m, 1 H) 4.04 (m, 1 H) 4.15 (m, 1 H) 4.17 (m, 1 H) 4.42 (m, 1 H) 4.89 (m, 1 H) 5.04 (m, 1 H)

TABLE I-continued

Example NMR's.
$^1$H NMR 400 MHz, DMSO-d6 (or otherwise specified) δ ppm

I-3  0.78-0.94 (m, 10 H), 0.94-1.18 (m, 23 H), 1.23 (br s, 4 H), 1.31-1.65 (m, 7 H), 1.66-1.84 (m, 4 H), 1.94 (br s, 3 H), 2.13 (br d, 2 H), 2.59-2.71 (m, 3 H), 2.76 (s, 4 H), 2.82-2.92 (m, 1 H), 2.92-3.05 (m, 3 H), 3.19 (s, 3 H), 3.46 (br s, 1 H), 3.66-3.77 (m, 2 H), 3.78-3.96 (m, 3 H), 4.08 (br s, 2 H), 4.42 (br d, 2 H), 4.80-4.89 (m, 2 H), 5.03 (br d, 1 H), 6.82 (br t, 1 H), 7.00-7.08 (m, 2 H), 7.16 (br d, 1 H)

I-4  0.76-0.94 (m, 11 H) 0.94-1.18 (m, 23 H) 1.23 (br s, 4 H) 1.31-1.49 (m, 5 H) 1.49-1.65 (m, 2 H) 1.74 (brd, J = 9.54 Hz, 4 H) 1.85-2.02 (m, 3 H) 2.13 (br d, J = 15.65 Hz, 3 H) 2.59-2.71 (m, 3 H) 2.76 (s, 4 H) 2.80-2.92 (m, 1 H) 2.92-3.18 (m, 4 H) 3.18-3.39 (m, 15 H) 3.46 (br s, 2 H) 3.59-3.77 (m, 3 H) 3.78-3.96 (m, 3 H) 4.08 (br s, 2 H) 4.42 (br d, J = 6.85 Hz, 3 H) 4.64-4.91 (m, 3 H) 5.03 (br, d, J = 4.89 Hz, 1 H) 6.82 (br t, J = 7.09 Hz, 1 H) 6.96-7.10 (m, 2 H) 7.16 (br d, J = 7.09 Hz, 1 H).

I-5  0.77-0.96 (m, 8 H) 0.96-1.22 (m, 21 H) 1.27-1.53 (m, 5 H) 1.61-1.88 (m, 6 H) 1.97-2.22 (m, 3 H) 2.39-2.65 (m, 10 H) 2.66-2.87 (m, 3 H) 3.22 (s, 4 H) 3.28-3.36 (m, 4 H) 3.44-3.56 (m, 2 H) 3.63-3.79 (m, 2 H) 3.81-4.04 (m, 2 H), 4.06-4.21 (m, 1 H) 4.21-4.34 (m, 1 H) 4.34-4.48 (m, 2 H) 4.74-4.94 (m, 2 H) 5.03 (d, J = 5.14 Hz, 1 H) 6.80 (br t, J = 7.46 Hz, 1 H) 6.96-7.08 (m, 3 H) 7.98 (br s, 1 H)

I-6  0.76-0.94 (m, 17 H) 0.94-1.15 (m, 31 H) 1.19 (s, 5 H) 1.29-1.57 (m, 9 H) 1.63-1.81 (m, 5 H) 1.81-1.95 (m, 5 H) 2.01 (br d, J = 11.25 Hz, 2 H) 2.06-2.25 (m, 2 H) 2.39-2.59 (m, 18 H) 2.60-2.74 (m, 10 H) 2.78-2.96 (m, 4 H) 3.13-3.38 (m, 11 H), 3.49 (br d, J = 5.87 Hz, 2 H) 3.64-3.71 (m, 3 H) 3.75 (br s, 2 H) 3.82-3.98 (m, 3 H) 3.98-4.18 (m, 4 H) 4.20-4.34 (m, 1 H) 4.34-4.50 (m, 3 H), 4.74-4.93 (m, 3 H) 5.25 (br d, J = 4.89 Hz, 2 H) 7.00-7.16 (m, 2 H) 7.21 (br s, 1 H) 7.45 (br t, J = 7.70 Hz, 2 H) 7.70 (d, J = 7.82 Hz, 2 H) 7.95 (s, 1 H).

I-7  METHANOL-d$_4$ 0.92-2.09 (51H, m), 2.34 (1H, m), 2.61 (1H, m), 2.89-3.61 (16H, m), 3.82-3.99 (2H, m), 4.15 (1H, m), 4.58-4.73 (4H, m), 4.93-5.04 (4H, m), 7.29 (4H, m)

The following Formula (1-A1b) compounds were prepared using the Schemes and procedures defined herein; and wherein R$^0$ is H; are shown in Table J. The respective compound names are provided below the table

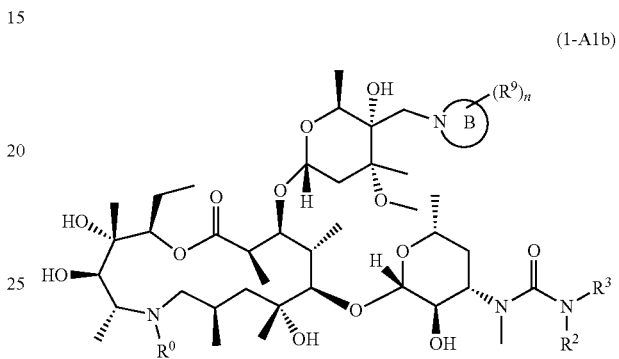

(1-A1b)

TABLE J

Formula (1-A1b) Compounds

| Ex # | R$^2$ | R$^3$ | Ring B ± (R$^9$)$_n$ | Mass [M+H]$^+$ |
|---|---|---|---|---|
| J-1 | H | cyclohexyl | -N(piperazine)N- | 958 |
| J-2 | H | ethyl | -N(piperazine)N- | 904 |
| J-3 | H | t-butyl | -N(piperazine)N- | 932 |
| J-4 | methyl | phenyl | -N(azetidine)-N(morpholine)O | 1009 |
| J-5 | H | H | -N(piperazine)N- | 876 |
| J-6 | H | -C$_6$H$_4$-N(CH$_3$)$_2$ | -N(piperazine)N- | 995 |
| J-7 | H | phenyl | -N(piperazine)N- | 952 |

TABLE J-continued
Formula (1-A1b) Compounds
| Ex # | R² | R³ | Ring B ± (R⁹)ₙ | Mass [M+H]⁺ |
|---|---|---|---|---|
| J-8 | H | pyridin-3yl | 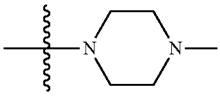 | 953 |
| J-9 | H | ethyl | 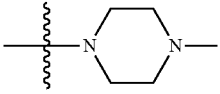 [SMILES: *N1CCN(C)CC1] | 975 |
| J-10 | methyl | phenyl | 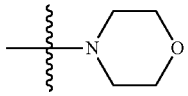 | 953 |
| J-11* | methyl | phenyl | 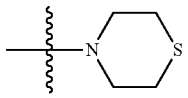 | 969 |
| J-12 | methyl | phenyl | 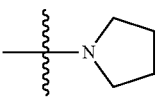 [SMILES: *N1CCCC1] | 937 |
| J-13 | methyl | phenyl | 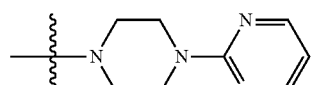 | 1030 |
| J-14* | methyl | phenyl | 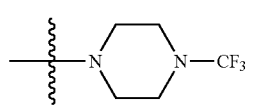 | 1019 |
| J-15 | methyl | phenyl | 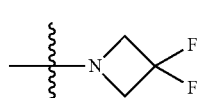 | 959 |
| J-16 | methyl | phenyl | 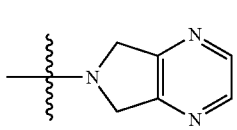 [SMILES: *N1Cc2nccnc2C1] | 987 |
| J-17* | methyl | phenyl | 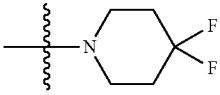 | 987 |
| J-18* | methyl | phenyl | 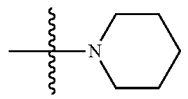 | 951 |
| J-19 | methyl | phenyl | 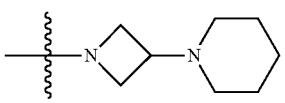 | 1006 |
| J-20 | methyl | phenyl | 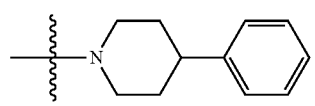 | 1027 |

TABLE J-continued

Formula (1-A1b) Compounds

| Ex # | R² | R³ | Ring B ± (R⁹)ₙ | Mass [M+H]⁺ |
|---|---|---|---|---|
| J-21 | methyl | phenyl | piperidine-N-SO₂Me | 1029 |
| J-22 | methyl | phenyl | azetidine | 923 |
| J-23 | methyl | phenyl | pyrazole | 934 |
| J-24 | methyl | phenyl | imidazole | 934 |
| J-25* | methyl | phenyl | tetrahydroisoquinoline | 999 |
| J-26 | methyl | phenyl | 3-(dimethylamino)azetidine | 966 |
| J-27 | methyl | phenyl | 1,2,4-triazole | 935 |
| J-28 | methyl | phenyl | 1,2,3-triazole | 935 |
| J-29 | methyl | phenyl | tetrazole | 936 |
| J-30 | methyl | phenyl | tetrazole | 936 |

*MIC ≤ 64 μg/mL for at least one of the bacterial strains

Table J Example Names:

J-1.  3-cyclohexyl-1-((2S,3R,4S,6R)-2-(((2R,3S,4R,5R, 8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

J-2. 3-ethyl-1-((2S,3R,4S,6R)-2-(((2R,3S,4R,5R,8R,10R, 11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

J-3. 3-(tert-butyl)-1-((2S,3R,4S,6R)-2-(((2R,3S,4R,5R, 8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

J-4. 1-((2S,3R,4S,6R)-2-(((2R,3S,4R,5R,8R,10R,11R, 12S,13S,14R)-2-ethyl-3,4,10-trihydroxy-13-(((2R,4R, 5S,6S)-5-hydroxy-4-methoxy-4,6-dimethyl-5-((3-morpholinoazetidin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-5. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

J-6. 3-(4-(dimethylamino)phenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

J-7. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

J-8. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-3-yl)urea;

J-9. 3-ethyl-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-methylpiperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

J-10. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(morpholinomethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-11. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(thiomorpholinomethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-12. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(pyrrolidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-13. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-(pyrimidin-2-yl)piperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-14. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-(trifluoromethyl)piperazin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-15. 1-((2S,3R,4S,6R)-2-(((2R,3S,4R,5R,8R,10R,11R,12S,13S,14R)-13-(((2R,4R,5S,6S)-5-((3,3-difluoroazetidin-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-16. 1-((2S,3R,4S,6R)-2-(((2R,3S,4R,5R,8R,10R,11R,12S,13S,14R)-13-(((2R,4R,5S,6S)-5-((5,7-dihydro-6H-pyrrolo[3,4-b]pyrazin-6-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-17. 1-((2S,3R,4S,6R)-2-(((2R,3S,4R,5R,8R,10R,11R,12S,13S,14R)-13-(((2R,4R,5S,6S)-5-((4,4-difluoropiperidin-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-18. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(piperidin-1-ylmethyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-19. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((3-(piperidin-1-yl)azetidin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-20. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-phenylpiperidin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-21. 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((4-(methylsulfonyl)piperidin-1-yl)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-22. 1-((2S,3R,4S,6R)-2-(((2R,3S,4R,5R,8R,10R,11R,12S,13S,14R)-13-(((2R,4R,5S,6S)-5-(azetidin-1-ylmethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-23. 1-((2S,3R,4S,6R)-2-(((2R,3S,4R,5R,8R,10R,11R,12S,13S,14R)-13-(((2R,4R,5S,6S)-5-((1H-pyrazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-24. 1-((2S,3R,4S,6R)-2-(((2R,3S,4R,5R,8R,10R,11R,12S,13S,14R)-13-(((2R,4R,5S,6S)-5-((1H-imidazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-25. 1-((2S,3R,4S,6R)-2-(((2R,3S,4R,5R,8R,10R,11R,12S,13S,14R)-13-(((2R,4R,5S,6S)-5-((3,4-dihydroisoquinolin-2(1H)-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-26. 1-((2S,3R,4S,6R)-2-(((2R,3S,4R,5R,8R,10R,11R,12S,13S,14R)-13-(((2R,4R,5S,6S)-5-((3-(dimethylamino)azetidin-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-27. 1-((2S,3R,4S,6R)-2-(((2R,3S,4R,5R,8R,10R,11R,12S,13S,14R)-13-(((2R,4R,5S,6S)-5-((1H-1,2,4-triazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-28. 1-((2S,3R,4S,6R)-2-(((2R,3S,4R,5R,8R,10R,11R,12S,13S,14R)-13-(((2R,4R,5S,6S)-5-((1H-1,2,3-triazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

J-29. 1-((2S,3R,4S,6R)-2-(((2R,3S,4R,5R,8R,10R,11R,12S,13S,14R)-13-(((2R,4R,5S,6S)-5-((1H-tetrazol-1-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; and J-30. 1-((2S,3R,4S,6R)-2-(((2R,3S,4R,5R,8R,10R,11R,12S,13S,14R)-13-(((2R,4R,5S,6S)-5-((2H-tetrazol-2-yl)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea.

TABLE J

| | Example NMR's $^1$H NMR (400 MHz, DMSO-d6) δ ppm |
|---|---|
| J-1 | 0.67-1.99 (m, 54 H) 1.99-2.74 (m, 25 H) 2.75-2.96 (m, 2 H) 3.03-3.57 (m, 12 H) 3.62-4.17 (m, 6 H) 4.35-4.53 (m, 3 H) 4.59-4.77 (m, 1 H) 4.77-4.92 (m, 2 H) 4.96-5.16 (m, 1 H) 5.65-5.92 (m, 1 H) |
| J-2 | 0.67-1.54 (m, 34 H) 1.58-1.83 (m, 3 H) 1.83-1.98 (m, 5 H) 2.07-2.19 (m, 3 H) 2.19-2.69 (m, 17 H) 2.77-2.89 (m, 1 H) 2.96-3.17 (m, 4 H) 3.41-3.52 (m, 3 H) 3.64-3.76 (m, 2 H) 3.97-4.18 (m, 2 H) 4.33-4.52 (m, 2 H) 4.52-4.71 (m, 1 H) 4.78-4.98 (m, 2 H) 6.03-6.28 (m, 1 H) |
| J-3 | 0.67-1.57 (m, 112 H) 1.59-2.19 (m, 35 H) 2.19-2.74 (m, 47 H), 2.79-3.00 (m, 2 H) 3.07-3.18 (m, 1 H) 3.19-3.52 (m, 12 H) 3.64-3.76 (m, 2 H) 3.81-4.01 (m, 1 H) 4.06-4.15 (m, 1 H) 4.33-4.52 (m, 5 H) 4.70-4.89 (m, 5 H) 4.97-5.06 (m, 2 H) 5.43-5.54 (m, 1 H) |
| J-4 | 0.5-1.5 (m, 36H), 1.7-2.3 (m, 9H), 2.4-2.9 (m, 10H), 3.0-3.4 (m, 14H), 3.5-3.9 (m, 8H), 4.1-4.4 (m, 4H), 4.84-4.86 (m, 3H), 7.05 (t, 1H, J = 8 Hz), 7.13 (d, 2H, J = 8 Hz), 7.29 (t, 2H, J = 8 Hz) |
| J-5 | 0.65-1.61 (m, 34 H) 1.61-1.82 (m, 2 H) 1.82-2.00 (m, 9 H) 2.05-2.19 (m, 4 H) 2.19-2.73 (m, 20 H), 2.77-2.94 (m, 1 H) 3.04-3.22 (m, 1 H) 3.22-3.39 (m, 4 H) 3.42-3.52 (m, 1 H) 3.63-3.79 (m, 1 H) 3.80-4.06 (m, 1 H) 4.06-4.16 (m, 1 H) 4.34-4.51 (m, 2 H) 4.62-4.79 (m, 1 H) 4.79-4.92 (m, 2 H) 5.63-5.75 (m, 2 H). |
| J-6 | 0.72-1.82 (m, 36 H) 1.84-1.99 (m, 6 H) 2.00-2.17 (m, 4 H) 2.17-2.71 (m, 17 H) 2.71-2.92 (m, 10 H) 3.11-3.81 (m, 18 H) 4.02-4.18 (m, 2 H) 4.41-4.56 (m, 2 H) 4.75-4.99 (m, 3 H) 6.55-6.72 (m, 2 H) 7.14-7.33 (m, 2 H) 7.85-8.06 (m, 1 H) |
| J-7 | 0.66-1.54 (m, 29 H) 1.55-1.83 (m, 4 H) 1.83-2.02 (m, 5 H) 2.05-2.20 (m, 4 H) 2.20-2.73 (m, 16 H) 2.73-2.96 (m, 4 H) 2.96-3.52 (m, 16 H) 3.67-3.85 (m, 2 H) 3.98-4.16 (m, 2 H) 4.39-4.54 (m, 4 H) 4.73-5.02 (m, 3 H) 6.83-7.00 (m, 1 H) 7.13-7.30 (m, 2 H) 7.37-7.58 (m, 2 H) 8.16-8.43 (m, 1 H) |
| J-8 | 0.73-1.57 (m, 37 H) 1.55-1.87 (m, 5 H) 1.85-2.03 (m, 8 H) 2.03-2.74 (m, 24 H) 2.72-2.94 (m, 4 H) 3.13-3.53 (m, 7 H) 3.69-3.88 (m, 1 H) 4.03-4.17 (m, 2 H) 4.38-4.55 (m, 1 H) 4.77-4.94 (m, 3 H) 7.13-7.35 (m, 1 H) 7.83-7.97 (m, 1 H) 8.07-8.19 (m, 1 H) 8.45-8.55 (m, 1 H) 8.55-8.73 (m, 1 H) |
| J-10^ | 0.5-1.5 (m, 36H), 1.7-2.3 (m, 15H), 2.4-2.8 (m, 10H), 3.0-3.4 (m, 14H), 3.5-3.9 (m, 3H), 4.1-4.4 (m, 4H), 4.81-4.87 (m, 3H), 7.05 (t, 1H, J = 8 Hz), 7.14 (d, 2H, J = 8 Hz), 7.30 (t, 2H, J = 8 Hz) |
| J-11^ | 0.5-1.5 (m, 36H), 1.7-2.3 (m, 12H), 2.4-2.8 (m, 16H), 3.0-3.4 (m, 8H), 3.5-3.9 (m, 4H), 4.1-4.5 (m, 3H), 4.81-4.87 (m, 3H), 7.05 (t, 1H, J = 8 Hz), 7.14 (d, 2H, J = 8 Hz), 7.29 (t, 2H, J = 8 Hz) |
| J-12 | 0.5-1.5 (m, 40H), 1.7-2.3 (m, 9H), 2.4-2.8 (m, 12H), 3.0-3.4 (m, 7H), 3.5-3.9 (m, 4H), 4.1-4.4 (m, 4H), 4.82-4.85 (m, 3H), 7.05 (t, 1H, J = 8 Hz), 7.15 (d, 2H, J = 8 Hz), 7.29 (t, 2H, J = 8 Hz) |
| J-13^ | 0.5-1.5 (m, 36H), 1.7-2.3 (m, 12H), 2.4-2.8 (m, 11H), 3.0-3.4 (m, 8H), 3.5-3.9 (m, 8H), 4.1-4.4 (m, 4H), 4.82-4.88 (m, 3H), 6.61 (t, 1H, J = 4.7 Hz), 7.05 (t, 1H, J = 8 Hz), 7.15 (d, 2H, J = 8 Hz), 7.30 (t, 2H, J = 8 Hz), 8.35 (d, 2H, J = 4.76 Hz) |
| J-14 | 0.5-1.5 (m, 40H), 1.7-2.3 (m, 9H), 2.4-2.8 (m, 12H), 3.0-3.4 (m, 9H), 3.5-3.9 (m, 4H), 4.1-4.4 (m, 3H), 4.82-4.87 (m, 3H), 7.05 (t, 1H, J = 8 Hz), 7.15 (d, 2H, J = 8 Hz), 7.29 (t, 2H, J = 8 Hz) |

TABLE J-continued

Example NMR's
¹H NMR (400 MHz, DMSO-d6) δ ppm

J-15^  0.5-1.5 (m, 36H), 1.7-2.3 (m, 12H), 2.4-2.8 (m, 9H), 3.0-3.4 (m, 7H), 3.5-3.9 (m, 8H), 4.1-4.4 (m, 3H), 4.82-4.88 (m, 3H), 7.05 (t, 1H, J = 8 Hz), 7.13 (d, 2H, J = 8 Hz), 7.29 (t, 2H, J = 8 Hz)

J-16^  0.5-1.5 (m, 36H), 1.7-2.3 (m, 12H), 2.4-2.8 (m, 8H), 3.0-3.4 (m, 10H),3.5-3.9 (m, 6H), 4.1-4.4 (m, 3H), 4.83-4.93 (m, 3H), 7.05 (t, 1H, J = 8 Hz), 7.15 (d, 2H, J = 8 Hz), 7.30 (t, 2H, J = 8 Hz), 8.39 (s, 2H)

J-17^  0.5-1.5 (m, 36H), 1.7-2.3 (m, 16H), 2.4-2.8 (m, 10H), 3.0-3.4 (m, 10H), 3.5-3.9 (m, 4H), 4.1-4.4 (m, 3H), 4.81-4.88 (m, 3H), 7.05 (t, 1H, J = 8 Hz), 7.14 (d, 2H, J = 8 Hz), 7.29 (t, 2H, J = 8 Hz)

J-18  0.5-1.5 (m, 43H), 1.7-2.3 (m, 9H), 2.4-2.8 (m, 12H), 3.0-3.4 (m, 6H), 3.5-3.9 (m, 4H), 4.1-4.4 (m, 4H), 4.81-4.84 (m, 3H), 7.05 (t, H, J = 8 Hz), 7.15 (d, 2H, J = 8 Hz), 7.29 (t, 2H, J = 8 Hz)

J-19^  0.5-1.5 (m, 43H), 1.7-2.3 (m, 14H), 2.4-2.8 (m, 10H), 3.0-3.4 (m, 12H), 3.5-3.9 (m, 4H), 4.1-4.4 (m, 3H), 4.81-4.84 (m, 3H), 7.06 (t, 1H, J = 8 Hz), 7.15 (d, 2H, J = 8 Hz), 7.28 (t, 2H, J = 8 Hz)

J-20^  0.5-1.5 (m, 42H), 1.7-2.3 (m, 12H), 2.4-2.8 (m, 9H), 3.0-3.4 (m, 10H), 3.5-3.9 (m, 4H), 4.1-4.4 (m, 3H), 4.82-4.87 (m, 3H), 7.06 (t, 1H, J = 8 Hz), 7.15-7.19 (m, 3H,), 7.24-7.31 (m, 6H)

J-21^  0.5-1.5 (m, 40H), 1.7-2.3 (m, 14H), 2.4-2.9 (m, 10H), 3.0-3.4 (m, 12H), 3.5-3.9 (m, 4H), 4.1-4.4 (m, 3H), 4.81-4.88 (m, 3H), 7.05 (t, 1H, J = 8 Hz), 7.15 (d, 2H, J = 8 Hz), 7.29 (t, 2H, J = 8 Hz)

J-22^  0.5-1.5 (m, 36H), 1.7-2.3 (m, 14H), 2.4-2.9 (m, 10H), 3.0-3.4 (m, 10H), 3.5-3.9 (m, 4H), 4.1-4.4 (m, 3H), 4.81-4.84 (m, 3H), 7.05 (t, 1H, J = 8 Hz), 7.14 (d, 2H, J = 8 Hz), 7.29 (t, 2H, J = 8 Hz)

J-23^  0.5-1.5 (m, 36H), 1.7-2.3 (m, 11H), 2.4-2.9 (m, 7H), 3.0-3.4 (m, 8H), 3.5-3.9 (m, 3H), 4.1-4.5 (m, 6H), 4.82-4.94 (m, 3H), 6.26 (s, 1H), 7.05-7.07 (m, 1H), 7.14 (d, 2H, J = 8 Hz), 7.29 (t, 2H, J = 8 Hz), 7.43 (s, 1H), 7.78 (s, 1H)

J-24^  0.5-1.5 (m, 36H), 1.7-2.3 (m, 11H), 2.4-2.9 (m, 7H), 3.0-3.4 (m, 8H), 3.5-3.9 (m, 4H), 4.1-4.5 (m, 5H), 4.83-5.02 (m, 3H), 6.84 (s, 1H), 7.06 (t, 1H, J = 7 Hz), 7.13 (d, 2H, J = 8 Hz), 7.25 (s, 1H), 7.30 (t, 2H, J = 8 Hz), 7.69 (s, 1H)

J-25^  0.5-1.5 (m, 35H), 1.7-2.3 (m, 14H), 2.4-2.9 (m, 10H), 3.0-3.4 (m, 8H), 3.5-3.9 (m, 6H), 4.1-4.5 (m, 4H), 4.82-4.90 (m, 3H), 7.03 7.16 (m, 7H), 7.29 (t, 2H, J = 8 Hz)

J-26^  0.5-1.5 (m, 36H), 1.7-2.3 (m, 18H), 2.4-2.9 (m, 10H), 3.0-3.4 (m, 10H), 3.5-3.9 (m, 4H), 4.1-4.4 (m, 4H), 4.81-4.86 (m, 3H), 7.05 (t, 1H, J = 8 Hz), 7.14 (d, 2H, J = 8 Hz), 7.29 (t, 2H, J = 8 Hz)

J-27^  0.5-1.5 (m, 36H), 1.7-2.3 (m, 14H), 2.4-2.9 (m, 7H), 3.0-3.4 (m, 8H), 3.5-3.9 (m, 4H), 4.1-4.5 (m, 5H), 4.83-4.94 (m, 3H), 6.84 (s, 1H), 7.06 (t, 1H, J = 7 Hz), 7.13 (d, 2H, J = 8 Hz), 7.25 (s, 1H), 7.30 (t, 2H, J = 8 Hz), 7.69 (s, 1H)

J-28^  .5-1.5 (m, 36H), 1.7-2.3 (m, 11H), 2.4-2.9 (m, 7H), 3.0-3.4 (m, 8H), 3.5-3.9 (m, 3H), 4.1-4.5 (m, 4H), 4.59-4.98 (m, 5H), 7.05 (t, 1H, J = 7 Hz), 7.13 (d, 2H, J = 8 Hz), 7.30 (t, 2H, J = 8 Hz), 7.72 (s, 1H), 8.06 (s, 1H)

J-29^  0.5-1.5 (m, 36H), 1.6-2.3 (m, 13H), 2.4-2.9 (m, 7H), 3.0-3.4 (m, 8H), 3.5-3.9 (m, 3H), 4.1-4.5 (m, 4H), 4.63-4.99 (m, 5H), 7.05 (t, 1H, J = 7 Hz), 7.13 (d, 2H, J = 8 Hz), 7.30 (t, 2H, J = 8 Hz), 7.72 (s, 1H), 9.24 (s, 1H)

J-30^  0.5-1.5 (m, 36H), 1.6-2.3 (m, 16H), 2.4-2.9 (m, 7H), 3.0-3.5 (m, 8H), 3.9-4.0 (m, 3H), 4.1-4.5 (m, 4H), 4.82-4.93 (m, 5H), 7.05 (t, 1H, J = 7 Hz), 7.13 (d, 2H, J = 8 Hz), 7.30 (t, 2H, J = 8 Hz), 7.72 (s, 1H), 8.92 (s, 1H)

BIOLOGICAL

BRD pathogens include, for example, *Pasteurella multocida*; *Mannheimia haemolytica*; *Histophilus somni*; and *Mycoplasma bovis*. There is some debate as to whether *M. bovis* is a primary pathogen, secondary invader or predisposing factor for other BRD agents. The polymicrobial nature of BRD makes it difficult to ascribe a specific pathogen(s) to an individual case of BRD, since affected animals typically present non-specific clinical signs. The epidemiology of BRD is well known, with cases occurring within 6-10 day of entry into the feedlot (FIG. 1). Therefore, antimicrobial metaphylaxis is routine for on-arrival cattle that are deemed high risk of developing BRD. Low risk cattle may also be administered a parenteral metaphylaxis. Macrolides tend to be the primary antimicrobials that are administered to high risk cattle.

Primary screening of the compounds of the invention included the evaluation of antibacterial activity of analogs through determination of microbial inhibition concentration (MIC) as per CLSI guidelines. The screening panel included the relevant BRD pathogens: 1) *M. haemolytica* (e.g., 12726, 46571 and 49023, all AHDRCC; and 33396 (ATCC)); and 2) *P. multocida* (e.g., 34135 and 46572 (both AHDRCC) and 43137 (ATCC)). In some instances, *H. somni* (A700025K) pathogens were also included in the screening panel. The AHDRCC strains originated from the Zoetis BRD/SRD surveillance program and refer to the Animal Health Development and Research Culture Collection. In addition, the screen assessed *S. aureus* (29213 ATCC) as a representative Gram-positive isolate, *E. faecalis* (19433 ATCC) as a commensal gram-positive gastrointestinal bacterium and *E. coli* (100, 3110 and 25922 (ATCC)) for the evaluation of efflux potential. The screening panel BRD pathogens were assessed in determining antibacterial activity of the Formula (1) compounds.

All relevant BRD pathogens were initially screened at a top concentration of 64 μg/mL of a Formula (1) compound in an eleven-point dilution series. The analogs were then characterized based on their minimum inhibitory concentration (MIC) values to the BRD pathogens with the goal to be >64 μg/mL for progression, and to be considered a non-antibiotic compound. Formula (1) compounds were considered to be non-antibacterial if the pathogen MIC was >64 μg/mL for *M. haemolytica* and *P. multocida* strains. In addition, if Formula (1) compounds were also tested against the *H. somni* strain, to be considered non-antibacterial, the MIC was also >64 μg/mL. Generally, if the analogs had an MIC >64 μg/mL for the BRD pathogens, then the MIC's reported for *S. aureus*, *E. faecalis* and *E. coli* were also >64 μg/mL. In most instances, compounds of the invention with an initial screening BRD pathogen MIC result >64 μg/mL were not tested beyond this top concentration since this MIC value was determinant for lack of antibacterial activity. In addition, it should be noted that some Examples described in the Tables that are flagged as antibacterial (i.e., MIC ≤64 μg/mL) may actually be non-antibacterial but for potential residual (minor impurity(s)) antibacterial starting material (i.e., tulathromycin epoxide, M9 epoxide, M8 epoxide or azithromycin) that was used in its preparation. If an Example was purified further, the MICs moved up essentially two dilutions across all strains tested in the screening panel.

In-Vitro MIC Model

Compounds were analyzed for antibacterial activity against a panel of Animal Health specific Gram-positive and Gram-negative clinical strains by diluting compounds in DMSO to an appropriate stock concentration to determine the Minimal Inhibitory Concentration (MIC) via a semi-automated broth micro-dilution method (CLSI reference method) with QC strains and anti-microbial agent(s). Specifically, bacteria were grown overnight on TSA w/5% sheep blood agar plates and diluted in saline buffer to a McFarland Standard 0.5, then further diluted in cation-ion adjusted Mueller Hinton Broth to a final concentration of approximately 5×10⁵ CFU/mL. 100 μL of inoculated media was added to 96-well plate(s) with 3 μL of serially diluted compound in each row. Depending on strain (see CLSI reference method), bacteria were incubated 18-22 hours at 35-37° C. in ambient air, with 5% $CO_2$ or anaerobically (up to 48 hours).

In-Vitro Immunological Assay(s)

Whole Blood Assay—Fresh whole bovine blood samples were collected into heparinized vacutainer tubes. Assay plates were prepared with 25 μL of drug diluted in PBS at varying concentration in 96 round bottom wells, then 225 μL of blood was added and plates incubated at 37° C. for 4 hours. Cells were stimulated with LPS (or PBS for controls) by adding 25 μL to the plates at a final concentration of 1 μg/mL and incubated at 37° C. for 18 hours. To collect plasma, plates were centrifuged at 2,000×g for 10 minutes and 100 μL of supernatant was transferred to a 96 well polypropylene plate that was sealed and stored at −80° C. Samples were assayed for cytokines using the Meso Scale Discovery (MSD) platform (described below) from plasma collected directly from drug treated animals as well as plasma collected from the whole blood assay.

Cytokine Detection—An MSD U-Plex cytokine assay was developed following the MSD U-Plex protocol guide and included biotinylated capture antibodies against: bovine Interleukin (IL)-1β (Biorad), bovine IL-6 (R&D Systems) and bovine tumor necrosis factor (TNF)-α (R&D Systems). The anti-IL-1β antibody was biotinylated using EZ-Link Sulfo-NHS-Biotin (Thermo Scientific) at a challenge ratio of 1:20 according to manufacturer instructions. Assay calibrators (Kingfisher) were diluted to a concentration of 40,000 μg/mL in control lithium heparin plasma, followed by 4-fold serial dilutions into plasma. The detection antibodies were sulfo-tagged following the MSD quick guide conjugation protocol using a challenge ratio of 1:20. Antibodies were used at the following concentrations: anti-IL-1β at 1 μg/mL, anti-IL-6 at 1 μg/mL and anti-TNF-α at 0.5 μg/mL. Cytokines were quantified according to manufacturer's instructions using a chemiluminescent readout. In brief, 0.5 mL of all biotinylated antibodies were diluted to 10 μg/mL with Diluent 100 and paired to their respective linkers by adding 750 μL of supplied Linker solution and incubated for 30 minutes followed by addition of Stop solution for another 30 minutes. The linked antibodies were then diluted 10-fold into Stop solution. Plates were coated by adding 50 μL of antibody solutions per well and incubated covered and shaking for 1 hour at room temperature. Plates were washed three times with PBS/Tween20 prior to samples or standards being added at 30 μL per well and incubated as above. Plates were washed three times before detection antibodies were added along with 2% goat and rabbit serum to block and incubated same as above. Plates were washed a further three times before addition of 150 μL 2× Read buffer and read immediately on the S16000 instrument (MSD). For soluble protein levels, a BCA protein kit (Thermofisher,) was used. The cytokine concentrations (pg/mL) were normalized to the total protein levels for each sample.

CD163 Expression by Flow Cytometry—Fresh whole bovine blood samples were placed on ice and processed within two hours of collection. Blood was placed in 96 well round bottom plates at 30 μL per well, 5 μL of goat serum was added as a blocking reagent and the plate was rocked at 4° C. for approximately 15 minutes. To label cells, 10 μL of a master mix panel of antibodies including anti-CD14 (BioLegend #301854), anti-CD172a (BioRad #MCA2041C), anti-CD163 (Kingfisher #WSC0832B-100) and anti-CD16 (BioRad #MCA5665F), was added to the samples and returned to 4° C. (protected from light) for 30 minutes. Single stain controls were included for use in compensation matrices. Red blood cells were removed by adding 200 μL of lysis buffer and incubating for 10 minutes at room temperature while rocking. The plate was then centrifuged at 270×g for three minutes and supernatant removed. This step was repeated until supernatant was clear. 200 μL of FACS buffer was added to each well to wash cells, centrifuged as above, resuspended in 80 μL of FACS buffer and read immediately on a digital FACS Canto II HTS (BD Bioscience) flow cytometer. Data was analyzed using FlowJo software (BD Bioscience). Macrophage subpopulations were determined using CD172, CD14, CD16 markers and assessed for expression of CD163.

In Vivo Mouse Lung Infection Challenge Model (Murine)

The challenge organism was *P. multocida* 46572. Target challenge concentration was $5\times10^2$ CFU/mouse. Isolated colonies from overnight growth (37° C. with 5% $CO_2$) on trypticase soy agar (TSA II) blood plates were transferred to room temperature Brain Heart Infusion Broth (BHIB). The broth culture was incubated 3.5-4 hours to approximately mid-log phase of growth, as measured by forward light scatter at 600 nm (OD600, 0.200). The culture was centrifuged to collect the bacterial pellet. The pellet was re-suspended in BHIB and adjusted to provide an approximate concentration of 2.7 $\log^{10}$ colony forming units (CFU) in 0.04 mL at the highest concentration. The challenge inoculum concentration was confirmed by serial dilutions of the inoculum for CFU enumeration. On Day −5, CD-1 female mice were received. Mice were given standard rodent diet and water ad libitum. On Day 0, bacterial inoculum (0.04 mL) was administered to each mouse (n=36) intranasally. Compounds of the invention were dosed at 20 mg/kg (0.1 mL) in a buffered (~pH 5.4) propylene glycol, monothioglycerol and water solution by subcutaneous injection. Animals were observed from Days 1-10. The study was terminated on Day 10. In addition, some treatment groups were sampled at 6, 24, and 48 hours post bacterial challenge for RNA sequence analysis of lung tissue.

In Vivo Bovine Lung Infection Challenge Model

The challenge organism was *M. haemolytica* (OSU-012103-BHI). The challenge organism was grown in 100 mL of brain heart infusion (BHI) medium in a 250 mL baffled flask and inoculated with 0.1 mL of thawed stock bacterial culture. The culture was incubated overnight (~15-18 hours) at 150 RPM in a 37° C. shaker-incubator. A 2 mL aliquot of the overnight culture was used to inoculate each 100 mL of media in a baffled flask containing fresh BHI medium at a ratio of ~1/3 broth to total volume of the flask. The culture was incubated for about 2 to 6 hours at 150 RPM at 37° C. When the optical density (OD) at 650 nm reached 0.800 (approximately $1\times10^9$ CFU/mL), the culture was chilled in an ice bath. The culture was centrifuged to collect the bacterial pellet. The pellet was re-suspended in a phosphate buffered saline (PBS) to the original absorbance value. The resulting suspension was further diluted to the appropriate challenge concentration. For each challenge dose, the appropriate amount of stock culture was added to a pre-measured volume of PBS medium to prepare the 120 mL dose. The dilution was prepared just prior to challenge administration. A 30 mL amount of BHI medium or PBS was infused into the lung immediately following administration of the challenge material. Male (or steer) Holstein cattle were received on Day −10. Animals received a pre-shipping dose of Advocin© and a) had *M. haemolytica* leukotoxin antibody titers less than 0.85 S/P ratio prior to allotment, as determined by a serological ELISA to leukotoxin of *M. haemolytica*; b) were negative for persistent BVDV infection as determined by ear notch sampling prior to arrival; c) free from systemic disease or indications of being immunecompromised; and d) in good health. Animals were fed a non-antibiotic diet and provided water ad libitum. A pre-challenge group of animals (N=4/group) received a challenge dose (~3.3×10$^8$ CFU/dose or ~1×10$^9$ CFU/dose) and treatment (10 mg/kg) on Day −8 to determine the optimal challenge dose. The challenge material was administered to the lungs via a plastic cannula subsequent to local lidocaine anesthesia. Treatment dose was administered by subcutaneous injection and the treatment drug was solubilized in a buffered (~pH 5-6) composition comprising propylene glycol and water. On Day 0, remaining animals (N=24/group) were challenged and then treated with either a 0.2, 0.5, 2.5, or 10 mg/kg amount of study compound (100 mg/mL). Animals were evaluated through the duration of the study which terminated on Day 6 for clinical signs of disease. Lungs were swabbed for bacterial presence and lung lesions were scored based on percent gross lung involvement and respiratory severity determined.

In Vivo Temporal Study

A clinical and genomics temporal study was conducted to mimic typical management cattle practices that result in the development of BRD. The design included extensive longitudinal genomics sampling, including the airway, as well as comprehensive clinical evaluation, with the goal of linking mechanism of disease to clinical phenotype. The study resulted in a 20% incidence of classic BRD as assessed by standard clinical scoring criteria. To allow data analysis, animals were assigned to phenotypic groups based on clinical signs, lung lesions, and treatment qualification as per feedlot standards. The study served as the framework to interpret the biological processes that resulted in healthy, subclinical, and diseased animals at the typical intervention point of arrival at the feedlot. For example, comparison of whole transcriptome RNA sequencing data of naso-pharyngeal swabs collected at the time analogous to arrival at the feedlot could be aligned with a known clinical outcome from the study results.

The study demonstrated that contrary to the dogma, there is an upregulation of innate inflammatory pathways prior to shipment and at the post-shipping feedlot arrival timepoint. This heightened inflammatory state is seen in virtually all animals despite the final clinical outcome. Further analysis of the comprehensive data revealed that animals that progressed to develop BRD continued to have elevated innate inflammatory pathway signatures expressed in the airway while the healthy and subclinical animals (healthy cohort) showed self-moderated decrease of the inflammatory signals within a couple of days (FIG. 2).

Of significance, is the presence of the unresolved exacerbated inflammation state at Days 4-6 which results in differential bacterial involvement of *H. somni* and *M. haemolytica* and the transition to the full BRD disease complex. Both healthy and diseased cohorts were confirmed by RNA sequence analysis to have similar viral and bacterial exposures from Day −1 through Day 4. The healthy cohort (no disease and subclinical) were able to resolve the inflammation state early, Day 0 or Day 1. The BRD (diseased) cohort did not resolve the inflammation state and progressed to the full BRD complex. A significant increase of typical BRD-associated microorganisms (*M. bovis, H. somni*, and *M. haemolytica*) was not detectable until after the innate inflammatory pathways failed to resolve at Day 4-6. It is believed that it is the unresolved inflammatory process that enables progression to the full BRD complex.

From this temporal study, pathways for intervention were identified. These include Pattern Recognition Receptor (PRR) TLR-4 activation, inflammasome signaling, NF-κB and STAT transcription, which were targeted to reduce the pathologic innate inflammatory cascade prior to disease onset. Some key inflammatory cytokines included IL-1β, IL-6, IL-36, and TNF-α which were further confirmed through in vitro cell-based assays and ex vivo bovine infection models. The study also served to identify biomarkers correlating with disease severity (CD163, IL-6, IL-36 and haptoglobin).

Plasma samples were collected from at-risk calves upon arrival at a feedlot, assessed for cytokine levels. The data was correlated with final disease (BRD) as assessed by clinical scoring for seven days. Of the cohort, 14 animals were healthy and 24 were diagnosed with BRD. As predicted for BRD etiology and pathogenesis, NF-κB mediated cytokines, including IL-6, were highest in animals that would develop clinical BRD. Interestingly, there was a correlation between higher levels of IFN-γ in animals at arrival associated with animals that did not progress to clinical BRD (FIG. 3). This data further supports that calves with heightened levels of some pro-inflammatory cytokines (IL-6 and IL-8) on arrival to the feedlot are associated with poor clinical outcome whereas calves that have increased IFN-γ, a cytokine associated with pathogen clearance, are associated with remaining healthy and not progressing to BRD.

In-Vitro Studies

The compounds of the invention had MIC values for multiple BRD pathogenic bacterial strains of *M. haemolytica* and *P. multocida* and from other pathogenic bacterial strains including *E. coli, S. aureus*, and *E. faecalis* that were considered to be non-antibacterial (i.e., MIC >64 μg/mL). Bacterial strains included the following: *E. coli* (A25922K/T, W3110WT, AG100T, AG100AT); *E. faecalis* (A19433K/T); *M. haemolytica* (12726K, 46571 K/T, A33396K/T, 49023T, and others); *P. multocida* (46572K, 43137K, 34135T, and others); *S. aureus* (A29213K/T); and *H. somni* (A7000025K). The K and T represent a specific strain at two study site locations. For Example, Example H-91 had MIC values that were >256 μg/mL in 25 different strains each of *M. haemolytica* and *P. multocida*; and an MIC >64 for *H. somni* (31 strains). Example H-11 had MIC values >64 for the same *M. haemolytica, P. multocida* and *H. somni* strains. As defined herein, the non-antibacterial compounds had MIC values >64 μg/mL in the BRD bacterial strains tested. Some compounds defined herein were considered to have some antibacterial properties as a result of at least one MIC value ≤64 μg/mL for any one of the bacterial strains tested. Except for a few compounds of the invention, most had MIC values >64 μg/mL for the BRD bacterial strains described above, and for the other non-BRD strains as well. The K and T represent a specific strain at two different study site locations.

Comparatively, gamithromycin had MIC values ranging from about 0.5-1 μg/mL and 1-2 μg/mL for the same *M. haemolytica* and *P. multocida* strains respectively; and about 0.25-8 μg/mL for the *H. somni* strains. For the same *H. somni* strains, florfenicol and enrofloxacin had MIC's ranging from 0.12-2 μg/mL and <0.06-1 μg/mL, respectively; clearly showing their antibacterial potential against these bacterial strains. In addition, the MIC's (μg/mL) for tulathromycin and M9 for the following bacterial isolates is shown in Table 1.

TABLE 1

Comparative MIC's (μg/mL) for Bacterial Isolates

| Bacterial Isolate | Tulathromycin | M9 |
|---|---|---|
| S. aureus ATCC 29213 | 8 | 64 |
| E. coli ATCC 25922 | 2 | >64 |
| E. coli W3110 | 8 | 64 |
| M. haemolytica ATCC 33396 | 1 | 32 |
| M. haemolytica 12726 | 2 | 32 |
| M. haemolytica 46571* | 1 | 32 |
| P. multocida ATCC 43137 | 1 | 16 |
| P. multocida 46572** | 1 | 8 |

*Indicates bovine efficacy challenge strain
**Indicates murine efficacy challenge strain.

In an Ames mutagenicity test, Example H-91 (1-5000 μg/plate; using the plate incorporation method and a standard panel of bacterial (E. coli and Salmonella isolates) was negative (non-mutagenic).

In summary, Examples H-11 and H-91 demonstrated a lack of in vitro activity vs. clinically relevant pathogenic strains for BRD (M. haemolytica and P. multocida) and a lack of clinically relevant MICs has been established against all zoonotic bacteria tested to date. Additionally, the compounds were non-mutagenic in Ames testing.

The compounds of the invention share the most commonly described immune-effects with the parent macrolide class including modulation of pro-inflammatory cytokine production and the trafficking/fate of granulocytes. Reductions in IL-1β, IL-6, IL-36 and TNFα with the compounds of the invention have been observed and have consistently been associated with a positive clinical outcome. The compounds of the invention also consistently mitigate the increase in biomarkers IL-6, IL-36, CD163 and haptoglobin which have also been associated with clinical disease outcome. Therefore, underlying mechanism of the compounds of the invention are likely the broad-spectrum modulation of innate inflammatory response.

In vitro systems were functional in demonstrating inhibition of cytokines TNF-α, IL-6 and IL-1β in BRD relevant primary cell types including bovine alveolar macrophages and nasopharyngeal epithelial cells. The effect of multiple cytokines was not easily quantified using single cell types. Therefore, a fresh whole bovine blood assay was developed with LPS as a stimulant (TLR-4 agonist) and with IL-1β and TNF-α as the read-out. Compounds of the invention were evaluated against a positive control for their ability to inhibit LPS-induced IL-1β and TNF-α as an overall evaluation of relative potency and modulation of target pathways (Table 6).

The second immunomodulation in vitro assay evaluated the potential for phospholipidosis with the compounds of the invention in bovine alveolar macrophages. This assay is utilized to determine cellular uptake of the compounds of the invention in relevant bovine and murine cell types. This assay utilized Invitrogen's commercially available HCS LipidTox detection kit with an Incucyte real time fluorescence reader to observe variations in $EC_{50}$ and phospholipidosis profiles based on compound concentrations. Murine intraperitoneal macrophages were also used in the same assay to evaluate species variability for potential correlation with mouse efficacy results. The combination of the bovine whole blood assay and phospholipidosis assays enabled rank ordering for progression into in vivo testing in the murine challenge model.

Transcriptional changes as do not always correlate with protein levels and observed phenotype. In order to correlate RNA sequencing data to cytokine changes the whole blood assay was utilized. Example H-11 downregulated LPS induced pathologic-associated cytokine production including IL-1β, TNF-α and IL-6. The results (Table 2) demonstrate a reduction in three cytokines which have been identified to be relevant to BRD disease state. Enhancement (enh), as indicated in Table 2, is observed in IL-1β cytokine levels when a compound is inhibitory at lower concentrations, however, fails to reach an $IC_{50}$ value. The enhancement result represents an overall stimulation of cytokine levels due to cellular stress or potential toxicity with increasing concentrations of the compound, representing a typical bell shape response curve for immunomodulatory activity. In addition, LPS stimulated whole bovine blood assays (4 independent studies with multiple blood donors) with Example H-11 showed a dose dependent reduction in the expression of key cytokines (IL-6, TNF-α and IL-1β) associated with BRD (FIG. 4); further supporting cytokine inhibition.

TABLE 2

Immunomodulation Assay Results

| Analog | M9 | H-11 | H-91 |
|---|---|---|---|
| TNF-α $IC_{50}$ (μM) | 250 | 8 | 90 |
| IL-1β $IC_{50}$ (μM) | 250 | 36* | 103* |
| Phospholipidosis $EC_{50}$ (mM) | 3.74 | 0.004 | 0.088 |
| logP | 2.2 | 3.2 | 3.1 |

*enhanced response at concentration indicating potential cytotoxicity

Further data supporting this hypothesis includes murine studies using a P. multocida infection in mice. For example, M9 and Example H-91 were clinically efficacious when airway tissues were collected longitudinally and evaluated for transcriptomic analysis. Using these results, specific transcriptional expression demonstrated regulators consistent with some key BRD pathways (PRRs, cytokines, STAT) and cellular cross-talk activity.

Mouse Murine Study

Compounds of the invention were selected for progression into murine efficacy and beyond based on a significant MIC increase (target >64 μg/mL) for all bacterial strains in the screening panel. This assessment was combined with an in vitro immunomodulation potency equal to or better than M9, TNF-α and IL-1β IC50 of ~250 μM for both cytokines and an $EC_{50}$ for phospholipidosis of 3.74 mM.

The murine efficacy model (P. multocida challenge) was optimized, and the treatment group size was powered to be able to observe statistically significant improvement of survival to expected ranges for immunomodulatory compounds. The experimental design was a randomized complete block design. Mice were individually identified and treatment groups comingled within a cage, with every treatment group equally represented across cages. Mortality was the primary variable. Mortality data was analyzed using a generalized mixed model with fixed effect of treatment and random effect of block. Survival time was also analyzed using the SAS PHREG (survival analysis) procedure to examine whether there were significant differences between treatment groups and the control group. Numerous compounds of the invention and M9 (positive control) were tested in this model at a dose of 20 mg/kg. Typical percent survival for no treatment control is in the range of 0-20% based on study to study variation in challenge inoculum and rate of infection. The analogs tested had an MIC vs. challenge strain at ≥64 μg/ml compared to M9 at (8 μg/mL).

Mouse survival for M9 was about 90-100%, further supporting its antibacterial properties against the bacterial strain (Table 3). Survival values presented are harmonized against the comparative vehicle survival rate.

TABLE 3

Mouse Murine Percent Survival

| Ex.# | % |
|---|---|
| B-2 | 28 |
| B-4 | 7 |
| B-5 | <1 |
| B-6 | 1 |
| B-13 | 48 |
| B-13a | 44 |
| H-3 | 8 |
| H-11 | 36 |
| H-13 | 59 |
| H-14 | 46 |
| H-39 | 44 |
| H-60 | 72 |
| H-72 | 4 |
| H-73 | 4 |
| H-74 | 11 |
| H-83 | 11 |
| H-87 | 14 |
| H-91 | 38 |
| H-95 | 39 |
| H-96 | 11 |
| H-100 | 19 |
| J-3 | 25 |
| J-4 | 5 |
| J-7 | 39 |

In one murine *P. multocida* intranasal challenge study, mice were administered tulathromycin (16 mg/kg; T02), M9 (32 mg/kg; T03), or ceftiofur (9 mg/kg; T04) by subcutaneous injection 18 hours after bacterial challenge ($5 \times 10^3$ CFU/mouse) for lung tissue RNA sequence analysis. Survival at Day 7 was about 80%, 50%, and 90% for T02, T03, and T04, respectively, compared to placebo at 0%. Differential gene expression from total lung tissue RNA sequence analysis indicated at least 226 unique genes were up or down regulated (with significance) for T03. Output from ingenuity pathway analysis of these unique genes predicted major upstream regulators of the involved pathways. Data was analyzed based on the number of genes being modulated in the same direction that were associated with a given upstream regulator. An activation z-score of 2 or greater is considered significant and the direction change is indicated by + (activated) or − (inhibited). The top 5 pathways included: IL-9 signaling, glucocorticoid receptor signaling, prolactin signaling, JAK STAT signaling, and IL-17 signaling. The top 6 upstream regulators (activation z-score) included: lipopolysaccharide (−6.725), TNF (−4.669), IFNG (−5.759), IL-1ß (−5.947), STAT1 (−2.787), and poly rI:rC-RNA (−5.289). Even though this study was run in the murine model, the top upstream regulators identified as being modulated by M9 include an almost ubiquitous overlap with the pathways identified in the natural disease study as being key mediators in BRD, and therefore is modulating highly relevant pathways in BRD pathobiology.

Single cell RNA sequencing was employed using the whole blood assay described above demonstrating drug-induced changes in protein cytokine expression to further substantiate cell type and pathway modulation by the compounds of the invention. Whole blood contains a variety of types of immune cells including both myeloid (e.g., neutrophils and macrophages) and lymphoid (e.g., T and B cells) derived cells as well as further differentiated cell-type specific subsets. Cells with transcriptional similarities were clustered together and identities were projected based on marker reference lists which were cross-checked with top differentially expressed genes against our established bovine antibody-based marker panels. In the absence of any stimulation, compound H-91 influenced genes that correlated in particular to cell clusters identified as neutrophils/macrophages, monocytes, and T and B lymphocytes. Samples were sequenced at 30 minutes, 4 hours, and 20 hours stimulation (LPS, as described above) with the relatively largest changes seen at 20-hours. Among the genes with the largest differentially expression values included but were not limited to cytokines such as IL-1ß, chemokines such as CXCL2 and CXCL8, and interferon-stimulated gene (ISG) family members (data not shown).

Focusing on the clusters of cells identified in the drug influence correlation, lists of significantly modulated genes (adjusted p <0.05 and absolute log(Fold Change) >0.25) were used to identify the predicted upstream regulators of the associated pathways. These regulators include (but are not limited to) components central to hypothesized pathological pathways in BRD such as TNFα, LPS (TLR4 agonist), NFκB, IL-1ß and IL-6. As described previously, the mitigation of these inflammatory pathways that are increased in BRD correlates with positive clinical outcome. In this experimental system, LPS was administered to activate the inflammatory pathways seen in calves at-risk for BRD and full transcriptome sequencing was used to determine drug effect on these key pathways. Within the myeloid cell populations, the neutrophil/activated macrophage cluster and monocyte cluster, the drug mitigated the activation of the majority of the inflammatory pathways described above. Within the B lymphocyte populations, the drug mitigated the LPS-induced activation within nearly all the top pathways regulators identified. This result makes sense as the PRR associated pathways described here are consistently expressed between the myeloid cell populations and B cells (both can serve as professional antigen-presenting cells). T cells express the family of PRRs to a much lesser extent so it follows that the pathways targeted by the drug are less affected in this cell type. Interestingly, the group of pathway regulators that were increased by drug in the context of stimulation (within myeloid and T cell clusters) represent pathways often associated with immunity against viral-type pathogens, interferons and STAT (which is a signaling molecule for the interferon family). This result expands on the mechanism of action description above where drug mitigates exacerbates innate proinflammatory pathways related to bacterial process pathobiology to may also upregulate immune defenses to viral pathogens known to be a major component in BRD.

Given the overlap between immunomodulatory properties of macrolides and the described target pathways, the desmethyl tulathromycin metabolite, M9, with reduced antimicrobial activity was utilized in a natural bovine respiratory disease study. The primary clinical endpoint for efficacy was treatment failure/success over a 14-day observation period. Clinically normal beef calves (150-200 kg) at moderate risk for BRD were dosed on arrival to the feedlot. Animals (N=114/group) received saline (T01), 5 mg/kg M9 (T02), 10 mg/kg M9 (T03) or Zactran (T04). Percent failure was 43%, 19.3%, 8.8%, and 29.8% for the T01, T02, T03, and T04 groups, respectively. Bacterial isolates were collected at necropsy and MICs were evaluated (Table 4). In a separate PK study, the maximum plasma concentration following a 10 mg/kg dose was 5 μg/mL. Based on the MICs observed (Table 4) and the maximum plasma concentration it was postulated that the residual MIC activity of M9 was not responsible for the significant overall outcome and the efficacy was primarily due to the immunomodulatory effects of M9. M9 demonstrated efficacy in a natural BRD infection study with statistical superiority demonstrated over untreated control groups in the reduction of lung lesions and treatment failure (attitude, rectal temperature, and respiratory rate/effort and nasal/ocular discharge). However, as can be seen for some of the BRD bacterial isolates, M9 has antibacterial (i.e., MIC <64 µg/mL) properties.

TABLE 4

MIC of Recovered Isolates: Natural Bovine Respiratory Disease Study Lung Bacteria Isolated at Necropsy

| Bacteria (n) | M9 | | | gamithromycin (Zactran) | | |
|---|---|---|---|---|---|---|
|  | MIC50 (µg/mL) | MIC90 (µg/mL) | Range (µg/mL) | MIC50 (µg/mL) | MIC90 (µg/mL) | Range (µg/mL) |
| M. haemolytica (116) | >64 | >64 | 32->64 | 1 | >64 | 0.5->64 |
| P. multocida (33) | 16 | >64 | 8->64 | 1 | >64 | 0.5->64 |
| H. somni (25) | 32 | 32 | 8-64 | 0.25 | 2 | 0.12-2 |

In a separate natural field study, using a compound of the invention (Example H-91), crossbred cattle (bulls, steers, heifers) ranging in age from 5 months or older weighing 300-500 pounds were used. Animals were penned and fed a non-antibiotic diet and provided water ad libitum. Animals (N=114/group) received a single saline placebo (T01) or treatment dose of Example H-91 at 0.5 mg/kg (T02) or 2.5 mg/kg H-91 (T03) on Day 0 by subcutaneous injection. The compound (20 mg/mL) was solubilized in a buffered (~pH 5-6) solution comprising propylene glycol and water. The study also included an active control group (N=57) wherein each animal received a labeled dose of Zuprevo (tildipirosin, 4 mg/kg, T04). A separate group of animals (N=3) received either the 0.5 mg/kg or 2.5 mg/kg dose of Example H-91 on Day 2. Animals were observed and clinically monitored (e.g., plasma, rectal temperature, attitude, respiratory (rate/effort and nasal/ocular discharge) until study termination on Day 7 to evaluate BRD. Bacterial swabs were also taken from cattle (treatment failures and lung lesions) and submitted for culture and isolation of M. haemolytica, P. multocida, H. somni, and M. bovis. Treatment success was 43.0% (T01), 57.9% (T02), 43.9% (T03), and 86.0% (T04). In view of the data presented, lower doses of a compound of the invention may be required for mitigating the innate immune and inflammatory response in the target animal. This correlates well with the in vitro assay data indicating at high concentration the immune response in cells is often increased as observed for IL-1ß.

In another natural field study, crossbred cattle (bulls, steers, heifers) ranging in age from 5 months or older weighing 300-500 pounds were used. Animals were penned and fed a non-antibiotic diet and provided water ad libitum. Animals (N=84/group) received a single treatment of Example H-11 at 0.03 mg/kg (T02), 0.1 mg/kg (T03), 0.3 mg/kg (T04), 1 mg/kg (T05), or 0.05 ml/kg saline (T01). A subset of 42 animals received a single 4 mg/kg dose of Zuprevo (T06; 180 mg/mL). Animals in the T01-T06 groups received the dose on Day 0. Route of administration for all treatment groups was by subcutaneous injection. Actives were solubilized in a buffered (~ pH 5-6) solution comprising propylene glycol and water to prepare 1.2 mg/mL (T02), 4 mg/mL (T03), 12 mg/mL (T04), and 40 mg/mL (T05). Animals were observed and clinically monitored (e.g., plasma, rectal temperature, attitude, respiratory (rate/effort and nasal/ocular discharge) until study termination on Day 7 to evaluate BRD. Bacterial swabs were also taken from cattle (treatment failures and lung lesions) and submitted for culture and isolation of M. haemolytica, P. multocida, H. somni, and M. bovis. Treatment success was 32.1% (T01), 58.3% (T02), 60.7% (T03), 51.2% (T04), 40.5% (T05) and 85.7% (T06). Compared to T01, T02 (0.0008), T03 (0.0003), T04 (0.0133), and T06 (<0.0001) were statistically significant at the 0.20 level.

Intensive sample collection was conducted over a 96-hour period in a subset of cattle treated with Example H-91 (0.5 mg/kg) or H-11 (0.1 mg/kg) in the natural bovine infection studies. These compounds demonstrated a rapid and transient increase in IL-36RA that increased to about 275% for Example H-91 and about 50% for Example H-11, compared to baseline, within 1 hour (FIG. 5). IL-36RA remained elevated for roughly 8 hours and then the concentrations dropped to −55% of the baseline concentration. A dose dependent reduction was observed from 48-96 hours. The compounds of the invention have shown an up-regulation of IL-36RA, which then binds to IL-36R limiting the pro-inflammatory response of IL-36. In addition, the IL-8 levels from one of the natural infection studies with Example H-91, increased 270% over the course of the study for control animals. In contrast, the IL-8 levels in animals dosed with Example H-91 decreased by about 15%.

To evaluate immunomodulation effects and potential biomarkers, a bovine M. haemolytica (strain: OSU-012103-BHI) intratracheal lung challenge model study was completed utilizing M9 treatment in the presence and absence of bacterial challenge and a Draxxin© comparator. It is important to note that the MIC for M9 to the challenge strain is >64 µg/mL indicating the effects observed were primarily through immunomodulation and not reduction of the bacterial challenge. Animals were administered 0.05 mL/kg saline (T01), 10 mg/kg M9 (T02); Draxxin 2.5 mg/kg (T03) and 10 mg/kg M9 (T04) by subcutaneous injection on Day −1. Dose was based on body weight. Animals were challenge on Day 0 with the exception of T04. Blood was collected longitudinally throughout the study for biomarker evaluation panel (e.g., IL-6 and CD163) including two baseline samples prior to treatment. Study results are presented in Table 5 and in FIG. 6. FIG. 6A depicts the area under the curve concentrations for IL-6 protein for individual animals against percent lung lesion scores and FIG. 6B depicts the CD163 fold change area under the curve for individual animals against percent lung lesion scores. Data is represented as percent lung lesion scores against the area under the curve (AUC) for IL-6 protein (immunoassay expressed in pg/mL) and CD163 (flow cytometric mean fluorescent intensity (MFI) in fold change from baseline). In both assays, a 2-fold change is typically considered to be relevant.

TABLE 5

M9 Intratracheal Lung Challenge Study

| Treatment Group | Challenge | No. Animals | Mortality |
|---|---|---|---|
| T01 | M. haemolytica | 6 | 4/6 |
| T02 |  | 6 | 1/6 |
| T03 |  | 6 | 0/6 |
| T04 | No challenge | 6 | 0/6 |

IL-6 was elevated and was correlated with higher rectal temperature (data not presented) and mortality. M9 and Draxxin© significantly reduced IL-6 levels which also correlated with overall animal survival or disease progression. CD163 mRNA expression followed the initial innate inflammatory cascade signaling in animals that showed clinical signs of BRD within a few days. The increased expression of CD163 on macrophages correlates to clinical disease progression in longitudinal sampling of whole blood. M9 mitigates the pathologic increase in CD163 expression.

In summary, M9 demonstrated statistically significant efficacy in both a natural BRD infection as compared to saline (T01) in the *M. haemolytica* challenge model. In a separate study, 10 mg/kg of M9 demonstrated statistical superiority versus saline control in reduction of lung lesions (20% vs. 31%, p=0.023) and mortality (13% vs. 38.9%, p=0.025). Additionally, reduction of biomarkers consistent with the proposed mechanism were observed. However, the residual antibacterial activity of M9 (MIC's≤64 μg/mL) against target pathogens was not in line with the non-antibiotic immunomodulator profile (>64 μg/mL).

In a separate bovine *M. haemolytica* intratracheal lung challenge study, Example H-91 was administered 24 hours prior to bacterial challenge consistent with the on-arrival control/prevention product profile. The study was designed to also include an assessment of immunomodulation biomarkers. Animals (n=24/group) received a subcutaneous dose of saline (0.05 mL/kg; T01); 0.5 mg/kg (T02) or 2.5 mg/kg (T03; n=23) of Example H-91; or a 10 mg/kg (T04) of M9. Dose amount was based on body weight. On Day 0, animals were challenged with *M. haemolytica*. T01-T04 animals were evaluated for clinical scores, lung lesions and mortality to assess statistical success. Outcomes included: respiratory severity score 0=normal, 1=mild clinical signs, 2=acute BRD clinical disease, 3=severe BRD clinical disease; attitude score 0=normal, 1=mild depression, 2=moderate to marked depression, 3=moribund. A treatment failure was considered if: a) the clinical score was 3 or b) a combination of scores of 2+2 with a rectal temperature of >104° F. Daily clinical scores were observed on a scale of 0-3; including attitude and respiratory, with rectal temperatures. Lung lesions were assessed at necropsy. On Day 6, the study was terminated and all remaining animals were euthanized. An animal will be described as surviving (euthanized due to end of study; no) or mortality/euthanized (euthanized or died prior to scheduled necropsy due to challenge; yes) based on data collected on the final disposition form and summarized by treatment. Tables 6 and 7, and FIG. 7 summarize the study results of this intratracheal study. FIG. 7A depicts the area under the curve concentrations for IL-6 protein for individual animals against percent lung lesion scores and FIG. 7B depicts the 00163 fold change area under the curve for individual animals against percent lung lesion scores, by flow cytometric analysis depicting the mean fluorescent intensity expressed as a fold change from baseline (>2 is considered biologically relevant).

TABLE 6

Intratracheal Lung Study—Lung Lesion Scoring For Example H-91

|  | Back Transform LS % Lung with Lesions | Standard Error % Lung with Lesions | Lower 80% Confidence Limit of Mean | Upper 80% Confidence Limit of Mean | Range % Lung with Lesions | P value | Significance at .20 level to T01 |
|---|---|---|---|---|---|---|---|
| T01 | 21 | 5 | 15 | 29 | 0 to 71 |  |  |
| T02 | 8 | 3 | 5 | 12 | 0 to 39 | 0.0027 | Yes |
| T03 | 9 | 3 | 6 | 13 | 0 to 58 | 0.0057 | Yes |
| T04 | 12 | 4 | 7 | 19 | 0 to 76 | 0.1244 | Yes |

As can be observed from Table 6, statistical significance (p≤50.2) was established for Example H-91 for T02 and T03, as well as for the positive control group, T04; when compared to T01.

TABLE 7

Intratracheal Study—Mortality for Example H-91

|  | Mortality/Euthanization (Yes/No) | | | | Total | | Significance |
|---|---|---|---|---|---|---|---|
|  | No | | Yes | | Observations | p- | cance |
|  | Number | % | Number | % | Number | value | to T01 |
| T01 | 16 | 66.7 | 8 | 33.3 | 24 | NA | NA |
| T02 | 23 | 100 | 0 | 0 | 23 | 0.0039 | Yes |
| T03 | 22 | 91.7 | 2 | 8.3 | 24 | 0.0723 | Yes |
| T04 | 21 | 87.5 | 3 | 12.5 | 24 | 0.1681 | Yes |

As can be observed from Table 7, statistical significance (p≤0.2) demonstrated in mortality as compared to no treatment saline control for Example H-91 for T02 and T03 as well as for the positive control group, T04; when compared to T01.

Data presented in FIG. 7 is represented as percent lung lesion scores against the area under the curve (AUC) for IL-6 protein (immunoassay expressed in pg/mL) and CD163 (flow cytometric mean fluorescent intensity (MFI) in fold change from baseline). In both assays, a 2-fold change is typically considered to be relevant.

Overall, the *M. haemolytica* intratracheal challenge study demonstrated efficacy for Example H-91 at 0.5 mg/kg and 2.5 mg/kg doses, administered subcutaneously. The compound demonstrated an MIC of >256 μg/mL against the M *haemolytica* challenge strain. Additionally, an MIC of >256 μg/mL was also established against all *M. haemolytica* target pathogens tested. Following a 2.5 mg/kg dose the H-91 plasma maximum concentration (Cmax) was 152 ng/mL. The efficacy generated by Example H-91 at both 0.5 mg/kg and 2.5 mg/kg doses is due to its activity as an immunomodulator and not as an antibiotic. Biomarker analysis demonstrated reduction in IL-6 and CD163 consistent with dose and clinical outcome. The biomarker assessment supports the proposed mechanism of immunomodulation.

In a separate *M. haemolytica* bovine intratracheal lung challenge study with a similar design as above, Example H-11 was assessed. Example H-11 was dosed at 0.5 mg/kg (T03) and 2.5 mg/kg (T04); saline placebo (negative control, T01) and M9 (positive control, 10 mg/kg, T05) were also assessed. Doses were administered to the animals by subcutaneous injection 24 hours prior to bacterial challenge. Lung lesion and mortality data is shown in Tables 8 and 9, respectively. Neutrophil counts, IL-6 and CD163 data is shown in FIG. 8. There was a 43% (median value) reduction in IL-6 levels at 32 hours post challenge while the geometric mean demonstrated a 51% reduction in IL-6 levels. Drug treatment at 24 hours prior to challenge reduced the number of blood neutrophils, plasma IL-6 and expression of scavenger receptor CD163 on blood macrophages; all of which correspond to clinical outcome

TABLE 8

Intratracheal Lung Study—Lung Lesion Scoring: Examples H-11

| | Back Transform LS % Lung with Lesions | Standard Error % Lung with Lesions | Lower 80% Confidence Limit of Mean | Upper 80% Confidence Limit of Mean | Range % Lung with Lesions | P value | Significance at .20 level to T01 |
|---|---|---|---|---|---|---|---|
| T01 | 33 | 7 | 23 | 44 | 2 to 75 | | |
| T03 (H-11) | 28 | 7 | 18 | 38 | 0 to 68 | 0.381 | No |
| T04 (H-11) | 21 | 6 | 13 | 31 | 2 to 70 | 0.0373 | Yes |
| T05 | 24 | 7 | 15 | 35 | 1 to 70 | 0.1481 | yes |

As can be observed from Table 8, statistical significance ($p \leq 0.2$) was established for Example H-11 (T04); as well as for the positive control group, T05; when compared to T01.

TABLE 9

Intratracheal Study—Mortality for Examples H-11

| | Mortality/Euthanization (Yes/No) | | | | Total | | Significance |
|---|---|---|---|---|---|---|---|
| | No | | Yes | | Observations | p- | cance |
| | Number | % | Number | % | Number | value | to T01 |
| T01 | 15 | 62.5 | 9 | 37.5 | 24 | | NA |
| T03 | 20 | 83.3 | 4 | 16.7 | 24 | 0.1028 | Yes |
| T04 | 18 | 75.0 | 6 | 25.0 | 24 | 0.3363 | No |
| T05 | 20 | 87.0 | 3 | 13.0 | 23 | 0.0652 | Yes |

As can be observed from Table 9, statistical significance ($p \leq 50.2$) demonstrated in mortality as compared to no treatment saline control for Example H-11 (T03) as well as for the positive control group (T05); when compared to T01.

As previously demonstrated, M9 and Example H-11 and H-91 downregulated exacerbated plasma IL-6 and CD163 (two independent studies). As described, CD163 is an acute phase protein receptor expressed on activated monocytes in the peripheral blood and macrophages in tissue that binds haptoglobin and hemoglobin to limit oxidative inflammation in the tissue. During chronic inflammatory diseases, expression of CD163 is increased and we see that same expression pattern in the *M. haemolytica* challenge model and in natural disease BRD. These data pointed to drug-mediated reduction in biomarkers of inflammatory pathways. This downregulation of these biomarkers was associated with a positive clinical outcome in naturally occurring BRD.

Lymphocyte populations were also assessed in a separate in vivo genomics challenge model conducted to further elucidate the drugs mechanism of action. Animals (n=8/ group; Holstein, 4-5 months old) were administered placebo (saline, T01), a 0.1 mg/kg dose of H-11 (T02) or a 2.5 mg/kg H-11 (T03) solution dose by subcutaneous injection 24 hours before *M. haemolytica* intratracheal challenge. As a genomics study, animals were not allowed to progree to final disease state; as such animals (n=4/group) were necropsied at 24 and 48 hours post challenge. As part of the study, biomarker and genomics time-course sampling was conducted. T cell surface markers included cytotoxic (CD8+) T cells, γδ-T cells and NK cells, with the most noted effects seen in the T helper cells. Cytokine production in T helper subtypes was assessed using intracellular staining which enables the identification of the specific cell type which is producing the cytokine. Drug treatment resulted in a shift in the balance between T helper type 1 (Th1) and type 17 (Th17) as assessed by production of IFN-γ and IL-17 (IL-17A, specifically), respectively. FIG. 9 shows the intracellular flow cytometric characterization of CD4+T helper cell subtype in the blood of animals at 24 and 48 hours post treatment with H-11 at 0.1 mg/kg (T02). T helper cells were identified by double expression of CD3 and CD4 while negative for CD8 with Th17 cells characterized by IL-17 expression and Th1 characterized by IFN-γ expression. The increase in Th1:Th17 ratio post-treatment suggests a functional shift consistent with promotion of more productive pathogen-fighting type immunity (Th1) over a response that has been associated with pathologic inflammatory responses (Th17) in BRD that is consistent with the role of IL-17-producing T helper cells in the recruitment and activation of neutrophils to affected tissue sites. The shift described in FIG. 9 with intracellular staining was subtle in scale but consistent with treatment-related decreases in IL-17 (IL-17A, specifically) observed in the bronchial alveolar lavage (BAL) fluid and affected consolidated lung tissue collected at necropsy (FIG. 10). FIG. 10 demonstrates the reduction of IL-17 levels as measured in the airway of animals challenged with *M. haemolytica* as a result of H-11 treatment. The noted absence of IL-17 in healthy lung tissue supports the relevance of the subtle protein changes. In addition, these results are consistent with transitional analyses from the airways of at-risk calves in the previously described investigative natural disease study where IL-17 expression levels correlated with poor clinical outcome. Given what is known regarding the pathobiology of BRD and the role of T helper lymphocyte populations in having significant influence on the type and/or direction of an inflammatory response, the shift away from Th17 suggests not only a way by which pathologic inflammation in BRD is being controlled, but potentially also suggests a mechanism by which treatment may enhance a more productive Th1 response which may promote pathogen clearance.

The data presented herein supports the immunomodulatory (non-antibiotic) effect of the compounds of the invention in that a) all animals in the investigative study demonstrated a heightened inflammatory state upon arrival at the feedlot as shown by elevated genomic signatures for PRRs, TLR4, IL-1β, TNF-α and JAK/STAT pathways; b) through genomic analysis it was confirmed that all animals were exposed to similar pathogens throughout the course of the study; c) it is the natural ability of the host to reduce this inflammatory state that predicates the animal for progression to the full BRD complex; d) reduction of this inflammatory state establishes a point of intervention for the use of an immunomodulator (compound of the invention); e) the immunomodulation effects seen with macrolides are consistent with the intervention required to combat the excessive innate immune inflammatory responses in the target animals and progression to BRD; and (f) use of M9 (antibiotic activity) had shown reduced MIC activity to target pathogens. Additional immunological marker data obtained from the in vitro immunological models is shown in Table 10. Compounds resulting in a ">" value for an immunological marker suggests that there was some inherent model effect that occurred such that an $IC_{50}$ and/or OS result could not be determined accurately.

TABLE 10

Immunological Data for the Urea's of Formula (1)

| Ex # | TNF-α ($IC_{50}$ μM) | IL-1β OS of LPS (μM) | IL-6 ($IC_{50}$ μM) |
|---|---|---|---|
| M9 | 250 | na | >250 |
| A-5 | >250 | 24 | >250 |
| A-8 | >250 | 101 | 16 |
| A-13 | 200 | >500 | >500 |
| A-22 | >250 | 100 | 246 |
| B-1 | 25 | 40 | 31 |
| B-1a | 32 | 40 | — |
| B-2 | 11 | 40 | 52 |
| B-2a | 9 | 16 | 23 |
| B-3 | 37 | 40 | 65 |
| B-3a | 12 | 16 | 26 |
| B-4 | 45 | 80 | — |
| B-6 | 12 | 40 | 41 |
| B-7 | 156 | 100 | 143 |
| B-8 | 2 | 6 | 8 |
| B-9 | 107 | 28 | 116 |
| B-13 | 14 | 16 | 51 |
| B-13a | 20 | 16 | — |
| C-2 | 200 | 100 | 100 |
| D-2 | 20 | 16 | 30 |
| E-2 | 40 | 40 | 35 |
| E-154 | 5 | 1 | 4 |
| E-155 | 8 | 6 | 8 |
| F-2 | 11 | 40 | 30 |
| G-2 | 80 | 100 | 70 |
| H-3 | 400 | >500 | — |
| H-8 | 6 | 1 | 5 |
| H-11 | 8 | 32 | 22 |
| H-13 | 12 | 6 | 9 |
| H-18 | 24 | 40 | 165 |
| H-19 | 70 | 100 | 181 |
| H-20 | 31 | 6 | >500 |
| H-22 | >500 | >500 | >500 |
| H-23 | — | 100 | 193 |
| H-24 | 23 | 16 | 30 |
| H-25 | 19 | 16 | 22 |
| H-26 | 30 | 250 | >250 |
| H-27 | 8 | 16 | 17 |
| H-28 | 13 | 17 | 8 |
| H-29 | 50 | 3 | 50 |
| H-30 | 250 | 250 | >250 |
| H-31 | 41 | 81 | 41 |
| H-32 | 11 | 44 | 8 |
| H-33 | 37 | 6 | 57 |
| H-37 | 8 | 40 | 12 |
| H-38 | 49 | >250 | 36 |
| H-39 | 21 | 6 | 19 |
| H-40 | 45 | 40 | — |
| H-42 | — | 100 | 177 |
| H-43 | 34 | 16 | 29 |
| H-45 | 109 | 250 | 130 |
| H-46 | >250 | 100 | — |
| H-50 | >250 | >250 | >250 |
| H-51 | 26 | 40 | 52 |
| H-54 | 9 | 6 | — |
| H-56 | 79 | 18 | 6 |
| H-58 | >250 | >250 | >250 |
| H-59 | 9 | 16 | 30 |
| H-60 | 5 | 3 | 7 |
| H-62 | 1 | <1 | 1 |
| H-64 | 28 | 16 | 28 |
| H-65 | 9 | 2 | 6 |
| H-66 | 106 | 250 | >250 |
| H-69 | 14 | 6 | 8 |
| H-70 | 13 | 6 | 4 |
| H-71 | 32 | 16 | 35 |
| H-72 | >500 | >500 | >500 |
| H-73 | >500 | >500 | — |
| H-74 | ~600 | >500 | >500 |
| H-76 | 179 | 100 | >500 |
| H-77 | 30 | 200 | — |
| H-81 | >250 | 39 | 47 |
| H-83 | 350 | 80 | — |
| H-87 | 100 | 500 | — |
| H-88 | 56 | 13 | 92 |
| H-91 | 85 | 130 | 181 |
| H-95 | 10 | 13 | — |
| H-100 | 6 | 16 | 10 |
| H-102 | 8 | 8 | 11 |
| H-103 | 5 | 3 | 4 |
| I-3 | 40 | 32 | — |
| I-7 | 8 | 6 | 16 |
| J-1 | 70 | 200 | 250 |
| J-2 | >500 | >500 | >500 |
| J-3 | 200 | 200 | 225 |
| J-4 | 7 | 1 | 3 |
| J-5 | >500 | >500 | >500 |
| J-6 | 225 | >500 | >500 |
| J-7 | 200 | 200 | >500 |
| J-8 | >500 | >500 | >500 |
| J-9 | >500 | >500 | >500 |
| J-10 | 20 | 40 | 45 |
| J-12 | 34 | 22 | 126 |
| J-15 | 14 | 16 | 28 |
| J-16 | 60 | 40 | — |
| J-17 | 14 | 40 | 25 |
| J-18 | 16 | >250 | 17 |
| J-19 | 19 | 16 | — |
| J-20 | 7 | 3 | 9 |
| J-21 | 65 | 20 | 75 |
| J-24 | 31 | 100 | 99 |
| J-25 | 6 | 16 | — |
| J-26 | 122 | 100 | >250 |
| J-27 | 48 | 250 | 124 |
| J-28 | 57 | 100 | 152 |
| J-29 | 19 | 40 | 56 |
| J-30 | 16 | 40 | 111 |
| J-32 | >500 | >500 | >500 |
| J-33 | 20 | 80 | 85 |
| J-34 | 40 | 32 | 65 |

The results presented in Table 10 demonstrate a significant increase in inhibition of TNFα, IL-1ß, and/or IL-6 for those Formula (1) compounds tested; compared to M9 at similar drug concentrations (250 µM). For M9, the top dose of 500 µM was not high enough to determine an overstimulation of IL-1ß which was recorded as not applicable (n/a). Further data supporting this hypothesis includes murine studies using a *P. multocida* infection in mice. For example, M9 was clinically efficacious when airway tissues were collected longitudinally and evaluated for transcriptomic analysis. Example H-11 and H-91 were also considered to be clinically efficacious. Using these results, specific transcriptional expression demonstrated regulators consistent with some key BRD pathways (PRRs, cytokines, STAT) and cellular cross-talk activity were assessed.

TNFα is a cell signaling protein, cytokine, that plays a key role in systemic inflammation when produced in excessive upregulated amounts. In the bovine whole blood in vitro screening assay the inhibition of TNFα as induced by stimulation by lipopolysaccharide (LPS) and as measured by half the maximal inhibitory concentration ($IC_{50}$) is recognized as the primary biomarker of immunomodulation potency upon pretreatment with the compounds of the invention. IL-1ß is a mediator of the inflammation response and is involved in a number of cellular activities including proliferation, differentiation and apoptosis. IL-1ß is also released upon cellular stress or cytotoxicity or upon TLR stimulation. In the bovine whole blood assay the stimulation of IL-1ß release upon increasing concentration of test compound is seen as a potential cellular toxicity signal as induced by the test compound. In order to estimate a therapeutic index from the in vitro assay a differential between the TNFα $IC_{50}$ (immunomodulation potency) versus the perceived cellular toxicity concentration (IL-1ß release or overstimulation) was utilized. Therefore, we propose for a compound to be efficacious in vivo, a therapeutic index of >2 (IL-1ß overstimulation/TNFα $IC_{50}$) is required, with higher indices predicting a greater potential for an efficacious dose in vivo. A lower TNFα $IC_{50}$ would indicate a lower overall mg/kg dose in vivo, assuming a sufficient therapeutic index of >2. As the in vitro assay index approaches 1 it is proposed that the balance between immunomodulation and cytotoxicity would be too narrow in order to achieve an efficacious dose in vivo.

Drug Binding Partners as Potential Biological Targets

The data provided herein relative to the immunological mechanistic activity of the compounds of the invention is consistent with the pathways presented herein that have been discovered to be important in the pathobiology of BRD. Key pathways associated with the onset of naturally occurring disease include NFκ, TLR4 (often represented by its agonist such as LPS), JAJ-STAT, TNFα and IL-1ß. Downstream signaling of these pathways lead to induction of pro-inflammatory cytokines such as TNFα and IL-1ß, and IL-6 and chemokines such as CXCL8. These same pathways and their respective components are modulated both in vitro and in vivo by these compounds. Additionally, the types of cells known to be involved in these pathways including macrophages, neutrophils and lymphocytes have been used via a whole blood LPS stimulation format (both in vitro and ex vivo) to demonstrate drug-induced changes in gene expression, cytokine expression, and cell surface receptor activation. In addition to classical immune cells, tissue-resident epithelial and endothelial cells can express innate immune receptors and activate the canonical pathway.

To further characterize the direct activity of the compounds of the invention, experiments to identify the drug's direct binding host partners(s) were performed with the aim of identifying the potential biological targets. Bovine primary cells (peripheral blood mononuclear cells [PBMCs] and polymorphonuclear cells [PMN/neutrophils]) and tissue (trachea, lung) protein homogenates were mixed with M9 and the macrolide, gamithromicin as a comparator. Tissue interactions were allowed to form using a heterogeneous assembly method (nematic protein organization technique, NPOT; Inoviem Scientific); and traditional western blots to identify native-structure proteins bound to the compound. Mass spectrometry analysis identified eight proteins involved in the interaction with M9 as compared to gamithromycin. The antibacterial macrolide gamithromycin was used as a comparator to differentiate specific binding to M9. These proteins were considered to be either direct binding partners of the drug or closely involved in the drug:target interaction (Table 11).

In order to add further clarity to binding partner identification, surface plasma resonance (SPR) technology was used. LCN2 and SLAMF9 was identified as direct binding targets at pH levels consistent with myeloid cell intracellular compartments and diseased tissue sites in BRD. These targets were unique to this drug class compared to gamithromycin, a macrolide antibiotic used in the treatment of BRD. Both targets fit the paradigm that the immunological mechanism of action is linked to the pathways that are both of key importance as being dysregulated in BRD and modulated by M9. LCN2 is expressed by neutrophils upon activation of toll-like receptors (TLRs) and is a component of the innate inflammatory response. Binding of drug to LCN suggests a direct interaction with and effect on neutrophils. Very little information exists to date on SLAMF9. It is a member of a family of signal adaptor proteins that is thought to lack signal transduction capabilities. Very recent studies have demonstrated that SLAMF9 can modulate the LPS-induced TNF response of macrophages and influence cellular functions. This finding is highly consistent with the immunological effects that have been demonstrated with the compounds of the invention further demonstrating the interplay with key innate inflammatory pathways.

TABLE 11

Drug/Protein Binding Partner Identification

| Target | Description | Tissue | Interaction KD (M) |
|---|---|---|---|
| LCN2 | Lipocalin 2 or neutrophil gelatinase-associated lipocalin | PMNs, Trachea | pH 6.5: 4.21E−03 pH 5.5: 4.35E−04 |
| SLAMF9 | Signaling lymphocyte activation molecule 9 | PBMCs, Trachea | pH 6.5: 2.15E−03 pH 5.5: 6.33E−03 |
| NLRX1 | Nod-like receptor X1 | PBMCs | Indirect |
| LPO | Lactoperoxidase | Trachea, PBMCs, PMNs | Indirect |
| TLR4 | Toll-like receptor 4 | PBMCs, Trachea | Indirect |

KD is the equilibrium dissociation constant that was used to present the drug/target affinity. The identified targets associated with drug were measured by surface plasmon resonance (SPR) to define the KD. As can be seen in the table, there was good drug/target binding for LCN2 and SLAMF9 at a biologically relevant pH; while binding for NLRX1, LPO, and TLR4 was indirect.

We claim:
1. A compound of Formula (1-A1)

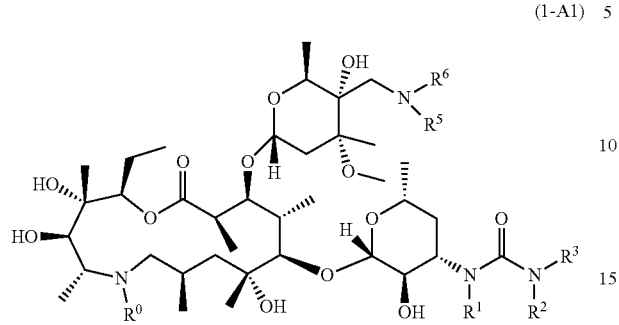

wherein
R$^a$, R$^b$ and R$^0$ are each independently H, methyl, ethyl or propyl;
R$^c$ is methyl, ethyl or propyl;
R$^1$ is methyl, ethyl, propyl, or isopropyl; or R$^1$ is benzyl, —CH$_2$pyridine, —CH$_2$pyrimidine, —CH$_2$pyrazole or —CH$_2$imidazole, wherein each is optionally substituted with at least one R$^9$ substituent;
R$^2$ and R$^3$ are each independently H, C$_1$-C$_6$alkyl, —CH$_2$N(CH$_3$)$_2$, or —CH$_2$CH$_2$N(CH$_3$)$_2$; or C$_0$-C$_2$alkylcyclopropyl, C$_0$-C$_2$alkylcyclobutyl, C$_0$-C$_2$alkylcyclopentyl, C$_0$-C$_2$alkylcyclohexyl, C$_0$-C$_2$alkylphenyl, C$_0$-C$_2$alkylpiperadinyl, piperazinyl, morpholinyl, tetrahydropyran, pyrrolyl, pyrazolyl, pyridinyl, pyrimidinyl, pyridazinyl or pyrazinyl, each of which is optionally substituted with at least one R$^9$ substituent;
R$^5$ and R$^6$ are each independently H; C$_1$-C$_6$alkyl or C$_1$-C$_6$alkoxy each optionally substituted with at least one hydroxy; or R$^5$ and R$^6$ are each independently cyano, C$_1$-C$_6$haloalkyl, C$_1$-C$_6$haloalkoxy, —C(O)R$^8$, —C(O)NR$^a$R$^8$, —C(O)R$^c$NR$^a$R$^b$, —C(O)OR$^8$, —C(O)ONR$^a$R$^b$, —R$^c$NR$^a$C(O)R$^8$, —R$^c$C(O)OH, —R$^c$C(O)NR$^a$R$^b$, —R$^c$NR$^a$C(O)H, —R$^c$S(O)$_p$R$^8$, —R$^c$NR$^a$R$^b$, —R$^c$OR$^a$, —S(O)$_p$R$^8$, —S(O)$_p$R$^8$NR$^a$R$^b$, —R$^c$S(O)$_p$NR$^a$R$^b$, —R$^c$NR$^a$S(O)$_p$R$^8$, phenyl, C$_1$alkylphenyl, cyclopropyl, cyclobutyl, cyclopentyl, cyclohexyl, C$_1$-C$_2$alkylcyclopropyl, C$_1$-C$_2$alkylcyclobutyl, C$_1$-C$_2$alkylcyclopentyl, C$_1$-C$_2$alkylcyclohexyl, tetrahydrofuranyl, tetrahydropyranyl, oxazolidinyl, pyrrolidinyl, piperidinyl, piperazinyl, morpholinyl, C$_1$-C$_2$alkyltetrahydrofuranyl, C$_1$-C$_2$alkyloxazolidinyl, C$_1$-C$_2$alkyltetrahydropyranyl, C$_1$-C$_2$alkylpyrrolidinyl, C$_1$-C$_2$alkylpiperidinyl, C$_1$-C$_2$alkylpiperazinyl, C$_1$-C$_2$alkylmorpholinyl, pyrazolyl, imidazolyl, triazolyl, tetrazolyl, oxazolyl, pyridinyl, pyridazinyl, pyrimidinyl, pyrazinyl, C$_1$-C$_2$alkylpyrazolyl, C$_1$-C$_2$alkylimidazolyl, C$_1$-C$_2$alkyltriazolyl, C$_1$-C$_2$alkyltetrazolyl, C$_1$-C$_2$alkyloxazolyl, C$_1$-C$_2$alkylpyridinyl, C$_1$-C$_2$alkylpyridazinyl, C$_1$-C$_2$alkylpyrimidinyl, or C$_1$-C$_2$alkylpyrazinyl; and wherein each phenyl, cycloalkyl ring, heterocycle ring and heteroaryl ring is optionally substituted with at least one R$^{10}$ substituent;
R$^8$ is methyl or ethyl; or cyclopropyl or phenyl each optionally substituted with at least one substituent selected from C$_1$-C$_4$alkyl, halogen, C$_1$-C$_4$alkoxy, —CF$_3$ and —OCF$_3$;

R$^9$ is independently selected from the group consisting of methyl, ethyl, propyl, isopropyl, t-butyl, methoxy, ethoxy, F, Cl, Br, cyano, —N(CH$_3$)$_2$, —CHF$_2$, —CF$_3$, —OCHF$_2$, hydroxyl and —OCF$_3$;
R$^{10}$ is independently selected from methyl, ethyl, propyl, methoxy, ethoxy, —CHF$_2$, —CF$_3$, —OCF$_3$, F, Cl, —NHCH$_3$, —N(CH$_3$)$_2$, —S(O)$_2$CH$_3$, nitro and cyano; and wherein p is the integer 0, 1 or 2; or a stereoisomer thereof, or a stereoisomer thereof, or a pharmaceutically acceptable salt thereof.

2. The compound of claim 1 that is selected from the group consisting of:
3-cyclopropyl-1-((2S,3R,4S,6R)-2-(((2R,3S,4R,5R,8R,10R,11R,12S,13S,14R)-13-(((2R,4R,5S,6S)-5-((3-cyclopropyl-1-(2-morpholinoethyl)ureido)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-13-(((2R,4R,5S,6S)-5-((dimethylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

1-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

1-((2S,3R,4S,6R)-2-(((2R,3S,4R,5R,8R,10R,11R,12S,13S,14R)-13-(((2R,4R,5S,6S)-5-((diethylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

1-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

3-(2-(dimethylamino)ethyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(2-(piperidin-1-yl)ethyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-propyl-3-(4-(trifluoromethyl)phenyl)urea;

1-((2S,3R,4S,6R)-2-(((2R,3S,4R,5R,8R,10R,11R,12S,13S,14R)-13-(((2R,4R,5S,6S)-5-(((2-(dimethylamino)ethyl)(propyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-13-(((2R,4R,5S,6S)-5-((3-(4-fluorophenyl)-1-propylureido)methyl)-5-hydroxy-4-methoxy-4,6-dimethyltetrahydro-2H-pyran-2-yl)oxy)-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-fluorophenyl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((1-propyl-3-(4-(trifluoromethyl)phenyl)ureido)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(4-(trifluoromethyl)phenyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

1-cyclopropyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-2-yl)urea;

1-ethyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-isopropyl-1-methyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-5-(((2-methoxyethyl)amino)methyl)-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-5-(((3-methoxypropyl)amino)methyl)-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-(((2-(dimethylamino)ethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(methylsulfonyl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((1-propylureido)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-13-(((2R,4R,5S,6S)-5-((ethylamino)methyl)-5-hydroxy-4-methoxy-4,6-dimethyltetrahydro-2H-pyran-2-yl)oxy)-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-5-((isobutylamino)methyl)-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((methylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-((cyclopropylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-((butylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-5-((isopentylamino)methyl)-4-methoxy-4,6-dimethyltetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((((1-methylpiperidin-4-yl)methyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-((((1-acetylpiperidin-4-yl)methyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((phenylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(tetrahydro-2H-pyran-4-yl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-(((2-cyclopropylethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-((cyclobutyl(methyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3,3-diphenylurea;

1-benzyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-13-(((2R,4R,5S,6S)-5-(((cyclopropylmethyl)amino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-morpholinoethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((2-(phenylsulfonyl)ethyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-2-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6- azacyclopentadecan-11-yl)oxy)-3-hydroxy-6-methyltetrahydro-2H-pyran-4-yl)-1,3-dimethyl-3-(pyrazin-2-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridazin-3-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrimidin-2-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrimidin-5-yl)urea;

1-(5-chloropyrimidin-2-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-3-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenyl-3-(2,2,2-trifluoroethyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenyl-3-(tetrahydro-2H-pyran-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(1,2,4-triazin-3-yl)urea;

1-(2,6-dimethylpyrimidin-4-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(1-methyl-1H-pyrazol-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-(4-methoxybenzyl)-3-methyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(3-methylpyridin-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((3-methyl-3-phenyl-1-propylureido)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-benzyl-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenylurea;

1-((2S,3R,4S,6R)-2-(((2R,3S,4R,5R,8R,10R,11R,12S,13S,14R)-13-(((2R,4R,5S,6S)-5-(aminomethyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8, 10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridazin-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenyl-1-propylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-isobutyl-3-methyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenyl-1-(pyridin-3-ylmethyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-3-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(pyridin-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(1-methyl-1H-pyrazol-4-yl)urea;

3-(1,5-dimethyl-1H-pyrazol-3-yl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(2-methoxyphenyl)-1-methylurea;

3-(4-cyanophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(3-(trifluoromethyl)phenyl)urea;

3-(3-cyanophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

3-(2-chlorophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(o-tolyl)urea);

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(2-fluorophenyl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-fluorophenyl)-1-methylurea;

3-(4-chlorophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6- azacyclopentadecan-11-yl)oxy)-3-hydroxy-6-methyltetrahydro-2H-pyran-4-yl)-3-(3-fluorophenyl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(3-methoxyphenyl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-methoxyphenyl)-1-methylurea;

3-(3-chlorophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(p-tolyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(m-tolyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-13-(((2R,4R,5S,6S)-5-((cyclopropylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

1-((2S,3R,4S,6R)-2-(((2R,3S,4R,5R,8R,10R,11R,12S,13S,14R)-13-(((2R,4R,5S,6S)-5-((cyclobutylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((4-(trifluoromethyl)phenyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

3-(2-(dimethylamino)ethyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(2-(piperidin-1-yl)ethyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(4-hydroxyphenyl)-1,3-dimethylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl-1,3-dimethyl-3-(4-(trifluoromethyl)phenyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6- azacyclopentadecan-11-yloxy)-3-hydroxy-6-methyltetrahydro-2H-pyran-4-yl)-1,3-dimethyl-3-phenylurea; and 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-6-propyl-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea, or a stereoisomer thereof, or a pharmaceutically acceptable salt thereof.

3. The compound of claim 1, wherein $R^0$ is each independently H, methyl or propyl;

$R^1$ is methyl, ethyl, propyl or isopropyl; or $R^1$ is benzyl optionally substituted with at least one $R^9$ substituent selected from methyl, ethyl, methoxy, ethoxy, F, Cl, hydroxy, —CF$_3$ and —OCF$_3$;

$R^2$ is H, methyl, ethyl or isopropyl;

$R^3$ is H, methyl, ethyl, propyl, isopropyl, t-butyl; —CH$_2$N(CH$_3$)$_2$, —CH$_2$CH$_2$N(CH$_3$)$_2$, cyclopropyl or cyclobutyl; or phenyl, pyridinyl, pyrimidinyl, pyrazinyl or pyridazinyl, each optionally substituted with at least one $R^9$ substituent selected from the group consisting of methyl, ethyl, hydroxy, methoxy, ethoxy, F, Cl, cyano, and —CF$_3$;

$R^5$ is H;

$R^6$ is H or C$_1$-C$_6$alkyl; or a stereoisomer thereof, or a pharmaceutically acceptable salt thereof.

4. The compound of claim 3 that is selected from the group consisting of:

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea;

1-ethyl-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-1-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-isopropyl-1-methyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((methylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-13-(((2R,4R,5S,6S)-5-((butylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-2-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrazin-2-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridazin-3-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrimidin-2-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyrimidin-5-yl)urea;

1-(5-chloropyrimidin-2-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-3-yl)urea;

1-(2,6-dimethylpyrimidin-4-yl)-3-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(pyridin-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-(3-methylpyridin-4-yl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-methyl-3-phenyl-1-propylurea;

3-(4-cyanophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

3-(3-cyanophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

3-(2-chlorophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-(o-tolyl)urea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(2-fluorophenyl)-1-methylurea;

3-(4-chlorophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(3-fluorophenyl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-3-(3-methoxyphenyl)-1-methylurea;

3-(3-chlorophenyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-phenylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethylurea;

1-((2S,3R,4S,6R)-2-(((2R,3S,4R,5R,8R,10R,11R,12S,13S,14R)-13-(((2R,4R,5S,6S)-5-((cyclopropylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

1-((2S,3R,4S,6R)-2-(((2R,3S,4R,5R,8R,10R,11R,12S,13S,14R)-13-(((2R,4R,5S,6S)-5-((cyclobutylamino)methyl)-5-hydroxy-4-methoxy-4,6-dimethyltetrahydro-2H-pyran-2-yl)oxy)-2-ethyl-3,4,10-trihydroxy-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-(((4-(trifluoromethyl)phenyl)amino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methyl-3-propylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

3-(2-(dimethylamino)ethyl)-1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1-methylurea;

1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1,3-dimethyl-3-(4-(trifluoromethyl)phenyl)urea; and 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,6,8,10,12,14-heptamethyl-15-oxo-1-oxa-6-azacyclopentadecan-11-yl)oxy)-3-hydroxy-6-methyltetrahydro-2H-pyran-4-yl)-1,3-dimethyl-3-phenylurea; or a stereoisomer thereof, or a pharmaceutically acceptable salt thereof.

5. The compound of claim 4 that is 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; or a stereoisomer thereof, or a pharmaceutically acceptable salt thereof.

6. A composition comprising a compound of claim 1, or a stereoisomer thereof or a pharmaceutically acceptable salt thereof, and wherein the composition further comprises a pharmaceutically acceptable carrier.

7. A composition comprising a compound of claim 4, or a stereoisomer thereof, or a pharmaceutically acceptable salt thereof; and wherein the composition further comprises a pharmaceutically acceptable carrier.

8. A composition comprising 1-((2S,3R,4S,6R)-2-(((2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyl-5-((propylamino)methyl)tetrahydro-2H-pyran-2-yl)oxy)-3,5,8,10,12,14-hexamethyl-15-oxo-1-oxa-6-azacyclopentadecan-11-yl)oxy)-3-hydroxy-6-methyltetrahydro-2H-pyran-4-yl)-1,3-dimethyl-3-phenylurea; or a stereoisomer thereof, or a pharmaceutically acceptable salt thereof; and wherein the composition further comprises a pharmaceutically acceptable carrier.

9. A method of treating a respiratory disease mediated by TNF-α, IL-1β or IL-6 in an animal in need thereof by administering to said animal a therapeutically effective amount of a compound of claim 1, or a stereoisomer thereof, or a pharmaceutically acceptable salt thereof.

10. A method of treating a respiratory disease mediated by TNF-α, IL-1β or IL-6 in an animal in need thereof by administering to said animal a therapeutically effective amount of the compound of claim 2 or 4, or a stereoisomer thereof, or a pharmaceutically acceptable salt thereof.

11. A method of treating a respiratory disease mediated by TNF-α, IL-1β or IL-6 in an animal in need thereof by administering to said animal a therapeutically effective amount of the compound of claim 5, or a stereoisomer thereof, or a pharmaceutically acceptable salt thereof.

* * * * *